US012655220B2

(12) United States Patent (10) Patent No.: US 12,655,220 B2

Igawa et al. (45) Date of Patent: Jun. 16, 2026

(54) LIGAND-BINDING FUSION PROTEINS

(71) Applicant: Chugai Seiyaku Kabushiki Kaisha, Tokyo (JP)

(72) Inventors: Tomoyuki Igawa, Singapore (SG); Vishnu Priyanka Reddy Chichili, Singapore (SG); Wei Shiong Adrian Ho, Singapore (SG); Yohei Yamamoto, Shizuoka (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 894 days.

(21) Appl. No.: 17/793,587

(22) PCT Filed: Jan. 20, 2021

(86) PCT No.: PCT/JP2021/001758

§ 371 (c)(1),
(2) Date: Jul. 18, 2022

(87) PCT Pub. No.: WO2021/149697

PCT Pub. Date: Jul. 29, 2021

(65) Prior Publication Data

US 2023/0069996 A1 Mar. 9, 2023

(30) Foreign Application Priority Data

Jan. 20, 2020 (JP) ................................. 2020-006806
Oct. 30, 2020 (JP) ................................. 2020-182089

(51) Int. Cl.

| | |
|---|---|
| *C07K 16/28* | (2006.01) |
| *C07K 14/54* | (2006.01) |
| *C07K 14/55* | (2006.01) |
| *C07K 16/24* | (2006.01) |
| *C12N 15/62* | (2006.01) |

(52) U.S. Cl.

CPC ........ *C07K 16/283* (2013.01); *C07K 14/5434* (2013.01); *C07K 14/55* (2013.01); *C07K 16/246* (2013.01); *C12N 15/62* (2013.01)

(58) Field of Classification Search

None
See application file for complete search history.

(56) References Cited

U.S. PATENT DOCUMENTS

| | | | |
|---|---|---|---|
| 7,666,817 | B2 | 2/2010 | Daugherty et al. |
| 7,901,684 | B2 | 3/2011 | Gill et al. |
| 8,518,404 | B2 | 8/2013 | Daugherty et al. |
| 8,809,504 | B2 | 8/2014 | Lauermann |
| 9,737,623 | B2 | 8/2017 | Desnoyers et al. |
| 10,011,858 | B2 | 7/2018 | Igawa et al. |
| 10,357,571 | B2 | 7/2019 | Williams et al. |
| 10,669,337 | B2 | 6/2020 | Irving et al. |
| 10,696,723 | B2 | 6/2020 | Winston et al. |
| 11,046,759 | B2 | 6/2021 | Moore et al. |
| 11,168,139 | B2 | 11/2021 | Igawa et al. |
| 11,932,697 | B2 | 3/2024 | Igawa et al. |
| 12,030,955 | B2 | 7/2024 | Igawa et al. |
| 12,060,654 | B2 | 8/2024 | Igawa et al. |
| 12,077,577 | B2 | 9/2024 | Kitamura et al. |
| 12,195,528 | B2 | 1/2025 | Igawa et al. |
| 2004/0259768 | A1 | 12/2004 | Lauermann |
| 2007/0065878 | A1 | 3/2007 | Daugherty et al. |
| 2007/0243589 | A1 | 10/2007 | Gill et al. |
| 2010/0015133 | A1 | 1/2010 | Igawa et al. |
| 2011/0064666 | A1 | 3/2011 | Ogawa et al. |
| 2012/0244154 | A1 | 9/2012 | Daugherty et al. |
| 2015/0064169 | A1 | 3/2015 | Wang et al. |
| 2015/0157748 | A1 | 6/2015 | Desnoyers et al. |
| 2016/0144042 | A1 | 5/2016 | Williams et al. |
| 2016/0194399 | A1 | 7/2016 | Irving et al. |
| 2016/0289324 | A1 | 10/2016 | Moore et al. |
| 2018/0057593 | A1 | 3/2018 | Dennis |
| 2019/0359721 | A1 | 11/2019 | Igawa et al. |
| 2019/0367576 | A1 | 12/2019 | Winston et al. |
| 2020/0207846 | A1 * | 7/2020 | Igawa ....................... A61P 1/16 |

(Continued)

FOREIGN PATENT DOCUMENTS

| | | |
|---|---|---|
| AU | 2016213702 A1 | 8/2016 |
| CA | 2548338 A1 | 6/2005 |

(Continued)

OTHER PUBLICATIONS

Dinarello, C. A., et al., "Treating inflammation by blocking interleukin-1 in a broad spectrum of diseases," Nat Rev Drug Discov., 11(8):633-652 (2012).

Gerspach, J., et al., "Target-Selective Activation of a TNF Prodrug by Urokinase-Type Plasminogen Activator (uPA) Mediated Proteolytic Processing at the Cell Surface," Cancer Immunology, Immunotherapy, 55(12):1590-1600 (2006).

Gladkov, O., et al., "Cyclophosphamide and Tucotuzumab (huKS-IL2) Following First-line Chemotherapy in Responding Patients With Extensive-disease Small-cell Lung Cancer," Anti-Cancer Drugs, 26(10):1061-1068 (2015).

Paoloni, M., et al., "Defining the Pharmacodynamic Profile and Therapeutic Index of NHS-IL12 Immunocytokine in Dogs With Malignant Melanoma," PLoS One, 10(6):e0129954 (2015).

Papadia, F., et al., "Isolated Limb Perfusion With the Tumor-targeting Human Monoclonal Antibody-cytokine Fusion Protein L19-TNF Plus Melphalan and Mild Hyperthermia in Patients With Locally Advanced Extremity Melanoma," Journal of Surgical Oncology, 107(2):173-179 (2013).

(Continued)

*Primary Examiner* — Brad Duffy

(74) *Attorney, Agent, or Firm* — Nixon & Vanderhye P.C.

(57) ABSTRACT

An objective of the present invention is to provide a fusion protein that can activate its ligand moiety such as a cytokine or chemokine selectively in a target tissue.

The present invention provides fusion proteins that include a ligand moiety such as a cytokine or chemokine connected via a peptide linker with a ligand-binding moiety that binds to the ligand moiety but is capable of releasing the ligand moiety in the presence of a protease. The present invention also provides their methods of production, their uses, and pharmaceutical compositions containing such a fusion protein. The present invention also relates to improved variants of such fusion proteins. Furthermore, for several cytokines, in vitro activities of the variants were evaluated.

14 Claims, 28 Drawing Sheets

Specification includes a Sequence Listing.

(56) References Cited

U.S. PATENT DOCUMENTS

| | | |
|---|---|---|
| 2020/0369781 A1 | 11/2020 | Igawa et al. |
| 2021/0155701 A1 | 5/2021 | Hoshino et al. |
| 2021/0206845 A1 | 7/2021 | Igawa et al. |
| 2021/0221875 A1 | 7/2021 | Kitamura et al. |
| 2021/0253672 A1 | 8/2021 | Ishikawa et al. |
| 2022/0073632 A1 | 3/2022 | Igawa et al. |
| 2022/0315909 A1 | 10/2022 | Sakurai et al. |
| 2022/0324975 A1 | 10/2022 | Sakurai et al. |
| 2024/0150476 A1 | 5/2024 | Igawa et al. |
| 2024/0270806 A1 | 8/2024 | Chichili et al. |
| 2024/0343771 A1 | 10/2024 | Chichili et al. |
| 2025/0026852 A1 | 1/2025 | Igawa et al. |
| 2025/0034756 A1 | 1/2025 | Igawa et al. |

FOREIGN PATENT DOCUMENTS

| | | |
|---|---|---|
| CA | 2591813 A1 | 6/2006 |
| CA | 2607147 A1 | 11/2006 |
| CA | 2666599 A1 | 2/2008 |
| CA | 2678626 A1 | 9/2008 |
| CA | 2548338 C | 6/2015 |
| CA | 2607147 C | 7/2018 |
| CA | 3083346 A1 | 6/2019 |
| CN | 1665932 A | 9/2005 |
| CN | 101821288 A | 9/2010 |
| CN | 1665932 B | 12/2010 |
| CN | 103068847 A | 4/2013 |
| CN | 103842383 A | 6/2014 |
| CN | 103958547 A | 7/2014 |
| CN | 104661676 A | 5/2015 |
| CN | 106459153 A | 2/2017 |
| CN | 107207564 A | 9/2017 |
| CN | 107602706 A | 1/2018 |
| CN | 103958547 B | 8/2018 |
| CN | 103068847 B | 5/2019 |
| CN | 111836828 A | 10/2020 |
| CN | 107602706 B | 12/2020 |
| CN | 106459153 B | 12/2021 |
| CN | 114127277 A | 3/2022 |
| EP | 1505154 A1 | 2/2005 |
| EP | 2957633 A1 | 12/2015 |
| EP | 3546480 A1 | 10/2019 |
| EP | 3546574 A1 | 10/2019 |
| EP | 3556773 A1 | 10/2019 |
| EP | 3719036 A1 | 10/2020 |
| EP | 3981428 A1 | 4/2022 |
| JP | 2005168328 A | 6/2005 |
| JP | 2010536370 A | 12/2010 |
| JP | 2011026298 A | 2/2011 |
| JP | 2012514982 A | 7/2012 |
| JP | 2013538204 A | 10/2013 |
| JP | 2014509605 A | 4/2014 |
| JP | 2015509952 A | 4/2015 |
| JP | 2015517320 A | 6/2015 |
| JP | 5753903 B2 | 7/2015 |
| JP | 5765894 B2 | 8/2015 |
| JP | 5851842 B2 | 2/2016 |
| JP | 6035009 B2 | 11/2016 |
| JP | 6130307 B2 | 5/2017 |
| JP | 6178846 B2 | 8/2017 |
| JP | 2017523176 A | 8/2017 |
| JP | 2017529853 A | 10/2017 |
| JP | 6273215 B2 | 1/2018 |
| JP | 2019520063 A | 7/2019 |
| JP | 7020909 B2 | 2/2022 |
| JP | 7301540 B2 | 7/2023 |
| RU | 2012110127 A | 9/2013 |
| RU | 2583876 C2 | 5/2016 |
| RU | 2015101803 A | 8/2016 |
| RU | 2636046 C2 | 11/2017 |
| WO | WO2004021861 A2 | 3/2004 |
| WO | WO2005110453 A2 | 11/2005 |
| WO | WO2007027935 A2 | 3/2007 |
| WO | WO-2007063311 A2 | 6/2007 |
| WO | WO2007076933 A1 | 7/2007 |
| WO | WO2008045148 A2 | 4/2008 |
| WO | WO2008157379 A2 | 12/2008 |
| WO | WO2009025846 A2 | 2/2009 |
| WO | WO2010081173 A2 | 7/2010 |
| WO | WO2010115998 A2 | 10/2010 |
| WO | WO2011020783 A3 | 4/2011 |
| WO | WO2011123683 A2 | 10/2011 |
| WO | WO2012025525 A1 | 3/2012 |
| WO | WO2012028697 A1 | 3/2012 |
| WO | WO2012123755 A1 | 9/2012 |
| WO | WO2012158818 A2 | 11/2012 |
| WO | WO2013046704 A2 | 4/2013 |
| WO | WO2013128194 A1 | 9/2013 |
| WO | WO2013148248 A1 | 10/2013 |
| WO | WO2013176730 A1 | 11/2013 |
| WO | WO2013180834 A2 | 12/2013 |
| WO | WO2013192550 A2 | 12/2013 |
| WO | WO2014052462 A2 | 4/2014 |
| WO | WO2014125955 A1 | 8/2014 |
| WO | WO2015066279 A2 | 5/2015 |
| WO | WO2015116933 A2 | 8/2015 |
| WO | WO2015117930 A1 | 8/2015 |
| WO | WO2016014974 A2 | 1/2016 |
| WO | WO2016046778 A2 | 3/2016 |
| WO | WO2016077505 A2 | 5/2016 |
| WO | WO2016118629 A1 | 7/2016 |
| WO | WO2016182064 A1 | 11/2016 |
| WO | WO2017025698 A1 | 2/2017 |
| WO | WO2017162587 A1 | 9/2017 |
| WO | WO2017205014 A1 | 11/2017 |
| WO | WO2017220990 A1 | 12/2017 |
| WO | WO2018085555 A1 | 5/2018 |
| WO | WO2018097307 A1 | 5/2018 |
| WO | WO-2018097308 A1 * | 5/2018 | ............. A61P 35/00 |
| WO | WO2018195506 A1 | 10/2018 |
| WO | WO2019010219 A1 | 1/2019 |
| WO | WO2019010224 A1 | 1/2019 |
| WO | WO2019032471 A1 | 2/2019 |
| WO | WO2019107380 A1 | 6/2019 |
| WO | WO2019107384 A1 | 6/2019 |
| WO | WO2019132472 A1 | 7/2019 |
| WO | WO2019173832 A2 | 9/2019 |
| WO | WO2019222294 A1 | 11/2019 |
| WO | WO2019222295 A1 | 11/2019 |
| WO | WO2019222296 A1 | 11/2019 |
| WO | WO2019230866 A1 | 12/2019 |
| WO | WO2019230867 A1 | 12/2019 |
| WO | WO2019230868 A1 | 12/2019 |
| WO | WO2020061526 A1 | 3/2020 |
| WO | WO2020069398 A1 | 4/2020 |
| WO | WO2020072821 A2 | 4/2020 |
| WO | WO2020086758 A1 | 4/2020 |
| WO | WO2020246567 A1 | 12/2020 |
| WO | WO2021016640 A1 | 1/2021 |
| WO | WO2021062406 A1 | 4/2021 |
| WO | WO2021149697 A1 | 7/2021 |
| WO | WO2021189139 A1 | 9/2021 |
| WO | WO2021202678 A1 | 10/2021 |
| WO | WO2021212083 A2 | 10/2021 |
| WO | WO2021236676 A1 | 11/2021 |
| WO | WO2022094046 A1 | 5/2022 |
| WO | WO2022155263 A2 | 7/2022 |
| WO | WO2023002952 A1 | 1/2023 |
| WO | WO2023004282 A2 | 1/2023 |
| WO | WO2023043978 A2 | 3/2023 |
| WO | WO2023050006 A1 | 4/2023 |
| WO | WO2023070038 A2 | 4/2023 |
| WO | WO2023242769 A1 | 12/2023 |
| WO | WO2024154744 A1 | 7/2024 |

OTHER PUBLICATIONS

Pavlou, A.K. and Belsey, M.J, "The Therapeutic Antibodies Market to 2008," European Journal of Pharmaceutics and Biopharmaceutics, 59(3):389-396 (2005).

Puskas, J., et al., "Development of an Attenuated Interleukin-2 Fusion Protein That Can Be Activated by Tumour-Expressed Proteases," Immunology, 133(2):206-220 (2011).

(56) References Cited

OTHER PUBLICATIONS

Reichert, J.M., et al., "Monoclonal Antibody Successes in the Clinic," Nature Biotechnology, 23(9):1073-1078 (2005).

Skrombolas, D., et al., "Development of an Interleukin-12 Fusion Protein That Is Activated by Cleavage with Matrix Metalloproteinase 9," J Interferon Cytokine Res., 39(4):233-245 (2019).

Tzeng, A., et al., "Antigen Specificity Can Be Irrelevant to Immunocytokine Efficacy and Biodistribution," Proceedings of the National Academy of Sciences of the United States of America, 112(11):3320-3325 (2015).

Weiner, L.M., et al., "Monoclonal Antibodies: Versatile Platforms for Cancer Immunotherapy," Nature Reviews. Immunology, 10(5):317-327 (2010).

Abi-Habib, R.J., et al., "A urokinase-activated recombinant diphtheria toxin targeting the granulocyte-macrophage colony-stimulating factor receptor is selectively cytotoxic to human acute myeloid leukemia blasts," Blood, 104(7):2143-2148 (2004).

Acchione, M., et al., "Impact of Linker and Conjugation Chemistry on Antigen Binding, Fc Receptor Binding and Thermal Stability of Model Antibody-drug Conjugates," MAbs, 4(3):362-372 (2012).

Alberts, B., et al., "Molecular Biology of The Cell," Fifth Edition, Chapter 3 "Proteins," 125, 136 (2008).

Allegra, C. J., et al., "Phase III Trial Assessing Bevacizumab in Stages II and III Carcinoma of the Colon: Results of NSABP Protocol C-08," J Clin Oncol., 29(1):11-16 (2011).

Alley, S.C., et al., "Antibody-drug Conjugates: Targeted Drug Delivery for Cancer," Curr Opin Chem Biol., 14(4):529-537 (2010).

Asano, R. and Kumagai, I., "Functionalization of Bispecific Therapeutic Antibodies Based on Protein Engineering," Yakugaku Zasshi, The Pharmaceutical Society of Japan, 135(7):851-856 (2015), with partial English translation.

Badri, H., et al., "Optimization of radiation dosing schedules for proneural glioblastoma," J Math Biol., 72(5):1301-1336 (2016).

Baeuerle, P.A., et al., "BiTE: Teaching Antibodies to Engage T-cells for Cancer Therapy," Curr Opin Mol Ther., 11(1):22-30 (2009).

Bannas, P., et al., "Nanobodies and Nanobody-Based Human Heavy Chain Antibodies as Antitumor Therapeutics," Front Immunol., 8:1603 (2017).

Baylot, V., et al., "TCTP Has a Crucial Role in the Different Stages of Prostate Cancer Malignant 4 Progression 5," TCTP/tpt1-Remodeling Signaling from Stem Cell to Disease. Results Probl in Cell Differ., 64:255-261 (2017).

Chen, X., et al., "Fusion Protein Linkers: Property, Design and Functionality," Adv Drug Deliv Rev., 65(10):1357-1369 (2013).

Chiu, M. L., et al., "Antibody Structure and Function: The Basis for Engineering Therapeutics," Antibodies, 8:55 (2019).

Colman, P. M., "Effects of Amino Acid Sequence Changes on Antibody-Antigen Interactions," Res Immunol., 145(1):33-36 (1994).

Dashivets, T., et al., "Oxidation in the Complementarity-determining Regions Differentially Influences the Properties of Therapeutic Antibodies," mAbs, 8(8):1525-1535 (2016).

De Bono, J.S., et al., "ING-1, A Monoclonal Antibody Targeting Ep-CAM in Patients With Advanced Adenocarcinomas," Clin Cancer Res., 10(22):7555-7565 (2004).

Derksen, P. W. B., et al., "Illegitimate WNT signaling promotes proliferation of multiple myeloma cells," PNAS, 101(16):6122-6127 (2004).

Desjarlais, J.R., et al., "Optimizing Engagement of the Immune System by Anti-Tumor Antibodies: An Engineer's Perspective," Drug Discov Today, 12(21-22):898-910 (2007).

Desnoyers, L.R., et al., "Tumor-specific Activation of an EGFR-targeting Probody Enhances Therapeutic Index," Sci Transl Med., 5(207):207ra144 (2013).

Dirks, P. B., "Brain Tumor Stem Cells: Bringing Order to the Chaos of Brain Cancer," J Clin Oncol., 26(17):2916-2924 (2008).

Drutskaya, M. S., et al., "Role of IL-6 in Experimental Arthritis Induced by Transfer of Arthritogenic Antibodies," Medical Immunology (Russia), 18(6):569-574 (2016).

Erster, O., et al., "Site-Specific Targeting of Antibody Activity in Vivo Mediated by Disease-Associated Proteases," J Control Release, 161(3):804-812 (2012).

Ginaldi, L., et al., "Increased levels of interleukin 31 (IL-31) in osteoporosis," BMC Immunol., 16:60 (2015).

Halin, C., et al., "Synergistic Therapeutic Effects of a Tumor Targeting Antibody Fragment, Fused to Interleukin 12 and to Tumor Necrosis Factor Alpha," Cancer Res., 63(12):3202-3210 (2003).

Harmsen, M., et al., "Selection and Optimization of Proteolytically Stable Llama Single-domain Antibody Fragments for Oral Immunotherapy," Appl Microbiol Biotechnol., 72(3):544-551 (2006).

Hussack, G., et al., "Engineered Single-Domain Antibodies with High Protease Resistance and Thermal Stability," PLoS One, 6(11):e28218 (2011).

Hutt, M., et al., "Plasma Half-life Extension of Small Recombinant Antibodies by Fusion to Immunoglobulin-Binding Domains," J Biol Chem., 287(7):4462-4469 (2012).

Ishii, A., et al., "A receptor involved in the regulation of the pharmacokinetics of antibody-based pharmaceuticals: FcRn," Folia Pharmacol Jpn., 136(5):280-284 (2010).

Juszczak, A., et al., "Ipilimumab: A Novel Immunomodulating Therapy Causing Autoimmune Hypophysitis: A Case Report and Review," Eur J Endocrinol., 167(1):1-5 (2012).

Keskin, O., et al., "A new, structurally nonredundant, diverse data set of protein-protein interfaces and its implications," Protein Sci., 13(4):1043-1055 (2004).

Kim, S.J., et al., "Antibody Engineering for the Development of Therapeutic Antibodies," Mol Cells, 20(1):17-29 (2005).

Knauf, M.J., et al., "Relationship of Effective Molecular Size to Systemic Clearance in Rats of Recombinant Interleukin-2 Chemically Modified with Water-Soluble Polymers," J Biol Chem., 263(29):15064-15070 (1988).

Kromann-Hansen, T., et al., "A Camelid-derived Antibody Fragment Targeting the Active Site of a Serine Protease Balances Between Inhibitor and Substrate Behavior," J Biol Chem., 291(29):15156-15168 (2016).

Lewis, G.D., et al., "Differential Responses of Human Tumor Cell Lines to Anti-p185HER2 Monoclonal Antibodies," Cancer Immunol Immunother., 37(4):255-263 (1993).

Lutterbuese, R., et al., "T cell-engaging BiTE antibodies specific for EGFR potently eliminate KRAS- and BRAF-mutated colorectal cancer cells," PNAS, 107(28):12605-12610 (2010).

Maeda, Y., et al., "Engineering of Functional Chimeric Protein G-Vargula Luciferase," Anal Biochem., 249(2):147-152 (1997).

Male, D., et al., "Immunology," 7th edition, Elsevier Ltd., 59-86 (2006).

Mariuzza, R.A., et al., "The Structural Basis of Antigen-Antibody Recognition," Ann Rev Biophys Biophys Chem., 16:139-159 (1987).

Muller, S., et al., "Spliceosomal Peptide P140 for Immunotherapy of Systemic Lupus Erythematosus," Arthritis Rheum., 58(12):3873-3883 (2008).

Nam, J.L., et al., "Current Evidence for the Management of Rheumatoid Arthritis With Biological Disease-modifying Antirheumatic Drugs: A Systematic Literature Review Informing the EULAR Recommendations for the Management of RA," Ann Rheum Dis., 69(6):976-986 (2010).

Neri, D. and Sondel, P. M., "Immunocytokines for cancer treatment: past, present and future," Curr Opin Immunol., 40:96-102 (2016).

Onuoha, S.C., et al., "Rational Design of Antirheumatic Prodrugs Specific for Sites of Inflammation," Arthritis Rheumatol., 67(10), pp. 2661-2672 (2015).

Polu, K.R., et al., "Probody Therapeutics for Targeting Antibodies to Diseased Tissue," Expert Opin Biol Ther., 14(8):1049-1053 (2014).

Qin, Z.-X. and Liu, Z.-M., "The Research Progress in Yapsin Protease Family," Lett Biotechnol., 19(4):591-596 (2008), with partial English translation.

Regsiter, A. and William, W., "Short-chain dehydrogenase/reductase SDR [uncultured *Sphingopyxis* sp.]," GenBank Accession No. SBV32674.1, May 15, 2017.

Riechelmann, H., et al., "Phase I Trial With the CD44v6-Targeting Immunoconjugate Bivatuzumab Mertansine in Head and Neck Squamous Cell Carcinoma," Oral Oncol., 44(9):823-829 (2008).

(56) References Cited

OTHER PUBLICATIONS

Robert, R. and Wark, K.L., "Engineered antibody approaches for Alzheimer's disease immunotherapy," Arch Biochem Biophys., 526(2):132-138 (2012).
Roitt, I., et al., Immunology, M., Mir, 109-111 (2000) (in Russian, with what is believed to be a published English equivalent of those pages taken from Roitt, et al., Immunology, Fifth Ed., 78-81 (1998).
Roitt, I., et al., "Immunology," Fifth Edition, Moscow, Mir, 97-113 (2000).
Rudikoff, S., et al. "Single amino acid substitution altering antigen-binding specificity," Proc Natl Acad Sci., 79(6):1979-1983 (1982).
Safdari, Y., et al., "Antibody Humanization Methods—A Review and Update," Biotechnol Genet Eng Rev., 29(2):175-186 (2013).
Sandersjoo, L., et al., "A New Prodrug Form of Affibody Molecules (Pro-affibody) is Selectively Activated by Cancer-associated Proteases," Cell Mol Life Sci., 72(7):1405-1415 (2015).
Satoh, M., et al., "Non-Fucosylated Therapeutic Antibodies as Next-Generation Therapeutic Antibodies," Expert Opin Biol Ther., 6(11):1161-1173 (2006).
Schlapschy, M., et al., "Fusion of a Recombinant Antibody Fragment with a Homo-amino-acid Polymer: Effects on Biophysical Properties and Prolonged Plasma Half-life," Protein Eng Des Sel., 20(6):273-284 (2007).
Seliverstov, Y.A., et al., "Spinal Muscular Atrophies: Conception," Differential Diagnostics and Prospects for Treatment, 3:9-17 (2015).
Severin, Y.S., editor, "Biochemistry, Textbook for Higher Education," Moscow, Geotar-Med, 39-45 (2004).
Singer, M. and Berg, P., "Genes and Genomes," Moscow, Mir, 63 (1998).
Takamori, A., et al., "IL-31 is crucial for induction of pruritus, but not inflammation, in contact hypersensitivity," Sci Rep., 8:6639 (2018).
Takeuchi, T., et al., "The Japanese Experience With Biologic Therapies for Rheumatoid Arthritis," Nat Rev Rheumatol., 6(11):644-652 (2010).
Thomas, D.A., et al., "A Broad-spectrum Fluorescence-based Peptide Library for the Rapid Identification of Protease Substrates," Proteomics, 6(7):2112-2120 (2006).
Torres, M. and Casadevall, A., "The Immunoglobulin Constant Region Contributes to Affinity and Specificity," Trends Immunol., 29(2):91-97 (2008).
Tran, B. and Rosenthal, M. A., "Survival comparison between glioblastoma multiforme and other incurable cancers," J Clin Neurosci., 17(4):417-421 (2010).
Trinh, V.A., et al., "Ipilimumab in the Treatment of Melanoma," Expert Opin Biol Ther., 12(6):773-782 (2012).
Turk, B.E., et al., "Determination of Protease Cleavage Site Motifs Using Mixture-based Oriented Peptide Libraries," Nat Biotechnol., 19(7):661-667 (2001).

Van Roy, M., et al., "The preclinical pharmacology of the high affinity anti-IL-6R Nanobody® ALX-0061 supports its clinical development in rheumatoid arthritis," Arthritis Res Ther., 17:135, (2015).
Vignali, D.A.A. and Kuchroo, V.K., "IL-12 Family Cytokines: Immunological Playmakers," Nat Immunol., 13(8):722-728 (2012).
Wei, S., editor, et al., Clinical Tumor Biological Immunotherapy, 186 (2006), with partial English translation.
Wuest, T., et al., "TNF-Selectokine: A Novel Prodrug Generated for Tumor Targeting and Site-specific Activation of Tumor Necrosis Factor," Oncogene, 21(27):4257-4265 (2002).
Yamane, B.H., et al., "The Development of Antibody-IL-2 based Immunotherapy with hu14.18-IL2 (EMD-273063) in Melanoma and Neuroblastoma," Expert Opin Investig Drugs, 18(7):991-1000 (2009).
Yarilin, A.A., "Fundamentals of Immunology," Moscow, Medicina, 172-174 (1999).
U.S. Appl. No. 10/651,584, filed Aug. 30, 2003, Lauermann.
U.S. Appl. No. 11/910,128, filed Oct. 7, 2008, Igawa et al.
U.S. Appl. No. 12/821,711, filed Jun. 23, 2010, Ogawa et al.
U.S. Appl. No. 16/463,218, filed May 22, 2019, Igawa et al., related application.
U.S. Appl. No. 16/463,222, filed May 22, 2019, Igawa et al., related application.
U.S. Appl. No. 16/766,600, filed May 22, 2020, Igawa et al., related application.
U.S. Appl. No. 16/767,085, filed May 26, 2020, Igawa et al., related application.
U.S. Appl. No. 17/058,889, filed Nov. 25, 2020, Hoshino et al., related application.
U.S. Appl. No. 17/058,896, filed Nov. 25, 2020, Ishikawa et al., related application.
U.S. Appl. No. 17/058,961, filed Nov. 25, 2020, Kitamura et al., related application.
U.S. Appl. No. 17/477,983, filed Sep. 17, 2021, Igawa et al., related application.
U.S. Appl. No. 17/615,633, filed Dec. 1, 2021, Sakurai et al., related application.
U.S. Appl. No. 17/615,748, filed Dec. 1, 2021, Sakurai et al.
U.S. Appl. No. 18/393,918, filed Dec. 22, 2023, Igawa et al., related application.
U.S. Appl. No. 18/414,813, filed Jan. 17, 2024, Chichili et al., related application.
U.S. Appl. No. 18/580,385, filed Jan. 18, 2024, Chichili et al., related application.
U.S. Appl. No. 18/656,351, filed May 6, 2024, Igawa et al., related application.
U.S. Appl. No. 18/672,417, filed May 23, 2024, Igawa et al., related application.

* cited by examiner

Ligand and VH molecule are released from anti-IL12 antibody complex by protease cleavage, and the released IL12 binds to receptor Ligand and VH molecule are released from anti-IL12 antibody complex by protease cleavage, and the released IL12 binds to receptor Ligand and VH molecule are released from anti-IL12 antibody complex by protease cleavage, and the released IL12 binds to receptor VH molecule is released from anti-IL12 antibody complex by protease cleavage, and the released IL12 fused to Fc binds to receptor VH molecule is released from anti-IL12
antibody complex by protease cleavage, and
the released IL12 fused to Fc binds to receptor VH molecule is released from anti-IL12
antibody complex by protease cleavage, and
the released IL12 fused to Fc binds to receptor VH molecule is released from anti-IL12
antibody complex by protease cleavage, and
the released IL12 fused to Fc binds to receptor VH molecule is released from anti-IL12
antibody complex by protease cleavage, and
the released IL12 fused to Fc binds to receptor Fig. 3C
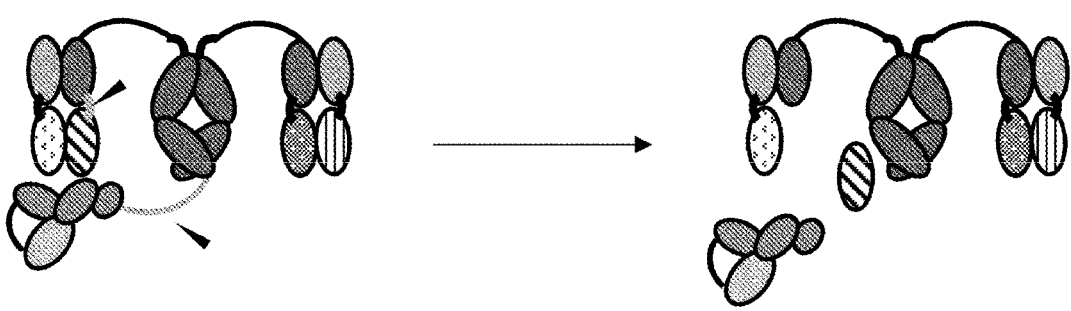
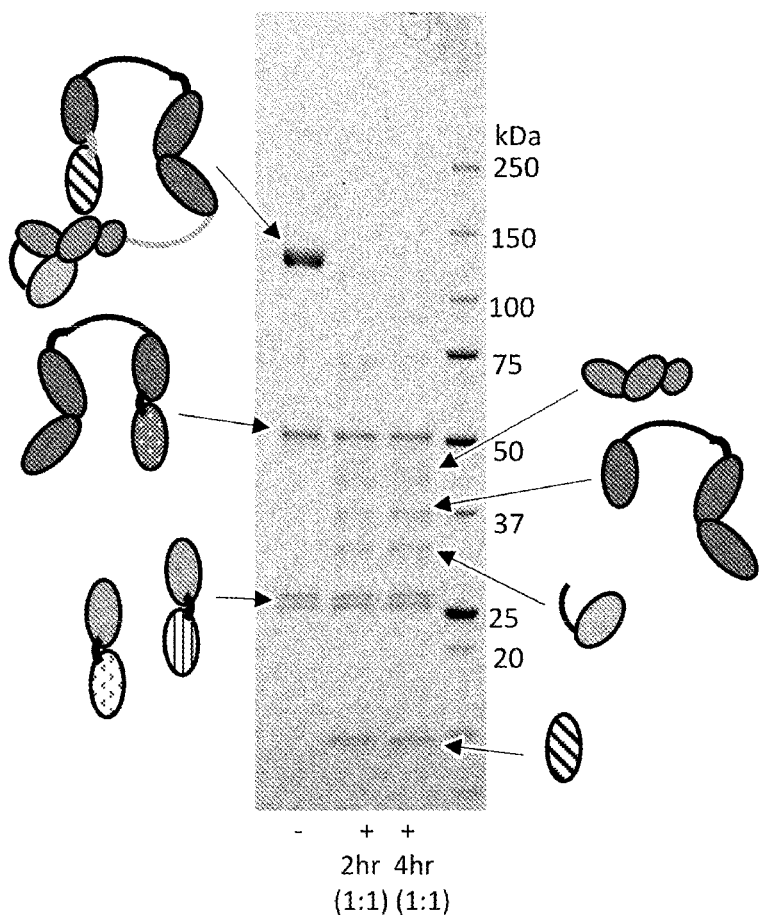

+  +  +  +  +  +  -

1hr 2hr 4hr 1hr 2hr 4hr
(10:1) (10:1) (10:1) (1:1) (1:1) (1:1)

Fig. 5
A
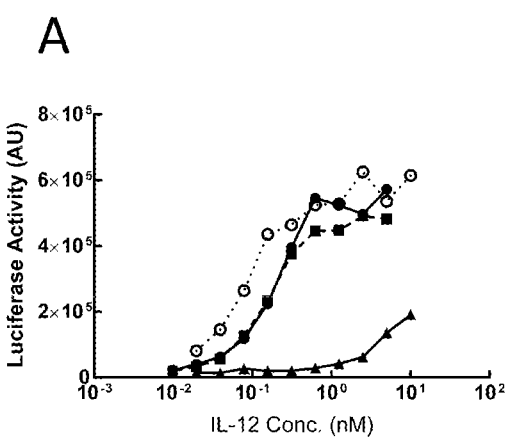
-●- hIL12_His tag
-■- hIL12_His tag + MTSP1
-▲- F4 monovalent IL-12 release Mab80
·○· F4 monovalent IL-12 release Mab80 + MTSP1
B
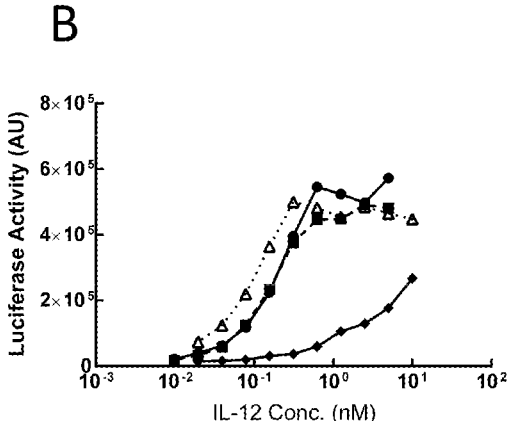
-●- hIL12_His tag
-■- hIL12_His tag + MTSP1
-◆- F4 bivalent IL-12 release Mab80
·△· F4 bivalent IL-12 release Mab80 + MTSP1
C
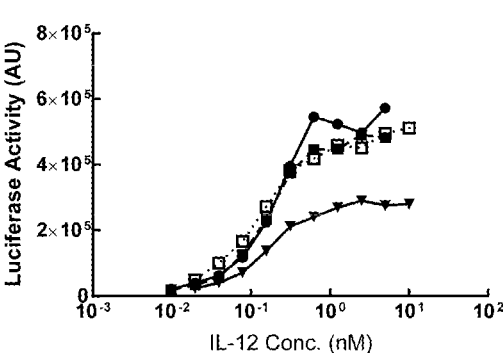
-●- hIL12_His tag
-■- hIL12_His tag + MTSP1
-▼- F2 bivalent IL-12 release Mab80
·□· F2 bivalent IL-12 release Mab80 + MTSP1

Fig. 6

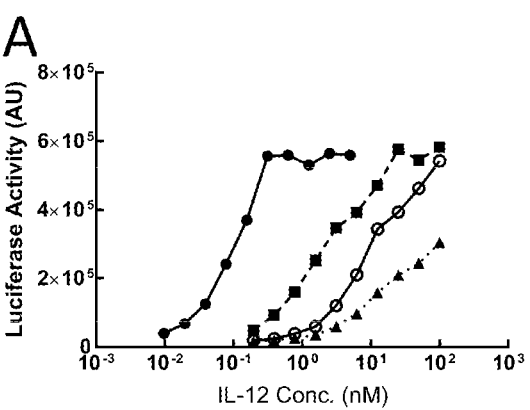

A

- hIL12_His tag
- F4 monovalent IL-12 fusion Mab80
- F4 monovalent IL-12 fusion Ustk
- F4 monovalent IL-12 fusion J695

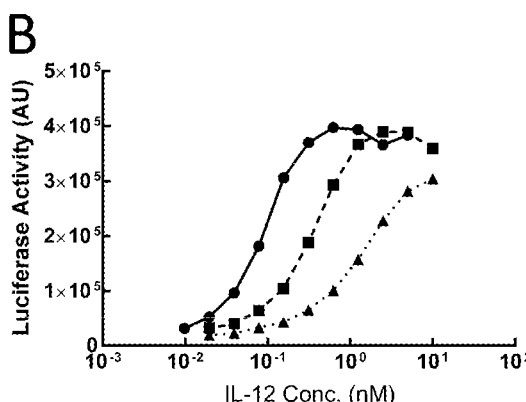

B

- hIL12_His tag + MTSP1
- F4 monovalent IL-12 fusion Ustk + MTSP1
- F4 monovalent IL-12 fusion J695 + MTSP1

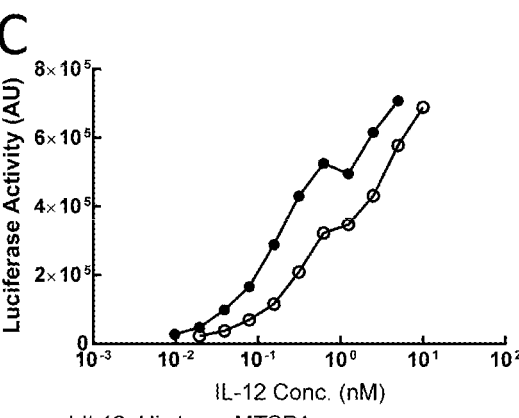

C

- hIL12_His tag + MTSP1
- F4 monovalent IL-12 fusion Mab80 + MTSP1

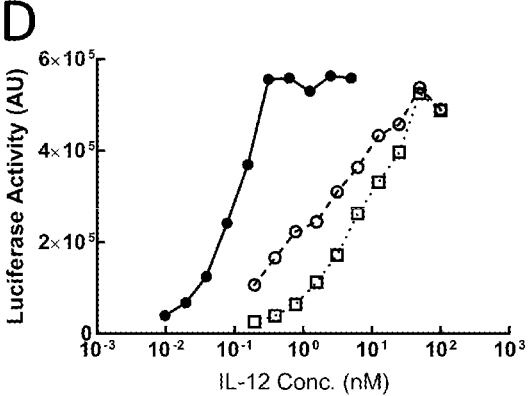

D

- hIL12_His tag
- F2 bivalent IL-12 fusion Mab80
- F4 bivalent IL-12 fusion Mab80

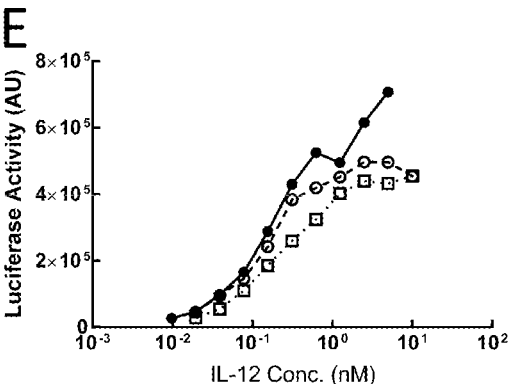

E

- hIL12_His tag + MTSP1
- F2 bivalent IL-12 fusion Mab80 + MTSP1
- F4 bivalent IL-12 fusion Mab80 + MTSP1

Fig. 7A

Fig. 9
087B03-L1-C1-L3-IL22
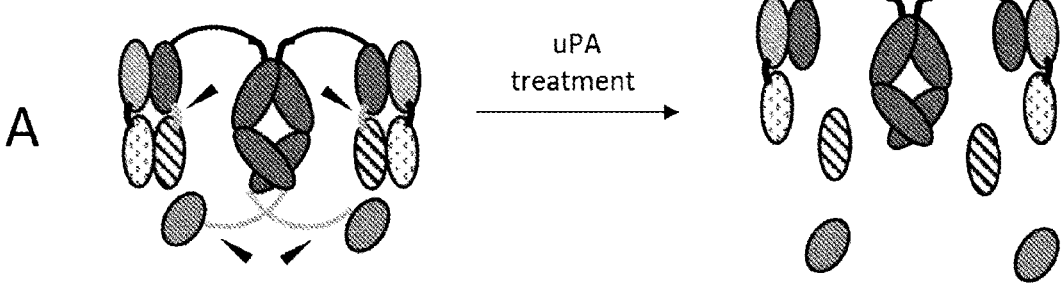
A       uPA treatment
087B03-C1-L4-IL22
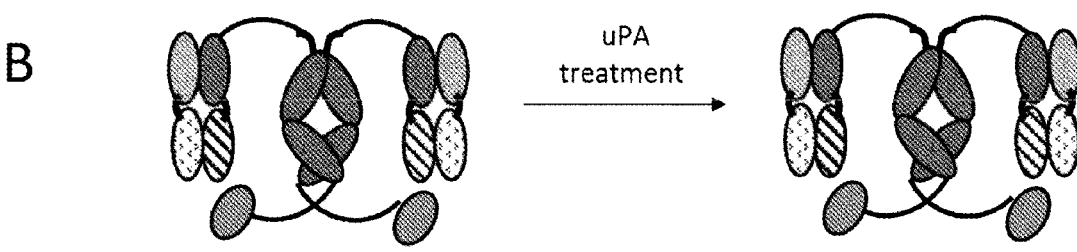
B       uPA treatment 1. 087B03-L1-C1-L3-IL22
2. 087B03-L1-C3-L3-IL22
3. 087B03-C1-L4-IL22
4. human IL-22
5. PBS
6. 087B03-L1-C1-L3-IL22
7. 087B03-L1-C3-L3-IL22
8. 087B03-C1-L4-IL22
9. human IL-22
10. PBS Fig. 12
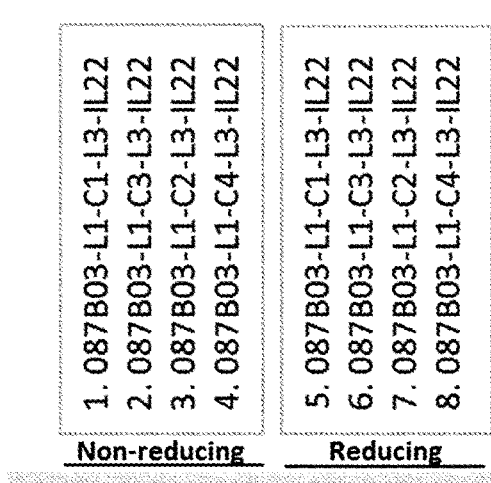
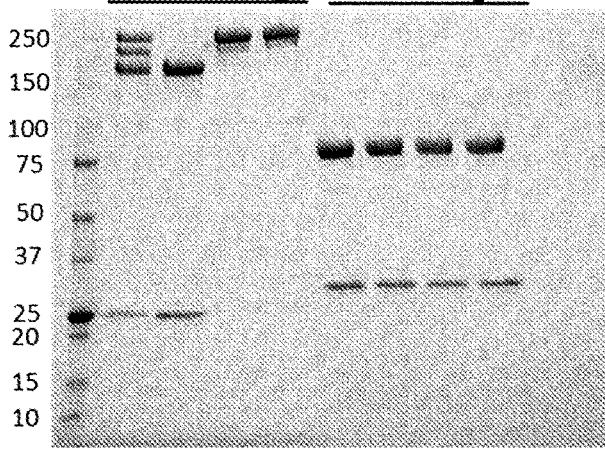

1. 087B03-L1-C2-L3-IL22
2. 087B03-L1-C4-L3-IL22
3. human IL-22
4. dPBS
5. 087B03-L1-C2-L3-IL22
6. 087B03-L1-C4-L3-IL22
7. human IL-22
8. dPBS 1. 087B03-L1-C2-L3-IL22
2. 087B03-L1-C4-L3-IL22
3. human IL-22
4. dPBS
5. 087B03-L1-C2-L3-IL22
6. 087B03-L1-C4-L3-IL22
7. human IL-22
8. dPBS Fig. 15
A    Activity of IL-22 fused antibodies with uPA
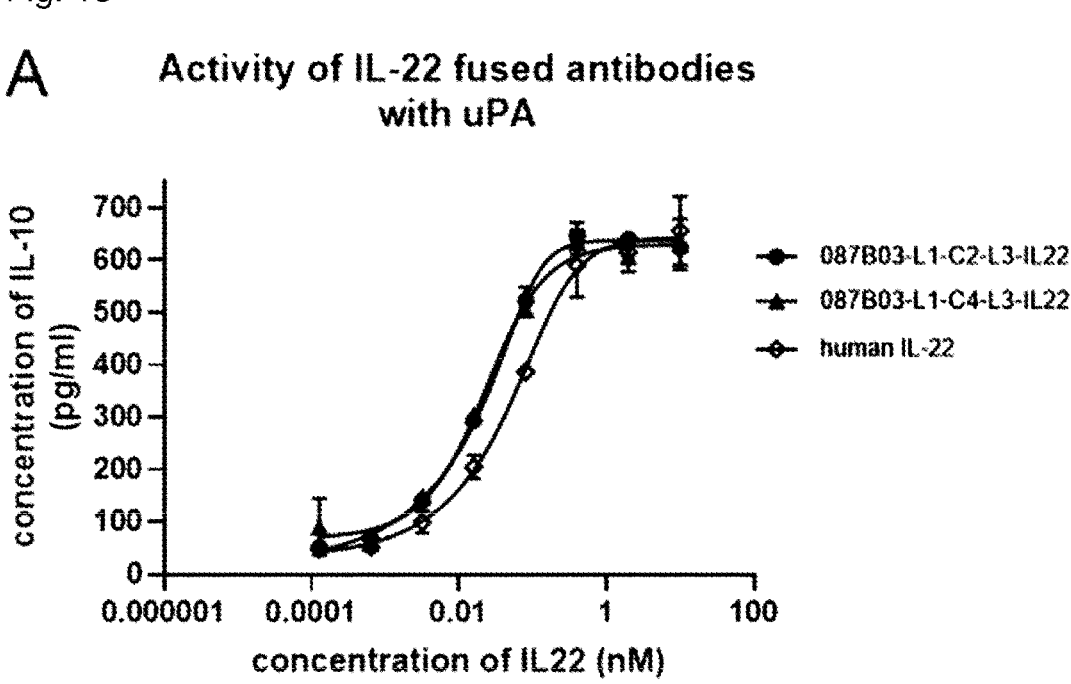
B    Activity of IL-22 fused antibodies without uPA
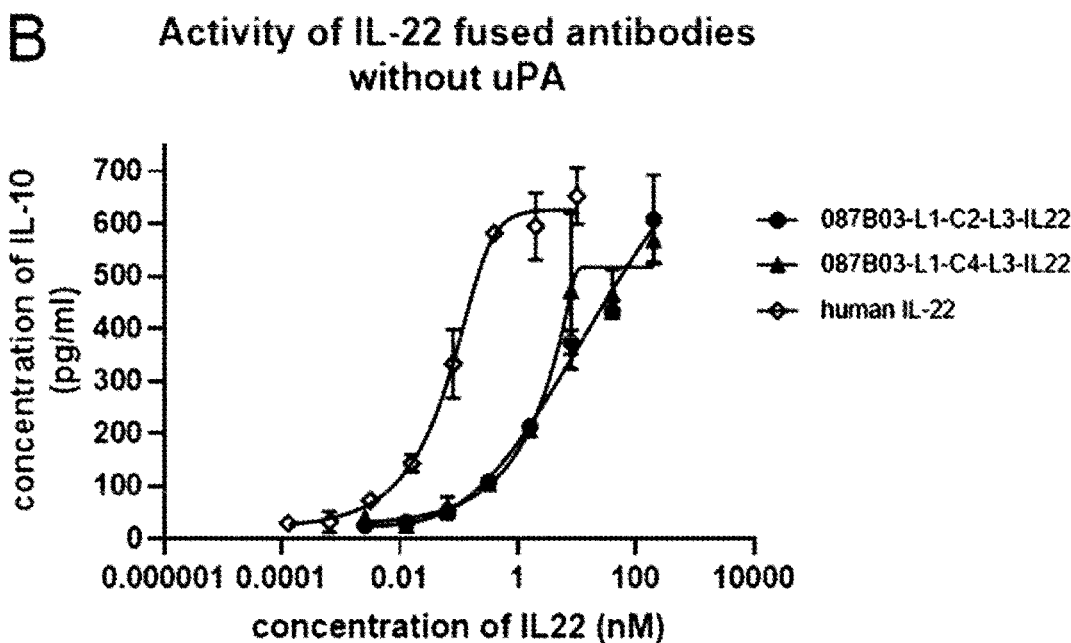

Fig. 16
Cx-L1-C5-L5-IL2.N88D/ 16C3-L1-C5-L5-IL2.N88D
A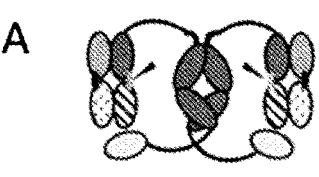
uPA
treatment
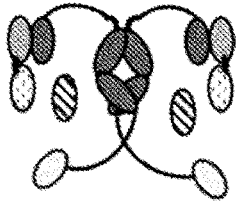
Cx-L6-C5-L5-IL2.N88D/ 16C3-L6-C5-L5-IL2.N88D
B
uPA
treatment
C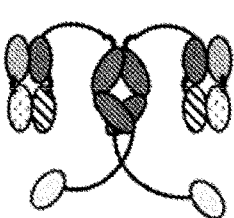
KLH-L6-C5-L5-IL2.N88D
uPA
treatment
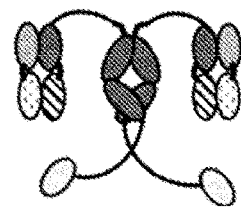

Fig. 17
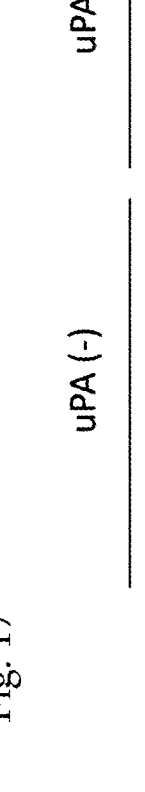
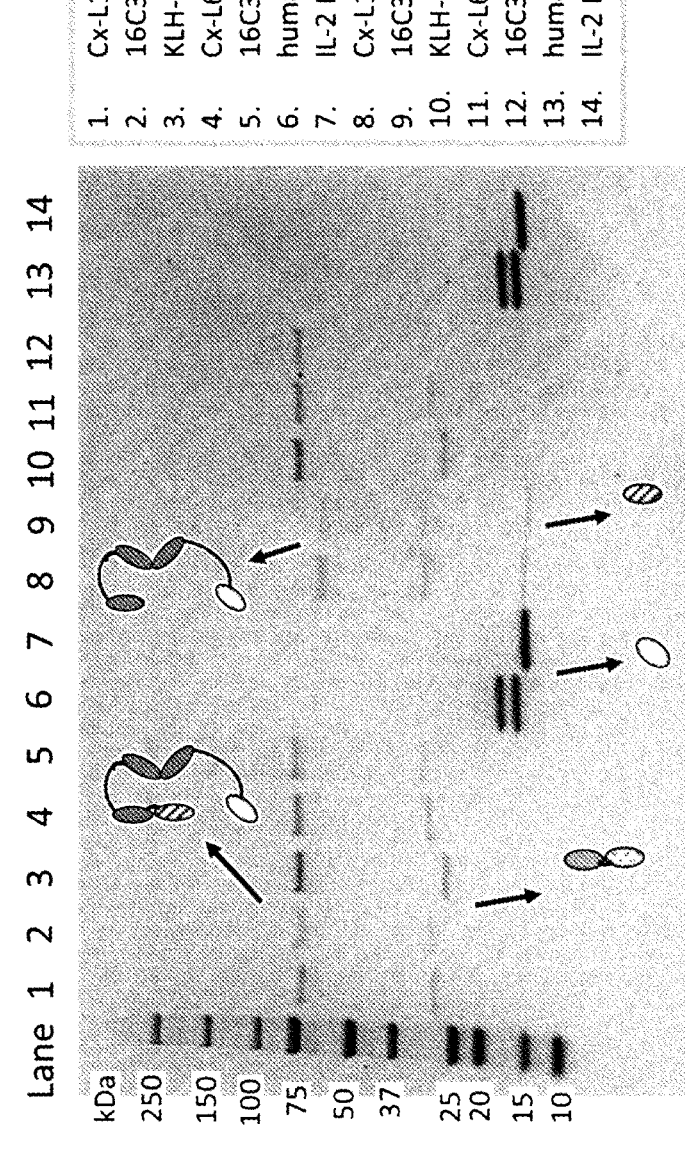
1. Cx-L1-C5-L5-IL2.N88D
2. 16C3-L1-C5-L5-IL2.N88D
3. KLH-L6-C5-L5-IL2.N88D
4. Cx-L6-C5-L5-IL2.N88D
5. 16C3-L6-C5-L5-IL2.N88D
6. human IL-2
7. IL-2 N88D
8. Cx-L1-C5-L5-IL2.N88D
9. 16C3-L1-C5-L5-IL2.N88D
10. KLH-L6-C5-L5-IL2.N88D
11. Cx-L6-C5-L5-IL2.N88D
12. 16C3-L6-C5-L5-IL2.N88D
13. human IL-2
14. IL-2 N88D

SEQUENCE LISTING

<160> NUMBER OF SEQ ID NOS: 938

<210> SEQ ID NO 1
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 1

Met Gly Trp Ser Cys Ile Ile Leu Phe Leu Val Ala Thr Ala Thr Gly
1               5                   10                  15

Val His Ser

<210> SEQ ID NO 2
<211> LENGTH: 8
<212> TYPE: PRT

```
<213> ORGANISM: Artificial Sequence
<220> FEATURE:
<223> OTHER INFORMATION: an artificially synthesized sequence

<400> SEQUENCE: 2

Leu Ser Gly Arg Ser Asp Asn His
1               5

<210> SEQ ID NO 3
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 3

Pro Leu Gly Leu Ala Gly
1               5

<210> SEQ ID NO 4
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 4

Val Pro Leu Ser Leu Thr Met Gly
1               5

<210> SEQ ID NO 5
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 5

Thr Ser Thr Ser Gly Arg Ser Ala Asn Pro Arg Gly
1               5                   10

<210> SEQ ID NO 6
<211> LENGTH: 13
<212> TYPE: PRT
<213> ORGANISM: Artificial Sequence
<220> FEATURE:
<223> OTHER INFORMATION: an artificially synthesized sequence

<400> SEQUENCE: 6

Ile Ser Ser Gly Leu Leu Ser Gly Arg Ser Asp Asn His
1               5                   10

<210> SEQ ID NO 7
<211> LENGTH: 18
<212> TYPE: PRT
<213> ORGANISM: Artificial Sequence
<220> FEATURE:
<223> OTHER INFORMATION: an artificially synthesized sequence

<400> SEQUENCE: 7

Ala Val Gly Leu Leu Ala Pro Pro Gly Gly Leu Ser Gly Arg Ser Asp
1               5                   10                  15

Asn His

<210> SEQ ID NO 8
<211> LENGTH: 13
```

<212> TYPE: PRT
<213> ORGANISM: Artificial Sequence
<220> FEATURE:
<223> OTHER INFORMATION: an artificially synthesized sequence

<400> SEQUENCE: 8

Gly Ala Gly Val Pro Met Ser Met Arg Gly Gly Ala Gly
1               5                   10

<210> SEQ ID NO 9
<211> LENGTH: 13
<212> TYPE: PRT
<213> ORGANISM: Artificial Sequence
<220> FEATURE:
<223> OTHER INFORMATION: an artificially synthesized sequence

<400> SEQUENCE: 9

Gly Ala Gly Ile Pro Val Ser Leu Arg Ser Gly Ala Gly
1               5                   10

<210> SEQ ID NO 10
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 10

Gly Pro Leu Gly Ile Ala Gly Gln
1               5

<210> SEQ ID NO 11
<211> LENGTH: 10
<212> TYPE: PRT
<213> ORGANISM: Artificial Sequence
<220> FEATURE:
<223> OTHER INFORMATION: an artificially synthesized sequence

<400> SEQUENCE: 11

Gly Gly Pro Leu Gly Met Leu Ser Gln Ser
1               5                   10

<210> SEQ ID NO 12
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 12

Pro Leu Gly Leu Trp Ala
1               5

<210> SEQ ID NO 13
<211> LENGTH: 13
<212> TYPE: PRT
<213> ORGANISM: Artificial Sequence
<220> FEATURE:
<223> OTHER INFORMATION: an artificially synthesized sequence

<400> SEQUENCE: 13

Gly Ala Gly Arg Pro Phe Ser Met Ile Met Gly Ala Gly
1               5                   10

<210> SEQ ID NO 14
<211> LENGTH: 13
<212> TYPE: PRT

-continued

```
<213> ORGANISM: Artificial Sequence
<220> FEATURE:
<223> OTHER INFORMATION: an artificially synthesized sequence

<400> SEQUENCE: 14

Gly Ala Gly Val Pro Leu Ser Leu Thr Met Gly Ala Gly
1               5                   10

<210> SEQ ID NO 15
<211> LENGTH: 13
<212> TYPE: PRT
<213> ORGANISM: Artificial Sequence
<220> FEATURE:
<223> OTHER INFORMATION: an artificially synthesized sequence

<400> SEQUENCE: 15

Gly Ala Gly Val Pro Leu Ser Leu Tyr Ser Gly Ala Gly
1               5                   10

<210> SEQ ID NO 16
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 16

Ala Ala Asn Leu Arg Asn
1               5

<210> SEQ ID NO 17
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 17

Ala Gln Ala Tyr Val Lys
1               5

<210> SEQ ID NO 18
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 18

Ala Ala Asn Tyr Met Arg
1               5

<210> SEQ ID NO 19
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 19

Ala Ala Ala Leu Thr Arg
1               5

<210> SEQ ID NO 20
<211> LENGTH: 6
<212> TYPE: PRT
<213> ORGANISM: Artificial Sequence
```

-continued

```
<220> FEATURE:
<223> OTHER INFORMATION: an artificially synthesized sequence

<400> SEQUENCE: 20

Ala Gln Asn Leu Met Arg
1               5

<210> SEQ ID NO 21
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 21

Ala Ala Asn Tyr Thr Lys
1               5

<210> SEQ ID NO 22
<211> LENGTH: 16
<212> TYPE: PRT
<213> ORGANISM: Artificial Sequence
<220> FEATURE:
<223> OTHER INFORMATION: an artificially synthesized sequence

<400> SEQUENCE: 22

Gly Ala Gly Pro Gln Gly Leu Ala Gly Gln Arg Gly Ile Val Ala Gly
1               5                   10                  15

<210> SEQ ID NO 23
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 23

Pro Arg Phe Lys Ile Ile Gly Gly
1               5

<210> SEQ ID NO 24
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 24

Pro Arg Phe Arg Ile Ile Gly Gly
1               5

<210> SEQ ID NO 25
<211> LENGTH: 9
<212> TYPE: PRT
<213> ORGANISM: Artificial Sequence
<220> FEATURE:
<223> OTHER INFORMATION: an artificially synthesized sequence

<400> SEQUENCE: 25

Gly Ala Gly Ser Gly Arg Ser Ala Gly
1               5

<210> SEQ ID NO 26
<211> LENGTH: 5
<212> TYPE: PRT
<213> ORGANISM: Artificial Sequence
<220> FEATURE:
```

-continued

---

<223> OTHER INFORMATION: an artificially synthesized sequence

<400> SEQUENCE: 26

Ser Gly Arg Ser Ala
1               5

<210> SEQ ID NO 27
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 27

Gly Ser Gly Arg Ser Ala
1               5

<210> SEQ ID NO 28
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 28

Ser Gly Lys Ser Ala
1               5

<210> SEQ ID NO 29
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 29

Ser Gly Arg Ser Ser
1               5

<210> SEQ ID NO 30
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 30

Ser Gly Arg Arg Ala
1               5

<210> SEQ ID NO 31
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 31

Ser Gly Arg Asn Ala
1               5

<210> SEQ ID NO 32
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 32

Ser Gly Arg Lys Ala
1               5

<210> SEQ ID NO 33
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 33

Gln Arg Gly Arg Ser Ala
1               5

<210> SEQ ID NO 34
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 34

Gly Ala Gly Ser Leu Leu Lys Ser Arg Met Val Pro Asn Phe Asn Ala
1               5                   10                  15

Gly

<210> SEQ ID NO 35
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 35

Thr Gln Gly Ala Ala Ala
1               5

<210> SEQ ID NO 36
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 36

Gly Ala Ala Ala Ala Ala
1               5

<210> SEQ ID NO 37
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 37

Gly Ala Gly Ala Ala Gly
1               5

<210> SEQ ID NO 38
<211> LENGTH: 6
<212> TYPE: PRT
<213> ORGANISM: Artificial Sequence
<220> FEATURE:

<223> OTHER INFORMATION: an artificially synthesized sequence

<400> SEQUENCE: 38

Ala Ala Ala Ala Ala Gly
1               5

<210> SEQ ID NO 39
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 39

Leu Cys Gly Ala Ala Ile
1               5

<210> SEQ ID NO 40
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 40

Phe Ala Gln Ala Leu Gly
1               5

<210> SEQ ID NO 41
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 41

Leu Leu Gln Ala Asn Pro
1               5

<210> SEQ ID NO 42
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 42

Leu Ala Ala Ala Asn Pro
1               5

<210> SEQ ID NO 43
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 43

Leu Tyr Gly Ala Gln Phe
1               5

<210> SEQ ID NO 44
<211> LENGTH: 6
<212> TYPE: PRT
<213> ORGANISM: Artificial Sequence
<220> FEATURE:
<223> OTHER INFORMATION: an artificially synthesized sequence

```
<400> SEQUENCE: 44

Leu Ser Gln Ala Gln Gly
1               5

<210> SEQ ID NO 45
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 45

Ala Ser Ala Ala Ser Gly
1               5

<210> SEQ ID NO 46
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 46

Phe Leu Gly Ala Ser Leu
1               5

<210> SEQ ID NO 47
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 47

Ala Tyr Gly Ala Thr Gly
1               5

<210> SEQ ID NO 48
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 48

Leu Ala Gln Ala Thr Gly
1               5

<210> SEQ ID NO 49
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 49

Gly Ala Gly Ser Gly Val Val Ile Ala Thr Val Ile Val Ile Thr Ala
1               5                   10                  15

Gly

<210> SEQ ID NO 50
<211> LENGTH: 8
<212> TYPE: PRT
<213> ORGANISM: Artificial Sequence
<220> FEATURE:
```

<223> OTHER INFORMATION: an artificially synthesized sequence

<400> SEQUENCE: 50

Ala Pro Met Ala Glu Gly Gly Gly
1               5

<210> SEQ ID NO 51
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 51

Glu Ala Gln Gly Asp Lys Ile Ile
1               5

<210> SEQ ID NO 52
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 52

Leu Ala Phe Ser Asp Ala Gly Pro
1               5

<210> SEQ ID NO 53
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 53

Tyr Val Ala Asp Ala Pro Lys
1               5

<210> SEQ ID NO 54
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 54

Arg Arg Arg Arg Arg
1               5

<210> SEQ ID NO 55
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 55

Arg Arg Arg Arg Arg Arg
1               5

<210> SEQ ID NO 56
<211> LENGTH: 10
<212> TYPE: PRT
<213> ORGANISM: Artificial Sequence
<220> FEATURE:
<223> OTHER INFORMATION: an artificially synthesized sequence

<400> SEQUENCE: 56

Gly Gln Ser Ser Arg His Arg Arg Ala Leu
1               5                   10

<210> SEQ ID NO 57
<211> LENGTH: 9
<212> TYPE: PRT
<213> ORGANISM: Artificial Sequence
<220> FEATURE:
<223> OTHER INFORMATION: an artificially synthesized sequence

<400> SEQUENCE: 57

Ser Ser Arg His Arg Arg Ala Leu Asp
1               5

<210> SEQ ID NO 58
<211> LENGTH: 14
<212> TYPE: PRT
<213> ORGANISM: Artificial Sequence
<220> FEATURE:
<223> OTHER INFORMATION: an artificially synthesized sequence

<400> SEQUENCE: 58

Arg Lys Ser Ser Ile Ile Ile Arg Met Arg Asp Val Val Leu
1               5                   10

<210> SEQ ID NO 59
<211> LENGTH: 15
<212> TYPE: PRT
<213> ORGANISM: Artificial Sequence
<220> FEATURE:
<223> OTHER INFORMATION: an artificially synthesized sequence

<400> SEQUENCE: 59

Ser Ser Ser Phe Asp Lys Gly Lys Tyr Lys Lys Gly Asp Asp Ala
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: an artificially synthesized sequence

<400> SEQUENCE: 60

Ser Ser Ser Phe Asp Lys Gly Lys Tyr Lys Arg Gly Asp Asp Ala
1               5                   10                  15

<210> SEQ ID NO 61
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 61

Ile Glu Gly Arg
1

<210> SEQ ID NO 62
<211> LENGTH: 4
<212> TYPE: PRT
<213> ORGANISM: Artificial Sequence
<220> FEATURE:
<223> OTHER INFORMATION: an artificially synthesized sequence -continued

```
<400> SEQUENCE: 62

Ile Asp Gly Arg
1

<210> SEQ ID NO 63
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 63

Gly Gly Ser Ile Asp Gly Arg
1               5

<210> SEQ ID NO 64
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 64

Gly Pro Gln Gly Ile Ala Gly Gln
1               5

<210> SEQ ID NO 65
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 65

Gly Pro Gln Gly Leu Leu Gly Ala
1               5

<210> SEQ ID NO 66
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 66

Gly Ile Ala Gly Gln
1               5

<210> SEQ ID NO 67
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 67

Gly Pro Leu Gly Ile Ala Gly
1               5

<210> SEQ ID NO 68
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 68
```

-continued

```
Gly Pro Glu Gly Leu Arg Val Gly
1               5

<210> SEQ ID NO 69
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 69

Tyr Gly Ala Gly Leu Gly Val Val
1               5

<210> SEQ ID NO 70
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 70

Ala Gly Leu Gly Val Val Glu Arg
1               5

<210> SEQ ID NO 71
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 71

Ala Gly Leu Gly Ile Ser Ser Thr
1               5

<210> SEQ ID NO 72
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 72

Glu Pro Gln Ala Leu Ala Met Ser
1               5

<210> SEQ ID NO 73
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 73

Gln Ala Leu Ala Met Ser Ala Ile
1               5

<210> SEQ ID NO 74
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 74
```

-continued

```
Ala Ala Tyr His Leu Val Ser Gln
1               5

<210> SEQ ID NO 75
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 75

Met Asp Ala Phe Leu Glu Ser Ser
1               5

<210> SEQ ID NO 76
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 76

Glu Ser Leu Pro Val Val Ala Val
1               5

<210> SEQ ID NO 77
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 77

Ser Ala Pro Ala Val Glu Ser Glu
1               5

<210> SEQ ID NO 78
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 78

Asp Val Ala Gln Phe Val Leu Thr
1               5

<210> SEQ ID NO 79
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 79

Val Ala Gln Phe Val Leu Thr Glu
1               5

<210> SEQ ID NO 80
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 80

Ala Gln Phe Val Leu Thr Glu Gly
```

1               5

<210> SEQ ID NO 81
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 81

Pro Val Gln Pro Ile Gly Pro Gln
1               5

<210> SEQ ID NO 82
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 82

Leu Val Pro Arg Gly Ser
1               5

<210> SEQ ID NO 83
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 83

Thr Ser Thr Ser Gly Arg Ser Ala Asn Pro Arg Gly
1               5                   10

<210> SEQ ID NO 84
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 84

Thr Ser Thr Ser Gly Arg Ser Ala Asn Pro Arg Gly
1               5                   10

<210> SEQ ID NO 85
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 85

Thr Ser Gly Ser Gly Arg Ser Ala Asn Ala Arg Gly
1               5                   10

<210> SEQ ID NO 86
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 86

Thr Ser Gln Ser Gly Arg Ser Ala Asn Gln Arg Gly
1               5                   10

-continued

```
<210> SEQ ID NO 87
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 87

Thr Ser Pro Ser Gly Arg Ser Ala Tyr Pro Arg Gly
1               5                   10

<210> SEQ ID NO 88
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 88

Thr Ser Gly Ser Gly Arg Ser Ala Thr Pro Arg Gly
1               5                   10

<210> SEQ ID NO 89
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 89

Thr Ser Gln Ser Gly Arg Ser Ala Thr Pro Arg Gly
1               5                   10

<210> SEQ ID NO 90
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 90

Thr Ser Ala Ser Gly Arg Ser Ala Thr Pro Arg Gly
1               5                   10

<210> SEQ ID NO 91
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 91

Thr Ser Tyr Ser Gly Arg Ser Ala Val Pro Arg Gly
1               5                   10

<210> SEQ ID NO 92
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 92

Thr Ser Tyr Ser Gly Arg Ser Ala Asn Phe Arg Gly
1               5                   10
```

-continued

```
<210> SEQ ID NO 93
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 93

Thr Ser Ser Ser Gly Arg Ser Ala Thr Pro Arg Gly
1               5                   10

<210> SEQ ID NO 94
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 94

Thr Ser Thr Thr Gly Arg Ser Ala Ser Pro Arg Gly
1               5                   10

<210> SEQ ID NO 95
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 95

Thr Ser Thr Ser Gly Arg Ser Ala Asn Pro Arg Gly
1               5                   10

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101
```

-continued

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

-continued

```
<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124
```

-continued

```
<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135
```

-continued

000

<210> SEQ ID NO 136
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 136

Gly Gly Gly Ser
1

<210> SEQ ID NO 137
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 137

Gly Gly Ser Gly
1

<210> SEQ ID NO 138
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 138

Gly Ser Gly Gly
1

<210> SEQ ID NO 139
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 139

Ser Gly Gly Gly
1

<210> SEQ ID NO 140
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 140

Gly Ser Ser Gly
1

<210> SEQ ID NO 141
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 141

Gly Gly Gly Gly Ser

-continued

```
1               5

<210> SEQ ID NO 142
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 142

Gly Gly Gly Ser Gly
1               5

<210> SEQ ID NO 143
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 143

Gly Gly Ser Gly Gly
1               5

<210> SEQ ID NO 144
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 144

Gly Ser Gly Gly Gly
1               5

<210> SEQ ID NO 145
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 145

Gly Ser Gly Gly Ser
1               5

<210> SEQ ID NO 146
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 146

Ser Gly Gly Gly Gly
1               5

<210> SEQ ID NO 147
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 147

Gly Ser Ser Gly Gly
1               5
```

<210> SEQ ID NO 148
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 148

Gly Ser Gly Ser Gly
1               5

<210> SEQ ID NO 149
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 149

Ser Gly Gly Ser Gly
1               5

<210> SEQ ID NO 150
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 150

Gly Ser Ser Ser Gly
1               5

<210> SEQ ID NO 151
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 151

Gly Gly Gly Gly Gly Ser
1               5

<210> SEQ ID NO 152
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 152

Ser Gly Gly Gly Gly Gly
1               5

<210> SEQ ID NO 153
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 153

Gly Gly Gly Gly Gly Gly Ser
1               5

<210> SEQ ID NO 154
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 154

Ser Gly Gly Gly Gly Gly Gly
1               5

<210> SEQ ID NO 155
<211> LENGTH: 330
<212> TYPE: PRT
<213> ORGANISM: Homo sapiens

<400> SEQUENCE: 155

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr

-continued

```
305              310              315              320

Gln Lys Ser Leu Ser Leu Ser Pro Gly Lys
                325              330

<210> SEQ ID NO 156
<211> LENGTH: 326
<212> TYPE: PRT
<213> ORGANISM: Homo sapiens

<400> SEQUENCE: 156

Ala Ser Thr Lys Gly Pro Ser Val Phe Pro Leu Ala Pro Cys Ser Arg
1               5               10               15

Ser Thr Ser Glu Ser Thr Ala Ala Leu Gly Cys Leu Val Lys Asp Tyr
                20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
        50              55              60

Leu Ser Ser Val Val Thr Val Pro Ser Ser Asn Phe Gly Thr Gln Thr
65              70              75              80

Tyr Thr Cys Asn Val Asp His Lys Pro Ser Asn Thr Lys Val Asp Lys
                85              90              95

Thr Val Glu Arg Lys Cys Cys Val Glu Cys Pro Pro Cys Pro Ala Pro
                100             105             110

Pro Val Ala Gly Pro Ser Val Phe Leu Phe Pro Pro Lys Pro Lys Asp
            115             120             125

Thr Leu Met Ile Ser Arg Thr Pro Glu Val Thr Cys Val Val Val Asp
        130             135             140

Val Ser His Glu Asp Pro Glu Val Gln Phe Asn Trp Tyr Val Asp Gly
145             150             155             160

Val Glu Val His Asn Ala Lys Thr Lys Pro Arg Glu Glu Gln Phe Asn
                165             170             175

Ser Thr Phe Arg Val Val Ser Val Leu Thr Val Val His Gln Asp Trp
            180             185             190

Leu Asn Gly Lys Glu Tyr Lys Cys Lys Val Ser Asn Lys Gly Leu Pro
            195             200             205

Ala Pro Ile Glu Lys Thr Ile Ser Lys Thr Lys Gly Gln Pro Arg Glu
        210             215             220

Pro Gln Val Tyr Thr Leu Pro Pro Ser Arg Glu Glu Met Thr Lys Asn
225             230             235             240

Gln Val Ser Leu Thr Cys Leu Val Lys Gly Phe Tyr Pro Ser Asp Ile
                245             250             255

Ala Val Glu Trp Glu Ser Asn Gly Gln Pro Glu Asn Asn Tyr Lys Thr
            260             265             270

Thr Pro Pro Met Leu Asp Ser Asp Gly Ser Phe Phe Leu Tyr Ser Lys
            275             280             285

Leu Thr Val Asp Lys Ser Arg Trp Gln Gln Gly Asn Val Phe Ser Cys
            290             295             300

Ser Val Met His Glu Ala Leu His Asn His Tyr Thr Gln Lys Ser Leu
305             310             315             320

Ser Leu Ser Pro Gly Lys
                325

<210> SEQ ID NO 157
<211> LENGTH: 377
```

<212> TYPE: PRT
<213> ORGANISM: Homo sapiens

<400> SEQUENCE: 157

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
        130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
            165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
        210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
        370                 375
```

<210> SEQ ID NO 158

<211> LENGTH: 327
<212> TYPE: PRT
<213> ORGANISM: Homo sapiens

<400> SEQUENCE: 158

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 159
<211> LENGTH: 6
<212> TYPE: PRT
<213> ORGANISM: Homo sapiens

<400> SEQUENCE: 159

Met Tyr Pro Pro Pro Tyr
1               5

```
<210> SEQ ID NO 160
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 160

Thr Ser Ala Ser Gly Arg Ser Ala Asn Pro Arg Gly
1               5                   10

<210> SEQ ID NO 161
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 161

Thr Ser Glu Ser Gly Arg Ser Ala Asn Pro Arg Gly
1               5                   10

<210> SEQ ID NO 162
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 162

Thr Ser Phe Ser Gly Arg Ser Ala Asn Pro Arg Gly
1               5                   10

<210> SEQ ID NO 163
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 163

Thr Ser Gly Ser Gly Arg Ser Ala Asn Pro Arg Gly
1               5                   10

<210> SEQ ID NO 164
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 164

Thr Ser His Ser Gly Arg Ser Ala Asn Pro Arg Gly
1               5                   10

<210> SEQ ID NO 165
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 165

Thr Ser Lys Ser Gly Arg Ser Ala Asn Pro Arg Gly
1               5                   10
```

```
<210> SEQ ID NO 166
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 166

Thr Ser Met Ser Gly Arg Ser Ala Asn Pro Arg Gly
1               5                   10

<210> SEQ ID NO 167
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 167

Thr Ser Asn Ser Gly Arg Ser Ala Asn Pro Arg Gly
1               5                   10

<210> SEQ ID NO 168
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 168

Thr Ser Pro Ser Gly Arg Ser Ala Asn Pro Arg Gly
1               5                   10

<210> SEQ ID NO 169
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 169

Thr Ser Gln Ser Gly Arg Ser Ala Asn Pro Arg Gly
1               5                   10

<210> SEQ ID NO 170
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 170

Thr Ser Trp Ser Gly Arg Ser Ala Asn Pro Arg Gly
1               5                   10

<210> SEQ ID NO 171
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 171

Thr Ser Tyr Ser Gly Arg Ser Ala Asn Pro Arg Gly
1               5                   10
```

-continued

```
<210> SEQ ID NO 172
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 172

Thr Ser Thr Ala Gly Arg Ser Ala Asn Pro Arg Gly
1               5                   10

<210> SEQ ID NO 173
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 173

Thr Ser Thr Asp Gly Arg Ser Ala Asn Pro Arg Gly
1               5                   10

<210> SEQ ID NO 174
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 174

Thr Ser Thr Glu Gly Arg Ser Ala Asn Pro Arg Gly
1               5                   10

<210> SEQ ID NO 175
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 175

Thr Ser Thr Phe Gly Arg Ser Ala Asn Pro Arg Gly
1               5                   10

<210> SEQ ID NO 176
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 176

Thr Ser Thr Leu Gly Arg Ser Ala Asn Pro Arg Gly
1               5                   10

<210> SEQ ID NO 177
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 177

Thr Ser Thr Met Gly Arg Ser Ala Asn Pro Arg Gly
1               5                   10

<210> SEQ ID NO 178
```

```
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 178

Thr Ser Thr Pro Gly Arg Ser Ala Asn Pro Arg Gly
1               5                   10

<210> SEQ ID NO 179
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 179

Thr Ser Thr Gln Gly Arg Ser Ala Asn Pro Arg Gly
1               5                   10

<210> SEQ ID NO 180
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 180

Thr Ser Thr Val Gly Arg Ser Ala Asn Pro Arg Gly
1               5                   10

<210> SEQ ID NO 181
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 181

Thr Ser Thr Trp Gly Arg Ser Ala Asn Pro Arg Gly
1               5                   10

<210> SEQ ID NO 182
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 182

Thr Ser Thr Ser Ala Arg Ser Ala Asn Pro Arg Gly
1               5                   10

<210> SEQ ID NO 183
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 183

Thr Ser Thr Ser Glu Arg Ser Ala Asn Pro Arg Gly
1               5                   10

<210> SEQ ID NO 184
<211> LENGTH: 12
```

-continued

```
<212> TYPE: PRT
<213> ORGANISM: Artificial Sequence
<220> FEATURE:
<223> OTHER INFORMATION: an artificially synthesized sequence

<400> SEQUENCE: 184

Thr Ser Thr Ser Phe Arg Ser Ala Asn Pro Arg Gly
1               5                   10

<210> SEQ ID NO 185
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 185

Thr Ser Thr Ser His Arg Ser Ala Asn Pro Arg Gly
1               5                   10

<210> SEQ ID NO 186
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 186

Thr Ser Thr Ser Ile Arg Ser Ala Asn Pro Arg Gly
1               5                   10

<210> SEQ ID NO 187
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 187

Thr Ser Thr Ser Lys Arg Ser Ala Asn Pro Arg Gly
1               5                   10

<210> SEQ ID NO 188
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 188

Thr Ser Thr Ser Leu Arg Ser Ala Asn Pro Arg Gly
1               5                   10

<210> SEQ ID NO 189
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 189

Thr Ser Thr Ser Met Arg Ser Ala Asn Pro Arg Gly
1               5                   10

<210> SEQ ID NO 190
<211> LENGTH: 12
<212> TYPE: PRT
```

-continued

```
<213> ORGANISM: Artificial Sequence
<220> FEATURE:
<223> OTHER INFORMATION: an artificially synthesized sequence

<400> SEQUENCE: 190

Thr Ser Thr Ser Asn Arg Ser Ala Asn Pro Arg Gly
1               5                   10

<210> SEQ ID NO 191
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 191

Thr Ser Thr Ser Pro Arg Ser Ala Asn Pro Arg Gly
1               5                   10

<210> SEQ ID NO 192
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 192

Thr Ser Thr Ser Gln Arg Ser Ala Asn Pro Arg Gly
1               5                   10

<210> SEQ ID NO 193
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 193

Thr Ser Thr Ser Arg Arg Ser Ala Asn Pro Arg Gly
1               5                   10

<210> SEQ ID NO 194
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 194

Thr Ser Thr Ser Thr Arg Ser Ala Asn Pro Arg Gly
1               5                   10

<210> SEQ ID NO 195
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 195

Thr Ser Thr Ser Val Arg Ser Ala Asn Pro Arg Gly
1               5                   10

<210> SEQ ID NO 196
<211> LENGTH: 12
<212> TYPE: PRT
<213> ORGANISM: Artificial Sequence
```

<220> FEATURE:
<223> OTHER INFORMATION: an artificially synthesized sequence

<400> SEQUENCE: 196

Thr Ser Thr Ser Trp Arg Ser Ala Asn Pro Arg Gly
1               5                   10

<210> SEQ ID NO 197
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 197

Thr Ser Thr Ser Tyr Arg Ser Ala Asn Pro Arg Gly
1               5                   10

<210> SEQ ID NO 198
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 198

Thr Ser Thr Ser Gly Arg Ala Ala Asn Pro Arg Gly
1               5                   10

<210> SEQ ID NO 199
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 199

Thr Ser Thr Ser Gly Arg Asp Ala Asn Pro Arg Gly
1               5                   10

<210> SEQ ID NO 200
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 200

Thr Ser Thr Ser Gly Arg Glu Ala Asn Pro Arg Gly
1               5                   10

<210> SEQ ID NO 201
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 201

Thr Ser Thr Ser Gly Arg Gly Ala Asn Pro Arg Gly
1               5                   10

<210> SEQ ID NO 202
<211> LENGTH: 12
<212> TYPE: PRT
<213> ORGANISM: Artificial Sequence
<220> FEATURE:

-continued

```
<223> OTHER INFORMATION: an artificially synthesized sequence

<400> SEQUENCE: 202

Thr Ser Thr Ser Gly Arg His Ala Asn Pro Arg Gly
1               5                   10

<210> SEQ ID NO 203
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 203

Thr Ser Thr Ser Gly Arg Ile Ala Asn Pro Arg Gly
1               5                   10

<210> SEQ ID NO 204
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 204

Thr Ser Thr Ser Gly Arg Lys Ala Asn Pro Arg Gly
1               5                   10

<210> SEQ ID NO 205
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 205

Thr Ser Thr Ser Gly Arg Leu Ala Asn Pro Arg Gly
1               5                   10

<210> SEQ ID NO 206
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 206

Thr Ser Thr Ser Gly Arg Met Ala Asn Pro Arg Gly
1               5                   10

<210> SEQ ID NO 207
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 207

Thr Ser Thr Ser Gly Arg Asn Ala Asn Pro Arg Gly
1               5                   10

<210> SEQ ID NO 208
<211> LENGTH: 12
<212> TYPE: PRT
<213> ORGANISM: Artificial Sequence
<220> FEATURE:
<223> OTHER INFORMATION: an artificially synthesized sequence
```

```
<400> SEQUENCE: 208

Thr Ser Thr Ser Gly Arg Pro Ala Asn Pro Arg Gly
1               5                   10

<210> SEQ ID NO 209
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 209

Thr Ser Thr Ser Gly Arg Gln Ala Asn Pro Arg Gly
1               5                   10

<210> SEQ ID NO 210
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 210

Thr Ser Thr Ser Gly Arg Arg Ala Asn Pro Arg Gly
1               5                   10

<210> SEQ ID NO 211
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 211

Thr Ser Thr Ser Gly Arg Thr Ala Asn Pro Arg Gly
1               5                   10

<210> SEQ ID NO 212
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 212

Thr Ser Thr Ser Gly Arg Val Ala Asn Pro Arg Gly
1               5                   10

<210> SEQ ID NO 213
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 213

Thr Ser Thr Ser Gly Arg Trp Ala Asn Pro Arg Gly
1               5                   10

<210> SEQ ID NO 214
<211> LENGTH: 12
<212> TYPE: PRT
<213> ORGANISM: Artificial Sequence
<220> FEATURE:
<223> OTHER INFORMATION: an artificially synthesized sequence
```

-continued

```
<400> SEQUENCE: 214

Thr Ser Thr Ser Gly Arg Tyr Ala Asn Pro Arg Gly
1               5                   10

<210> SEQ ID NO 215
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 215

Thr Ser Thr Ser Gly Arg Ser Glu Asn Pro Arg Gly
1               5                   10

<210> SEQ ID NO 216
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 216

Thr Ser Thr Ser Gly Arg Ser Phe Asn Pro Arg Gly
1               5                   10

<210> SEQ ID NO 217
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 217

Thr Ser Thr Ser Gly Arg Ser Lys Asn Pro Arg Gly
1               5                   10

<210> SEQ ID NO 218
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 218

Thr Ser Thr Ser Gly Arg Ser Met Asn Pro Arg Gly
1               5                   10

<210> SEQ ID NO 219
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 219

Thr Ser Thr Ser Gly Arg Ser Asn Asn Pro Arg Gly
1               5                   10

<210> SEQ ID NO 220
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 220
```

-continued

```
Thr Ser Thr Ser Gly Arg Ser Pro Asn Pro Arg Gly
1               5               10

<210> SEQ ID NO 221
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 221

Thr Ser Thr Ser Gly Arg Ser Gln Asn Pro Arg Gly
1               5               10

<210> SEQ ID NO 222
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 222

Thr Ser Thr Ser Gly Arg Ser Arg Asn Pro Arg Gly
1               5               10

<210> SEQ ID NO 223
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 223

Thr Ser Thr Ser Gly Arg Ser Ser Asn Pro Arg Gly
1               5               10

<210> SEQ ID NO 224
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 224

Thr Ser Thr Ser Gly Arg Ser Trp Asn Pro Arg Gly
1               5               10

<210> SEQ ID NO 225
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 225

Thr Ser Thr Ser Gly Arg Ser Tyr Asn Pro Arg Gly
1               5               10

<210> SEQ ID NO 226
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 226
```

```
Thr Ser Thr Ser Gly Arg Ser Ala Ala Pro Arg Gly
1               5                   10

<210> SEQ ID NO 227
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 227

Thr Ser Thr Ser Gly Arg Ser Ala Asp Pro Arg Gly
1               5                   10

<210> SEQ ID NO 228
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 228

Thr Ser Thr Ser Gly Arg Ser Ala Glu Pro Arg Gly
1               5                   10

<210> SEQ ID NO 229
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 229

Thr Ser Thr Ser Gly Arg Ser Ala Phe Pro Arg Gly
1               5                   10

<210> SEQ ID NO 230
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 230

Thr Ser Thr Ser Gly Arg Ser Ala Gly Pro Arg Gly
1               5                   10

<210> SEQ ID NO 231
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 231

Thr Ser Thr Ser Gly Arg Ser Ala Lys Pro Arg Gly
1               5                   10

<210> SEQ ID NO 232
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 232

Thr Ser Thr Ser Gly Arg Ser Ala Leu Pro Arg Gly
```

-continued

```
1               5                   10

<210> SEQ ID NO 233
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 233

Thr Ser Thr Ser Gly Arg Ser Ala Met Pro Arg Gly
1               5                   10

<210> SEQ ID NO 234
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 234

Thr Ser Thr Ser Gly Arg Ser Ala Pro Pro Arg Gly
1               5                   10

<210> SEQ ID NO 235
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 235

Thr Ser Thr Ser Gly Arg Ser Ala Gln Pro Arg Gly
1               5                   10

<210> SEQ ID NO 236
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 236

Thr Ser Thr Ser Gly Arg Ser Ala Val Pro Arg Gly
1               5                   10

<210> SEQ ID NO 237
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 237

Thr Ser Thr Ser Gly Arg Ser Ala Trp Pro Arg Gly
1               5                   10

<210> SEQ ID NO 238
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 238

Thr Ser Thr Ser Gly Arg Ser Ala Tyr Pro Arg Gly
1               5                   10
```

```
<210> SEQ ID NO 239
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 239

Thr Ser Thr Ser Gly Arg Ser Ala Asn Ala Arg Gly
1               5                   10

<210> SEQ ID NO 240
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 240

Thr Ser Thr Ser Gly Arg Ser Ala Asn Asp Arg Gly
1               5                   10

<210> SEQ ID NO 241
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 241

Thr Ser Thr Ser Gly Arg Ser Ala Asn Glu Arg Gly
1               5                   10

<210> SEQ ID NO 242
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 242

Thr Ser Thr Ser Gly Arg Ser Ala Asn Phe Arg Gly
1               5                   10

<210> SEQ ID NO 243
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 243

Thr Ser Thr Ser Gly Arg Ser Ala Asn Gly Arg Gly
1               5                   10

<210> SEQ ID NO 244
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 244

Thr Ser Thr Ser Gly Arg Ser Ala Asn Ile Arg Gly
1               5                   10
```

<210> SEQ ID NO 245
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 245

Thr Ser Thr Ser Gly Arg Ser Ala Asn Lys Arg Gly
1               5                   10

<210> SEQ ID NO 246
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 246

Thr Ser Thr Ser Gly Arg Ser Ala Asn Asn Arg Gly
1               5                   10

<210> SEQ ID NO 247
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 247

Thr Ser Thr Ser Gly Arg Ser Ala Asn Gln Arg Gly
1               5                   10

<210> SEQ ID NO 248
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 248

Thr Ser Thr Ser Gly Arg Ser Ala Asn Ser Arg Gly
1               5                   10

<210> SEQ ID NO 249
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 249

Thr Ser Thr Ser Gly Arg Ser Ala Asn Thr Arg Gly
1               5                   10

<210> SEQ ID NO 250
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 250

Thr Ser Thr Ser Gly Arg Ser Ala Asn Trp Arg Gly
1               5                   10

```
<210> SEQ ID NO 251
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 251

Thr Ser Asp Ser Gly Arg Ser Ala Asn Pro Arg Gly
1               5                   10

<210> SEQ ID NO 252
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 252

Thr Ser Ile Ser Gly Arg Ser Ala Asn Pro Arg Gly
1               5                   10

<210> SEQ ID NO 253
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 253

Thr Ser Ser Ser Gly Arg Ser Ala Asn Pro Arg Gly
1               5                   10

<210> SEQ ID NO 254
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 254

Thr Ser Thr His Gly Arg Ser Ala Asn Pro Arg Gly
1               5                   10

<210> SEQ ID NO 255
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 255

Thr Ser Thr Lys Gly Arg Ser Ala Asn Pro Arg Gly
1               5                   10

<210> SEQ ID NO 256
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 256

Thr Ser Thr Thr Gly Arg Ser Ala Asn Pro Arg Gly
1               5                   10

<210> SEQ ID NO 257
```

```
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 257

Thr Ser Thr Tyr Gly Arg Ser Ala Asn Pro Arg Gly
1               5                   10

<210> SEQ ID NO 258
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 258

Thr Ser Thr Ser Asp Arg Ser Ala Asn Pro Arg Gly
1               5                   10

<210> SEQ ID NO 259
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 259

Thr Ser Thr Ser Ser Arg Ser Ala Asn Pro Arg Gly
1               5                   10

<210> SEQ ID NO 260
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 260

Thr Ser Thr Ser Gly Arg Phe Ala Asn Pro Arg Gly
1               5                   10

<210> SEQ ID NO 261
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 261

Thr Ser Thr Ser Gly Arg Ser Asp Asn Pro Arg Gly
1               5                   10

<210> SEQ ID NO 262
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 262

Thr Ser Thr Ser Gly Arg Ser His Asn Pro Arg Gly
1               5                   10

<210> SEQ ID NO 263
<211> LENGTH: 12
```

```
<212> TYPE: PRT
<213> ORGANISM: Artificial Sequence
<220> FEATURE:
<223> OTHER INFORMATION: an artificially synthesized sequence

<400> SEQUENCE: 263

Thr Ser Thr Ser Gly Arg Ser Ile Asn Pro Arg Gly
1               5                   10

<210> SEQ ID NO 264
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 264

Thr Ser Thr Ser Gly Arg Ser Leu Asn Pro Arg Gly
1               5                   10

<210> SEQ ID NO 265
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 265

Thr Ser Thr Ser Gly Arg Ser Thr Asn Pro Arg Gly
1               5                   10

<210> SEQ ID NO 266
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 266

Thr Ser Thr Ser Gly Arg Ser Val Asn Pro Arg Gly
1               5                   10

<210> SEQ ID NO 267
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 267

Thr Ser Thr Ser Gly Arg Ser Ala His Pro Arg Gly
1               5                   10

<210> SEQ ID NO 268
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 268

Thr Ser Thr Ser Gly Arg Ser Ala Ile Pro Arg Gly
1               5                   10

<210> SEQ ID NO 269
<211> LENGTH: 12
<212> TYPE: PRT
```

<213> ORGANISM: Artificial Sequence
<220> FEATURE:
<223> OTHER INFORMATION: an artificially synthesized sequence

<400> SEQUENCE: 269

Thr Ser Thr Ser Gly Arg Ser Ala Arg Pro Arg Gly
1               5                   10

<210> SEQ ID NO 270
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 270

Thr Ser Thr Ser Gly Arg Ser Ala Ser Pro Arg Gly
1               5                   10

<210> SEQ ID NO 271
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 271

Thr Ser Thr Ser Gly Arg Ser Ala Thr Pro Arg Gly
1               5                   10

<210> SEQ ID NO 272
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 272

Thr Ser Thr Ser Gly Arg Ser Ala Asn His Arg Gly
1               5                   10

<210> SEQ ID NO 273
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 273

Thr Ser Thr Ser Gly Arg Ser Ala Asn Leu Arg Gly
1               5                   10

<210> SEQ ID NO 274
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 274

Thr Ser Thr Ser Gly Arg Ser Ala Asn Met Arg Gly
1               5                   10

<210> SEQ ID NO 275
<211> LENGTH: 12
<212> TYPE: PRT
<213> ORGANISM: Artificial Sequence

```
<220> FEATURE:
<223> OTHER INFORMATION: an artificially synthesized sequence

<400> SEQUENCE: 275

Thr Ser Thr Ser Gly Arg Ser Ala Asn Arg Arg Gly
1               5                   10

<210> SEQ ID NO 276
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 276

Thr Ser Thr Ser Gly Arg Ser Ala Asn Val Arg Gly
1               5                   10

<210> SEQ ID NO 277
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 277

Thr Ser Thr Ser Gly Arg Ser Ala Asn Tyr Arg Gly
1               5                   10

<210> SEQ ID NO 278
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 278

Thr Ser Gly Ser Gly Arg Ser Ala Val Pro Arg Gly
1               5                   10

<210> SEQ ID NO 279
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 279

Thr Ser Gly Ser Gly Arg Ser Ala Tyr Pro Arg Gly
1               5                   10

<210> SEQ ID NO 280
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 280

Thr Ser Gly Ser Gly Arg Ser Ala Asn Gln Arg Gly
1               5                   10

<210> SEQ ID NO 281
<211> LENGTH: 12
<212> TYPE: PRT
<213> ORGANISM: Artificial Sequence
<220> FEATURE:
```

-continued

```
<223> OTHER INFORMATION: an artificially synthesized sequence

<400> SEQUENCE: 281

Thr Ser Gly Ser Gly Arg Ser Ala Asn Ile Arg Gly
1               5                   10

<210> SEQ ID NO 282
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 282

Thr Ser Gly Ser Gly Arg Ser Ala Asn Phe Arg Gly
1               5                   10

<210> SEQ ID NO 283
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 283

Thr Ser Gly Ser Gly Arg Ser Ala Asn Ser Arg Gly
1               5                   10

<210> SEQ ID NO 284
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 284

Thr Ser Gln Ser Gly Arg Ser Ala Val Pro Arg Gly
1               5                   10

<210> SEQ ID NO 285
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 285

Thr Ser Gln Ser Gly Arg Ser Ala Tyr Pro Arg Gly
1               5                   10

<210> SEQ ID NO 286
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 286

Thr Ser Gln Ser Gly Arg Ser Ala Asn Ala Arg Gly
1               5                   10

<210> SEQ ID NO 287
<211> LENGTH: 12
<212> TYPE: PRT
<213> ORGANISM: Artificial Sequence
<220> FEATURE:
<223> OTHER INFORMATION: an artificially synthesized sequence
```

```
<400> SEQUENCE: 287

Thr Ser Gln Ser Gly Arg Ser Ala Asn Ile Arg Gly
1               5                   10

<210> SEQ ID NO 288
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 288

Thr Ser Gln Ser Gly Arg Ser Ala Asn Phe Arg Gly
1               5                   10

<210> SEQ ID NO 289
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 289

Thr Ser Gln Ser Gly Arg Ser Ala Asn Ser Arg Gly
1               5                   10

<210> SEQ ID NO 290
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 290

Thr Ser Pro Ser Gly Arg Ser Ala Val Pro Arg Gly
1               5                   10

<210> SEQ ID NO 291
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 291

Thr Ser Pro Ser Gly Arg Ser Ala Asn Gln Arg Gly
1               5                   10

<210> SEQ ID NO 292
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 292

Thr Ser Pro Ser Gly Arg Ser Ala Asn Ala Arg Gly
1               5                   10

<210> SEQ ID NO 293
<211> LENGTH: 12
<212> TYPE: PRT
<213> ORGANISM: Artificial Sequence
<220> FEATURE:
<223> OTHER INFORMATION: an artificially synthesized sequence
```

<400> SEQUENCE: 293

Thr Ser Pro Ser Gly Arg Ser Ala Asn Ile Arg Gly
1               5                   10

<210> SEQ ID NO 294
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 294

Thr Ser Pro Ser Gly Arg Ser Ala Asn Phe Arg Gly
1               5                   10

<210> SEQ ID NO 295
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 295

Thr Ser Pro Ser Gly Arg Ser Ala Asn Ser Arg Gly
1               5                   10

<210> SEQ ID NO 296
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 296

Thr Ser Ala Ser Gly Arg Ser Ala Val Pro Arg Gly
1               5                   10

<210> SEQ ID NO 297
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 297

Thr Ser Ala Ser Gly Arg Ser Ala Tyr Pro Arg Gly
1               5                   10

<210> SEQ ID NO 298
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 298

Thr Ser Ala Ser Gly Arg Ser Ala Asn Gln Arg Gly
1               5                   10

<210> SEQ ID NO 299
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 299

-continued

```
Thr Ser Ala Ser Gly Arg Ser Ala Asn Ala Arg Gly
1               5                   10

<210> SEQ ID NO 300
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 300

Thr Ser Ala Ser Gly Arg Ser Ala Asn Ile Arg Gly
1               5                   10

<210> SEQ ID NO 301
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 301

Thr Ser Ala Ser Gly Arg Ser Ala Asn Phe Arg Gly
1               5                   10

<210> SEQ ID NO 302
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 302

Thr Ser Ala Ser Gly Arg Ser Ala Asn Ser Arg Gly
1               5                   10

<210> SEQ ID NO 303
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 303

Thr Ser Tyr Ser Gly Arg Ser Glu Asn Pro Arg Gly
1               5                   10

<210> SEQ ID NO 304
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 304

Thr Ser Gly Ser Gly Arg Ser Glu Asn Pro Arg Gly
1               5                   10

<210> SEQ ID NO 305
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 305
```

-continued

```
Thr Ser Gln Ser Gly Arg Ser Glu Asn Pro Arg Gly
1               5                   10

<210> SEQ ID NO 306
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 306

Thr Ser Pro Ser Gly Arg Ser Glu Asn Pro Arg Gly
1               5                   10

<210> SEQ ID NO 307
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 307

Thr Ser Ala Ser Gly Arg Ser Glu Asn Pro Arg Gly
1               5                   10

<210> SEQ ID NO 308
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 308

Thr Ser His Ser Gly Arg Ser Glu Asn Pro Arg Gly
1               5                   10

<210> SEQ ID NO 309
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 309

Thr Ser Thr Ser Gly Arg Ser Glu Asn Gln Arg Gly
1               5                   10

<210> SEQ ID NO 310
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 310

Thr Ser Thr Ser Gly Arg Ser Glu Asn Ala Arg Gly
1               5                   10

<210> SEQ ID NO 311
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 311

Thr Ser Thr Ser Gly Arg Ser Glu Asn Ile Arg Gly
```

-continued

```
1               5               10

<210> SEQ ID NO 312
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 312

Thr Ser Thr Ser Gly Arg Ser Glu Asn Phe Arg Gly
1               5               10

<210> SEQ ID NO 313
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 313

Thr Ser Thr Ser Gly Arg Ser Glu Asn Ser Arg Gly
1               5               10

<210> SEQ ID NO 314
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 314

Thr Ser Tyr Ser Gly Arg Ser Ala Glu Pro Arg Gly
1               5               10

<210> SEQ ID NO 315
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 315

Thr Ser Gly Ser Gly Arg Ser Ala Glu Pro Arg Gly
1               5               10

<210> SEQ ID NO 316
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 316

Thr Ser Gln Ser Gly Arg Ser Ala Glu Pro Arg Gly
1               5               10

<210> SEQ ID NO 317
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 317

Thr Ser Pro Ser Gly Arg Ser Ala Glu Pro Arg Gly
1               5               10
```

```
<210> SEQ ID NO 318
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 318

Thr Ser Ala Ser Gly Arg Ser Ala Glu Pro Arg Gly
1               5                   10

<210> SEQ ID NO 319
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 319

Thr Ser His Ser Gly Arg Ser Ala Glu Pro Arg Gly
1               5                   10

<210> SEQ ID NO 320
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 320

Thr Ser Thr Ser Gly Arg Ser Ala Glu Gln Arg Gly
1               5                   10

<210> SEQ ID NO 321
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 321

Thr Ser Thr Ser Gly Arg Ser Ala Glu Ala Arg Gly
1               5                   10

<210> SEQ ID NO 322
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 322

Thr Ser Thr Ser Gly Arg Ser Ala Glu Ile Arg Gly
1               5                   10

<210> SEQ ID NO 323
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 323

Thr Ser Thr Ser Gly Arg Ser Ala Glu Phe Arg Gly
1               5                   10
```

-continued

```
<210> SEQ ID NO 324
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 324

Thr Ser Thr Ser Gly Arg Ser Ala Glu Ser Arg Gly
1               5                   10

<210> SEQ ID NO 325
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 325

Thr Ser Gly Thr Gly Arg Ser Ala Asn Pro Arg Gly
1               5                   10

<210> SEQ ID NO 326
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 326

Thr Ser Gly Lys Gly Arg Ser Ala Asn Pro Arg Gly
1               5                   10

<210> SEQ ID NO 327
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 327

Thr Ser Gly Ser Gly Arg Ser Ala Ile Pro Arg Gly
1               5                   10

<210> SEQ ID NO 328
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 328

Thr Ser Gly Ser Gly Arg Ser Ala Ser Pro Arg Gly
1               5                   10

<210> SEQ ID NO 329
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 329

Thr Ser Gly Ser Gly Arg Ser Ala His Pro Arg Gly
1               5                   10
```

```
<210> SEQ ID NO 330
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 330

Thr Ser Gly Ser Gly Arg Ser Ala Asn Tyr Arg Gly
1               5                   10

<210> SEQ ID NO 331
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 331

Thr Ser Gly Ser Gly Arg Ser Ala Asn Val Arg Gly
1               5                   10

<210> SEQ ID NO 332
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 332

Thr Ser Gly Ser Gly Arg Ser Ala Asn His Arg Gly
1               5                   10

<210> SEQ ID NO 333
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 333

Thr Ser Gln Thr Gly Arg Ser Ala Asn Pro Arg Gly
1               5                   10

<210> SEQ ID NO 334
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 334

Thr Ser Gln Lys Gly Arg Ser Ala Asn Pro Arg Gly
1               5                   10

<210> SEQ ID NO 335
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 335

Thr Ser Gln Ser Gly Arg Ser Ala Ile Pro Arg Gly
1               5                   10

<210> SEQ ID NO 336
```

```
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 336

Thr Ser Gln Ser Gly Arg Ser Ala Ser Pro Arg Gly
1               5                   10

<210> SEQ ID NO 337
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 337

Thr Ser Gln Ser Gly Arg Ser Ala His Pro Arg Gly
1               5                   10

<210> SEQ ID NO 338
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 338

Thr Ser Gln Ser Gly Arg Ser Ala Asn Tyr Arg Gly
1               5                   10

<210> SEQ ID NO 339
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 339

Thr Ser Gln Ser Gly Arg Ser Ala Asn Val Arg Gly
1               5                   10

<210> SEQ ID NO 340
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 340

Thr Ser Gln Ser Gly Arg Ser Ala Asn His Arg Gly
1               5                   10

<210> SEQ ID NO 341
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 341

Thr Ser Pro Thr Gly Arg Ser Ala Asn Pro Arg Gly
1               5                   10

<210> SEQ ID NO 342
<211> LENGTH: 12
```

```
<212> TYPE: PRT
<213> ORGANISM: Artificial Sequence
<220> FEATURE:
<223> OTHER INFORMATION: an artificially synthesized sequence

<400> SEQUENCE: 342

Thr Ser Pro Lys Gly Arg Ser Ala Asn Pro Arg Gly
1               5                   10

<210> SEQ ID NO 343
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 343

Thr Ser Pro Ser Gly Arg Ser Ala Ile Pro Arg Gly
1               5                   10

<210> SEQ ID NO 344
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 344

Thr Ser Pro Ser Gly Arg Ser Ala Thr Pro Arg Gly
1               5                   10

<210> SEQ ID NO 345
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 345

Thr Ser Pro Ser Gly Arg Ser Ala Ser Pro Arg Gly
1               5                   10

<210> SEQ ID NO 346
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 346

Thr Ser Pro Ser Gly Arg Ser Ala His Pro Arg Gly
1               5                   10

<210> SEQ ID NO 347
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 347

Thr Ser Pro Ser Gly Arg Ser Ala Asn Tyr Arg Gly
1               5                   10

<210> SEQ ID NO 348
<211> LENGTH: 12
<212> TYPE: PRT
```

-continued

<213> ORGANISM: Artificial Sequence
<220> FEATURE:
<223> OTHER INFORMATION: an artificially synthesized sequence

<400> SEQUENCE: 348

Thr Ser Pro Ser Gly Arg Ser Ala Asn Val Arg Gly
1               5                   10

<210> SEQ ID NO 349
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 349

Thr Ser Pro Ser Gly Arg Ser Ala Asn His Arg Gly
1               5                   10

<210> SEQ ID NO 350
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 350

Thr Ser Ala Thr Gly Arg Ser Ala Asn Pro Arg Gly
1               5                   10

<210> SEQ ID NO 351
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 351

Thr Ser Ala Lys Gly Arg Ser Ala Asn Pro Arg Gly
1               5                   10

<210> SEQ ID NO 352
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 352

Thr Ser Ala Ser Gly Arg Ser Ala Ile Pro Arg Gly
1               5                   10

<210> SEQ ID NO 353
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 353

Thr Ser Ala Ser Gly Arg Ser Ala Ser Pro Arg Gly
1               5                   10

<210> SEQ ID NO 354
<211> LENGTH: 12
<212> TYPE: PRT
<213> ORGANISM: Artificial Sequence -continued

```
<220> FEATURE:
<223> OTHER INFORMATION: an artificially synthesized sequence

<400> SEQUENCE: 354

Thr Ser Ala Ser Gly Arg Ser Ala His Pro Arg Gly
1               5               10

<210> SEQ ID NO 355
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 355

Thr Ser Ala Ser Gly Arg Ser Ala Asn Tyr Arg Gly
1               5               10

<210> SEQ ID NO 356
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 356

Thr Ser Ala Ser Gly Arg Ser Ala Asn Val Arg Gly
1               5               10

<210> SEQ ID NO 357
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 357

Thr Ser Ala Ser Gly Arg Ser Ala Asn His Arg Gly
1               5                  10

<210> SEQ ID NO 358
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 358

Thr Ser Tyr Thr Gly Arg Ser Ala Asn Pro Arg Gly
1               5                  10

<210> SEQ ID NO 359
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 359

Thr Ser Tyr Lys Gly Arg Ser Ala Asn Pro Arg Gly
1               5                  10

<210> SEQ ID NO 360
<211> LENGTH: 12
<212> TYPE: PRT
<213> ORGANISM: Artificial Sequence
<220> FEATURE:
```

-continued

<223> OTHER INFORMATION: an artificially synthesized sequence

<400> SEQUENCE: 360

Thr Ser Tyr Ser Gly Arg Ser Ala Ile Pro Arg Gly
1               5                   10

<210> SEQ ID NO 361
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 361

Thr Ser Tyr Ser Gly Arg Ser Ala Thr Pro Arg Gly
1               5                   10

<210> SEQ ID NO 362
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 362

Thr Ser Tyr Ser Gly Arg Ser Ala Ser Pro Arg Gly
1               5                   10

<210> SEQ ID NO 363
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 363

Thr Ser Tyr Ser Gly Arg Ser Ala His Pro Arg Gly
1               5                   10

<210> SEQ ID NO 364
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 364

Thr Ser Tyr Ser Gly Arg Ser Ala Asn Ala Arg Gly
1               5                   10

<210> SEQ ID NO 365
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 365

Thr Ser Tyr Ser Gly Arg Ser Ala Asn Tyr Arg Gly
1               5                   10

<210> SEQ ID NO 366
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 366

Thr Ser Tyr Ser Gly Arg Ser Ala Asn Val Arg Gly
1               5                   10

<210> SEQ ID NO 367
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 367

Thr Ser Tyr Ser Gly Arg Ser Ala Asn His Arg Gly
1               5                   10

<210> SEQ ID NO 368
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 368

Thr Ser Ser Thr Gly Arg Ser Ala Asn Pro Arg Gly
1               5                   10

<210> SEQ ID NO 369
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 369

Thr Ser Ser Lys Gly Arg Ser Ala Asn Pro Arg Gly
1               5                   10

<210> SEQ ID NO 370
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 370

Thr Ser Ser Ser Gly Arg Ser Ala Val Pro Arg Gly
1               5                   10

<210> SEQ ID NO 371
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 371

Thr Ser Ser Ser Gly Arg Ser Ala Ile Pro Arg Gly
1               5                   10

<210> SEQ ID NO 372
<211> LENGTH: 12
<212> TYPE: PRT
<213> ORGANISM: Artificial Sequence
<220> FEATURE:
<223> OTHER INFORMATION: an artificially synthesized sequence -continued

<400> SEQUENCE: 372

Thr Ser Ser Ser Gly Arg Ser Ala Ser Pro Arg Gly
1               5                   10

<210> SEQ ID NO 373
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 373

Thr Ser Ser Ser Gly Arg Ser Ala His Pro Arg Gly
1               5                   10

<210> SEQ ID NO 374
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 374

Thr Ser Ser Ser Gly Arg Ser Ala Asn Ala Arg Gly
1               5                   10

<210> SEQ ID NO 375
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 375

Thr Ser Ser Ser Gly Arg Ser Ala Asn Phe Arg Gly
1               5                   10

<210> SEQ ID NO 376
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 376

Thr Ser Ser Ser Gly Arg Ser Ala Asn Tyr Arg Gly
1               5                   10

<210> SEQ ID NO 377
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 377

Thr Ser Ser Ser Gly Arg Ser Ala Asn Val Arg Gly
1               5                   10

<210> SEQ ID NO 378
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 378

-continued

Thr Ser Ser Ser Gly Arg Ser Ala Asn His Arg Gly
1               5               10

<210> SEQ ID NO 379
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 379

Thr Ser Ile Thr Gly Arg Ser Ala Asn Pro Arg Gly
1               5               10

<210> SEQ ID NO 380
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 380

Thr Ser Ile Lys Gly Arg Ser Ala Asn Pro Arg Gly
1               5               10

<210> SEQ ID NO 381
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 381

Thr Ser Ile Ser Gly Arg Ser Ala Val Pro Arg Gly
1               5               10

<210> SEQ ID NO 382
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 382

Thr Ser Ile Ser Gly Arg Ser Ala Ile Pro Arg Gly
1               5               10

<210> SEQ ID NO 383
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 383

Thr Ser Ile Ser Gly Arg Ser Ala Thr Pro Arg Gly
1               5               10

<210> SEQ ID NO 384
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 384

-continued

```
Thr Ser Ile Ser Gly Arg Ser Ala Ser Pro Arg Gly
1               5                   10

<210> SEQ ID NO 385
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 385

Thr Ser Ile Ser Gly Arg Ser Ala His Pro Arg Gly
1               5                   10

<210> SEQ ID NO 386
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 386

Thr Ser Ile Ser Gly Arg Ser Ala Asn Ala Arg Gly
1               5                   10

<210> SEQ ID NO 387
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 387

Thr Ser Ile Ser Gly Arg Ser Ala Asn Phe Arg Gly
1               5                   10

<210> SEQ ID NO 388
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 388

Thr Ser Ile Ser Gly Arg Ser Ala Asn Tyr Arg Gly
1               5                   10

<210> SEQ ID NO 389
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 389

Thr Ser Ile Ser Gly Arg Ser Ala Asn Val Arg Gly
1               5                   10

<210> SEQ ID NO 390
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 390

Thr Ser Ile Ser Gly Arg Ser Ala Asn His Arg Gly
```

-continued

```
1               5                  10

<210> SEQ ID NO 391
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 391

Thr Ser Thr Thr Gly Arg Ser Ala Val Pro Arg Gly
1               5                  10

<210> SEQ ID NO 392
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 392

Thr Ser Thr Thr Gly Arg Ser Ala Ile Pro Arg Gly
1               5                  10

<210> SEQ ID NO 393
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 393

Thr Ser Thr Thr Gly Arg Ser Ala Thr Pro Arg Gly
1               5                  10

<210> SEQ ID NO 394
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 394

Thr Ser Thr Thr Gly Arg Ser Ala His Pro Arg Gly
1               5                  10

<210> SEQ ID NO 395
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 395

Thr Ser Thr Thr Gly Arg Ser Ala Asn Ala Arg Gly
1               5                  10

<210> SEQ ID NO 396
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 396

Thr Ser Thr Thr Gly Arg Ser Ala Asn Phe Arg Gly
1               5                  10
```

-continued

```
<210> SEQ ID NO 397
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 397

Thr Ser Thr Thr Gly Arg Ser Ala Asn Tyr Arg Gly
1               5                   10

<210> SEQ ID NO 398
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 398

Thr Ser Thr Thr Gly Arg Ser Ala Asn Val Arg Gly
1               5                   10

<210> SEQ ID NO 399
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 399

Thr Ser Thr Thr Gly Arg Ser Ala Asn His Arg Gly
1               5                   10

<210> SEQ ID NO 400
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 400

Thr Ser Thr Lys Gly Arg Ser Ala Val Pro Arg Gly
1               5                   10

<210> SEQ ID NO 401
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 401

Thr Ser Thr Lys Gly Arg Ser Ala Ile Pro Arg Gly
1               5                   10

<210> SEQ ID NO 402
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 402

Thr Ser Thr Lys Gly Arg Ser Ala Thr Pro Arg Gly
1               5                   10
```

-continued

<210> SEQ ID NO 403
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 403

Thr Ser Thr Lys Gly Arg Ser Ala Ser Pro Arg Gly
1               5                   10

<210> SEQ ID NO 404
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 404

Thr Ser Thr Lys Gly Arg Ser Ala His Pro Arg Gly
1               5                   10

<210> SEQ ID NO 405
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 405

Thr Ser Thr Lys Gly Arg Ser Ala Asn Ala Arg Gly
1               5                   10

<210> SEQ ID NO 406
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 406

Thr Ser Thr Lys Gly Arg Ser Ala Asn Phe Arg Gly
1               5                   10

<210> SEQ ID NO 407
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 407

Thr Ser Thr Lys Gly Arg Ser Ala Asn Tyr Arg Gly
1               5                   10

<210> SEQ ID NO 408
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 408

Thr Ser Thr Lys Gly Arg Ser Ala Asn Val Arg Gly
1               5                   10

```
<210> SEQ ID NO 409
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 409

Thr Ser Thr Lys Gly Arg Ser Ala Asn His Arg Gly
1               5                   10

<210> SEQ ID NO 410
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 410

Thr Ser Thr Ser Gly Arg Ser Ala Val Tyr Arg Gly
1               5                   10

<210> SEQ ID NO 411
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 411

Thr Ser Thr Ser Gly Arg Ser Ala Val Val Arg Gly
1               5                   10

<210> SEQ ID NO 412
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 412

Thr Ser Thr Ser Gly Arg Ser Ala Val His Arg Gly
1               5                   10

<210> SEQ ID NO 413
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 413

Thr Ser Thr Ser Gly Arg Ser Ala Ile Tyr Arg Gly
1               5                   10

<210> SEQ ID NO 414
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 414

Thr Ser Thr Ser Gly Arg Ser Ala Ile Val Arg Gly
1               5                   10

<210> SEQ ID NO 415
```

```
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 415

Thr Ser Thr Ser Gly Arg Ser Ala Ile His Arg Gly
1               5                   10

<210> SEQ ID NO 416
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 416

Thr Ser Thr Ser Gly Arg Ser Ala Ser Tyr Arg Gly
1               5                   10

<210> SEQ ID NO 417
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 417

Thr Ser Thr Ser Gly Arg Ser Ala Ser Val Arg Gly
1               5                   10

<210> SEQ ID NO 418
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 418

Thr Ser Thr Ser Gly Arg Ser Ala Ser His Arg Gly
1               5                   10

<210> SEQ ID NO 419
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 419

Thr Ser Thr Ser Gly Arg Ser Ala His Tyr Arg Gly
1               5                   10

<210> SEQ ID NO 420
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 420

Thr Ser Thr Ser Gly Arg Ser Ala His Val Arg Gly
1               5                   10

<210> SEQ ID NO 421
<211> LENGTH: 12
```

-continued

<212> TYPE: PRT
<213> ORGANISM: Artificial Sequence
<220> FEATURE:
<223> OTHER INFORMATION: an artificially synthesized sequence

<400> SEQUENCE: 421

Thr Ser Thr Ser Gly Arg Ser Ala His His Arg Gly
1               5                   10

<210> SEQ ID NO 422
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 422

Thr Ser Pro Ser Gly Arg Ser Glu Val Pro Arg Gly
1               5                   10

<210> SEQ ID NO 423
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 423

Thr Ser Pro Ser Gly Arg Ser Ala Glu Pro Arg Gly
1               5                   10

<210> SEQ ID NO 424
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 424

Thr Ser Pro Ser Gly Arg Ser Ala Gly Pro Arg Gly
1               5                   10

<210> SEQ ID NO 425
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 425

Thr Ser Ala Ser Gly Arg Ser Glu Asn Ala Arg Gly
1               5                   10

<210> SEQ ID NO 426
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 426

Thr Ser Ala Ser Gly Arg Ser Ala Glu Ala Arg Gly
1               5                   10

<210> SEQ ID NO 427
<211> LENGTH: 12
<212> TYPE: PRT

-continued

```
<213> ORGANISM: Artificial Sequence
<220> FEATURE:
<223> OTHER INFORMATION: an artificially synthesized sequence

<400> SEQUENCE: 427

Thr Ser Ala Ser Gly Arg Ser Ala Gly Ala Arg Gly
1               5                   10

<210> SEQ ID NO 428
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 428

Thr Ser Gly Thr Gly Arg Ser Ala Thr Pro Arg Gly
1               5                   10

<210> SEQ ID NO 429
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 429

Thr Ser Gly Ser Gly Arg Ser Ala Thr Tyr Arg Gly
1               5                   10

<210> SEQ ID NO 430
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 430

Thr Ser Gly Ser Gly Arg Ser Ala Thr Val Arg Gly
1               5                   10

<210> SEQ ID NO 431
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 431

Thr Ser Gly Ser Gly Arg Ser Ala Thr His Arg Gly
1               5                   10

<210> SEQ ID NO 432
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 432

Thr Ser Gly Thr Gly Arg Ser Ala Thr Tyr Arg Gly
1               5                   10

<210> SEQ ID NO 433
<211> LENGTH: 12
<212> TYPE: PRT
<213> ORGANISM: Artificial Sequence
```

```
<220> FEATURE:
<223> OTHER INFORMATION: an artificially synthesized sequence

<400> SEQUENCE: 433

Thr Ser Gly Thr Gly Arg Ser Ala Thr Val Arg Gly
1               5                   10

<210> SEQ ID NO 434
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 434

Thr Ser Gly Thr Gly Arg Ser Ala Thr His Arg Gly
1               5                   10

<210> SEQ ID NO 435
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 435

Thr Ser Gly Ser Gly Arg Ser Glu Thr Pro Arg Gly
1               5                   10

<210> SEQ ID NO 436
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 436

Thr Ser Gly Thr Gly Arg Ser Glu Thr Pro Arg Gly
1               5                   10

<210> SEQ ID NO 437
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 437

Thr Ser Gly Ser Gly Arg Ser Glu Thr Tyr Arg Gly
1               5                   10

<210> SEQ ID NO 438
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 438

Thr Ser Gly Ser Gly Arg Ser Glu Thr Val Arg Gly
1               5                   10

<210> SEQ ID NO 439
<211> LENGTH: 12
<212> TYPE: PRT
<213> ORGANISM: Artificial Sequence
<220> FEATURE:
```

-continued

```
<223> OTHER INFORMATION: an artificially synthesized sequence

<400> SEQUENCE: 439

Thr Ser Gly Ser Gly Arg Ser Glu Thr His Arg Gly
1               5                   10

<210> SEQ ID NO 440
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 440

Thr Ser Tyr Thr Gly Arg Ser Ala Val Pro Arg Gly
1               5                   10

<210> SEQ ID NO 441
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 441

Thr Ser Tyr Ser Gly Arg Ser Ala Val Tyr Arg Gly
1               5                   10

<210> SEQ ID NO 442
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 442

Thr Ser Tyr Ser Gly Arg Ser Ala Val Val Arg Gly
1               5                   10

<210> SEQ ID NO 443
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 443

Thr Ser Tyr Ser Gly Arg Ser Ala Val His Arg Gly
1               5                   10

<210> SEQ ID NO 444
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 444

Thr Ser Tyr Thr Gly Arg Ser Ala Val Tyr Arg Gly
1               5                   10

<210> SEQ ID NO 445
<211> LENGTH: 12
<212> TYPE: PRT
<213> ORGANISM: Artificial Sequence
<220> FEATURE:
<223> OTHER INFORMATION: an artificially synthesized sequence
```

<400> SEQUENCE: 445

Thr Ser Tyr Thr Gly Arg Ser Ala Val Val Arg Gly
1               5                   10

<210> SEQ ID NO 446
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 446

Thr Ser Tyr Thr Gly Arg Ser Ala Val His Arg Gly
1               5                   10

<210> SEQ ID NO 447
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 447

Thr Ser Tyr Ser Gly Arg Ser Glu Val Pro Arg Gly
1               5                   10

<210> SEQ ID NO 448
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 448

Thr Ser Tyr Thr Gly Arg Ser Glu Val Pro Arg Gly
1               5                   10

<210> SEQ ID NO 449
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 449

Thr Ser Tyr Ser Gly Arg Ser Glu Val Tyr Arg Gly
1               5                   10

<210> SEQ ID NO 450
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 450

Thr Ser Tyr Ser Gly Arg Ser Glu Val Val Arg Gly
1               5                   10

<210> SEQ ID NO 451
<211> LENGTH: 12
<212> TYPE: PRT
<213> ORGANISM: Artificial Sequence
<220> FEATURE:
<223> OTHER INFORMATION: an artificially synthesized sequence -continued

<400> SEQUENCE: 451

Thr Ser Tyr Ser Gly Arg Ser Glu Val His Arg Gly
1               5                   10

<210> SEQ ID NO 452
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 452

Thr Ser Tyr Thr Gly Arg Ser Ala Val Pro Gly Gly
1               5                   10

<210> SEQ ID NO 453
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 453

Thr Ser Tyr Ser Gly Arg Ser Ala Val Tyr Gly Gly
1               5                   10

<210> SEQ ID NO 454
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 454

Thr Ser Tyr Ser Gly Arg Ser Ala Val Val Gly Gly
1               5                   10

<210> SEQ ID NO 455
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 455

Thr Ser Tyr Ser Gly Arg Ser Ala Val His Gly Gly
1               5                   10

<210> SEQ ID NO 456
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 456

Thr Ser Tyr Thr Gly Arg Ser Ala Val Tyr Gly Gly
1               5                   10

<210> SEQ ID NO 457
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 457

```
Thr Ser Tyr Thr Gly Arg Ser Ala Val Val Gly Gly
1               5                   10

<210> SEQ ID NO 458
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 458

Thr Ser Tyr Thr Gly Arg Ser Ala Val His Gly Gly
1               5                   10

<210> SEQ ID NO 459
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 459

Ala Ser Gly Arg Ser Ala Asn Pro
1               5

<210> SEQ ID NO 460
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 460

Glu Ser Gly Arg Ser Ala Asn Pro
1               5

<210> SEQ ID NO 461
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 461

Phe Ser Gly Arg Ser Ala Asn Pro
1               5

<210> SEQ ID NO 462
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 462

Gly Ser Gly Arg Ser Ala Asn Pro
1               5

<210> SEQ ID NO 463
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 463
```

```
His Ser Gly Arg Ser Ala Asn Pro
1               5

<210> SEQ ID NO 464
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 464

Lys Ser Gly Arg Ser Ala Asn Pro
1               5

<210> SEQ ID NO 465
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 465

Met Ser Gly Arg Ser Ala Asn Pro
1               5

<210> SEQ ID NO 466
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 466

Asn Ser Gly Arg Ser Ala Asn Pro
1               5

<210> SEQ ID NO 467
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 467

Pro Ser Gly Arg Ser Ala Asn Pro
1               5

<210> SEQ ID NO 468
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 468

Gln Ser Gly Arg Ser Ala Asn Pro
1               5

<210> SEQ ID NO 469
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 469

Trp Ser Gly Arg Ser Ala Asn Pro
```

-continued

```
1               5

<210> SEQ ID NO 470
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 470

Tyr Ser Gly Arg Ser Ala Asn Pro
1               5

<210> SEQ ID NO 471
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 471

Thr Ala Gly Arg Ser Ala Asn Pro
1               5

<210> SEQ ID NO 472
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 472

Thr Asp Gly Arg Ser Ala Asn Pro
1               5

<210> SEQ ID NO 473
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 473

Thr Glu Gly Arg Ser Ala Asn Pro
1               5

<210> SEQ ID NO 474
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 474

Thr Phe Gly Arg Ser Ala Asn Pro
1               5

<210> SEQ ID NO 475
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 475

Thr Leu Gly Arg Ser Ala Asn Pro
1               5
```

```
<210> SEQ ID NO 476
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 476

Thr Met Gly Arg Ser Ala Asn Pro
1               5

<210> SEQ ID NO 477
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 477

Thr Pro Gly Arg Ser Ala Asn Pro
1               5

<210> SEQ ID NO 478
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 478

Thr Gln Gly Arg Ser Ala Asn Pro
1               5

<210> SEQ ID NO 479
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 479

Thr Val Gly Arg Ser Ala Asn Pro
1               5

<210> SEQ ID NO 480
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 480

Thr Trp Gly Arg Ser Ala Asn Pro
1               5

<210> SEQ ID NO 481
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 481

Thr Ser Ala Arg Ser Ala Asn Pro
1               5
```

```
<210> SEQ ID NO 482
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 482

Thr Ser Glu Arg Ser Ala Asn Pro
1               5

<210> SEQ ID NO 483
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 483

Thr Ser Phe Arg Ser Ala Asn Pro
1               5

<210> SEQ ID NO 484
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 484

Thr Ser His Arg Ser Ala Asn Pro
1               5

<210> SEQ ID NO 485
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 485

Thr Ser Ile Arg Ser Ala Asn Pro
1               5

<210> SEQ ID NO 486
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 486

Thr Ser Lys Arg Ser Ala Asn Pro
1               5

<210> SEQ ID NO 487
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 487

Thr Ser Leu Arg Ser Ala Asn Pro
1               5
```

-continued

```
<210> SEQ ID NO 488
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 488

Thr Ser Met Arg Ser Ala Asn Pro
1               5

<210> SEQ ID NO 489
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 489

Thr Ser Asn Arg Ser Ala Asn Pro
1               5

<210> SEQ ID NO 490
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 490

Thr Ser Pro Arg Ser Ala Asn Pro
1               5

<210> SEQ ID NO 491
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 491

Thr Ser Gln Arg Ser Ala Asn Pro
1               5

<210> SEQ ID NO 492
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 492

Thr Ser Arg Arg Ser Ala Asn Pro
1               5

<210> SEQ ID NO 493
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 493

Thr Ser Thr Arg Ser Ala Asn Pro
1               5

<210> SEQ ID NO 494
```

-continued

```
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 494

Thr Ser Val Arg Ser Ala Asn Pro
1               5

<210> SEQ ID NO 495
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 495

Thr Ser Trp Arg Ser Ala Asn Pro
1               5

<210> SEQ ID NO 496
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 496

Thr Ser Tyr Arg Ser Ala Asn Pro
1               5

<210> SEQ ID NO 497
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 497

Thr Ser Gly Arg Ala Ala Asn Pro
1               5

<210> SEQ ID NO 498
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 498

Thr Ser Gly Arg Asp Ala Asn Pro
1               5

<210> SEQ ID NO 499
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 499

Thr Ser Gly Arg Glu Ala Asn Pro
1               5

<210> SEQ ID NO 500
<211> LENGTH: 8
```

-continued

```
<212> TYPE: PRT
<213> ORGANISM: Artificial Sequence
<220> FEATURE:
<223> OTHER INFORMATION: an artificially synthesized sequence

<400> SEQUENCE: 500

Thr Ser Gly Arg Gly Ala Asn Pro
1               5

<210> SEQ ID NO 501
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 501

Thr Ser Gly Arg His Ala Asn Pro
1               5

<210> SEQ ID NO 502
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 502

Thr Ser Gly Arg Ile Ala Asn Pro
1               5

<210> SEQ ID NO 503
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 503

Thr Ser Gly Arg Lys Ala Asn Pro
1               5

<210> SEQ ID NO 504
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 504

Thr Ser Gly Arg Leu Ala Asn Pro
1               5

<210> SEQ ID NO 505
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 505

Thr Ser Gly Arg Met Ala Asn Pro
1               5

<210> SEQ ID NO 506
<211> LENGTH: 8
<212> TYPE: PRT
```

-continued

```
<213> ORGANISM: Artificial Sequence
<220> FEATURE:
<223> OTHER INFORMATION: an artificially synthesized sequence

<400> SEQUENCE: 506

Thr Ser Gly Arg Asn Ala Asn Pro
1               5

<210> SEQ ID NO 507
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 507

Thr Ser Gly Arg Pro Ala Asn Pro
1               5

<210> SEQ ID NO 508
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 508

Thr Ser Gly Arg Gln Ala Asn Pro
1               5

<210> SEQ ID NO 509
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 509

Thr Ser Gly Arg Arg Ala Asn Pro
1               5

<210> SEQ ID NO 510
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 510

Thr Ser Gly Arg Thr Ala Asn Pro
1               5

<210> SEQ ID NO 511
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 511

Thr Ser Gly Arg Val Ala Asn Pro
1               5

<210> SEQ ID NO 512
<211> LENGTH: 8
<212> TYPE: PRT
<213> ORGANISM: Artificial Sequence
```

-continued

```
<220> FEATURE:
<223> OTHER INFORMATION: an artificially synthesized sequence

<400> SEQUENCE: 512

Thr Ser Gly Arg Trp Ala Asn Pro
1               5

<210> SEQ ID NO 513
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 513

Thr Ser Gly Arg Tyr Ala Asn Pro
1               5

<210> SEQ ID NO 514
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 514

Thr Ser Gly Arg Ser Glu Asn Pro
1               5

<210> SEQ ID NO 515
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 515

Thr Ser Gly Arg Ser Phe Asn Pro
1               5

<210> SEQ ID NO 516
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 516

Thr Ser Gly Arg Ser Lys Asn Pro
1               5

<210> SEQ ID NO 517
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 517

Thr Ser Gly Arg Ser Met Asn Pro
1               5

<210> SEQ ID NO 518
<211> LENGTH: 8
<212> TYPE: PRT
<213> ORGANISM: Artificial Sequence
<220> FEATURE:
```

-continued

<223> OTHER INFORMATION: an artificially synthesized sequence

<400> SEQUENCE: 518

Thr Ser Gly Arg Ser Asn Asn Pro
1               5

<210> SEQ ID NO 519
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 519

Thr Ser Gly Arg Ser Pro Asn Pro
1               5

<210> SEQ ID NO 520
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 520

Thr Ser Gly Arg Ser Gln Asn Pro
1               5

<210> SEQ ID NO 521
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 521

Thr Ser Gly Arg Ser Arg Asn Pro
1               5

<210> SEQ ID NO 522
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 522

Thr Ser Gly Arg Ser Ser Asn Pro
1               5

<210> SEQ ID NO 523
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 523

Thr Ser Gly Arg Ser Trp Asn Pro
1               5

<210> SEQ ID NO 524
<211> LENGTH: 8
<212> TYPE: PRT
<213> ORGANISM: Artificial Sequence
<220> FEATURE:
<223> OTHER INFORMATION: an artificially synthesized sequence -continued

<400> SEQUENCE: 524

Thr Ser Gly Arg Ser Tyr Asn Pro
1               5

<210> SEQ ID NO 525
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 525

Thr Ser Gly Arg Ser Ala Ala Pro
1               5

<210> SEQ ID NO 526
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 526

Thr Ser Gly Arg Ser Ala Asp Pro
1               5

<210> SEQ ID NO 527
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 527

Thr Ser Gly Arg Ser Ala Glu Pro
1               5

<210> SEQ ID NO 528
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 528

Thr Ser Gly Arg Ser Ala Phe Pro
1               5

<210> SEQ ID NO 529
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 529

Thr Ser Gly Arg Ser Ala Gly Pro
1               5

<210> SEQ ID NO 530
<211> LENGTH: 8
<212> TYPE: PRT
<213> ORGANISM: Artificial Sequence
<220> FEATURE:
<223> OTHER INFORMATION: an artificially synthesized sequence

```
<400> SEQUENCE: 530

Thr Ser Gly Arg Ser Ala Lys Pro
1               5

<210> SEQ ID NO 531
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 531

Thr Ser Gly Arg Ser Ala Leu Pro
1               5

<210> SEQ ID NO 532
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 532

Thr Ser Gly Arg Ser Ala Met Pro
1               5

<210> SEQ ID NO 533
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 533

Thr Ser Gly Arg Ser Ala Pro Pro
1               5

<210> SEQ ID NO 534
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 534

Thr Ser Gly Arg Ser Ala Gln Pro
1               5

<210> SEQ ID NO 535
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 535

Thr Ser Gly Arg Ser Ala Val Pro
1               5

<210> SEQ ID NO 536
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 536
```

```
Thr Ser Gly Arg Ser Ala Trp Pro
1               5

<210> SEQ ID NO 537
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 537

Thr Ser Gly Arg Ser Ala Tyr Pro
1               5

<210> SEQ ID NO 538
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 538

Thr Ser Gly Arg Ser Ala Asn Ala
1               5

<210> SEQ ID NO 539
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 539

Thr Ser Gly Arg Ser Ala Asn Asp
1               5

<210> SEQ ID NO 540
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 540

Thr Ser Gly Arg Ser Ala Asn Glu
1               5

<210> SEQ ID NO 541
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 541

Thr Ser Gly Arg Ser Ala Asn Phe
1               5

<210> SEQ ID NO 542
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 542
```

-continued

```
Thr Ser Gly Arg Ser Ala Asn Gly
1               5

<210> SEQ ID NO 543
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 543

Thr Ser Gly Arg Ser Ala Asn Ile
1               5

<210> SEQ ID NO 544
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 544

Thr Ser Gly Arg Ser Ala Asn Lys
1               5

<210> SEQ ID NO 545
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 545

Thr Ser Gly Arg Ser Ala Asn Asn
1               5

<210> SEQ ID NO 546
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 546

Thr Ser Gly Arg Ser Ala Asn Gln
1               5

<210> SEQ ID NO 547
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 547

Thr Ser Gly Arg Ser Ala Asn Ser
1               5

<210> SEQ ID NO 548
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 548

Thr Ser Gly Arg Ser Ala Asn Thr
```

-continued

```
1               5

<210> SEQ ID NO 549
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 549

Thr Ser Gly Arg Ser Ala Asn Trp
1               5

<210> SEQ ID NO 550
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 550

Asp Ser Gly Arg Ser Ala Asn Pro
1               5

<210> SEQ ID NO 551
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 551

Ile Ser Gly Arg Ser Ala Asn Pro
1               5

<210> SEQ ID NO 552
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 552

Ser Ser Gly Arg Ser Ala Asn Pro
1               5

<210> SEQ ID NO 553
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 553

Thr His Gly Arg Ser Ala Asn Pro
1               5

<210> SEQ ID NO 554
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 554

Thr Lys Gly Arg Ser Ala Asn Pro
1               5
```

-continued

```
<210> SEQ ID NO 555
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 555

Thr Thr Gly Arg Ser Ala Asn Pro
1               5

<210> SEQ ID NO 556
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 556

Thr Tyr Gly Arg Ser Ala Asn Pro
1               5

<210> SEQ ID NO 557
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 557

Thr Ser Asp Arg Ser Ala Asn Pro
1               5

<210> SEQ ID NO 558
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 558

Thr Ser Ser Arg Ser Ala Asn Pro
1               5

<210> SEQ ID NO 559
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 559

Thr Ser Gly Arg Phe Ala Asn Pro
1               5

<210> SEQ ID NO 560
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 560

Thr Ser Gly Arg Ser Asp Asn Pro
1               5
```

```
<210> SEQ ID NO 561
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 561

Thr Ser Gly Arg Ser His Asn Pro
1               5

<210> SEQ ID NO 562
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 562

Thr Ser Gly Arg Ser Ile Asn Pro
1               5

<210> SEQ ID NO 563
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 563

Thr Ser Gly Arg Ser Leu Asn Pro
1               5

<210> SEQ ID NO 564
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 564

Thr Ser Gly Arg Ser Thr Asn Pro
1               5

<210> SEQ ID NO 565
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 565

Thr Ser Gly Arg Ser Val Asn Pro
1               5

<210> SEQ ID NO 566
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 566

Thr Ser Gly Arg Ser Ala His Pro
1               5
```

-continued

```
<210> SEQ ID NO 567
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 567

Thr Ser Gly Arg Ser Ala Ile Pro
1               5

<210> SEQ ID NO 568
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 568

Thr Ser Gly Arg Ser Ala Arg Pro
1               5

<210> SEQ ID NO 569
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 569

Thr Ser Gly Arg Ser Ala Ser Pro
1               5

<210> SEQ ID NO 570
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 570

Thr Ser Gly Arg Ser Ala Thr Pro
1               5

<210> SEQ ID NO 571
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 571

Thr Ser Gly Arg Ser Ala Asn His
1               5

<210> SEQ ID NO 572
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 572

Thr Ser Gly Arg Ser Ala Asn Leu
1               5

<210> SEQ ID NO 573
```

```
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 573

Thr Ser Gly Arg Ser Ala Asn Met
1               5

<210> SEQ ID NO 574
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 574

Thr Ser Gly Arg Ser Ala Asn Arg
1               5

<210> SEQ ID NO 575
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 575

Thr Ser Gly Arg Ser Ala Asn Val
1               5

<210> SEQ ID NO 576
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 576

Thr Ser Gly Arg Ser Ala Asn Tyr
1               5

<210> SEQ ID NO 577
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 577

Gly Ser Gly Arg Ser Ala Val Pro
1               5

<210> SEQ ID NO 578
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 578

Gly Ser Gly Arg Ser Ala Tyr Pro
1               5

<210> SEQ ID NO 579
<211> LENGTH: 8
```

<212> TYPE: PRT
<213> ORGANISM: Artificial Sequence
<220> FEATURE:
<223> OTHER INFORMATION: an artificially synthesized sequence

<400> SEQUENCE: 579

Gly Ser Gly Arg Ser Ala Asn Gln
1               5

<210> SEQ ID NO 580
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 580

Gly Ser Gly Arg Ser Ala Asn Ala
1               5

<210> SEQ ID NO 581
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 581

Gly Ser Gly Arg Ser Ala Asn Ile
1               5

<210> SEQ ID NO 582
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 582

Gly Ser Gly Arg Ser Ala Asn Phe
1               5

<210> SEQ ID NO 583
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 583

Gly Ser Gly Arg Ser Ala Asn Ser
1               5

<210> SEQ ID NO 584
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 584

Gln Ser Gly Arg Ser Ala Val Pro
1               5

<210> SEQ ID NO 585
<211> LENGTH: 8
<212> TYPE: PRT

-continued

```
<213> ORGANISM: Artificial Sequence
<220> FEATURE:
<223> OTHER INFORMATION: an artificially synthesized sequence

<400> SEQUENCE: 585

Gln Ser Gly Arg Ser Ala Tyr Pro
1               5

<210> SEQ ID NO 586
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 586

Gln Ser Gly Arg Ser Ala Asn Gln
1               5

<210> SEQ ID NO 587
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 587

Gln Ser Gly Arg Ser Ala Asn Ala
1               5

<210> SEQ ID NO 588
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 588

Gln Ser Gly Arg Ser Ala Asn Ile
1               5

<210> SEQ ID NO 589
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 589

Gln Ser Gly Arg Ser Ala Asn Phe
1               5

<210> SEQ ID NO 590
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 590

Gln Ser Gly Arg Ser Ala Asn Ser
1               5

<210> SEQ ID NO 591
<211> LENGTH: 8
<212> TYPE: PRT
<213> ORGANISM: Artificial Sequence
```

-continued

```
<220> FEATURE:
<223> OTHER INFORMATION: an artificially synthesized sequence

<400> SEQUENCE: 591

Pro Ser Gly Arg Ser Ala Val Pro
1               5

<210> SEQ ID NO 592
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 592

Pro Ser Gly Arg Ser Ala Tyr Pro
1               5

<210> SEQ ID NO 593
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 593

Pro Ser Gly Arg Ser Ala Asn Gln
1               5

<210> SEQ ID NO 594
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 594

Pro Ser Gly Arg Ser Ala Asn Ala
1               5

<210> SEQ ID NO 595
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 595

Pro Ser Gly Arg Ser Ala Asn Ile
1               5

<210> SEQ ID NO 596
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 596

Pro Ser Gly Arg Ser Ala Asn Phe
1               5

<210> SEQ ID NO 597
<211> LENGTH: 8
<212> TYPE: PRT
<213> ORGANISM: Artificial Sequence
<220> FEATURE:
```

-continued

<223> OTHER INFORMATION: an artificially synthesized sequence

<400> SEQUENCE: 597

Pro Ser Gly Arg Ser Ala Asn Ser
1               5

<210> SEQ ID NO 598
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 598

Ala Ser Gly Arg Ser Ala Val Pro
1               5

<210> SEQ ID NO 599
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 599

Ala Ser Gly Arg Ser Ala Tyr Pro
1               5

<210> SEQ ID NO 600
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 600

Ala Ser Gly Arg Ser Ala Asn Gln
1               5

<210> SEQ ID NO 601
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 601

Ala Ser Gly Arg Ser Ala Asn Ala
1               5

<210> SEQ ID NO 602
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 602

Ala Ser Gly Arg Ser Ala Asn Ile
1               5

<210> SEQ ID NO 603
<211> LENGTH: 8
<212> TYPE: PRT
<213> ORGANISM: Artificial Sequence
<220> FEATURE:
<223> OTHER INFORMATION: an artificially synthesized sequence

```
<400> SEQUENCE: 603

Ala Ser Gly Arg Ser Ala Asn Phe
1               5

<210> SEQ ID NO 604
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 604

Ala Ser Gly Arg Ser Ala Asn Ser
1               5

<210> SEQ ID NO 605
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 605

Tyr Ser Gly Arg Ser Glu Asn Pro
1               5

<210> SEQ ID NO 606
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 606

Gly Ser Gly Arg Ser Glu Asn Pro
1               5

<210> SEQ ID NO 607
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 607

Gln Ser Gly Arg Ser Glu Asn Pro
1               5

<210> SEQ ID NO 608
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 608

Pro Ser Gly Arg Ser Glu Asn Pro
1               5

<210> SEQ ID NO 609
<211> LENGTH: 8
<212> TYPE: PRT
<213> ORGANISM: Artificial Sequence
<220> FEATURE:
<223> OTHER INFORMATION: an artificially synthesized sequence
```

-continued

```
<400> SEQUENCE: 609

Ala Ser Gly Arg Ser Glu Asn Pro
1               5

<210> SEQ ID NO 610
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 610

His Ser Gly Arg Ser Glu Asn Pro
1               5

<210> SEQ ID NO 611
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 611

Thr Ser Gly Arg Ser Glu Asn Gln
1               5

<210> SEQ ID NO 612
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 612

Thr Ser Gly Arg Ser Glu Asn Ala
1               5

<210> SEQ ID NO 613
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 613

Thr Ser Gly Arg Ser Glu Asn Ile
1               5

<210> SEQ ID NO 614
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 614

Thr Ser Gly Arg Ser Glu Asn Phe
1               5

<210> SEQ ID NO 615
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 615
```

Thr Ser Gly Arg Ser Glu Asn Ser
1               5

<210> SEQ ID NO 616
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 616

Tyr Ser Gly Arg Ser Ala Glu Pro
1               5

<210> SEQ ID NO 617
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 617

Gly Ser Gly Arg Ser Ala Glu Pro
1               5

<210> SEQ ID NO 618
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 618

Gln Ser Gly Arg Ser Ala Glu Pro
1               5

<210> SEQ ID NO 619
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 619

Pro Ser Gly Arg Ser Ala Glu Pro
1               5

<210> SEQ ID NO 620
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 620

Ala Ser Gly Arg Ser Ala Glu Pro
1               5

<210> SEQ ID NO 621
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 621

```
His Ser Gly Arg Ser Ala Glu Pro
1               5

<210> SEQ ID NO 622
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 622

Thr Ser Gly Arg Ser Ala Glu Gln
1               5

<210> SEQ ID NO 623
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 623

Thr Ser Gly Arg Ser Ala Glu Ala
1               5

<210> SEQ ID NO 624
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 624

Thr Ser Gly Arg Ser Ala Glu Ile
1               5

<210> SEQ ID NO 625
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 625

Thr Ser Gly Arg Ser Ala Glu Phe
1               5

<210> SEQ ID NO 626
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 626

Thr Ser Gly Arg Ser Ala Glu Ser
1               5

<210> SEQ ID NO 627
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 627

Gly Thr Gly Arg Ser Ala Asn Pro
```

-continued

```
1                 5

<210> SEQ ID NO 628
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 628

Gly Lys Gly Arg Ser Ala Asn Pro
1                 5

<210> SEQ ID NO 629
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 629

Gly Ser Gly Arg Ser Ala Ile Pro
1                 5

<210> SEQ ID NO 630
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 630

Gly Ser Gly Arg Ser Ala Thr Pro
1                 5

<210> SEQ ID NO 631
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 631

Gly Ser Gly Arg Ser Ala Ser Pro
1                 5

<210> SEQ ID NO 632
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 632

Gly Ser Gly Arg Ser Ala His Pro
1                 5

<210> SEQ ID NO 633
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 633

Gly Ser Gly Arg Ser Ala Asn Tyr
1                 5
```

```
<210> SEQ ID NO 634
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 634

Gly Ser Gly Arg Ser Ala Asn Val
1               5

<210> SEQ ID NO 635
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 635

Gly Ser Gly Arg Ser Ala Asn His
1               5

<210> SEQ ID NO 636
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 636

Gln Thr Gly Arg Ser Ala Asn Pro
1               5

<210> SEQ ID NO 637
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 637

Gln Lys Gly Arg Ser Ala Asn Pro
1               5

<210> SEQ ID NO 638
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 638

Gln Ser Gly Arg Ser Ala Ile Pro
1               5

<210> SEQ ID NO 639
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 639

Gln Ser Gly Arg Ser Ala Thr Pro
1               5
```

-continued

```
<210> SEQ ID NO 640
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 640

Gln Ser Gly Arg Ser Ala Ser Pro
1               5

<210> SEQ ID NO 641
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 641

Gln Ser Gly Arg Ser Ala His Pro
1               5

<210> SEQ ID NO 642
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 642

Gln Ser Gly Arg Ser Ala Asn Tyr
1               5

<210> SEQ ID NO 643
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 643

Gln Ser Gly Arg Ser Ala Asn Val
1               5

<210> SEQ ID NO 644
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 644

Gln Ser Gly Arg Ser Ala Asn His
1               5

<210> SEQ ID NO 645
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 645

Pro Thr Gly Arg Ser Ala Asn Pro
1               5
```

-continued

```
<210> SEQ ID NO 646
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 646

Pro Lys Gly Arg Ser Ala Asn Pro
1               5

<210> SEQ ID NO 647
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 647

Pro Ser Gly Arg Ser Ala Ile Pro
1               5

<210> SEQ ID NO 648
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 648

Pro Ser Gly Arg Ser Ala Thr Pro
1               5

<210> SEQ ID NO 649
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 649

Pro Ser Gly Arg Ser Ala Ser Pro
1               5

<210> SEQ ID NO 650
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 650

Pro Ser Gly Arg Ser Ala His Pro
1               5

<210> SEQ ID NO 651
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 651

Pro Ser Gly Arg Ser Ala Asn Tyr
1               5

<210> SEQ ID NO 652
```

-continued

```
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 652

Pro Ser Gly Arg Ser Ala Asn Val
1               5

<210> SEQ ID NO 653
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 653

Pro Ser Gly Arg Ser Ala Asn His
1               5

<210> SEQ ID NO 654
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 654

Ala Thr Gly Arg Ser Ala Asn Pro
1               5

<210> SEQ ID NO 655
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 655

Ala Lys Gly Arg Ser Ala Asn Pro
1               5

<210> SEQ ID NO 656
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 656

Ala Ser Gly Arg Ser Ala Ile Pro
1               5

<210> SEQ ID NO 657
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 657

Ala Ser Gly Arg Ser Ala Thr Pro
1               5

<210> SEQ ID NO 658
<211> LENGTH: 8
```

<212> TYPE: PRT
<213> ORGANISM: Artificial Sequence
<220> FEATURE:
<223> OTHER INFORMATION: an artificially synthesized sequence

<400> SEQUENCE: 658

Ala Ser Gly Arg Ser Ala Ser Pro
1               5

<210> SEQ ID NO 659
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 659

Ala Ser Gly Arg Ser Ala His Pro
1               5

<210> SEQ ID NO 660
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 660

Ala Ser Gly Arg Ser Ala Asn Tyr
1               5

<210> SEQ ID NO 661
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 661

Ala Ser Gly Arg Ser Ala Asn Val
1               5

<210> SEQ ID NO 662
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 662

Ala Ser Gly Arg Ser Ala Asn His
1               5

<210> SEQ ID NO 663
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 663

Tyr Thr Gly Arg Ser Ala Asn Pro
1               5

<210> SEQ ID NO 664
<211> LENGTH: 8
<212> TYPE: PRT

<213> ORGANISM: Artificial Sequence
<220> FEATURE:
<223> OTHER INFORMATION: an artificially synthesized sequence

<400> SEQUENCE: 664

Tyr Lys Gly Arg Ser Ala Asn Pro
1               5

<210> SEQ ID NO 665
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 665

Tyr Ser Gly Arg Ser Ala Val Pro
1               5

<210> SEQ ID NO 666
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 666

Tyr Ser Gly Arg Ser Ala Ile Pro
1               5

<210> SEQ ID NO 667
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 667

Tyr Ser Gly Arg Ser Ala Thr Pro
1               5

<210> SEQ ID NO 668
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 668

Tyr Ser Gly Arg Ser Ala Ser Pro
1               5

<210> SEQ ID NO 669
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 669

Tyr Ser Gly Arg Ser Ala His Pro
1               5

<210> SEQ ID NO 670
<211> LENGTH: 8
<212> TYPE: PRT
<213> ORGANISM: Artificial Sequence

```
<220> FEATURE:
<223> OTHER INFORMATION: an artificially synthesized sequence

<400> SEQUENCE: 670

Tyr Ser Gly Arg Ser Ala Asn Ala
1               5

<210> SEQ ID NO 671
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 671

Tyr Ser Gly Arg Ser Ala Asn Phe
1               5

<210> SEQ ID NO 672
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 672

Tyr Ser Gly Arg Ser Ala Asn Tyr
1               5

<210> SEQ ID NO 673
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 673

Tyr Ser Gly Arg Ser Ala Asn Val
1               5

<210> SEQ ID NO 674
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 674

Tyr Ser Gly Arg Ser Ala Asn His
1               5

<210> SEQ ID NO 675
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 675

Ser Thr Gly Arg Ser Ala Asn Pro
1               5

<210> SEQ ID NO 676
<211> LENGTH: 8
<212> TYPE: PRT
<213> ORGANISM: Artificial Sequence
<220> FEATURE:
```

-continued

```
<223> OTHER INFORMATION: an artificially synthesized sequence

<400> SEQUENCE: 676

Ser Lys Gly Arg Ser Ala Asn Pro
1               5

<210> SEQ ID NO 677
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 677

Ser Ser Gly Arg Ser Ala Val Pro
1               5

<210> SEQ ID NO 678
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 678

Ser Ser Gly Arg Ser Ala Ile Pro
1               5

<210> SEQ ID NO 679
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 679

Ser Ser Gly Arg Ser Ala Thr Pro
1               5

<210> SEQ ID NO 680
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 680

Ser Ser Gly Arg Ser Ala Ser Pro
1               5

<210> SEQ ID NO 681
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 681

Ser Ser Gly Arg Ser Ala His Pro
1               5

<210> SEQ ID NO 682
<211> LENGTH: 8
<212> TYPE: PRT
<213> ORGANISM: Artificial Sequence
<220> FEATURE:
<223> OTHER INFORMATION: an artificially synthesized sequence
```

-continued

```
<400> SEQUENCE: 682

Ser Ser Gly Arg Ser Ala Asn Ala
1               5

<210> SEQ ID NO 683
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 683

Ser Ser Gly Arg Ser Ala Asn Phe
1               5

<210> SEQ ID NO 684
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 684

Ser Ser Gly Arg Ser Ala Asn Tyr
1               5

<210> SEQ ID NO 685
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 685

Ser Ser Gly Arg Ser Ala Asn Val
1               5

<210> SEQ ID NO 686
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 686

Ser Ser Gly Arg Ser Ala Asn His
1               5

<210> SEQ ID NO 687
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 687

Ile Thr Gly Arg Ser Ala Asn Pro
1               5

<210> SEQ ID NO 688
<211> LENGTH: 8
<212> TYPE: PRT
<213> ORGANISM: Artificial Sequence
<220> FEATURE:
<223> OTHER INFORMATION: an artificially synthesized sequence
```

-continued

```
<400> SEQUENCE: 688

Ile Lys Gly Arg Ser Ala Asn Pro
1               5

<210> SEQ ID NO 689
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 689

Ile Ser Gly Arg Ser Ala Val Pro
1               5

<210> SEQ ID NO 690
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 690

Ile Ser Gly Arg Ser Ala Ile Pro
1               5

<210> SEQ ID NO 691
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 691

Ile Ser Gly Arg Ser Ala Thr Pro
1               5

<210> SEQ ID NO 692
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 692

Ile Ser Gly Arg Ser Ala Ser Pro
1               5

<210> SEQ ID NO 693
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 693

Ile Ser Gly Arg Ser Ala His Pro
1               5

<210> SEQ ID NO 694
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 694
```

Ile Ser Gly Arg Ser Ala Asn Ala
1               5

<210> SEQ ID NO 695
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 695

Ile Ser Gly Arg Ser Ala Asn Phe
1               5

<210> SEQ ID NO 696
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 696

Ile Ser Gly Arg Ser Ala Asn Tyr
1               5

<210> SEQ ID NO 697
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 697

Ile Ser Gly Arg Ser Ala Asn Val
1               5

<210> SEQ ID NO 698
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 698

Ile Ser Gly Arg Ser Ala Asn His
1               5

<210> SEQ ID NO 699
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 699

Thr Thr Gly Arg Ser Ala Val Pro
1               5

<210> SEQ ID NO 700
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 700

```
Thr Thr Gly Arg Ser Ala Ile Pro
1               5

<210> SEQ ID NO 701
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 701

Thr Thr Gly Arg Ser Ala Thr Pro
1               5

<210> SEQ ID NO 702
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 702

Thr Thr Gly Arg Ser Ala Ser Pro
1               5

<210> SEQ ID NO 703
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 703

Thr Thr Gly Arg Ser Ala His Pro
1               5

<210> SEQ ID NO 704
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 704

Thr Thr Gly Arg Ser Ala Asn Ala
1               5

<210> SEQ ID NO 705
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 705

Thr Thr Gly Arg Ser Ala Asn Phe
1               5

<210> SEQ ID NO 706
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 706

Thr Thr Gly Arg Ser Ala Asn Tyr
```

-continued

```
1               5

<210> SEQ ID NO 707
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 707

Thr Thr Gly Arg Ser Ala Asn Val
1               5

<210> SEQ ID NO 708
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 708

Thr Thr Gly Arg Ser Ala Asn His
1               5

<210> SEQ ID NO 709
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 709

Thr Lys Gly Arg Ser Ala Val Pro
1               5

<210> SEQ ID NO 710
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 710

Thr Lys Gly Arg Ser Ala Ile Pro
1               5

<210> SEQ ID NO 711
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 711

Thr Lys Gly Arg Ser Ala Thr Pro
1               5

<210> SEQ ID NO 712
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 712

Thr Lys Gly Arg Ser Ala Ser Pro
1               5
```

-continued

```
<210> SEQ ID NO 713
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 713

Thr Lys Gly Arg Ser Ala His Pro
1               5

<210> SEQ ID NO 714
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 714

Thr Lys Gly Arg Ser Ala Asn Ala
1               5

<210> SEQ ID NO 715
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 715

Thr Lys Gly Arg Ser Ala Asn Phe
1               5

<210> SEQ ID NO 716
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 716

Thr Lys Gly Arg Ser Ala Asn Tyr
1               5

<210> SEQ ID NO 717
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 717

Thr Lys Gly Arg Ser Ala Asn Val
1               5

<210> SEQ ID NO 718
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 718

Thr Lys Gly Arg Ser Ala Asn His
1               5
```

-continued

```
<210> SEQ ID NO 719
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 719

Thr Ser Gly Arg Ser Ala Val Tyr
1               5

<210> SEQ ID NO 720
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 720

Thr Ser Gly Arg Ser Ala Val Val
1               5

<210> SEQ ID NO 721
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 721

Thr Ser Gly Arg Ser Ala Val His
1               5

<210> SEQ ID NO 722
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 722

Thr Ser Gly Arg Ser Ala Ile Tyr
1               5

<210> SEQ ID NO 723
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 723

Thr Ser Gly Arg Ser Ala Ile Val
1               5

<210> SEQ ID NO 724
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 724

Thr Ser Gly Arg Ser Ala Ile His
1               5
```

-continued

```
<210> SEQ ID NO 725
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 725

Thr Ser Gly Arg Ser Ala Ser Tyr
1               5

<210> SEQ ID NO 726
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 726

Thr Ser Gly Arg Ser Ala Ser Val
1               5

<210> SEQ ID NO 727
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 727

Thr Ser Gly Arg Ser Ala Ser His
1               5

<210> SEQ ID NO 728
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 728

Thr Ser Gly Arg Ser Ala His Tyr
1               5

<210> SEQ ID NO 729
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 729

Thr Ser Gly Arg Ser Ala His Val
1               5

<210> SEQ ID NO 730
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 730

Thr Ser Gly Arg Ser Ala His His
1               5

<210> SEQ ID NO 731
```

-continued

```
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 731

Pro Ser Gly Arg Ser Glu Val Pro
1               5

<210> SEQ ID NO 732
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 732

Pro Ser Gly Arg Ser Ala Glu Pro
1               5

<210> SEQ ID NO 733
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 733

Pro Ser Gly Arg Ser Ala Gly Pro
1               5

<210> SEQ ID NO 734
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 734

Ala Ser Gly Arg Ser Glu Asn Ala
1               5

<210> SEQ ID NO 735
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 735

Ala Ser Gly Arg Ser Ala Glu Ala
1               5

<210> SEQ ID NO 736
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 736

Ala Ser Gly Arg Ser Ala Gly Ala
1               5

<210> SEQ ID NO 737
<211> LENGTH: 8
```

-continued

```
<212> TYPE: PRT
<213> ORGANISM: Artificial Sequence
<220> FEATURE:
<223> OTHER INFORMATION: an artificially synthesized sequence

<400> SEQUENCE: 737

Gly Thr Gly Arg Ser Ala Thr Pro
1               5

<210> SEQ ID NO 738
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 738

Gly Ser Gly Arg Ser Ala Thr Tyr
1               5

<210> SEQ ID NO 739
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 739

Gly Ser Gly Arg Ser Ala Thr Val
1               5

<210> SEQ ID NO 740
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 740

Gly Ser Gly Arg Ser Ala Thr His
1               5

<210> SEQ ID NO 741
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 741

Gly Thr Gly Arg Ser Ala Thr Tyr
1               5

<210> SEQ ID NO 742
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 742

Gly Thr Gly Arg Ser Ala Thr Val
1               5

<210> SEQ ID NO 743
<211> LENGTH: 8
<212> TYPE: PRT
```

<213> ORGANISM: Artificial Sequence
<220> FEATURE:
<223> OTHER INFORMATION: an artificially synthesized sequence

<400> SEQUENCE: 743

Gly Thr Gly Arg Ser Ala Thr His
1               5

<210> SEQ ID NO 744
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 744

Gly Ser Gly Arg Ser Glu Thr Pro
1               5

<210> SEQ ID NO 745
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 745

Gly Thr Gly Arg Ser Glu Thr Pro
1               5

<210> SEQ ID NO 746
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 746

Gly Ser Gly Arg Ser Glu Thr Tyr
1               5

<210> SEQ ID NO 747
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 747

Gly Ser Gly Arg Ser Glu Thr Val
1               5

<210> SEQ ID NO 748
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 748

Gly Ser Gly Arg Ser Glu Thr His
1               5

<210> SEQ ID NO 749
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 749

Tyr Thr Gly Arg Ser Ala Val Pro
1               5

<210> SEQ ID NO 750
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 750

Tyr Ser Gly Arg Ser Ala Val Tyr
1               5

<210> SEQ ID NO 751
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 751

Tyr Ser Gly Arg Ser Ala Val Val
1               5

<210> SEQ ID NO 752
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 752

Tyr Ser Gly Arg Ser Ala Val His
1               5

<210> SEQ ID NO 753
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 753

Tyr Thr Gly Arg Ser Ala Val Tyr
1               5

<210> SEQ ID NO 754
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 754

Tyr Thr Gly Arg Ser Ala Val Val
1               5

<210> SEQ ID NO 755
<211> LENGTH: 8
<212> TYPE: PRT
<213> ORGANISM: Artificial Sequence
<220> FEATURE:

<223> OTHER INFORMATION: an artificially synthesized sequence

<400> SEQUENCE: 755

Tyr Thr Gly Arg Ser Ala Val His
1               5

<210> SEQ ID NO 756
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 756

Tyr Ser Gly Arg Ser Glu Val Pro
1               5

<210> SEQ ID NO 757
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 757

Tyr Thr Gly Arg Ser Glu Val Pro
1               5

<210> SEQ ID NO 758
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 758

Tyr Ser Gly Arg Ser Glu Val Tyr
1               5

<210> SEQ ID NO 759
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 759

Tyr Ser Gly Arg Ser Glu Val Val
1               5

<210> SEQ ID NO 760
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 760

Tyr Ser Gly Arg Ser Glu Val His
1               5

<210> SEQ ID NO 761
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 761

Tyr Thr Gly Arg Ser Ala Val Pro
1               5

<210> SEQ ID NO 762
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 762

Tyr Ser Gly Arg Ser Ala Val Tyr
1               5

<210> SEQ ID NO 763
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 763

Tyr Ser Gly Arg Ser Ala Val Val
1               5

<210> SEQ ID NO 764
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 764

Tyr Ser Gly Arg Ser Ala Val His
1               5

<210> SEQ ID NO 765
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 765

Tyr Thr Gly Arg Ser Ala Val Tyr
1               5

<210> SEQ ID NO 766
<211> LENGTH: 8
<212> TYPE: PRT
<213> ORGANISM: Artificial Sequence
<220> FEATURE:
<223> OTHER INFORMATION: an artificially synthesized sequence

<400> SEQUENCE: 766

Tyr Thr Gly Arg Ser Ala Val Val
1               5

<210> SEQ ID NO 767
<211> LENGTH: 8
<212> TYPE: PRT
<213> ORGANISM: Artificial Sequence
<220> FEATURE:
<223> OTHER INFORMATION: an artificially synthesized sequence -continued

```
<400> SEQUENCE: 767

Tyr Thr Gly Arg Ser Ala Val His
1               5

<210> SEQ ID NO 768
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 768

Thr Ser Thr Ser Gly Arg Ser Ala Asn Pro Arg Gly
1               5                   10

<210> SEQ ID NO 769
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 769

Thr Ser Thr Ser Gly Arg Ser Ala Asn Pro Ala Gly
1               5                   10

<210> SEQ ID NO 770
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 770

Thr Ser Thr Ser Gly Arg Ser Ala Asn Pro His Gly
1               5                   10

<210> SEQ ID NO 771
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 771

Thr Ser Thr Ser Gly Arg Ser Ala Asn Pro Ile Gly
1               5                   10

<210> SEQ ID NO 772
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 772

Thr Ser Thr Ser Gly Arg Ser Ala Asn Pro Leu Gly
1               5                   10

<210> SEQ ID NO 773
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 773
```

-continued

```
Thr Ser Thr Ser Gly Arg Ser Ala Asn Pro Ser Gly
1               5                   10

<210> SEQ ID NO 774
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 774

Ile Ser Thr Ser Gly Arg Ser Ala Asn Pro Ile Gly
1               5                   10

<210> SEQ ID NO 775
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 775

Tyr Ser Thr Ser Gly Arg Ser Ala Asn Pro Ile Gly
1               5                   10

<210> SEQ ID NO 776
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 776

Thr Ser Tyr Ser Gly Arg Ser Ala Val Pro Ala Gly
1               5                   10

<210> SEQ ID NO 777
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 777

Thr Ser Pro Ser Gly Arg Ser Ala Asn Ile Ala Gly
1               5                   10

<210> SEQ ID NO 778
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 778

Thr Ser Pro Ser Gly Arg Ser Ala Asn Phe Ala Gly
1               5                   10

<210> SEQ ID NO 779
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 779
```

-continued

```
Thr Ser Pro Thr Gly Arg Ser Ala Asn Pro Ala Gly
1               5                   10

<210> SEQ ID NO 780
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 780

Thr Ser Pro Ser Gly Arg Ser Ala Ile Pro Ala Gly
1               5                   10

<210> SEQ ID NO 781
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 781

Thr Ser Tyr Thr Gly Arg Ser Ala Asn Pro Ala Gly
1               5                   10

<210> SEQ ID NO 782
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 782

Thr Ser Tyr Ser Gly Arg Ser Ala Ile Pro Ala Gly
1               5                   10

<210> SEQ ID NO 783
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 783

Thr Ser Ile Ser Gly Arg Ser Ala Asn Tyr Ala Gly
1               5                   10

<210> SEQ ID NO 784
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 784

Thr Ser Pro Ser Gly Arg Ser Ala Gly Pro Ala Gly
1               5                   10

<210> SEQ ID NO 785
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 785

Thr Ser Tyr Thr Gly Arg Ser Ala Val Pro Ala Gly
```

-continued

```
1               5                    10

<210> SEQ ID NO 786
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 786

Thr Ser Tyr Thr Gly Arg Ser Ala Val Tyr Ala Gly
1               5                    10

<210> SEQ ID NO 787
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 787

Thr Ser Tyr Thr Gly Arg Ser Ala Val Val Ala Gly
1               5                    10

<210> SEQ ID NO 788
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 788

Thr Ser Tyr Thr Gly Arg Ser Ala Val His Ala Gly
1               5                    10

<210> SEQ ID NO 789
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 789

Thr Ser Tyr Ser Gly Arg Ser Ala Val Pro His Gly
1               5                    10

<210> SEQ ID NO 790
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 790

Thr Ser Pro Ser Gly Arg Ser Ala Asn Ile His Gly
1               5                    10

<210> SEQ ID NO 791
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 791

Thr Ser Pro Ser Gly Arg Ser Ala Asn Phe His Gly
1               5                    10
```

-continued

```
<210> SEQ ID NO 792
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 792

Thr Ser Pro Thr Gly Arg Ser Ala Asn Pro His Gly
1               5                   10

<210> SEQ ID NO 793
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 793

Thr Ser Pro Ser Gly Arg Ser Ala Ile Pro His Gly
1               5                   10

<210> SEQ ID NO 794
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 794

Thr Ser Tyr Thr Gly Arg Ser Ala Asn Pro His Gly
1               5                   10

<210> SEQ ID NO 795
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 795

Thr Ser Tyr Ser Gly Arg Ser Ala Ile Pro His Gly
1               5                   10

<210> SEQ ID NO 796
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 796

Thr Ser Ile Ser Gly Arg Ser Ala Asn Tyr His Gly
1               5                   10

<210> SEQ ID NO 797
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 797

Thr Ser Pro Ser Gly Arg Ser Ala Gly Pro His Gly
1               5                   10
```

-continued

```
<210> SEQ ID NO 798
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 798

Thr Ser Tyr Thr Gly Arg Ser Ala Val Pro His Gly
1               5                   10

<210> SEQ ID NO 799
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 799

Thr Ser Tyr Thr Gly Arg Ser Ala Val Tyr His Gly
1               5                   10

<210> SEQ ID NO 800
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 800

Thr Ser Tyr Thr Gly Arg Ser Ala Val Val His Gly
1               5                   10

<210> SEQ ID NO 801
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 801

Thr Ser Tyr Thr Gly Arg Ser Ala Val His His Gly
1               5                   10

<210> SEQ ID NO 802
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 802

Thr Ser Tyr Ser Gly Arg Ser Ala Val Pro Ile Gly
1               5                   10

<210> SEQ ID NO 803
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 803

Thr Ser Pro Ser Gly Arg Ser Ala Asn Ile Ile Gly
1               5                   10
```

<210> SEQ ID NO 804
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 804

Thr Ser Pro Ser Gly Arg Ser Ala Asn Phe Ile Gly
1               5                   10

<210> SEQ ID NO 805
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 805

Thr Ser Pro Thr Gly Arg Ser Ala Asn Pro Ile Gly
1               5                   10

<210> SEQ ID NO 806
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 806

Thr Ser Pro Ser Gly Arg Ser Ala Ile Pro Ile Gly
1               5                   10

<210> SEQ ID NO 807
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 807

Thr Ser Tyr Thr Gly Arg Ser Ala Asn Pro Ile Gly
1               5                   10

<210> SEQ ID NO 808
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 808

Thr Ser Tyr Ser Gly Arg Ser Ala Ile Pro Ile Gly
1               5                   10

<210> SEQ ID NO 809
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 809

Thr Ser Ile Ser Gly Arg Ser Ala Asn Tyr Ile Gly
1               5                   10

<210> SEQ ID NO 810

```
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 810

Thr Ser Pro Ser Gly Arg Ser Ala Gly Pro Ile Gly
1               5                   10

<210> SEQ ID NO 811
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 811

Thr Ser Tyr Thr Gly Arg Ser Ala Val Pro Ile Gly
1               5                   10

<210> SEQ ID NO 812
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 812

Thr Ser Tyr Thr Gly Arg Ser Ala Val Tyr Ile Gly
1               5                   10

<210> SEQ ID NO 813
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 813

Thr Ser Tyr Thr Gly Arg Ser Ala Val Val Ile Gly
1               5                   10

<210> SEQ ID NO 814
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 814

Thr Ser Tyr Thr Gly Arg Ser Ala Val His Ile Gly
1               5                   10

<210> SEQ ID NO 815
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 815

Thr Ser Tyr Ser Gly Arg Ser Ala Val Pro Leu Gly
1               5                   10

<210> SEQ ID NO 816
<211> LENGTH: 12
```

-continued

```
<212> TYPE: PRT
<213> ORGANISM: Artificial Sequence
<220> FEATURE:
<223> OTHER INFORMATION: an artificially synthesized sequence

<400> SEQUENCE: 816

Thr Ser Pro Ser Gly Arg Ser Ala Asn Ile Leu Gly
1               5                   10

<210> SEQ ID NO 817
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 817

Thr Ser Pro Ser Gly Arg Ser Ala Asn Phe Leu Gly
1               5                   10

<210> SEQ ID NO 818
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 818

Thr Ser Pro Thr Gly Arg Ser Ala Asn Pro Leu Gly
1               5                   10

<210> SEQ ID NO 819
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 819

Thr Ser Pro Ser Gly Arg Ser Ala Ile Pro Leu Gly
1               5                   10

<210> SEQ ID NO 820
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 820

Thr Ser Tyr Thr Gly Arg Ser Ala Asn Pro Leu Gly
1               5                   10

<210> SEQ ID NO 821
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 821

Thr Ser Tyr Ser Gly Arg Ser Ala Ile Pro Leu Gly
1               5                   10

<210> SEQ ID NO 822
<211> LENGTH: 12
<212> TYPE: PRT
```

-continued

```
<213> ORGANISM: Artificial Sequence
<220> FEATURE:
<223> OTHER INFORMATION: an artificially synthesized sequence

<400> SEQUENCE: 822

Thr Ser Ile Ser Gly Arg Ser Ala Asn Tyr Leu Gly
1               5                   10

<210> SEQ ID NO 823
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 823

Thr Ser Pro Ser Gly Arg Ser Ala Gly Pro Leu Gly
1               5                   10

<210> SEQ ID NO 824
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 824

Thr Ser Tyr Thr Gly Arg Ser Ala Val Pro Leu Gly
1               5                   10

<210> SEQ ID NO 825
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 825

Thr Ser Tyr Thr Gly Arg Ser Ala Val Tyr Leu Gly
1               5                   10

<210> SEQ ID NO 826
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 826

Thr Ser Tyr Thr Gly Arg Ser Ala Val Val Leu Gly
1               5                   10

<210> SEQ ID NO 827
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 827

Thr Ser Tyr Thr Gly Arg Ser Ala Val His Leu Gly
1               5                   10

<210> SEQ ID NO 828
<211> LENGTH: 12
<212> TYPE: PRT
<213> ORGANISM: Artificial Sequence
```

```
<220> FEATURE:
<223> OTHER INFORMATION: an artificially synthesized sequence

<400> SEQUENCE: 828

Thr Ser Tyr Ser Gly Arg Ser Ala Val Pro Ser Gly
1               5                   10

<210> SEQ ID NO 829
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 829

Thr Ser Pro Ser Gly Arg Ser Ala Asn Ile Ser Gly
1               5                   10

<210> SEQ ID NO 830
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 830

Thr Ser Pro Ser Gly Arg Ser Ala Asn Phe Ser Gly
1               5                   10

<210> SEQ ID NO 831
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 831

Thr Ser Pro Thr Gly Arg Ser Ala Asn Pro Ser Gly
1               5                   10

<210> SEQ ID NO 832
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 832

Thr Ser Pro Ser Gly Arg Ser Ala Ile Pro Ser Gly
1               5                   10

<210> SEQ ID NO 833
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 833

Thr Ser Tyr Thr Gly Arg Ser Ala Asn Pro Ser Gly
1               5                   10

<210> SEQ ID NO 834
<211> LENGTH: 12
<212> TYPE: PRT
<213> ORGANISM: Artificial Sequence
<220> FEATURE:
```

-continued

<223> OTHER INFORMATION: an artificially synthesized sequence

<400> SEQUENCE: 834

Thr Ser Tyr Ser Gly Arg Ser Ala Ile Pro Ser Gly
1               5                   10

<210> SEQ ID NO 835
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 835

Thr Ser Ile Ser Gly Arg Ser Ala Asn Tyr Ser Gly
1               5                   10

<210> SEQ ID NO 836
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 836

Thr Ser Pro Ser Gly Arg Ser Ala Gly Pro Ser Gly
1               5                   10

<210> SEQ ID NO 837
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 837

Thr Ser Tyr Thr Gly Arg Ser Ala Val Pro Ser Gly
1               5                   10

<210> SEQ ID NO 838
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 838

Thr Ser Tyr Thr Gly Arg Ser Ala Val Tyr Ser Gly
1               5                   10

<210> SEQ ID NO 839
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 839

Thr Ser Tyr Thr Gly Arg Ser Ala Val Val Ser Gly
1               5                   10

<210> SEQ ID NO 840
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 840

Thr Ser Tyr Thr Gly Arg Ser Ala Val His Ser Gly
1               5                   10

<210> SEQ ID NO 841
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 841

Ile Ser Tyr Ser Gly Arg Ser Ala Val Pro Ile Gly
1               5                   10

<210> SEQ ID NO 842
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 842

Ile Ser Pro Ser Gly Arg Ser Ala Asn Ile Ile Gly
1               5                   10

<210> SEQ ID NO 843
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 843

Ile Ser Pro Ser Gly Arg Ser Ala Asn Phe Ile Gly
1               5                   10

<210> SEQ ID NO 844
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 844

Ile Ser Pro Thr Gly Arg Ser Ala Asn Pro Ile Gly
1               5                   10

<210> SEQ ID NO 845
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 845

Ile Ser Pro Ser Gly Arg Ser Ala Ile Pro Ile Gly
1               5                   10

<210> SEQ ID NO 846
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 846

Ile Ser Tyr Thr Gly Arg Ser Ala Asn Pro Ile Gly
1               5                   10

<210> SEQ ID NO 847
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 847

Ile Ser Tyr Ser Gly Arg Ser Ala Ile Pro Ile Gly
1               5                   10

<210> SEQ ID NO 848
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 848

Ile Ser Ile Ser Gly Arg Ser Ala Asn Tyr Ile Gly
1               5                   10

<210> SEQ ID NO 849
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 849

Ile Ser Pro Ser Gly Arg Ser Ala Gly Pro Ile Gly
1               5                   10

<210> SEQ ID NO 850
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 850

Ile Ser Tyr Thr Gly Arg Ser Ala Val Pro Ile Gly
1               5                   10

<210> SEQ ID NO 851
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 851

Ile Ser Tyr Thr Gly Arg Ser Ala Val Tyr Ile Gly
1               5                   10

<210> SEQ ID NO 852
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 852

```
Ile Ser Tyr Thr Gly Arg Ser Ala Val Val Ile Gly
1               5                   10

<210> SEQ ID NO 853
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 853

Ile Ser Tyr Thr Gly Arg Ser Ala Val His Ile Gly
1               5                   10

<210> SEQ ID NO 854
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 854

Tyr Ser Tyr Ser Gly Arg Ser Ala Val Pro Ile Gly
1               5                   10

<210> SEQ ID NO 855
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 855

Tyr Ser Pro Ser Gly Arg Ser Ala Asn Ile Ile Gly
1               5                   10

<210> SEQ ID NO 856
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 856

Tyr Ser Pro Ser Gly Arg Ser Ala Asn Phe Ile Gly
1               5                   10

<210> SEQ ID NO 857
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 857

Tyr Ser Pro Thr Gly Arg Ser Ala Asn Pro Ile Gly
1               5                   10

<210> SEQ ID NO 858
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 858
```

-continued

```
Tyr Ser Pro Ser Gly Arg Ser Ala Ile Pro Ile Gly
1               5                   10

<210> SEQ ID NO 859
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 859

Tyr Ser Tyr Thr Gly Arg Ser Ala Asn Pro Ile Gly
1               5                   10

<210> SEQ ID NO 860
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 860

Tyr Ser Tyr Ser Gly Arg Ser Ala Ile Pro Ile Gly
1               5                   10

<210> SEQ ID NO 861
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 861

Tyr Ser Ile Ser Gly Arg Ser Ala Asn Tyr Ile Gly
1               5                   10

<210> SEQ ID NO 862
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 862

Tyr Ser Pro Ser Gly Arg Ser Ala Gly Pro Ile Gly
1               5                   10

<210> SEQ ID NO 863
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 863

Tyr Ser Tyr Thr Gly Arg Ser Ala Val Pro Ile Gly
1               5                   10

<210> SEQ ID NO 864
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 864

Tyr Ser Tyr Thr Gly Arg Ser Ala Val Tyr Ile Gly
```

-continued

```
1               5                  10
```

<210> SEQ ID NO 865
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 865

```
Tyr Ser Tyr Thr Gly Arg Ser Ala Val Val Ile Gly
1               5                  10
```

<210> SEQ ID NO 866
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 866

```
Tyr Ser Tyr Thr Gly Arg Ser Ala Val His Ile Gly
1               5                  10
```

<210> SEQ ID NO 867
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 867

```
Thr Ser Tyr Thr Gly Arg Ser Ala Val Pro Arg Gly
1               5                  10
```

<210> SEQ ID NO 868
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 868

```
Thr Ser Tyr Ser Gly Arg Ser Ala Val Val Arg Gly
1               5                  10
```

<210> SEQ ID NO 869
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 869

```
Thr Ser Tyr Thr Gly Arg Ser Ala Val Tyr Arg Gly
1               5                  10
```

<210> SEQ ID NO 870
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 870

```
Thr Ser Tyr Thr Gly Arg Ser Ala Val His Arg Gly
1               5                  10
```

-continued

```
<210> SEQ ID NO 871
<211> LENGTH: 306
<212> TYPE: PRT
<213> ORGANISM: Homo sapiens

<400> SEQUENCE: 871

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
            195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305

<210> SEQ ID NO 872
<211> LENGTH: 197
<212> TYPE: PRT
<213> ORGANISM: Homo sapiens

<400> SEQUENCE: 872

Arg Asn Leu Pro Val Ala Thr Pro Asp Pro Gly Met Phe Pro Cys Leu
1               5                   10                  15
```

```
His His Ser Gln Asn Leu Leu Arg Ala Val Ser Asn Met Leu Gln Lys
        20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
            195

<210> SEQ ID NO 873
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 873

Thr Ser Thr Ser Gly Arg Ser Ala Asn Pro Arg Gly
1               5                   10

<210> SEQ ID NO 874
<211> LENGTH: 550
<212> TYPE: PRT
<213> ORGANISM: Artificial Sequence
<220> FEATURE:
<223> OTHER INFORMATION: an artificially synthesized sequence

<400> SEQUENCE: 874

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
        50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
```

-continued

```
            100               105               110
Asn Tyr Ser Gly Arg Phe Thr Cys Trp Trp Leu Thr Thr Ile Ser Thr
        115               120               125
Asp Leu Thr Phe Ser Val Lys Ser Ser Arg Gly Ser Ser Asp Pro Gln
    130               135               140
Gly Val Thr Cys Gly Ala Ala Thr Leu Ser Ala Glu Arg Val Arg Gly
145               150               155               160
Asp Asn Lys Glu Tyr Glu Tyr Ser Val Glu Cys Gln Glu Asp Ser Ala
                165               170               175
Cys Pro Ala Ala Glu Glu Ser Leu Pro Ile Glu Val Met Val Asp Ala
            180               185               190
Val His Lys Leu Lys Tyr Glu Asn Tyr Thr Ser Ser Phe Phe Ile Arg
        195               200               205
Asp Ile Ile Lys Pro Asp Pro Pro Lys Asn Leu Gln Leu Lys Pro Leu
    210               215               220
Lys Asn Ser Arg Gln Val Glu Val Ser Trp Glu Tyr Pro Asp Thr Trp
225               230               235               240
Ser Thr Pro His Ser Tyr Phe Ser Leu Thr Phe Cys Val Gln Val Gln
            245               250               255
Gly Lys Ser Lys Arg Glu Lys Lys Asp Arg Val Phe Thr Asp Lys Thr
        260               265               270
Ser Ala Thr Val Ile Cys Arg Lys Asn Ala Ser Ile Ser Val Arg Ala
        275               280               285
Gln Asp Arg Tyr Tyr Ser Ser Ser Trp Ser Glu Trp Ala Ser Val Pro
    290               295               300
Cys Ser Gly Gly Ser Gly Gly Ser Gly Gly Ser Thr Ser Thr Ser Gly
305               310               315               320
Arg Ser Ala Asn Pro Arg Gly Gly Gly Ser Gly Gly Ser Gly Gly Ser
            325               330               335
Glu Ile Val Met Thr Gln Ser Pro Ala Thr Leu Ser Val Ser Pro Gly
            340               345               350
Glu Arg Ala Thr Leu Ser Cys Arg Ala Ser Gln Ser Ile Ser Ile Asn
        355               360               365
Leu His Trp Tyr Gln Gln Lys Pro Gly Gln Ala Pro Arg Leu Leu Ile
    370               375               380
Tyr Phe Ala Ser Gln Ser Ile Ser Gly Ile Pro Ala Arg Phe Ser Gly
385               390               395               400
Ser Gly Ser Gly Thr Glu Phe Thr Leu Thr Ile Ser Ser Leu Gln Ser
            405               410               415
Glu Asp Phe Ala Val Tyr Tyr Cys Gln Gln Ser Asn Ser Phe Pro Leu
            420               425               430
Thr Phe Gly Gly Gly Thr Lys Val Glu Ile Lys Arg Thr Val Ala Ala
        435               440               445
Pro Ser Val Phe Ile Phe Pro Pro Ser Asp Glu Gln Leu Lys Ser Gly
    450               455               460
Thr Ala Ser Val Val Cys Leu Leu Asn Asn Phe Tyr Pro Arg Glu Ala
465               470               475               480
Lys Val Gln Trp Lys Val Asp Asn Ala Leu Gln Ser Gly Asn Ser Gln
            485               490               495
Glu Ser Val Thr Glu Gln Asp Ser Lys Asp Ser Thr Tyr Ser Leu Ser
            500               505               510
Ser Thr Leu Thr Leu Ser Lys Ala Asp Tyr Glu Lys His Lys Val Tyr
            515               520               525
```

-continued

```
Ala Cys Glu Val Thr His Gln Gly Leu Ser Ser Pro Val Thr Lys Ser
    530                 535                 540

Phe Asn Arg Gly Glu Cys
545                 550

<210> SEQ ID NO 875
<211> LENGTH: 683
<212> TYPE: PRT
<213> ORGANISM: Artificial Sequence
<220> FEATURE:
<223> OTHER INFORMATION: an artificially synthesized sequence

<400> SEQUENCE: 875

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Leu His Trp Val Arg Gln Ala Pro Gly Gln Gly Leu Glu Trp Met
            35                  40                  45

Gly Trp Ile Asp Pro Glu Asn Gly Asp Thr Glu Tyr Ala Pro Lys Phe
        50                  55                  60

Gln Gly Arg Val Thr Met Thr Thr Asp Thr Ser Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
                100                 105                 110

Met Val Thr Val Ser Ser Thr Ser Thr Ser Gly Arg Ser Ala Asn Pro
            115                 120                 125

Arg Gly Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
            195                 200                 205

Gln Thr Tyr Ile Cys Asn Val Asn His Lys Pro Ser Asn Thr Lys Val
    210                 215                 220

Asp Lys Lys Val Gly Gly Gly Gly Ser Gly Gly Gly Gly Ser Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335
```

-continued

```
Leu Asn Gly Lys Glu Tyr Lys Cys Lys Val Ser Asn Lys Ala Leu Pro
        340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
        450                 455                 460

Ser Leu Ser Pro Gly Gly Ser Thr Ser Thr Ser Gly Arg Ser Ala Asn
465                 470                 475                 480

Pro Arg Gly Gly Gly Ser Arg Asn Leu Pro Val Ala Thr Pro Asp Pro
                485                 490                 495

Gly Met Phe Pro Cys Leu His His Ser Gln Asn Leu Leu Arg Ala Val
                500                 505                 510

Ser Asn Met Leu Gln Lys Ala Arg Gln Thr Leu Glu Phe Tyr Pro Cys
        515                 520                 525

Thr Ser Glu Glu Ile Asp His Glu Asp Ile Thr Lys Asp Lys Thr Ser
        530                 535                 540

Thr Val Glu Ala Cys Leu Pro Leu Glu Leu Thr Lys Asn Glu Ser Cys
545                 550                 555                 560

Leu Asn Ser Arg Glu Thr Ser Phe Ile Thr Asn Gly Ser Cys Leu Ala
                565                 570                 575

Ser Arg Lys Thr Ser Phe Met Met Ala Leu Cys Leu Ser Ser Ile Tyr
                580                 585                 590

Glu Asp Leu Lys Met Tyr Gln Val Glu Phe Lys Thr Met Asn Ala Lys
                595                 600                 605

Leu Leu Met Asp Pro Lys Arg Gln Ile Phe Leu Asp Gln Asn Met Leu
        610                 615                 620

Ala Val Ile Asp Glu Leu Met Gln Ala Leu Asn Phe Asn Ser Glu Thr
625                 630                 635                 640

Val Pro Gln Lys Ser Ser Leu Glu Glu Pro Asp Phe Tyr Lys Thr Lys
                645                 650                 655

Ile Lys Leu Cys Ile Leu Leu His Ala Phe Arg Ile Arg Ala Val Thr
                660                 665                 670

Ile Asp Arg Val Met Ser Tyr Leu Asn Ala Ser
        675                 680
```

<210> SEQ ID NO 876
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 876

```
Glu Ile Val Met Thr Gln Ser Pro Ala Thr Leu Ser Val Ser Pro Gly
1               5                   10                  15
```

-continued

```
Glu Arg Ala Thr Leu Ser Cys Arg Ala Ser Gln Ser Ile Ser Ile Asn
            20                  25                  30

Leu His Trp Tyr Gln Gln Lys Pro Gly Gln Ala Pro Arg Leu Leu Ile
            35                  40                  45

Tyr Phe Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 877
<211> LENGTH: 30
<212> TYPE: PRT
<213> ORGANISM: Artificial Sequence
<220> FEATURE:
<223> OTHER INFORMATION: an artificially synthesized sequence

<400> SEQUENCE: 877

Gly Gly Ser Gly Gly Ser Gly Gly Ser Thr Ser Thr Ser Gly Arg Ser
1               5                   10                  15

Ala Asn Pro Arg Gly Gly Gly Ser Gly Gly Ser Gly Gly Ser
            20                  25                  30
```

```
<210> SEQ ID NO 878
<211> LENGTH: 118
<212> TYPE: PRT
<213> ORGANISM: Artificial Sequence
<220> FEATURE:
<223> OTHER INFORMATION: an artificially synthesized sequence

<400> SEQUENCE: 878

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
            35                  40                  45

Gly Trp Ile Asp Pro Glu Asn Gly Asp Thr Glu Tyr Ala Pro Lys Phe
    50                  55                  60

Gln Gly Arg Val Thr Met Thr Thr Asp Thr Ser Thr Ser Thr Ala Tyr
```

-continued

```
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
            100                 105                 110

Met Val Thr Val Ser Ser
        115

<210> SEQ ID NO 879
<211> LENGTH: 18
<212> TYPE: PRT
<213> ORGANISM: Artificial Sequence
<220> FEATURE:
<223> OTHER INFORMATION: an artificially synthesized sequence

<400> SEQUENCE: 879

Gly Gly Ser Thr Ser Thr Ser Gly Arg Ser Ala Asn Pro Arg Gly Gly
1               5                   10                  15

Gly Ser

<210> SEQ ID NO 880
<211> LENGTH: 1009
<212> TYPE: PRT
<213> ORGANISM: Artificial Sequence
<220> FEATURE:
<223> OTHER INFORMATION: an artificially synthesized sequence

<400> SEQUENCE: 880

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
            100                 105                 110

Met Val Thr Val Ser Ser Thr Ser Thr Ser Gly Arg Ser Ala Asn Pro
        115                 120                 125

Arg Gly Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
            195                 200                 205

Gln Thr Tyr Ile Cys Asn Val Asn His Lys Pro Ser Asn Thr Lys Val
        210                 215                 220

Asp Lys Lys Val Gly Gly Gly Gly Ser Gly Gly Gly Gly Ser Glu Pro
```

```
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
                275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Glu Glu Met Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
        450                 455                 460

Ser Leu Ser Pro Gly Gly Ser Thr Ser Thr Ser Gly Arg Ser Ala Asn
465                 470                 475                 480

Pro Arg Gly Gly Gly Ser Ile Trp Glu Leu Lys Lys Asp Val Tyr Val
                485                 490                 495

Val Glu Leu Asp Trp Tyr Pro Asp Ala Pro Gly Glu Met Val Val Leu
                500                 505                 510

Thr Cys Asp Thr Pro Glu Glu Asp Gly Ile Thr Trp Thr Leu Asp Gln
                515                 520                 525

Ser Ser Glu Val Leu Gly Ser Gly Lys Thr Leu Thr Ile Gln Val Lys
        530                 535                 540

Glu Phe Gly Asp Ala Gly Gln Tyr Thr Cys His Lys Gly Gly Glu Val
545                 550                 555                 560

Leu Ser His Ser Leu Leu Leu Leu His Lys Lys Glu Asp Gly Ile Trp
                565                 570                 575

Ser Thr Asp Ile Leu Lys Asp Gln Lys Glu Pro Lys Asn Lys Thr Phe
                580                 585                 590

Leu Arg Cys Glu Ala Lys Asn Tyr Ser Gly Arg Phe Thr Cys Trp Trp
                595                 600                 605

Leu Thr Thr Ile Ser Thr Asp Leu Thr Phe Ser Val Lys Ser Ser Arg
        610                 615                 620

Gly Ser Ser Asp Pro Gln Gly Val Thr Cys Gly Ala Ala Thr Leu Ser
625                 630                 635                 640

Ala Glu Arg Val Arg Gly Asp Asn Lys Glu Tyr Glu Tyr Ser Val Glu
                645                 650                 655
```

-continued

```
Cys Gln Glu Asp Ser Ala Cys Pro Ala Ala Glu Glu Ser Leu Pro Ile
        660                 665                 670

Glu Val Met Val Asp Ala Val His Lys Leu Lys Tyr Glu Asn Tyr Thr
        675                 680                 685

Ser Ser Phe Phe Ile Arg Asp Ile Ile Lys Pro Asp Pro Pro Lys Asn
        690                 695                 700

Leu Gln Leu Lys Pro Leu Lys Asn Ser Arg Gln Val Glu Val Ser Trp
705                 710                 715                 720

Glu Tyr Pro Asp Thr Trp Ser Thr Pro His Ser Tyr Phe Ser Leu Thr
                725                 730                 735

Phe Cys Val Gln Val Gln Gly Lys Ser Lys Arg Glu Lys Lys Asp Arg
                740                 745                 750

Val Phe Thr Asp Lys Thr Ser Ala Thr Val Ile Cys Arg Lys Asn Ala
                755                 760                 765

Ser Ile Ser Val Arg Ala Gln Asp Arg Tyr Tyr Ser Ser Ser Trp Ser
        770                 775                 780

Glu Trp Ala Ser Val Pro Cys Ser Gly Gly Gly Gly Ser Gly Gly Gly
785                 790                 795                 800

Gly Ser Gly Gly Gly Gly Ser Gly Gly Gly Gly Ser Arg Asn Leu Pro
                805                 810                 815

Val Ala Thr Pro Asp Pro Gly Met Phe Pro Cys Leu His His Ser Gln
                820                 825                 830

Asn Leu Leu Arg Ala Val Ser Asn Met Leu Gln Lys Ala Arg Gln Thr
                835                 840                 845

Leu Glu Phe Tyr Pro Cys Thr Ser Glu Glu Ile Asp His Glu Asp Ile
        850                 855                 860

Thr Lys Asp Lys Thr Ser Thr Val Glu Ala Cys Leu Pro Leu Glu Leu
865                 870                 875                 880

Thr Lys Asn Glu Ser Cys Leu Asn Ser Arg Glu Thr Ser Phe Ile Thr
                885                 890                 895

Asn Gly Ser Cys Leu Ala Ser Arg Lys Thr Ser Phe Met Met Ala Leu
                900                 905                 910

Cys Leu Ser Ser Ile Tyr Glu Asp Leu Lys Met Tyr Gln Val Glu Phe
        915                 920                 925

Lys Thr Met Asn Ala Lys Leu Leu Met Asp Pro Lys Arg Gln Ile Phe
        930                 935                 940

Leu Asp Gln Asn Met Leu Ala Val Ile Asp Glu Leu Met Gln Ala Leu
945                 950                 955                 960

Asn Phe Asn Ser Glu Thr Val Pro Gln Lys Ser Ser Leu Glu Glu Pro
                965                 970                 975

Asp Phe Tyr Lys Thr Lys Ile Lys Leu Cys Ile Leu Leu His Ala Phe
                980                 985                 990

Arg Ile Arg Ala Val Thr Ile Asp  Arg Val Met Ser Tyr  Leu Asn Ala
        995                 1000                1005

Ser
```

<210> SEQ ID NO 881
<211> LENGTH: 1009
<212> TYPE: PRT
<213> ORGANISM: Artificial Sequence
<220> FEATURE:
<223> OTHER INFORMATION: an artificially synthesized sequence

<400> SEQUENCE: 881

-continued

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
            100                 105                 110

Met Val Thr Val Ser Ser Thr Ser Thr Ser Gly Arg Ser Ala Asn Pro
            115                 120                 125

Arg Gly Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
            195                 200                 205

Gln Thr Tyr Ile Cys Asn Val Asn His Lys Pro Ser Asn Thr Lys Val
    210                 215                 220

Asp Lys Arg Val Gly Gly Gly Gly Ser Gly Gly Gly Gly Ser Glu Pro
225                 230                 235                 240

Lys Ser Cys Asp Lys Thr His Thr Cys Pro Pro Cys Pro Ala Pro Glu
            245                 250                 255

Leu Arg Arg Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Cys Thr Leu Pro Pro Ser Arg Glu Glu Met Thr Lys Asn
    370                 375                 380

Gln Val Ser Leu Trp Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
```

-continued

```
            420               425               430
Leu Thr Val Asp Lys Ser Arg Trp Gln Gln Gly Asn Val Phe Ser Cys
        435               440               445

Ser Val Met His Glu Ala Leu His Asn Arg Tyr Thr Gln Lys Ser Leu
        450               455               460

Ser Leu Ser Pro Gly Gly Ser Thr Ser Thr Ser Gly Arg Ser Ala Asn
465               470               475               480

Pro Arg Gly Gly Gly Ser Ile Trp Glu Leu Lys Lys Asp Val Tyr Val
                485               490               495

Val Glu Leu Asp Trp Tyr Pro Asp Ala Pro Gly Glu Met Val Val Leu
                500               505               510

Thr Cys Asp Thr Pro Glu Glu Asp Gly Ile Thr Trp Thr Leu Asp Gln
        515               520               525

Ser Ser Glu Val Leu Gly Ser Gly Lys Thr Leu Thr Ile Gln Val Lys
        530               535               540

Glu Phe Gly Asp Ala Gly Gln Tyr Thr Cys His Lys Gly Gly Glu Val
545               550               555               560

Leu Ser His Ser Leu Leu Leu Leu His Lys Lys Glu Asp Gly Ile Trp
                565               570               575

Ser Thr Asp Ile Leu Lys Asp Gln Lys Glu Pro Lys Asn Lys Thr Phe
                580               585               590

Leu Arg Cys Glu Ala Lys Asn Tyr Ser Gly Arg Phe Thr Cys Trp Trp
        595               600               605

Leu Thr Thr Ile Ser Thr Asp Leu Thr Phe Ser Val Lys Ser Ser Arg
        610               615               620

Gly Ser Ser Asp Pro Gln Gly Val Thr Cys Gly Ala Ala Thr Leu Ser
625               630               635               640

Ala Glu Arg Val Arg Gly Asp Asn Lys Glu Tyr Glu Tyr Ser Val Glu
                645               650               655

Cys Gln Glu Asp Ser Ala Cys Pro Ala Ala Glu Glu Ser Leu Pro Ile
                660               665               670

Glu Val Met Val Asp Ala Val His Lys Leu Lys Tyr Glu Asn Tyr Thr
        675               680               685

Ser Ser Phe Phe Ile Arg Asp Ile Ile Lys Pro Asp Pro Pro Lys Asn
        690               695               700

Leu Gln Leu Lys Pro Leu Lys Asn Ser Arg Gln Val Glu Val Ser Trp
705               710               715               720

Glu Tyr Pro Asp Thr Trp Ser Thr Pro His Ser Tyr Phe Ser Leu Thr
                725               730               735

Phe Cys Val Gln Val Gln Gly Lys Ser Lys Arg Glu Lys Lys Asp Arg
                740               745               750

Val Phe Thr Asp Lys Thr Ser Ala Thr Val Ile Cys Arg Lys Asn Ala
        755               760               765

Ser Ile Ser Val Arg Ala Gln Asp Arg Tyr Tyr Ser Ser Ser Trp Ser
        770               775               780

Glu Trp Ala Ser Val Pro Cys Ser Gly Gly Gly Ser Gly Gly Gly
785               790               795               800

Gly Ser Gly Gly Gly Gly Ser Gly Gly Gly Gly Ser Arg Asn Leu Pro
                805               810               815

Val Ala Thr Pro Asp Pro Gly Met Phe Pro Cys Leu His His Ser Gln
                820               825               830

Asn Leu Leu Arg Ala Val Ser Asn Met Leu Gln Lys Ala Arg Gln Thr
        835               840               845
```

-continued

```
Leu Glu Phe Tyr Pro Cys Thr Ser Glu Glu Ile Asp His Glu Asp Ile
    850             855             860

Thr Lys Asp Lys Thr Ser Thr Val Glu Ala Cys Leu Pro Leu Glu Leu
865             870             875             880

Thr Lys Asn Glu Ser Cys Leu Asn Ser Arg Glu Thr Ser Phe Ile Thr
                885             890             895

Asn Gly Ser Cys Leu Ala Ser Arg Lys Thr Ser Phe Met Met Ala Leu
                900             905             910

Cys Leu Ser Ser Ile Tyr Glu Asp Leu Lys Met Tyr Gln Val Glu Phe
                915             920             925

Lys Thr Met Asn Ala Lys Leu Leu Met Asp Pro Lys Arg Gln Ile Phe
    930             935             940

Leu Asp Gln Asn Met Leu Ala Val Ile Asp Glu Leu Met Gln Ala Leu
945             950             955             960

Asn Phe Asn Ser Glu Thr Val Pro Gln Lys Ser Ser Leu Glu Glu Pro
                965             970             975

Asp Phe Tyr Lys Thr Lys Ile Lys Leu Cys Ile Leu Leu His Ala Phe
                980             985             990

Arg Ile Arg Ala Val Thr Ile Asp Arg Val Met Ser Tyr Leu Asn Ala
    995             1000            1005

Ser
```

<210> SEQ ID NO 882
<211> LENGTH: 223
<212> TYPE: PRT
<213> ORGANISM: Artificial Sequence
<220> FEATURE:
<223> OTHER INFORMATION: an artificially synthesized sequence

<400> SEQUENCE: 882

```
Gln Val Gln Leu Gln Gln Ser Gly Pro Gln Leu Val Arg Pro Gly Ala
1               5               10              15

Ser Val Lys Ile Ser Cys Lys Ala Ser Gly Tyr Ser Phe Thr Ser Tyr
                20              25              30

Trp Met His Trp Val Asn Gln Arg Pro Gly Gln Gly Leu Glu Trp Ile
            35              40              45

Gly Met Ile Asp Pro Ser Tyr Ser Glu Thr Arg Leu Asn Gln Lys Phe
    50              55              60

Lys Asp Lys Ala Thr Leu Thr Val Asp Lys Ser Ser Ser Thr Ala Tyr
65              70              75              80

Met Gln Leu Ser Ser Pro Thr Ser Glu Asp Ser Ala Val Tyr Tyr Cys
                85              90              95

Ala Leu Tyr Gly Asn Tyr Phe Asp Tyr Trp Gly Gln Gly Thr Thr Leu
                100             105             110

Thr Val Ser Ser Ala Ser Val Ala Ala Pro Ser Val Phe Ile Phe Pro
            115             120             125

Pro Ser Asp Glu Gln Leu Lys Ser Gly Thr Ala Ser Val Val Cys Leu
    130             135             140

Leu Asn Asn Phe Tyr Pro Arg Glu Ala Lys Val Gln Trp Lys Val Asp
145             150             155             160

Asn Ala Leu Gln Ser Gly Asn Ser Gln Glu Ser Val Thr Glu Gln Asp
                165             170             175

Ser Lys Asp Ser Thr Tyr Ser Leu Ser Ser Thr Leu Thr Leu Ser Lys
                180             185             190
```

-continued

```
Ala Asp Tyr Glu Lys His Lys Val Tyr Ala Cys Glu Val Thr His Gln
        195                 200                 205

Gly Leu Ser Ser Pro Val Thr Lys Ser Phe Asn Arg Gly Glu Cys
    210                 215                 220

<210> SEQ ID NO 883
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 883

Asp Ile Gln Met Thr Gln Ser Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Tyr
                85                  90                  95

Thr Phe Gly Gly Gly Thr Lys Leu Glu Val Lys Ser Ser Ala Ser Thr
                100                 105                 110

Lys Gly Pro Ser Val Phe Pro Leu Ala Pro Ser Ser Lys Ser Thr Ser
                115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
                180                 185                 190

Asn Val Asn His Lys Pro Ser Asn Thr Lys Val Asp Lys Arg Val Gly
                195                 200                 205

Gly Gly Gly Ser Gly Gly Gly Ser Glu Pro Lys Ser Cys Asp Lys
    210                 215                 220

Thr His Thr Cys Pro Pro Cys Pro Ala Pro Glu Leu Arg Arg Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

-continued

```
Thr Ile Ser Lys Ala Lys Gly Gln Pro Arg Glu Pro Gln Val Tyr Thr
            340                 345                 350

Leu Pro Pro Ser Arg Cys Glu Met Thr Lys Asn Gln Val Ser Leu Ser
            355                 360                 365

Cys Ala Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                    405                 410                 415

Ser Arg Trp Gln Gln Gly Asn Val Phe Ser Cys Ser Val Met His Glu
                    420                 425                 430

Ala Leu His Asn His Tyr Thr Gln Lys Ser Leu Ser Leu Ser Pro
            435                 440                 445

<210> SEQ ID NO 884
<211> LENGTH: 683
<212> TYPE: PRT
<213> ORGANISM: Artificial Sequence
<220> FEATURE:
<223> OTHER INFORMATION: an artificially synthesized sequence

<400> SEQUENCE: 884

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
            35                  40                  45

Gly Trp Ile Asp Pro Glu Asn Gly Asp Thr Glu Tyr Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
            100                 105                 110

Met Val Thr Val Ser Ser Thr Ser Thr Ser Gly Arg Ser Ala Asn Pro
            115                 120                 125

Arg Gly Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
            165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
            195                 200                 205

Gln Thr Tyr Ile Cys Asn Val Asn His Lys Pro Ser Asn Thr Lys Val
            210                 215                 220

Asp Lys Arg Val Gly Gly Gly Gly Ser Gly Gly Gly Ser Glu Pro
225                 230                 235                 240

Lys Ser Cys Asp Lys Thr His Thr Cys Pro Pro Cys Pro Ala Pro Glu
                245                 250                 255
```

-continued

```
Leu Arg Arg Gly Pro Ser Val Phe Leu Phe Pro Pro Lys Pro Lys Asp
            260             265             270

Thr Leu Met Ile Ser Arg Thr Pro Glu Val Thr Cys Val Val Val Asp
            275             280             285

Val Ser His Glu Asp Pro Glu Val Lys Phe Asn Trp Tyr Val Asp Gly
            290             295             300

Val Glu Val His Asn Ala Lys Thr Lys Pro Arg Glu Glu Gln Tyr Asn
305             310             315             320

Ser Thr Tyr Arg Val Val Ser Val Leu Thr Val Leu His Gln Asp Trp
            325             330             335

Leu Asn Gly Lys Glu Tyr Lys Cys Lys Val Ser Asn Lys Ala Leu Pro
            340             345             350

Ala Pro Ile Glu Lys Thr Ile Ser Lys Ala Lys Gly Gln Pro Arg Glu
            355             360             365

Pro Gln Val Tyr Thr Leu Pro Pro Ser Arg Glu Glu Met Thr Lys Asn
            370             375             380

Gln Val Ser Leu Thr Cys Leu Val Lys Gly Phe Tyr Pro Ser Asp Ile
385             390             395             400

Ala Val Glu Trp Glu Ser Asn Gly Gln Pro Glu Asn Asn Tyr Lys Thr
            405             410             415

Thr Pro Pro Val Leu Asp Ser Asp Gly Ser Phe Phe Leu Tyr Ser Lys
            420             425             430

Leu Thr Val Asp Lys Ser Arg Trp Gln Gln Gly Asn Val Phe Ser Cys
            435             440             445

Ser Val Met His Glu Ala Leu His Asn His Tyr Thr Gln Lys Ser Leu
            450             455             460

Ser Leu Ser Pro Gly Gly Ser Gly Gly Ser Gly Gly Ser Gly Gly Ser
465             470             475             480

Gly Gly Ser Gly Gly Ser Arg Asn Leu Pro Val Ala Thr Pro Asp Pro
            485             490             495

Gly Met Phe Pro Cys Leu His His Ser Gln Asn Leu Leu Arg Ala Val
            500             505             510

Ser Asn Met Leu Gln Lys Ala Arg Gln Thr Leu Glu Phe Tyr Pro Cys
            515             520             525

Thr Ser Glu Glu Ile Asp His Glu Asp Ile Thr Lys Asp Lys Thr Ser
            530             535             540

Thr Val Glu Ala Cys Leu Pro Leu Glu Leu Thr Lys Asn Glu Ser Cys
545             550             555             560

Leu Asn Ser Arg Glu Thr Ser Phe Ile Thr Asn Gly Ser Cys Leu Ala
            565             570             575

Ser Arg Lys Thr Ser Phe Met Met Ala Leu Cys Leu Ser Ser Ile Tyr
            580             585             590

Glu Asp Leu Lys Met Tyr Gln Val Glu Phe Lys Thr Met Asn Ala Lys
            595             600             605

Leu Leu Met Asp Pro Lys Arg Gln Ile Phe Leu Asp Gln Asn Met Leu
            610             615             620

Ala Val Ile Asp Glu Leu Met Gln Ala Leu Asn Phe Asn Ser Glu Thr
625             630             635             640

Val Pro Gln Lys Ser Ser Leu Glu Glu Pro Asp Phe Tyr Lys Thr Lys
            645             650             655

Ile Lys Leu Cys Ile Leu Leu His Ala Phe Arg Ile Arg Ala Val Thr
            660             665             670

Ile Asp Arg Val Met Ser Tyr Leu Asn Ala Ser
```

-continued

```
        675                 680

<210> SEQ ID NO 885
<211> LENGTH: 1009
<212> TYPE: PRT
<213> ORGANISM: Artificial Sequence
<220> FEATURE:
<223> OTHER INFORMATION: an artificially synthesized sequence

<400> SEQUENCE: 885

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Leu His Trp Val Arg Gln Ala Pro Gly Gln Gly Leu Glu Trp Met
            35                  40                  45

Gly Trp Ile Asp Pro Glu Asn Gly Asp Thr Glu Tyr Ala Pro Lys Phe
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
                100                 105                 110

Met Val Thr Val Ser Ser Thr Ser Thr Ser Gly Arg Ser Ala Asn Pro
            115                 120                 125

Arg Gly Ala Ser Thr Lys Gly Pro Ser Val Phe Pro Leu Ala Pro Ser
        130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
            195                 200                 205

Gln Thr Tyr Ile Cys Asn Val Asn His Lys Pro Ser Asn Thr Lys Val
        210                 215                 220

Asp Lys Arg Val Gly Gly Gly Gly Ser Gly Gly Gly Gly Ser Glu Pro
225                 230                 235                 240

Lys Ser Cys Asp Lys Thr His Thr Cys Pro Pro Cys Pro Ala Pro Glu
                245                 250                 255

Leu Arg Arg Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
```

-continued

```
            355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
    450                 455                 460

Ser Leu Ser Pro Gly Gly Ser Gly Gly Ser Gly Gly Ser Gly Gly Ser
465                 470                 475                 480

Gly Gly Ser Gly Gly Ser Ile Trp Glu Leu Lys Lys Asp Val Tyr Val
                485                 490                 495

Val Glu Leu Asp Trp Tyr Pro Asp Ala Pro Gly Glu Met Val Val Leu
                500                 505                 510

Thr Cys Asp Thr Pro Glu Glu Asp Gly Ile Thr Trp Thr Leu Asp Gln
                515                 520                 525

Ser Ser Glu Val Leu Gly Ser Gly Lys Thr Leu Thr Ile Gln Val Lys
    530                 535                 540

Glu Phe Gly Asp Ala Gly Gln Tyr Thr Cys His Lys Gly Gly Glu Val
545                 550                 555                 560

Leu Ser His Ser Leu Leu Leu Leu His Lys Lys Glu Asp Gly Ile Trp
                565                 570                 575

Ser Thr Asp Ile Leu Lys Asp Gln Lys Glu Pro Lys Asn Lys Thr Phe
                580                 585                 590

Leu Arg Cys Glu Ala Lys Asn Tyr Ser Gly Arg Phe Thr Cys Trp Trp
                595                 600                 605

Leu Thr Thr Ile Ser Thr Asp Leu Thr Phe Ser Val Lys Ser Ser Arg
    610                 615                 620

Gly Ser Ser Asp Pro Gln Gly Val Thr Cys Gly Ala Ala Thr Leu Ser
625                 630                 635                 640

Ala Glu Arg Val Arg Gly Asp Asn Lys Glu Tyr Glu Tyr Ser Val Glu
                645                 650                 655

Cys Gln Glu Asp Ser Ala Cys Pro Ala Ala Glu Glu Ser Leu Pro Ile
                660                 665                 670

Glu Val Met Val Asp Ala Val His Lys Leu Lys Tyr Glu Asn Tyr Thr
                675                 680                 685

Ser Ser Phe Phe Ile Arg Asp Ile Ile Lys Pro Asp Pro Pro Lys Asn
    690                 695                 700

Leu Gln Leu Lys Pro Leu Lys Asn Ser Arg Gln Val Glu Val Ser Trp
705                 710                 715                 720

Glu Tyr Pro Asp Thr Trp Ser Thr Pro His Ser Tyr Phe Ser Leu Thr
                725                 730                 735

Phe Cys Val Gln Val Gln Gly Lys Ser Lys Arg Glu Lys Lys Asp Arg
                740                 745                 750

Val Phe Thr Asp Lys Thr Ser Ala Thr Val Ile Cys Arg Lys Asn Ala
                755                 760                 765

Ser Ile Ser Val Arg Ala Gln Asp Arg Tyr Tyr Ser Ser Ser Trp Ser
    770                 775                 780
```

-continued

```
Glu Trp Ala Ser Val Pro Cys Ser Gly Gly Gly Ser Gly Gly Gly
785                 790                 795                 800

Gly Ser Gly Gly Gly Gly Ser Gly Gly Gly Gly Ser Arg Asn Leu Pro
                805                 810                 815

Val Ala Thr Pro Asp Pro Gly Met Phe Pro Cys Leu His His Ser Gln
            820                 825                 830

Asn Leu Leu Arg Ala Val Ser Asn Met Leu Gln Lys Ala Arg Gln Thr
                835                 840                 845

Leu Glu Phe Tyr Pro Cys Thr Ser Glu Glu Ile Asp His Glu Asp Ile
        850                 855                 860

Thr Lys Asp Lys Thr Ser Thr Val Glu Ala Cys Leu Pro Leu Glu Leu
865                 870                 875                 880

Thr Lys Asn Glu Ser Cys Leu Asn Ser Arg Glu Thr Ser Phe Ile Thr
                885                 890                 895

Asn Gly Ser Cys Leu Ala Ser Arg Lys Thr Ser Phe Met Met Ala Leu
            900                 905                 910

Cys Leu Ser Ser Ile Tyr Glu Asp Leu Lys Met Tyr Gln Val Glu Phe
        915                 920                 925

Lys Thr Met Asn Ala Lys Leu Leu Met Asp Pro Lys Arg Gln Ile Phe
        930                 935                 940

Leu Asp Gln Asn Met Leu Ala Val Ile Asp Glu Leu Met Gln Ala Leu
945                 950                 955                 960

Asn Phe Asn Ser Glu Thr Val Pro Gln Lys Ser Ser Leu Glu Glu Pro
                965                 970                 975

Asp Phe Tyr Lys Thr Lys Ile Lys Leu Cys Ile Leu Leu His Ala Phe
            980                 985                 990

Arg Ile Arg Ala Val Thr Ile Asp  Arg Val Met Ser Tyr  Leu Asn Ala
        995                 1000                1005

Ser
```

<210> SEQ ID NO 886
<211> LENGTH: 1009
<212> TYPE: PRT
<213> ORGANISM: Artificial Sequence
<220> FEATURE:
<223> OTHER INFORMATION: an artificially synthesized sequence

<400> SEQUENCE: 886

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
            100                 105                 110

Met Val Thr Val Ser Ser Thr Ser Thr Ser Gly Arg Ser Ala Asn Pro
        115                 120                 125
```

-continued

```
Arg Gly Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
            165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Arg Val Gly Gly Gly Ser Gly Gly Gly Ser Glu Pro
225                 230                 235                 240

Lys Ser Cys Asp Lys Thr His Thr Cys Pro Pro Cys Pro Ala Pro Glu
            245                 250                 255

Leu Arg Arg Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
    275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Cys Thr Leu Pro Pro Ser Arg Glu Glu Met Thr Lys Asn
    370                 375                 380

Gln Val Ser Leu Trp Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn Arg Tyr Thr Gln Lys Ser Leu
    450                 455                 460

Ser Leu Ser Pro Gly Gly Ser Gly Gly Ser Gly Gly Ser Gly Gly Ser
465                 470                 475                 480

Gly Gly Ser Gly Gly Ser Ile Trp Glu Leu Lys Lys Asp Val Tyr Val
            485                 490                 495

Val Glu Leu Asp Trp Tyr Pro Asp Ala Pro Gly Glu Met Val Val Leu
            500                 505                 510

Thr Cys Asp Thr Pro Glu Glu Asp Gly Ile Thr Trp Thr Leu Asp Gln
        515                 520                 525

Ser Ser Glu Val Leu Gly Ser Gly Lys Thr Leu Thr Ile Gln Val Lys
    530                 535                 540

Glu Phe Gly Asp Ala Gly Gln Tyr Thr Cys His Lys Gly Gly Glu Val
```

-continued

```
545                 550                 555                 560

Leu Ser His Ser Leu Leu Leu Leu His Lys Lys Glu Asp Gly Ile Trp
                565                 570                 575

Ser Thr Asp Ile Leu Lys Asp Gln Lys Glu Pro Lys Asn Lys Thr Phe
                580                 585                 590

Leu Arg Cys Glu Ala Lys Asn Tyr Ser Gly Arg Phe Thr Cys Trp Trp
                595                 600                 605

Leu Thr Thr Ile Ser Thr Asp Leu Thr Phe Ser Val Lys Ser Ser Arg
                610                 615                 620

Gly Ser Ser Asp Pro Gln Gly Val Thr Cys Gly Ala Ala Thr Leu Ser
625                 630                 635                 640

Ala Glu Arg Val Arg Gly Asp Asn Lys Glu Tyr Glu Tyr Ser Val Glu
                645                 650                 655

Cys Gln Glu Asp Ser Ala Cys Pro Ala Ala Glu Glu Ser Leu Pro Ile
                660                 665                 670

Glu Val Met Val Asp Ala Val His Lys Leu Lys Tyr Glu Asn Tyr Thr
                675                 680                 685

Ser Ser Phe Phe Ile Arg Asp Ile Ile Lys Pro Asp Pro Pro Lys Asn
                690                 695                 700

Leu Gln Leu Lys Pro Leu Lys Asn Ser Arg Gln Val Glu Val Ser Trp
705                 710                 715                 720

Glu Tyr Pro Asp Thr Trp Ser Thr Pro His Ser Tyr Phe Ser Leu Thr
                725                 730                 735

Phe Cys Val Gln Val Gln Gly Lys Ser Lys Arg Glu Lys Lys Asp Arg
                740                 745                 750

Val Phe Thr Asp Lys Thr Ser Ala Thr Val Ile Cys Arg Lys Asn Ala
                755                 760                 765

Ser Ile Ser Val Arg Ala Gln Asp Arg Tyr Tyr Ser Ser Ser Trp Ser
                770                 775                 780

Glu Trp Ala Ser Val Pro Cys Ser Gly Gly Gly Ser Gly Gly Gly
785                 790                 795                 800

Gly Ser Gly Gly Gly Gly Ser Gly Gly Gly Ser Arg Asn Leu Pro
                805                 810                 815

Val Ala Thr Pro Asp Pro Gly Met Phe Pro Cys Leu His His Ser Gln
                820                 825                 830

Asn Leu Leu Arg Ala Val Ser Asn Met Leu Gln Lys Ala Arg Gln Thr
                835                 840                 845

Leu Glu Phe Tyr Pro Cys Thr Ser Glu Glu Ile Asp His Glu Asp Ile
                850                 855                 860

Thr Lys Asp Lys Thr Ser Thr Val Glu Ala Cys Leu Pro Leu Glu Leu
865                 870                 875                 880

Thr Lys Asn Glu Ser Cys Leu Asn Ser Arg Glu Thr Ser Phe Ile Thr
                885                 890                 895

Asn Gly Ser Cys Leu Ala Ser Arg Lys Thr Ser Phe Met Met Ala Leu
                900                 905                 910

Cys Leu Ser Ser Ile Tyr Glu Asp Leu Lys Met Tyr Gln Val Glu Phe
                915                 920                 925

Lys Thr Met Asn Ala Lys Leu Leu Met Asp Pro Lys Arg Gln Ile Phe
                930                 935                 940

Leu Asp Gln Asn Met Leu Ala Val Ile Asp Glu Leu Met Gln Ala Leu
945                 950                 955                 960

Asn Phe Asn Ser Glu Thr Val Pro Gln Lys Ser Ser Leu Glu Glu Pro
                965                 970                 975
```

-continued

```
Asp Phe Tyr Lys Thr Lys Ile Lys Leu Cys Ile Leu Leu His Ala Phe
            980                 985                 990

Arg Ile Arg Ala Val Thr Ile Asp  Arg Val Met Ser Tyr  Leu Asn Ala
        995                 1000                 1005

Ser
```

<210> SEQ ID NO 887
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 887

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 888
<211> LENGTH: 1010
<212> TYPE: PRT
<213> ORGANISM: Artificial Sequence
<220> FEATURE:
<223> OTHER INFORMATION: an artificially synthesized sequence

<400> SEQUENCE: 888

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Leu Gly Trp Val Arg Gln Met Pro Gly Lys Gly Leu Asp Trp Ile
        35                  40                  45
```

```
Gly Ile Met Ser Pro Val Asp Ser Asp Ile Arg Tyr Ser Pro Ser Phe
    50              55              60
Gln Gly Gln Val Thr Met Ser Val Asp Lys Ser Ile Thr Thr Ala Tyr
65              70              75              80
Leu Gln Trp Asn Ser Leu Lys Ala Ser Asp Thr Ala Met Tyr Tyr Cys
            85              90              95
Ala Arg Arg Arg Pro Gly Gln Gly Tyr Phe Asp Phe Trp Gly Gln Gly
            100             105             110
Thr Leu Val Thr Val Ser Ser Thr Ser Thr Ser Gly Arg Ser Ala Asn
        115             120             125
Pro Arg Gly Ala Ser Thr Lys Gly Pro Ser Val Phe Pro Leu Ala Pro
    130             135             140
Ser Ser Lys Ser Thr Ser Gly Gly Thr Ala Ala Leu Gly Cys Leu Val
145             150             155             160
Lys Asp Tyr Phe Pro Glu Pro Val Thr Val Ser Trp Asn Ser Gly Ala
            165             170             175
Leu Thr Ser Gly Val His Thr Phe Pro Ala Val Leu Gln Ser Ser Gly
        180             185             190
Leu Tyr Ser Leu Ser Ser Val Val Thr Val Pro Ser Ser Ser Leu Gly
        195             200             205
Thr Gln Thr Tyr Ile Cys Asn Val Asn His Lys Pro Ser Asn Thr Lys
    210             215             220
Val Asp Lys Arg Val Gly Gly Gly Gly Ser Gly Gly Gly Ser Glu
225             230             235             240
Pro Lys Ser Cys Asp Lys Thr His Thr Cys Pro Pro Cys Pro Ala Pro
            245             250             255
Glu Leu Arg Arg Gly Pro Ser Val Phe Leu Phe Pro Pro Lys Pro Lys
            260             265             270
Asp Thr Leu Met Ile Ser Arg Thr Pro Glu Val Thr Cys Val Val Val
        275             280             285
Asp Val Ser His Glu Asp Pro Glu Val Lys Phe Asn Trp Tyr Val Asp
    290             295             300
Gly Val Glu Val His Asn Ala Lys Thr Lys Pro Arg Glu Glu Gln Tyr
305             310             315             320
Asn Ser Thr Tyr Arg Val Val Ser Val Leu Thr Val Leu His Gln Asp
            325             330             335
Trp Leu Asn Gly Lys Glu Tyr Lys Cys Lys Val Ser Asn Lys Ala Leu
        340             345             350
Pro Ala Pro Ile Glu Lys Thr Ile Ser Lys Ala Lys Gly Gln Pro Arg
    355             360             365
Glu Pro Gln Val Cys Thr Leu Pro Pro Ser Arg Glu Glu Met Thr Lys
    370             375             380
Asn Gln Val Ser Leu Trp Cys Leu Val Lys Gly Phe Tyr Pro Ser Asp
385             390             395             400
Ile Ala Val Glu Trp Glu Ser Asn Gly Gln Pro Glu Asn Asn Tyr Lys
            405             410             415
Thr Thr Pro Pro Val Leu Asp Ser Asp Gly Ser Phe Phe Leu Tyr Ser
            420             425             430
Lys Leu Thr Val Asp Lys Ser Arg Trp Gln Gln Gly Asn Val Phe Ser
        435             440             445
Cys Ser Val Met His Glu Ala Leu His Asn Arg Tyr Thr Gln Lys Ser
    450             455             460
```

-continued

Leu Ser Leu Ser Pro Gly Gly Ser Gly Gly Ser Gly Gly Ser Gly Gly
465                 470                 475                 480

Ser Gly Gly Ser Gly Gly Ser Ile Trp Glu Leu Lys Lys Asp Val Tyr
                    485                 490                 495

Val Val Glu Leu Asp Trp Tyr Pro Asp Ala Pro Gly Glu Met Val Val
                500                 505                 510

Leu Thr Cys Asp Thr Pro Glu Glu Asp Gly Ile Thr Trp Thr Leu Asp
            515                 520                 525

Gln Ser Ser Glu Val Leu Gly Ser Gly Lys Thr Leu Thr Ile Gln Val
530                 535                 540

Lys Glu Phe Gly Asp Ala Gly Gln Tyr Thr Cys His Lys Gly Gly Glu
545                 550                 555                 560

Val Leu Ser His Ser Leu Leu Leu Leu His Lys Lys Glu Asp Gly Ile
                565                 570                 575

Trp Ser Thr Asp Ile Leu Lys Asp Gln Lys Glu Pro Lys Asn Lys Thr
                580                 585                 590

Phe Leu Arg Cys Glu Ala Lys Asn Tyr Ser Gly Arg Phe Thr Cys Trp
                595                 600                 605

Trp Leu Thr Thr Ile Ser Thr Asp Leu Thr Phe Ser Val Lys Ser Ser
            610                 615                 620

Arg Gly Ser Ser Asp Pro Gln Gly Val Thr Cys Gly Ala Ala Thr Leu
625                 630                 635                 640

Ser Ala Glu Arg Val Arg Gly Asp Asn Lys Glu Tyr Glu Tyr Ser Val
                645                 650                 655

Glu Cys Gln Glu Asp Ser Ala Cys Pro Ala Ala Glu Glu Ser Leu Pro
                660                 665                 670

Ile Glu Val Met Val Asp Ala Val His Lys Leu Lys Tyr Glu Asn Tyr
                675                 680                 685

Thr Ser Ser Phe Phe Ile Arg Asp Ile Ile Lys Pro Asp Pro Pro Lys
            690                 695                 700

Asn Leu Gln Leu Lys Pro Leu Lys Asn Ser Arg Gln Val Glu Val Ser
705                 710                 715                 720

Trp Glu Tyr Pro Asp Thr Trp Ser Thr Pro His Ser Tyr Phe Ser Leu
                725                 730                 735

Thr Phe Cys Val Gln Val Gln Gly Lys Ser Lys Arg Glu Lys Lys Asp
                740                 745                 750

Arg Val Phe Thr Asp Lys Thr Ser Ala Thr Val Ile Cys Arg Lys Asn
                755                 760                 765

Ala Ser Ile Ser Val Arg Ala Gln Asp Arg Tyr Tyr Ser Ser Ser Trp
            770                 775                 780

Ser Glu Trp Ala Ser Val Pro Cys Ser Gly Gly Gly Ser Gly Gly
785                 790                 795                 800

Gly Gly Ser Gly Gly Gly Ser Gly Gly Gly Ser Arg Asn Leu
                805                 810                 815

Pro Val Ala Thr Pro Asp Pro Gly Met Phe Pro Cys Leu His His Ser
            820                 825                 830

Gln Asn Leu Leu Arg Ala Val Ser Asn Met Leu Gln Lys Ala Arg Gln
            835                 840                 845

Thr Leu Glu Phe Tyr Pro Cys Thr Ser Glu Glu Ile Asp His Glu Asp
            850                 855                 860

Ile Thr Lys Asp Lys Thr Ser Thr Val Glu Ala Cys Leu Pro Leu Glu
865                 870                 875                 880

Leu Thr Lys Asn Glu Ser Cys Leu Asn Ser Arg Glu Thr Ser Phe Ile

-continued

```
                885               890               895
Thr Asn Gly Ser Cys Leu Ala Ser Arg Lys Thr Ser Phe Met Met Ala
            900               905               910

Leu Cys Leu Ser Ser Ile Tyr Glu Asp Leu Lys Met Tyr Gln Val Glu
            915               920               925

Phe Lys Thr Met Asn Ala Lys Leu Leu Met Asp Pro Lys Arg Gln Ile
        930               935               940

Phe Leu Asp Gln Asn Met Leu Ala Val Ile Asp Glu Leu Met Gln Ala
945               950               955               960

Leu Asn Phe Asn Ser Glu Thr Val Pro Gln Lys Ser Ser Leu Glu Glu
            965               970               975

Pro Asp Phe Tyr Lys Thr Lys Ile Lys Leu Cys Ile Leu Leu His Ala
            980               985               990

Phe Arg Ile Arg Ala Val Thr Ile  Asp Arg Val Met Ser  Tyr Leu Asn
        995               1000              1005

Ala Ser
    1010
```

```
<210> SEQ ID NO 889
<211> LENGTH: 119
<212> TYPE: PRT
<213> ORGANISM: Artificial Sequence
<220> FEATURE:
<223> OTHER INFORMATION: an artificially synthesized sequence

<400> SEQUENCE: 889

Glu Val Gln Leu Val Gln Ser Gly Ala Glu Val Lys Lys Pro Gly Glu
1               5               10              15

Ser Leu Lys Ile Ser Cys Lys Gly Ser Gly Tyr Ser Phe Thr Thr Tyr
            20              25              30

Trp Leu Gly Trp Val Arg Gln Met Pro Gly Lys Gly Leu Asp Trp Ile
        35              40              45

Gly Ile Met Ser Pro Val Asp Ser Asp Ile Arg Tyr Ser Pro Ser Phe
    50              55              60

Gln Gly Gln Val Thr Met Ser Val Asp Lys Ser Ile Thr Thr Ala Tyr
65              70              75              80

Leu Gln Trp Asn Ser Leu Lys Ala Ser Asp Thr Ala Met Tyr Tyr Cys
            85              90              95

Ala Arg Arg Arg Pro Gly Gln Gly Tyr Phe Asp Phe Trp Gly Gln Gly
            100             105             110

Thr Leu Val Thr Val Ser Ser
        115
```

```
<210> SEQ ID NO 890
<211> LENGTH: 219
<212> TYPE: PRT
<213> ORGANISM: Artificial Sequence
<220> FEATURE:
<223> OTHER INFORMATION: an artificially synthesized sequence

<400> SEQUENCE: 890

Gln Ser Val Leu Thr Gln Pro Pro Ser Val Ser Gly Ala Pro Gly Gln
1               5               10              15

Arg Val Thr Ile Ser Cys Ser Gly Ser Arg Ser Asn Ile Gly Ser Asn
            20              25              30

Thr Val Lys Trp Tyr Gln Gln Leu Pro Gly Thr Ala Pro Lys Leu Leu
        35              40              45
```

```
Ile Tyr Tyr Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Tyr Thr
                85                  90                  95

His Pro Ala Leu Leu Phe Gly Thr Gly Thr Lys Val Thr Val Leu Gly
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 891
<211> LENGTH: 1006
<212> TYPE: PRT
<213> ORGANISM: Artificial Sequence
<220> FEATURE:
<223> OTHER INFORMATION: an artificially synthesized sequence

<400> SEQUENCE: 891

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser Thr Ser Thr Ser Gly Arg Ser Ala Asn Pro Arg Gly Ala
            115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190
```

-continued

```
Ser Ser Val Val Thr Val Pro Ser Ser Ser Leu Gly Thr Gln Thr Tyr
        195                 200             205

Ile Cys Asn Val Asn His Lys Pro Ser Asn Thr Lys Val Asp Lys Arg
    210                 215             220

Val Gly Gly Gly Gly Ser Gly Gly Gly Gly Ser Glu Pro Lys Ser Cys
225                 230             235                 240

Asp Lys Thr His Thr Cys Pro Pro Cys Pro Ala Pro Glu Leu Arg Arg
            245             250             255

Gly Pro Ser Val Phe Leu Phe Pro Pro Lys Pro Lys Asp Thr Leu Met
            260             265             270

Ile Ser Arg Thr Pro Glu Val Thr Cys Val Val Val Asp Val Ser His
        275             280             285

Glu Asp Pro Glu Val Lys Phe Asn Trp Tyr Val Asp Gly Val Glu Val
    290             295             300

His Asn Ala Lys Thr Lys Pro Arg Glu Glu Gln Tyr Asn Ser Thr Tyr
305             310             315             320

Arg Val Val Ser Val Leu Thr Val Leu His Gln Asp Trp Leu Asn Gly
            325             330             335

Lys Glu Tyr Lys Cys Lys Val Ser Asn Lys Ala Leu Pro Ala Pro Ile
            340             345             350

Glu Lys Thr Ile Ser Lys Ala Lys Gly Gln Pro Arg Glu Pro Gln Val
        355             360             365

Cys Thr Leu Pro Pro Ser Arg Glu Glu Met Thr Lys Asn Gln Val Ser
        370             375             380

Leu Trp Cys Leu Val Lys Gly Phe Tyr Pro Ser Asp Ile Ala Val Glu
385             390             395             400

Trp Glu Ser Asn Gly Gln Pro Glu Asn Asn Tyr Lys Thr Thr Pro Pro
                405             410             415

Val Leu Asp Ser Asp Gly Ser Phe Phe Leu Tyr Ser Lys Leu Thr Val
            420             425             430

Asp Lys Ser Arg Trp Gln Gln Gly Asn Val Phe Ser Cys Ser Val Met
            435             440             445

His Glu Ala Leu His Asn Arg Tyr Thr Gln Lys Ser Leu Ser Leu Ser
    450             455             460

Pro Gly Gly Ser Gly Gly Ser Gly Gly Ser Gly Gly Ser Gly Gly Ser
465             470             475             480

Gly Gly Ser Ile Trp Glu Leu Lys Lys Asp Val Tyr Val Val Glu Leu
            485             490             495

Asp Trp Tyr Pro Asp Ala Pro Gly Glu Met Val Val Leu Thr Cys Asp
            500             505             510

Thr Pro Glu Glu Asp Gly Ile Thr Trp Thr Leu Asp Gln Ser Ser Glu
        515             520             525

Val Leu Gly Ser Gly Lys Thr Leu Thr Ile Gln Val Lys Glu Phe Gly
    530             535             540

Asp Ala Gly Gln Tyr Thr Cys His Lys Gly Gly Glu Val Leu Ser His
545             550             555             560

Ser Leu Leu Leu Leu His Lys Lys Glu Asp Gly Ile Trp Ser Thr Asp
            565             570             575

Ile Leu Lys Asp Gln Lys Glu Pro Lys Asn Lys Thr Phe Leu Arg Cys
            580             585             590

Glu Ala Lys Asn Tyr Ser Gly Arg Phe Thr Cys Trp Trp Leu Thr Thr
            595             600             605

Ile Ser Thr Asp Leu Thr Phe Ser Val Lys Ser Ser Arg Gly Ser Ser
```

```
          610             615             620

Asp Pro Gln Gly Val Thr Cys Gly Ala Ala Thr Leu Ser Ala Glu Arg
625             630             635             640

Val Arg Gly Asp Asn Lys Glu Tyr Glu Tyr Ser Val Glu Cys Gln Glu
                645             650             655

Asp Ser Ala Cys Pro Ala Ala Glu Glu Ser Leu Pro Ile Glu Val Met
                660             665             670

Val Asp Ala Val His Lys Leu Lys Tyr Glu Asn Tyr Thr Ser Ser Phe
        675             680             685

Phe Ile Arg Asp Ile Ile Lys Pro Asp Pro Pro Lys Asn Leu Gln Leu
        690             695             700

Lys Pro Leu Lys Asn Ser Arg Gln Val Glu Val Ser Trp Glu Tyr Pro
705             710             715             720

Asp Thr Trp Ser Thr Pro His Ser Tyr Phe Ser Leu Thr Phe Cys Val
                725             730             735

Gln Val Gln Gly Lys Ser Lys Arg Glu Lys Lys Asp Arg Val Phe Thr
                740             745             750

Asp Lys Thr Ser Ala Thr Val Ile Cys Arg Lys Asn Ala Ser Ile Ser
        755             760             765

Val Arg Ala Gln Asp Arg Tyr Tyr Ser Ser Ser Trp Ser Glu Trp Ala
        770             775             780

Ser Val Pro Cys Ser Gly Gly Gly Ser Gly Gly Gly Ser Gly
785             790             795             800

Gly Gly Gly Ser Gly Gly Gly Gly Ser Arg Asn Leu Pro Val Ala Thr
                805             810             815

Pro Asp Pro Gly Met Phe Pro Cys Leu His His Ser Gln Asn Leu Leu
                820             825             830

Arg Ala Val Ser Asn Met Leu Gln Lys Ala Arg Gln Thr Leu Glu Phe
                835             840             845

Tyr Pro Cys Thr Ser Glu Glu Ile Asp His Glu Asp Ile Thr Lys Asp
        850             855             860

Lys Thr Ser Thr Val Glu Ala Cys Leu Pro Leu Glu Leu Thr Lys Asn
865             870             875             880

Glu Ser Cys Leu Asn Ser Arg Glu Thr Ser Phe Ile Thr Asn Gly Ser
                885             890             895

Cys Leu Ala Ser Arg Lys Thr Ser Phe Met Met Ala Leu Cys Leu Ser
        900             905             910

Ser Ile Tyr Glu Asp Leu Lys Met Tyr Gln Val Glu Phe Lys Thr Met
        915             920             925

Asn Ala Lys Leu Leu Met Asp Pro Lys Arg Gln Ile Phe Leu Asp Gln
        930             935             940

Asn Met Leu Ala Val Ile Asp Glu Leu Met Gln Ala Leu Asn Phe Asn
945             950             955             960

Ser Glu Thr Val Pro Gln Lys Ser Ser Leu Glu Glu Pro Asp Phe Tyr
                965             970             975

Lys Thr Lys Ile Lys Leu Cys Ile Leu Leu His Ala Phe Arg Ile Arg
                980             985             990

Ala Val Thr Ile Asp Arg Val Met  Ser Tyr Leu Asn Ala  Ser
        995             1000            1005
```

<210> SEQ ID NO 892
<211> LENGTH: 115
<212> TYPE: PRT
<213> ORGANISM: Artificial Sequence -continued

```
<220> FEATURE:
<223> OTHER INFORMATION: an artificially synthesized sequence

<400> SEQUENCE: 892

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser
        115

<210> SEQ ID NO 893
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 893

Gly Gly Gly Gly Ala
1               5

<210> SEQ ID NO 894
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 894

Gly Gly Gly Gly Glu
1               5

<210> SEQ ID NO 895
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 895

Gly Gly Gly Ala
1

<210> SEQ ID NO 896
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 896

Gly Gly Gly Glu
```

1

```
<210> SEQ ID NO 897
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 897

Gln Gln Gln Gly
1

<210> SEQ ID NO 898
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 898

Gln Gln Gln Gln Gly
1               5

<210> SEQ ID NO 899
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 899

Ser Ser Ser Gly
1

<210> SEQ ID NO 900
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 900

Ser Ser Ser Ser Gly
1               5

<210> SEQ ID NO 901
<211> LENGTH: 338
<212> TYPE: PRT
<213> ORGANISM: Artificial sequence
<220> FEATURE:
<223> OTHER INFORMATION: an artificially synthesized sequence

<400> SEQUENCE: 901

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

-continued

```
Tyr Ile Cys Asn Val Asn His Lys Pro Ser Asn Thr Lys Val Asp Lys
                85                  90                  95

Arg Val Gly Gly Gly Gly Ser Gly Gly Gly Gly Ser Glu Pro Lys Ser
            100                 105                 110

Cys Asp Lys Thr His Thr Cys Pro Pro Cys Pro Ala Pro Glu Leu Arg
            115                 120                 125

Arg Gly Pro Ser Val Phe Leu Phe Pro Pro Lys Pro Lys Asp Thr Leu
    130                 135                 140

Met Ile Ser Arg Thr Pro Glu Val Thr Cys Val Val Val Asp Val Ser
145                 150                 155                 160

His Glu Asp Pro Glu Val Lys Phe Asn Trp Tyr Val Asp Gly Val Glu
                165                 170                 175

Val His Asn Ala Lys Thr Lys Pro Arg Glu Glu Gln Tyr Asn Ser Thr
            180                 185                 190

Tyr Arg Val Val Ser Val Leu Thr Val Leu His Gln Asp Trp Leu Asn
            195                 200                 205

Gly Lys Glu Tyr Lys Cys Lys Val Ser Asn Lys Ala Leu Pro Ala Pro
    210                 215                 220

Ile Glu Lys Thr Ile Ser Lys Ala Lys Gly Gln Pro Arg Glu Pro Gln
225                 230                 235                 240

Val Tyr Thr Leu Pro Pro Ser Arg Glu Glu Met Thr Lys Asn Gln Val
                245                 250                 255

Ser Leu Thr Cys Leu Val Lys Gly Phe Tyr Pro Ser Asp Ile Ala Val
            260                 265                 270

Glu Trp Glu Ser Asn Gly Gln Pro Glu Asn Asn Tyr Lys Thr Thr Pro
            275                 280                 285

Pro Val Leu Asp Ser Asp Gly Ser Phe Phe Leu Tyr Ser Lys Leu Thr
    290                 295                 300

Val Asp Lys Ser Arg Trp Gln Gln Gly Asn Val Phe Ser Cys Ser Val
305                 310                 315                 320

Met His Glu Ala Leu His Asn His Tyr Thr Gln Lys Ser Leu Ser Leu
                325                 330                 335

Ser Pro
```

```
<210> SEQ ID NO 902
<211> LENGTH: 523
<212> TYPE: PRT
<213> ORGANISM: Artificial sequence
<220> FEATURE:
<223> OTHER INFORMATION: an artificially synthesized sequence

<400> SEQUENCE: 902
```

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
                20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
```

-continued

```
                100                 105                 110
Asn Tyr Ser Gly Arg Phe Thr Cys Trp Trp Leu Thr Thr Ile Ser Thr
            115                 120                 125

Asp Leu Thr Phe Ser Val Lys Ser Ser Arg Gly Ser Ser Asp Pro Gln
        130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
                180                 185                 190

Val His Lys Leu Lys Tyr Glu Asn Tyr Thr Ser Ser Phe Phe Ile Arg
            195                 200                 205

Asp Ile Ile Lys Pro Asp Pro Pro Lys Asn Leu Gln Leu Lys Pro Leu
            210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
            275                 280                 285

Gln Asp Arg Tyr Tyr Ser Ser Ser Trp Ser Glu Trp Ala Ser Val Pro
        290                 295                 300

Cys Ser Gly Gly Gly Gly Ser Gly Gly Gly Ser Gly Gly Gly Gly
305                 310                 315                 320

Ser Gly Gly Gly Gly Ser Arg Asn Leu Pro Val Ala Thr Pro Asp Pro
                325                 330                 335

Gly Met Phe Pro Cys Leu His His Ser Gln Asn Leu Leu Arg Ala Val
            340                 345                 350

Ser Asn Met Leu Gln Lys Ala Arg Gln Thr Leu Glu Phe Tyr Pro Cys
        355                 360                 365

Thr Ser Glu Glu Ile Asp His Glu Asp Ile Thr Lys Asp Lys Thr Ser
    370                 375                 380

Thr Val Glu Ala Cys Leu Pro Leu Glu Leu Thr Lys Asn Glu Ser Cys
385                 390                 395                 400

Leu Asn Ser Arg Glu Thr Ser Phe Ile Thr Asn Gly Ser Cys Leu Ala
                405                 410                 415

Ser Arg Lys Thr Ser Phe Met Met Ala Leu Cys Leu Ser Ser Ile Tyr
            420                 425                 430

Glu Asp Leu Lys Met Tyr Gln Val Glu Phe Lys Thr Met Asn Ala Lys
        435                 440                 445

Leu Leu Met Asp Pro Lys Arg Gln Ile Phe Leu Asp Gln Asn Met Leu
    450                 455                 460

Ala Val Ile Asp Glu Leu Met Gln Ala Leu Asn Phe Asn Ser Glu Thr
465                 470                 475                 480

Val Pro Gln Lys Ser Ser Leu Glu Glu Pro Asp Phe Tyr Lys Thr Lys
                485                 490                 495

Ile Lys Leu Cys Ile Leu Leu His Ala Phe Arg Ile Arg Ala Val Thr
            500                 505                 510

Ile Asp Arg Val Met Ser Tyr Leu Asn Ala Ser
            515                 520
```

-continued

```
<210> SEQ ID NO 903
<211> LENGTH: 18
<212> TYPE: PRT
<213> ORGANISM: Artificial sequence
<220> FEATURE:
<223> OTHER INFORMATION: an artificially synthesized sequence

<400> SEQUENCE: 903

Gly Gly Ser Gly Gly Ser Gly Gly Ser Gly Gly Ser Gly Gly Ser Gly
1               5                   10                  15

Gly Ser

<210> SEQ ID NO 904
<211> LENGTH: 1009
<212> TYPE: PRT
<213> ORGANISM: Artificial sequence
<220> FEATURE:
<223> OTHER INFORMATION: an artificially synthesized sequence

<400> SEQUENCE: 904

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
            100                 105                 110

Met Val Thr Val Ser Ser Thr Ser Thr Ser Gly Arg Ser Ala Asn Pro
        115                 120                 125

Arg Gly Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Arg Val Glu Pro Lys Ser Cys Gly Gly Gly Ser Gly Gly
225                 230                 235                 240

Gly Gly Ser Asp Lys Thr His Thr Cys Pro Pro Cys Pro Ala Pro Glu
                245                 250                 255

Leu Arg Arg Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285
```

-continued

```
Val Ser His Glu Asp Pro Glu Val Lys Phe Asn Trp Tyr Val Asp Gly
    290             295             300

Val Glu Val His Asn Ala Lys Thr Lys Pro Arg Glu Glu Gln Tyr Asn
305             310             315             320

Ser Thr Tyr Arg Val Val Ser Val Leu Thr Val Leu His Gln Asp Trp
            325             330             335

Leu Asn Gly Lys Glu Tyr Lys Cys Lys Val Ser Asn Lys Ala Leu Pro
            340             345             350

Ala Pro Ile Glu Lys Thr Ile Ser Lys Ala Lys Gly Gln Pro Arg Glu
            355             360             365

Pro Gln Val Tyr Thr Leu Pro Pro Ser Arg Glu Glu Met Thr Lys Asn
    370             375             380

Gln Val Ser Leu Thr Cys Leu Val Lys Gly Phe Tyr Pro Ser Asp Ile
385             390             395             400

Ala Val Glu Trp Glu Ser Asn Gly Gln Pro Glu Asn Asn Tyr Lys Thr
            405             410             415

Thr Pro Pro Val Leu Asp Ser Asp Gly Ser Phe Phe Leu Tyr Ser Lys
            420             425             430

Leu Thr Val Asp Lys Ser Arg Trp Gln Gln Gly Asn Val Phe Ser Cys
            435             440             445

Ser Val Met His Glu Ala Leu His Asn His Tyr Thr Gln Lys Ser Leu
    450             455             460

Ser Leu Ser Pro Gly Gly Ser Gly Gly Ser Gly Gly Ser Gly Gly Ser
465             470             475             480

Gly Gly Ser Gly Gly Ser Ile Trp Glu Leu Lys Lys Asp Val Tyr Val
            485             490             495

Val Glu Leu Asp Trp Tyr Pro Asp Ala Pro Gly Glu Met Val Val Leu
            500             505             510

Thr Cys Asp Thr Pro Glu Glu Asp Gly Ile Thr Trp Thr Leu Asp Gln
            515             520             525

Ser Ser Glu Val Leu Gly Ser Gly Lys Thr Leu Thr Ile Gln Val Lys
    530             535             540

Glu Phe Gly Asp Ala Gly Gln Tyr Thr Cys His Lys Gly Gly Glu Val
545             550             555             560

Leu Ser His Ser Leu Leu Leu Leu His Lys Lys Glu Asp Gly Ile Trp
            565             570             575

Ser Thr Asp Ile Leu Lys Asp Gln Lys Glu Pro Lys Asn Lys Thr Phe
            580             585             590

Leu Arg Cys Glu Ala Lys Asn Tyr Ser Gly Arg Phe Thr Cys Trp Trp
            595             600             605

Leu Thr Thr Ile Ser Thr Asp Leu Thr Phe Ser Val Lys Ser Ser Arg
            610             615             620

Gly Ser Ser Asp Pro Gln Gly Val Thr Cys Gly Ala Ala Thr Leu Ser
625             630             635             640

Ala Glu Arg Val Arg Gly Asp Asn Lys Glu Tyr Glu Tyr Ser Val Glu
            645             650             655

Cys Gln Glu Asp Ser Ala Cys Pro Ala Ala Glu Glu Ser Leu Pro Ile
            660             665             670

Glu Val Met Val Asp Ala Val His Lys Leu Lys Tyr Glu Asn Tyr Thr
            675             680             685

Ser Ser Phe Phe Ile Arg Asp Ile Ile Lys Pro Asp Pro Pro Lys Asn
    690             695             700
```

```
Leu Gln Leu Lys Pro Leu Lys Asn Ser Arg Gln Val Glu Val Ser Trp
705             710             715             720

Glu Tyr Pro Asp Thr Trp Ser Thr Pro His Ser Tyr Phe Ser Leu Thr
            725             730             735

Phe Cys Val Gln Val Gln Gly Lys Ser Lys Arg Glu Lys Lys Asp Arg
                740             745             750

Val Phe Thr Asp Lys Thr Ser Ala Thr Val Ile Cys Arg Lys Asn Ala
            755             760             765

Ser Ile Ser Val Arg Ala Gln Asp Arg Tyr Tyr Ser Ser Ser Trp Ser
        770             775             780

Glu Trp Ala Ser Val Pro Cys Ser Gly Gly Gly Ser Gly Gly Gly
785             790             795             800

Gly Ser Gly Gly Gly Gly Ser Gly Gly Gly Gly Ser Arg Asn Leu Pro
            805             810             815

Val Ala Thr Pro Asp Pro Gly Met Phe Pro Cys Leu His His Ser Gln
            820             825             830

Asn Leu Leu Arg Ala Val Ser Asn Met Leu Gln Lys Ala Arg Gln Thr
            835             840             845

Leu Glu Phe Tyr Pro Cys Thr Ser Glu Glu Ile Asp His Glu Asp Ile
        850             855             860

Thr Lys Asp Lys Thr Ser Thr Val Glu Ala Cys Leu Pro Leu Glu Leu
865             870             875             880

Thr Lys Asn Glu Ser Cys Leu Asn Ser Arg Glu Thr Ser Phe Ile Thr
            885             890             895

Asn Gly Ser Cys Leu Ala Ser Arg Lys Thr Ser Phe Met Met Ala Leu
            900             905             910

Cys Leu Ser Ser Ile Tyr Glu Asp Leu Lys Met Tyr Gln Val Glu Phe
        915             920             925

Lys Thr Met Asn Ala Lys Leu Leu Met Asp Pro Lys Arg Gln Ile Phe
        930             935             940

Leu Asp Gln Asn Met Leu Ala Val Ile Asp Glu Leu Met Gln Ala Leu
945             950             955             960

Asn Phe Asn Ser Glu Thr Val Pro Gln Lys Ser Ser Leu Glu Glu Pro
            965             970             975

Asp Phe Tyr Lys Thr Lys Ile Lys Leu Cys Ile Leu Leu His Ala Phe
            980             985             990

Arg Ile Arg Ala Val Thr Ile Asp Arg Val Met Ser Tyr Leu Asn Ala
        995             1000            1005

Ser

<210> SEQ ID NO 905
<211> LENGTH: 338
<212> TYPE: PRT
<213> ORGANISM: Artificial sequence
<220> FEATURE:
<223> OTHER INFORMATION: an artificially synthesized sequence

<400> SEQUENCE: 905

Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
```

-continued

```
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Gly Gly Gly Ser Gly Gly Gly Gly
            100                 105                 110

Ser Asp Lys Thr His Thr Cys Pro Pro Cys Pro Ala Pro Glu Leu Arg
            115                 120                 125

Arg Gly Pro Ser Val Phe Leu Phe Pro Pro Lys Pro Lys Asp Thr Leu
            130                 135                 140

Met Ile Ser Arg Thr Pro Glu Val Thr Cys Val Val Val Asp Val Ser
145                 150                 155                 160

His Glu Asp Pro Glu Val Lys Phe Asn Trp Tyr Val Asp Gly Val Glu
                165                 170                 175

Val His Asn Ala Lys Thr Lys Pro Arg Glu Glu Gln Tyr Asn Ser Thr
                180                 185                 190

Tyr Arg Val Val Ser Val Leu Thr Val Leu His Gln Asp Trp Leu Asn
                195                 200                 205

Gly Lys Glu Tyr Lys Cys Lys Val Ser Asn Lys Ala Leu Pro Ala Pro
            210                 215                 220

Ile Glu Lys Thr Ile Ser Lys Ala Lys Gly Gln Pro Arg Glu Pro Gln
225                 230                 235                 240

Val Tyr Thr Leu Pro Pro Ser Arg Glu Glu Met Thr Lys Asn Gln Val
                245                 250                 255

Ser Leu Thr Cys Leu Val Lys Gly Phe Tyr Pro Ser Asp Ile Ala Val
                260                 265                 270

Glu Trp Glu Ser Asn Gly Gln Pro Glu Asn Asn Tyr Lys Thr Thr Pro
            275                 280                 285

Pro Val Leu Asp Ser Asp Gly Ser Phe Phe Leu Tyr Ser Lys Leu Thr
            290                 295                 300

Val Asp Lys Ser Arg Trp Gln Gln Gly Asn Val Phe Ser Cys Ser Val
305                 310                 315                 320

Met His Glu Ala Leu His Asn His Tyr Thr Gln Lys Ser Leu Ser Leu
                325                 330                 335

Ser Pro

<210> SEQ ID NO 906
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 906

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ile Asn
                20                  25                  30

Leu His Trp Tyr Gln Gln Lys Pro Gly Gln Ala Pro Arg Leu Leu Ile
            35                  40                  45

Tyr Phe Ala Ser Gln Ser Ile Ser Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80
```

```
Glu Asp Phe Ala Val Tyr Tyr Cys Gln Gln Ser Asn Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Ser
    210
```

<210> SEQ ID NO 907
<211> LENGTH: 1009
<212> TYPE: PRT
<213> ORGANISM: Artificial sequence
<220> FEATURE:
<223> OTHER INFORMATION: an artificially synthesized sequence

<400> SEQUENCE: 907

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Asn Ala Asn Lys Glu Leu Arg Tyr Phe Asp Val Trp Gly Gln Gly Thr
            100                 105                 110

Met Val Thr Val Ser Ser Thr Ser Thr Ser Gly Arg Ser Ala Asn Pro
            115                 120                 125

Arg Gly Ala Ser Thr Lys Gly Pro Ser Val Phe Pro Leu Ala Pro Ser
        130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
            195                 200                 205

Gln Thr Tyr Ile Cys Asn Val Asn His Lys Pro Ser Asn Thr Lys Val
        210                 215                 220
```

-continued

```
Asp Lys Arg Val Gly Gly Gly Gly Ser Gly Gly Gly Gly Ser Glu Pro
225             230             235             240

Lys Ser Ser Asp Lys Thr His Thr Cys Pro Pro Cys Pro Ala Pro Glu
                245             250             255

Leu Arg Arg Gly Pro Ser Val Phe Leu Phe Pro Pro Lys Pro Lys Asp
            260             265             270

Thr Leu Met Ile Ser Arg Thr Pro Glu Val Thr Cys Val Val Val Asp
        275             280             285

Val Ser His Glu Asp Pro Glu Val Lys Phe Asn Trp Tyr Val Asp Gly
    290             295             300

Val Glu Val His Asn Ala Lys Thr Lys Pro Arg Glu Glu Gln Tyr Asn
305             310             315             320

Ser Thr Tyr Arg Val Val Ser Val Leu Thr Val Leu His Gln Asp Trp
            325             330             335

Leu Asn Gly Lys Glu Tyr Lys Cys Lys Val Ser Asn Lys Ala Leu Pro
            340             345             350

Ala Pro Ile Glu Lys Thr Ile Ser Lys Ala Lys Gly Gln Pro Arg Glu
        355             360             365

Pro Gln Val Tyr Thr Leu Pro Pro Ser Arg Glu Glu Met Thr Lys Asn
    370             375             380

Gln Val Ser Leu Thr Cys Leu Val Lys Gly Phe Tyr Pro Ser Asp Ile
385             390             395             400

Ala Val Glu Trp Glu Ser Asn Gly Gln Pro Glu Asn Asn Tyr Lys Thr
            405             410             415

Thr Pro Pro Val Leu Asp Ser Asp Gly Ser Phe Phe Leu Tyr Ser Lys
            420             425             430

Leu Thr Val Asp Lys Ser Arg Trp Gln Gln Gly Asn Val Phe Ser Cys
            435             440             445

Ser Val Met His Glu Ala Leu His Asn His Tyr Thr Gln Lys Ser Leu
    450             455             460

Ser Leu Ser Pro Gly Gly Ser Gly Gly Ser Gly Gly Ser Gly Gly Ser
465             470             475             480

Gly Gly Ser Gly Gly Ser Ile Trp Glu Leu Lys Lys Asp Val Tyr Val
            485             490             495

Val Glu Leu Asp Trp Tyr Pro Asp Ala Pro Gly Glu Met Val Val Leu
            500             505             510

Thr Cys Asp Thr Pro Glu Glu Asp Gly Ile Thr Trp Thr Leu Asp Gln
        515             520             525

Ser Ser Glu Val Leu Gly Ser Gly Lys Thr Leu Thr Ile Gln Val Lys
    530             535             540

Glu Phe Gly Asp Ala Gly Gln Tyr Thr Cys His Lys Gly Gly Glu Val
545             550             555             560

Leu Ser His Ser Leu Leu Leu Leu His Lys Lys Glu Asp Gly Ile Trp
            565             570             575

Ser Thr Asp Ile Leu Lys Asp Gln Lys Glu Pro Lys Asn Lys Thr Phe
            580             585             590

Leu Arg Cys Glu Ala Lys Asn Tyr Ser Gly Arg Phe Thr Cys Trp Trp
            595             600             605

Leu Thr Thr Ile Ser Thr Asp Leu Thr Phe Ser Val Lys Ser Ser Arg
            610             615             620

Gly Ser Ser Asp Pro Gln Gly Val Thr Cys Gly Ala Ala Thr Leu Ser
625             630             635             640
```

Ala Glu Arg Val Arg Gly Asp Asn Lys Glu Tyr Glu Tyr Ser Val Glu
                    645               650             655

Cys Gln Glu Asp Ser Ala Cys Pro Ala Ala Glu Glu Ser Leu Pro Ile
            660               665               670

Glu Val Met Val Asp Ala Val His Lys Leu Lys Tyr Glu Asn Tyr Thr
            675               680               685

Ser Ser Phe Phe Ile Arg Asp Ile Ile Lys Pro Asp Pro Pro Lys Asn
    690               695               700

Leu Gln Leu Lys Pro Leu Lys Asn Ser Arg Gln Val Glu Val Ser Trp
705               710               715               720

Glu Tyr Pro Asp Thr Trp Ser Thr Pro His Ser Tyr Phe Ser Leu Thr
            725               730               735

Phe Cys Val Gln Val Gln Gly Lys Ser Lys Arg Glu Lys Lys Asp Arg
            740               745               750

Val Phe Thr Asp Lys Thr Ser Ala Thr Val Ile Cys Arg Lys Asn Ala
            755               760               765

Ser Ile Ser Val Arg Ala Gln Asp Arg Tyr Tyr Ser Ser Ser Trp Ser
    770               775               780

Glu Trp Ala Ser Val Pro Cys Ser Gly Gly Gly Ser Gly Gly Gly
785               790               795               800

Gly Ser Gly Gly Gly Gly Ser Gly Gly Gly Gly Ser Arg Asn Leu Pro
            805               810               815

Val Ala Thr Pro Asp Pro Gly Met Phe Pro Cys Leu His His Ser Gln
            820               825               830

Asn Leu Leu Arg Ala Val Ser Asn Met Leu Gln Lys Ala Arg Gln Thr
            835               840               845

Leu Glu Phe Tyr Pro Cys Thr Ser Glu Glu Ile Asp His Glu Asp Ile
    850               855               860

Thr Lys Asp Lys Thr Ser Thr Val Glu Ala Cys Leu Pro Leu Glu Leu
865               870               875               880

Thr Lys Asn Glu Ser Cys Leu Asn Ser Arg Glu Thr Ser Phe Ile Thr
            885               890               895

Asn Gly Ser Cys Leu Ala Ser Arg Lys Thr Ser Phe Met Met Ala Leu
            900               905               910

Cys Leu Ser Ser Ile Tyr Glu Asp Leu Lys Met Tyr Gln Val Glu Phe
            915               920               925

Lys Thr Met Asn Ala Lys Leu Leu Met Asp Pro Lys Arg Gln Ile Phe
            930               935               940

Leu Asp Gln Asn Met Leu Ala Val Ile Asp Glu Leu Met Gln Ala Leu
945               950               955               960

Asn Phe Asn Ser Glu Thr Val Pro Gln Lys Ser Ser Leu Glu Glu Pro
            965               970               975

Asp Phe Tyr Lys Thr Lys Ile Lys Leu Cys Ile Leu Leu His Ala Phe
            980               985               990

Arg Ile Arg Ala Val Thr Ile Asp  Arg Val Met Ser Tyr  Leu Asn Ala
            995               1000              1005

Ser

<210> SEQ ID NO 908
<211> LENGTH: 338
<212> TYPE: PRT
<213> ORGANISM: Artificial sequence
<220> FEATURE:
<223> OTHER INFORMATION: an artificially synthesized sequence -continued

```
<400> SEQUENCE: 908

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Gly Gly Gly Gly Ser Gly Gly Gly Gly Ser Glu Pro Lys Ser
            100                 105                 110

Ser Asp Lys Thr His Thr Cys Pro Pro Cys Pro Ala Pro Glu Leu Arg
        115                 120                 125

Arg Gly Pro Ser Val Phe Leu Phe Pro Pro Lys Pro Lys Asp Thr Leu
    130                 135                 140

Met Ile Ser Arg Thr Pro Glu Val Thr Cys Val Val Val Asp Val Ser
145                 150                 155                 160

His Glu Asp Pro Glu Val Lys Phe Asn Trp Tyr Val Asp Gly Val Glu
                165                 170                 175

Val His Asn Ala Lys Thr Lys Pro Arg Glu Glu Gln Tyr Asn Ser Thr
            180                 185                 190

Tyr Arg Val Val Ser Val Leu Thr Val Leu His Gln Asp Trp Leu Asn
        195                 200                 205

Gly Lys Glu Tyr Lys Cys Lys Val Ser Asn Lys Ala Leu Pro Ala Pro
    210                 215                 220

Ile Glu Lys Thr Ile Ser Lys Ala Lys Gly Gln Pro Arg Glu Pro Gln
225                 230                 235                 240

Val Tyr Thr Leu Pro Pro Ser Arg Glu Glu Met Thr Lys Asn Gln Val
                245                 250                 255

Ser Leu Thr Cys Leu Val Lys Gly Phe Tyr Pro Ser Asp Ile Ala Val
            260                 265                 270

Glu Trp Glu Ser Asn Gly Gln Pro Glu Asn Asn Tyr Lys Thr Thr Pro
        275                 280                 285

Pro Val Leu Asp Ser Asp Gly Ser Phe Phe Leu Tyr Ser Lys Leu Thr
    290                 295                 300

Val Asp Lys Ser Arg Trp Gln Gln Gly Asn Val Phe Ser Cys Ser Val
305                 310                 315                 320

Met His Glu Ala Leu His Asn His Tyr Thr Gln Lys Ser Leu Ser Leu
                325                 330                 335

Ser Pro

<210> SEQ ID NO 909
<211> LENGTH: 1009
<212> TYPE: PRT
<213> ORGANISM: Artificial sequence
<220> FEATURE:
<223> OTHER INFORMATION: an artificially synthesized sequence

<400> SEQUENCE: 909

Gln Val Gln Leu Val Gln Ser Gly Ala Glu Val Lys Lys Pro Gly Ala
1               5                   10                  15
```

-continued

Ser Val Lys Val Ser Cys Lys Ala Ser Gly Tyr Thr Phe Thr Asp Tyr
          20                  25                  30

Tyr Leu His Trp Val Arg Gln Ala Pro Gly Gln Gly Leu Glu Trp Met
          35                  40                  45

Gly Trp Ile Asp Pro Glu Asn Gly Asp Thr Glu Tyr Ala Pro Lys Phe
      50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
              85                  90                  95

Asn Ala Asn Lys Glu Leu Arg Tyr Phe Asp Val Trp Gly Gln Gly Thr
          100                 105                 110

Met Val Thr Val Ser Ser Thr Ser Thr Ser Gly Arg Ser Ala Asn Pro
          115                 120                 125

Arg Gly Ala Ser Thr Lys Gly Pro Ser Val Phe Pro Leu Ala Pro Cys
      130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
              165                 170                 175

Thr Ser Gly Val His Thr Phe Pro Ala Val Leu Gln Ser Ser Gly Leu
          180                 185                 190

Tyr Ser Leu Ser Ser Val Val Thr Val Pro Ser Ser Ser Leu Gly Thr
          195                 200                 205

Gln Thr Tyr Ile Cys Asn Val Asn His Lys Pro Ser Asn Thr Lys Val
      210                 215                 220

Asp Lys Arg Val Gly Gly Gly Gly Ser Gly Gly Gly Ser Glu Pro
225                 230                 235                 240

Lys Ser Ser Asp Lys Thr His Thr Cys Pro Pro Cys Pro Ala Pro Glu
              245                 250                 255

Leu Arg Arg Gly Pro Ser Val Phe Leu Phe Pro Pro Lys Pro Lys Asp
              260                 265                 270

Thr Leu Met Ile Ser Arg Thr Pro Glu Val Thr Cys Val Val Val Asp
          275                 280                 285

Val Ser His Glu Asp Pro Glu Val Lys Phe Asn Trp Tyr Val Asp Gly
      290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
              325                 330                 335

Leu Asn Gly Lys Glu Tyr Lys Cys Lys Val Ser Asn Lys Ala Leu Pro
          340                 345                 350

Ala Pro Ile Glu Lys Thr Ile Ser Lys Ala Lys Gly Gln Pro Arg Glu
          355                 360                 365

Pro Gln Val Tyr Thr Leu Pro Pro Ser Arg Glu Glu Met Thr Lys Asn
      370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
              405                 410                 415

Thr Pro Pro Val Leu Asp Ser Asp Gly Ser Phe Phe Leu Tyr Ser Lys
          420                 425                 430

```
Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
        450                 455                 460

Ser Leu Ser Pro Gly Gly Ser Gly Gly Ser Gly Gly Ser Gly Gly Ser
465                 470                 475                 480

Gly Gly Ser Gly Gly Ser Ile Trp Glu Leu Lys Lys Asp Val Tyr Val
                485                 490                 495

Val Glu Leu Asp Trp Tyr Pro Asp Ala Pro Gly Glu Met Val Val Leu
                500                 505                 510

Thr Cys Asp Thr Pro Glu Glu Asp Gly Ile Thr Trp Thr Leu Asp Gln
        515                 520                 525

Ser Ser Glu Val Leu Gly Ser Gly Lys Thr Leu Thr Ile Gln Val Lys
        530                 535                 540

Glu Phe Gly Asp Ala Gly Gln Tyr Thr Cys His Lys Gly Gly Glu Val
545                 550                 555                 560

Leu Ser His Ser Leu Leu Leu Leu His Lys Lys Glu Asp Gly Ile Trp
                565                 570                 575

Ser Thr Asp Ile Leu Lys Asp Gln Lys Glu Pro Lys Asn Lys Thr Phe
                580                 585                 590

Leu Arg Cys Glu Ala Lys Asn Tyr Ser Gly Arg Phe Thr Cys Trp Trp
        595                 600                 605

Leu Thr Thr Ile Ser Thr Asp Leu Thr Phe Ser Val Lys Ser Ser Arg
        610                 615                 620

Gly Ser Ser Asp Pro Gln Gly Val Thr Cys Gly Ala Ala Thr Leu Ser
625                 630                 635                 640

Ala Glu Arg Val Arg Gly Asp Asn Lys Glu Tyr Glu Tyr Ser Val Glu
                645                 650                 655

Cys Gln Glu Asp Ser Ala Cys Pro Ala Ala Glu Glu Ser Leu Pro Ile
                660                 665                 670

Glu Val Met Val Asp Ala Val His Lys Leu Lys Tyr Glu Asn Tyr Thr
                675                 680                 685

Ser Ser Phe Phe Ile Arg Asp Ile Ile Lys Pro Asp Pro Pro Lys Asn
        690                 695                 700

Leu Gln Leu Lys Pro Leu Lys Asn Ser Arg Gln Val Glu Val Ser Trp
705                 710                 715                 720

Glu Tyr Pro Asp Thr Trp Ser Thr Pro His Ser Tyr Phe Ser Leu Thr
                725                 730                 735

Phe Cys Val Gln Val Gln Gly Lys Ser Lys Arg Glu Lys Lys Asp Arg
                740                 745                 750

Val Phe Thr Asp Lys Thr Ser Ala Thr Val Ile Cys Arg Lys Asn Ala
        755                 760                 765

Ser Ile Ser Val Arg Ala Gln Asp Arg Tyr Tyr Ser Ser Ser Trp Ser
        770                 775                 780

Glu Trp Ala Ser Val Pro Cys Ser Gly Gly Gly Ser Gly Gly Gly
785                 790                 795                 800

Gly Ser Gly Gly Gly Gly Ser Gly Gly Gly Ser Arg Asn Leu Pro
                805                 810                 815

Val Ala Thr Pro Asp Pro Gly Met Phe Pro Cys Leu His His Ser Gln
        820                 825                 830

Asn Leu Leu Arg Ala Val Ser Asn Met Leu Gln Lys Ala Arg Gln Thr
        835                 840                 845

Leu Glu Phe Tyr Pro Cys Thr Ser Glu Glu Ile Asp His Glu Asp Ile
```

-continued

```
     850                 855                 860

Thr Lys Asp Lys Thr Ser Thr Val Glu Ala Cys Leu Pro Leu Glu Leu
865                 870                 875                 880

Thr Lys Asn Glu Ser Cys Leu Asn Ser Arg Glu Thr Ser Phe Ile Thr
                885                 890                 895

Asn Gly Ser Cys Leu Ala Ser Arg Lys Thr Ser Phe Met Met Ala Leu
                900                 905                 910

Cys Leu Ser Ser Ile Tyr Glu Asp Leu Lys Met Tyr Gln Val Glu Phe
                915                 920                 925

Lys Thr Met Asn Ala Lys Leu Leu Met Asp Pro Lys Arg Gln Ile Phe
                930                 935                 940

Leu Asp Gln Asn Met Leu Ala Val Ile Asp Glu Leu Met Gln Ala Leu
945                 950                 955                 960

Asn Phe Asn Ser Glu Thr Val Pro Gln Lys Ser Ser Leu Glu Glu Pro
                965                 970                 975

Asp Phe Tyr Lys Thr Lys Ile Lys Leu Cys Ile Leu Leu His Ala Phe
                980                 985                 990

Arg Ile Arg Ala Val Thr Ile Asp  Arg Val Met Ser Tyr  Leu Asn Ala
                995                 1000                1005

Ser
```

```
<210> SEQ ID NO 910
<211> LENGTH: 338
<212> TYPE: PRT
<213> ORGANISM: Artificial sequence
<220> FEATURE:
<223> OTHER INFORMATION: an artificially synthesized sequence

<400> SEQUENCE: 910

Ala Ser Thr Lys Gly Pro Ser Val Phe Pro Leu Ala Pro Cys Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Gly Gly Gly Gly Ser Gly Gly Gly Gly Ser Glu Pro Lys Ser
                100                 105                 110

Ser Asp Lys Thr His Thr Cys Pro Pro Cys Pro Ala Pro Glu Leu Arg
                115                 120                 125

Arg Gly Pro Ser Val Phe Leu Phe Pro Pro Lys Pro Lys Asp Thr Leu
        130                 135                 140

Met Ile Ser Arg Thr Pro Glu Val Thr Cys Val Val Val Asp Val Ser
145                 150                 155                 160

His Glu Asp Pro Glu Val Lys Phe Asn Trp Tyr Val Asp Gly Val Glu
                165                 170                 175

Val His Asn Ala Lys Thr Lys Pro Arg Glu Glu Gln Tyr Asn Ser Thr
                180                 185                 190

Tyr Arg Val Val Ser Val Leu Thr Val Leu His Gln Asp Trp Leu Asn
        195                 200                 205
```

```
Gly Lys Glu Tyr Lys Cys Lys Val Ser Asn Lys Ala Leu Pro Ala Pro
    210             215             220

Ile Glu Lys Thr Ile Ser Lys Ala Lys Gly Gln Pro Arg Glu Pro Gln
225             230             235             240

Val Tyr Thr Leu Pro Pro Ser Arg Glu Glu Met Thr Lys Asn Gln Val
                245             250             255

Ser Leu Thr Cys Leu Val Lys Gly Phe Tyr Pro Ser Asp Ile Ala Val
                260             265             270

Glu Trp Glu Ser Asn Gly Gln Pro Glu Asn Asn Tyr Lys Thr Thr Pro
                275             280             285

Pro Val Leu Asp Ser Asp Gly Ser Phe Phe Leu Tyr Ser Lys Leu Thr
    290             295             300

Val Asp Lys Ser Arg Trp Gln Gln Gly Asn Val Phe Ser Cys Ser Val
305             310             315             320

Met His Glu Ala Leu His Asn His Tyr Thr Gln Lys Ser Leu Ser Leu
                325             330             335

Ser Pro

<210> SEQ ID NO 911
<211> LENGTH: 146
<212> TYPE: PRT
<213> ORGANISM: Artificial sequence
<220> FEATURE:
<223> OTHER INFORMATION: an artificially synthesized sequence

<400> SEQUENCE: 911

Ala Pro Ile Ser Ser His Cys Arg Leu Asp Lys Ser Asn Phe Gln Gln
1               5               10              15

Pro Tyr Ile Thr Asn Arg Thr Phe Met Leu Ala Lys Glu Ala Ser Leu
                20              25              30

Ala Asp Asn Asn Thr Asp Val Arg Leu Ile Gly Glu Lys Leu Phe His
            35              40              45

Gly Val Ser Met Ser Glu Arg Cys Tyr Leu Met Lys Gln Val Leu Asn
    50              55              60

Phe Thr Leu Glu Glu Val Leu Phe Pro Gln Ser Asp Arg Phe Gln Pro
65              70              75              80

Tyr Met Gln Glu Val Val Pro Phe Leu Ala Arg Leu Ser Asn Arg Leu
                85              90              95

Ser Thr Cys His Ile Glu Gly Asp Asp Leu His Ile Gln Arg Asn Val
            100             105             110

Gln Lys Leu Lys Asp Thr Val Lys Lys Leu Gly Glu Ser Gly Glu Ile
        115             120             125

Lys Ala Ile Gly Glu Leu Asp Leu Leu Phe Met Ser Leu Arg Asn Ala
    130             135             140

Cys Ile
145

<210> SEQ ID NO 912
<211> LENGTH: 216
<212> TYPE: PRT
<213> ORGANISM: Artificial sequence
<220> FEATURE:
<223> OTHER INFORMATION: an artificially synthesized sequence

<400> SEQUENCE: 912

Gln Ala Ala Leu Thr Gln Pro Ala Ser Val Ser Gly Ser Pro Gly Gln
1               5               10              15
```

-continued

```
Ser Ile Thr Ile Ser Cys Thr Gly Ala Ser Gly Asp Val Gly Ala Tyr
            20              25              30

Asn Phe Val Ser Trp Tyr Gln Gln His Pro Gly Lys Ala Pro Lys Leu
            35              40              45

Ile Ile Tyr Asp Val Asn Lys Arg Pro Ser Gly Val Ser Asn Arg Phe
    50              55              60

Ser Gly Ser Lys Ser Gly Asn Thr Ala Ser Leu Thr Ile Ser Gly Leu
65              70              75              80

Gln Ala Glu Asp Glu Ala Asp Tyr Tyr Cys Ser Ser Tyr Thr Ser Thr
            85              90              95

Phe Ser Val Val Phe Gly Gly Gly Thr Lys Leu Thr Val Leu Gly Gln
            100             105             110

Pro Lys Ala Ala Pro Ser Val Thr Leu Phe Pro Pro Ser Ser Glu Glu
            115             120             125

Leu Gln Ala Asn Lys Ala Thr Leu Val Cys Leu Ile Ser Asp Phe Tyr
    130             135             140

Pro Gly Ala Val Thr Val Ala Trp Lys Ala Asp Ser Ser Pro Val Lys
145             150             155             160

Ala Gly Val Glu Thr Thr Thr Pro Ser Lys Gln Ser Asn Asn Lys Tyr
            165             170             175

Ala Ala Ser Ser Tyr Leu Ser Leu Thr Pro Glu Gln Trp Lys Ser His
            180             185             190

Arg Ser Tyr Ser Cys Gln Val Thr His Glu Gly Ser Thr Val Glu Lys
            195             200             205

Thr Val Ala Pro Thr Glu Cys Ser
    210             215
```

```
<210> SEQ ID NO 913
<211> LENGTH: 635
<212> TYPE: PRT
<213> ORGANISM: Artificial sequence
<220> FEATURE:
<223> OTHER INFORMATION: an artificially synthesized sequence

<400> SEQUENCE: 913
```

```
Glu Val Gln Leu Val Glu Ser Gly Gly Gly Val Val Arg Pro Gly Gly
1               5               10              15

Ser Leu Arg Leu Ser Cys Ala Ala Ser Gly Phe Thr Phe Asp Asp Tyr
            20              25              30

Gly Met Asn Trp Val Arg Gln Ala Pro Gly Lys Gly Leu Glu Trp Val
            35              40              45

Ser Gly Val Asn Trp Asn Gly Gly Thr Arg Asp Tyr Ala Ala Ser Val
    50              55              60

Lys Gly Arg Phe Thr Ile Ser Arg Asp Asn Ala Lys Asn Ser Leu Tyr
65              70              75              80

Leu Gln Met Asn Ser Leu Arg Ala Glu Asp Thr Ala Leu Tyr His Cys
            85              90              95

Ala Arg Gly Trp Tyr Ser Gly Ala Ala Trp Asn Met Gly Tyr Trp Gly
            100             105             110

Arg Gly Thr Leu Val Thr Val Ser Ser Thr Ser Thr Ser Gly Arg Ser
            115             120             125

Ala Asn Pro Arg Gly Ala Ser Thr Lys Gly Pro Ser Val Phe Pro Leu
    130             135             140

Ala Pro Ser Ser Lys Ser Thr Ser Gly Gly Thr Ala Ala Leu Gly Cys
145             150             155             160
```

-continued

```
Leu Val Lys Asp Tyr Phe Pro Glu Pro Val Thr Val Ser Trp Asn Ser
            165             170             175

Gly Ala Leu Thr Ser Gly Val His Thr Phe Pro Ala Val Leu Gln Ser
            180             185             190

Ser Gly Leu Tyr Ser Leu Ser Ser Val Val Thr Val Pro Ser Ser Ser
            195             200             205

Leu Gly Thr Gln Thr Tyr Ile Cys Asn Val Asn His Lys Pro Ser Asn
        210             215             220

Thr Lys Val Asp Lys Arg Val Gly Gly Gly Ser Gly Gly Gly Gly
225             230             235             240

Ser Glu Pro Lys Ser Cys Asp Lys Thr His Thr Cys Pro Pro Cys Pro
                245             250             255

Ala Pro Glu Leu Arg Arg Gly Pro Ser Val Phe Leu Phe Pro Pro Lys
            260             265             270

Pro Lys Asp Thr Leu Met Ile Ser Arg Thr Pro Glu Val Thr Cys Val
            275             280             285

Val Val Asp Val Ser His Glu Asp Pro Glu Val Lys Phe Asn Trp Tyr
        290             295             300

Val Asp Gly Val Glu Val His Asn Ala Lys Thr Lys Pro Arg Glu Glu
305             310             315             320

Gln Tyr Asn Ser Thr Tyr Arg Val Val Ser Val Leu Thr Val Leu His
            325             330             335

Gln Asp Trp Leu Asn Gly Lys Glu Tyr Lys Cys Lys Val Ser Asn Lys
            340             345             350

Ala Leu Pro Ala Pro Ile Glu Lys Thr Ile Ser Lys Ala Lys Gly Gln
            355             360             365

Pro Arg Glu Pro Gln Val Tyr Thr Leu Pro Pro Ser Arg Glu Glu Met
            370             375             380

Thr Lys Asn Gln Val Ser Leu Thr Cys Leu Val Lys Gly Phe Tyr Pro
385             390             395             400

Ser Asp Ile Ala Val Glu Trp Glu Ser Asn Gly Gln Pro Glu Asn Asn
            405             410             415

Tyr Lys Thr Thr Pro Pro Val Leu Asp Ser Asp Gly Ser Phe Phe Leu
            420             425             430

Tyr Ser Lys Leu Thr Val Asp Lys Ser Arg Trp Gln Gln Gly Asn Val
            435             440             445

Phe Ser Cys Ser Val Met His Glu Ala Leu His Asn His Tyr Thr Gln
    450             455             460

Lys Ser Leu Ser Leu Ser Pro Gly Gly Ser Thr Ser Thr Ser Gly Arg
465             470             475             480

Ser Ala Asn Pro Arg Gly Gly Gly Ser Ala Pro Ile Ser Ser His Cys
                485             490             495

Arg Leu Asp Lys Ser Asn Phe Gln Gln Pro Tyr Ile Thr Asn Arg Thr
            500             505             510

Phe Met Leu Ala Lys Glu Ala Ser Leu Ala Asp Asn Asn Thr Asp Val
            515             520             525

Arg Leu Ile Gly Glu Lys Leu Phe His Gly Val Ser Met Ser Glu Arg
        530             535             540

Cys Tyr Leu Met Lys Gln Val Leu Asn Phe Thr Leu Glu Glu Val Leu
545             550             555             560

Phe Pro Gln Ser Asp Arg Phe Gln Pro Tyr Met Gln Glu Val Val Pro
                565             570             575
```

-continued

```
Phe Leu Ala Arg Leu Ser Asn Arg Leu Ser Thr Cys His Ile Glu Gly
            580                 585                 590

Asp Asp Leu His Ile Gln Arg Asn Val Gln Lys Leu Lys Asp Thr Val
            595                 600                 605

Lys Lys Leu Gly Glu Ser Gly Glu Ile Lys Ala Ile Gly Glu Leu Asp
        610                 615                 620

Leu Leu Phe Met Ser Leu Arg Asn Ala Cys Ile
625                 630                 635
```

```
<210> SEQ ID NO 914
<211> LENGTH: 121
<212> TYPE: PRT
<213> ORGANISM: Artificial sequence
<220> FEATURE:
<223> OTHER INFORMATION: an artificially synthesized sequence

<400> SEQUENCE: 914
```

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
            35                  40                  45

Ser Gly Val Asn Trp Asn Gly Gly Thr Arg Asp Tyr Ala Ala Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Gly Trp Tyr Ser Gly Ala Ala Trp Asn Met Gly Tyr Trp Gly
            100                 105                 110

Arg Gly Thr Leu Val Thr Val Ser Ser
        115                 120
```

```
<210> SEQ ID NO 915
<211> LENGTH: 216
<212> TYPE: PRT
<213> ORGANISM: Artificial sequence
<220> FEATURE:
<223> OTHER INFORMATION: an artificially synthesized sequence

<400> SEQUENCE: 915
```

```
Gln Ala Ala Leu Thr Gln Pro Ala Ser Val Ser Gly Ser Pro Gly Gln
1               5                   10                  15

Ser Ile Thr Ile Ser Cys Thr Gly Ala Ser Gly Asp Val Gly Ala Tyr
            20                  25                  30

Asn Phe Val Ser Trp Tyr Gln Gln His Pro Gly Lys Ala Pro Lys Leu
            35                  40                  45

Ile Ile Tyr Asp Val Asn Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Thr
                85                  90                  95

Phe Ser Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125
```

-continued

```
Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Ser Ser
    210                 215
```

```
<210> SEQ ID NO 916
<211> LENGTH: 635
<212> TYPE: PRT
<213> ORGANISM: Artificial sequence
<220> FEATURE:
<223> OTHER INFORMATION: an artificially synthesized sequence

<400> SEQUENCE: 916
```

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
            35                  40                  45

Ser Gly Val Asn Trp Asn Gly Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
            85                  90                  95

Ala Arg Gly Trp Tyr Ser Gly Ala Ala Trp Asn Met Gly Tyr Trp Gly
            100                 105                 110

Arg Gly Thr Leu Val Thr Val Ser Ser Thr Ser Thr Ser Gly Arg Ser
        115                 120                 125

Ala Asn Pro Arg Gly Ala Ser Thr Lys Gly Pro Ser Val Phe Pro Leu
    130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
    210                 215                 220

Thr Lys Val Asp Lys Arg Val Gly Gly Gly Ser Gly Gly Gly Gly
225                 230                 235                 240

Ser Glu Pro Lys Ser Ser Asp Lys Thr His Thr Cys Pro Pro Cys Pro
                245                 250                 255

Ala Pro Glu Leu Arg Arg Gly Pro Ser Val Phe Leu Phe Pro Pro Lys
    260                 265                 270
```

-continued

```
Pro Lys Asp Thr Leu Met Ile Ser Arg Thr Pro Glu Val Thr Cys Val
    275                 280             285

Val Val Asp Val Ser His Glu Asp Pro Glu Val Lys Phe Asn Trp Tyr
    290                 295             300

Val Asp Gly Val Glu Val His Asn Ala Lys Thr Lys Pro Arg Glu Glu
305                 310             315                 320

Gln Tyr Asn Ser Thr Tyr Arg Val Val Ser Val Leu Thr Val Leu His
                325             330             335

Gln Asp Trp Leu Asn Gly Lys Glu Tyr Lys Cys Lys Val Ser Asn Lys
            340             345             350

Ala Leu Pro Ala Pro Ile Glu Lys Thr Ile Ser Lys Ala Lys Gly Gln
            355             360             365

Pro Arg Glu Pro Gln Val Tyr Thr Leu Pro Pro Ser Arg Glu Glu Met
    370             375             380

Thr Lys Asn Gln Val Ser Leu Thr Cys Leu Val Lys Gly Phe Tyr Pro
385             390             395                 400

Ser Asp Ile Ala Val Glu Trp Glu Ser Asn Gly Gln Pro Glu Asn Asn
            405             410             415

Tyr Lys Thr Thr Pro Pro Val Leu Asp Ser Asp Gly Ser Phe Phe Leu
            420             425             430

Tyr Ser Lys Leu Thr Val Asp Lys Ser Arg Trp Gln Gln Gly Asn Val
            435             440             445

Phe Ser Cys Ser Val Met His Glu Ala Leu His Asn His Tyr Thr Gln
    450             455             460

Lys Ser Leu Ser Leu Ser Pro Gly Gly Ser Thr Ser Thr Ser Gly Arg
465             470             475                 480

Ser Ala Asn Pro Arg Gly Gly Gly Ser Ala Pro Ile Ser Ser His Cys
            485             490             495

Arg Leu Asp Lys Ser Asn Phe Gln Gln Pro Tyr Ile Thr Asn Arg Thr
            500             505             510

Phe Met Leu Ala Lys Glu Ala Ser Leu Ala Asp Asn Asn Thr Asp Val
            515             520             525

Arg Leu Ile Gly Glu Lys Leu Phe His Gly Val Ser Met Ser Glu Arg
    530             535             540

Cys Tyr Leu Met Lys Gln Val Leu Asn Phe Thr Leu Glu Glu Val Leu
545             550             555                 560

Phe Pro Gln Ser Asp Arg Phe Gln Pro Tyr Met Gln Glu Val Val Pro
            565             570             575

Phe Leu Ala Arg Leu Ser Asn Arg Leu Ser Thr Cys His Ile Glu Gly
            580             585             590

Asp Asp Leu His Ile Gln Arg Asn Val Gln Lys Leu Lys Asp Thr Val
            595             600             605

Lys Lys Leu Gly Glu Ser Gly Glu Ile Lys Ala Ile Gly Glu Leu Asp
    610             615             620

Leu Leu Phe Met Ser Leu Arg Asn Ala Cys Ile
625             630             635
```

<210> SEQ ID NO 917
<211> LENGTH: 623
<212> TYPE: PRT
<213> ORGANISM: Artificial sequence
<220> FEATURE:
<223> OTHER INFORMATION: an artificially synthesized sequence

<400> SEQUENCE: 917

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Trp Asn Gly Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Gly Trp Tyr Ser Gly Ala Ala Trp Asn Met Gly Tyr Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Gly Gly Gly Gly Ser
    210                 215                 220

Gly Gly Gly Gly Ser Glu Pro Lys Ser Cys Asp Lys Thr His Thr Cys
225                 230                 235                 240

Pro Pro Cys Pro Ala Pro Glu Leu Arg Arg Gly Pro Ser Val Phe Leu
            245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
            275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
            325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
            355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415
```

```
Ser Phe Phe Leu Tyr Ser Lys Leu Thr Val Asp Lys Ser Arg Trp Gln
            420             425             430

Gln Gly Asn Val Phe Ser Cys Ser Val Met His Glu Ala Leu His Asn
        435             440             445

His Tyr Thr Gln Lys Ser Leu Ser Leu Ser Pro Gly Gly Ser Gly Gly
    450             455             460

Ser Gly Gly Ser Gly Gly Ser Gly Gly Ser Gly Gly Ser Ala Pro Ile
465             470             475             480

Ser Ser His Cys Arg Leu Asp Lys Ser Asn Phe Gln Gln Pro Tyr Ile
                485             490             495

Thr Asn Arg Thr Phe Met Leu Ala Lys Glu Ala Ser Leu Ala Asp Asn
            500             505             510

Asn Thr Asp Val Arg Leu Ile Gly Glu Lys Leu Phe His Gly Val Ser
            515             520             525

Met Ser Glu Arg Cys Tyr Leu Met Lys Gln Val Leu Asn Phe Thr Leu
    530             535             540

Glu Glu Val Leu Phe Pro Gln Ser Asp Arg Phe Gln Pro Tyr Met Gln
545             550             555             560

Glu Val Val Pro Phe Leu Ala Arg Leu Ser Asn Arg Leu Ser Thr Cys
            565             570             575

His Ile Glu Gly Asp Asp Leu His Ile Gln Arg Asn Val Gln Lys Leu
            580             585             590

Lys Asp Thr Val Lys Lys Leu Gly Glu Ser Gly Glu Ile Lys Ala Ile
            595             600             605

Gly Glu Leu Asp Leu Leu Phe Met Ser Leu Arg Asn Ala Cys Ile
    610             615             620
```

```
<210> SEQ ID NO 918
<211> LENGTH: 141
<212> TYPE: PRT
<213> ORGANISM: Artificial sequence
<220> FEATURE:
<223> OTHER INFORMATION: an artificially synthesized sequence

<400> SEQUENCE: 918
```

```
Ala Pro Thr Ser Ser Ser Thr Lys Lys Thr Gln Leu Gln Leu Glu His
1               5               10              15

Leu Leu Leu Asp Leu Gln Met Ile Leu Asn Gly Ile Asn Asn Tyr Lys
            20              25              30

Asn Pro Lys Leu Thr Arg Met Leu Thr Phe Lys Phe Tyr Met Pro Lys
        35              40              45

Lys Ala Thr Glu Leu Lys His Leu Gln Cys Leu Glu Glu Glu Leu Lys
    50              55              60

Pro Leu Glu Glu Val Leu Asn Leu Ala Gln Ser Lys Asn Phe His Leu
65              70              75              80

Arg Pro Arg Asp Leu Ile Ser Asp Ile Asn Val Ile Val Leu Glu Leu
            85              90              95

Lys Gly Ser Glu Thr Thr Phe Met Cys Glu Tyr Ala Asp Glu Thr Ala
            100             105             110

Thr Ile Val Glu Phe Leu Asn Arg Trp Ile Thr Phe Ala Gln Ser Ile
            115             120             125

Ile Ser Thr Leu Thr His His His His His His
    130             135             140
```

```
<210> SEQ ID NO 919
<211> LENGTH: 637
```

<212> TYPE: PRT
<213> ORGANISM: Artificial sequence
<220> FEATURE:
<223> OTHER INFORMATION: an artificially synthesized sequence

<400> SEQUENCE: 919

```
Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
                20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Trp Arg Gly Asp Gly Tyr Tyr Ala Tyr Phe Asp Val Trp Gly
            100                 105                 110

Ala Gly Thr Thr Val Thr Val Ser Ser Thr Ser Thr Ser Gly Arg Ser
            115                 120                 125

Ala Asn Pro Arg Gly Ala Ser Thr Lys Gly Pro Ser Val Phe Pro Leu
    130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
            195                 200                 205

Leu Gly Thr Gln Thr Tyr Ile Cys Asn Val Asn His Lys Pro Ser Asn
    210                 215                 220

Thr Lys Val Asp Lys Arg Val Glu Pro Lys Ser Cys Asp Lys Thr His
225                 230                 235                 240

Thr Gly Gly Gly Gly Ser Gly Gly Gly Gly Ser Cys Pro Pro Cys Pro
            245                 250                 255

Ala Pro Glu Leu Arg Arg Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Gly Leu Pro Ser Ser Ile Glu Lys Thr Ile Ser Lys Ala Lys Gly Gln
            355                 360                 365

Pro Arg Glu Pro Gln Val Tyr Thr Leu Pro Pro Ser Arg Glu Glu Met
    370                 375                 380
```

-continued

```
Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
                420                 425                 430

Tyr Ser Lys Leu Thr Val Asp Lys Ser Arg Trp Gln Glu Gly Asn Val
                435                 440                 445

Phe Ser Cys Ser Val Met His Glu Ala Leu His Asn His Tyr Thr Gln
    450                 455                 460

Lys Ser Leu Ser Leu Ser Pro Gly Gly Gly Ser Gly Gly Gly Gly
465                 470                 475                 480

Ser Gly Gly Gly Gly Ser Gly Gly Gly Gly Ser Gly Gly Gly Gly Ser
                485                 490                 495

Ala Pro Thr Ser Ser Ser Thr Lys Lys Thr Gln Leu Gln Leu Glu His
                500                 505                 510

Leu Leu Leu Asp Leu Gln Met Ile Leu Asn Gly Ile Asn Asn Tyr Lys
                515                 520                 525

Asn Pro Lys Leu Thr Arg Met Leu Thr Phe Lys Phe Tyr Met Pro Lys
    530                 535                 540

Lys Ala Thr Glu Leu Lys His Leu Gln Cys Leu Glu Glu Glu Leu Lys
545                 550                 555                 560

Pro Leu Glu Glu Val Leu Asn Leu Ala Gln Ser Lys Asn Phe His Leu
                565                 570                 575

Arg Pro Arg Asp Leu Ile Ser Asp Ile Asn Val Ile Val Leu Glu Leu
                580                 585                 590

Lys Gly Ser Glu Thr Thr Phe Met Cys Glu Tyr Ala Asp Glu Thr Ala
                595                 600                 605

Thr Ile Val Glu Phe Leu Asn Arg Trp Ile Thr Phe Ala Gln Ser Ile
    610                 615                 620

Ile Ser Thr Leu Thr His His His His His His His
625                 630                 635
```

```
<210> SEQ ID NO 920
<211> LENGTH: 218
<212> TYPE: PRT
<213> ORGANISM: Artificial sequence
<220> FEATURE:
<223> OTHER INFORMATION: an artificially synthesized sequence

<400> SEQUENCE: 920

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys Arg
            100                 105                 110
```

-continued

```
Thr Val Ala Ala Pro Ser Val Phe Ile Phe Pro Pro Ser Asp Glu Gln
        115                 120             125

Leu Lys Ser Gly Thr Ala Ser Val Val Cys Leu Leu Asn Asn Phe Tyr
    130                 135             140

Pro Arg Glu Ala Lys Val Gln Trp Lys Val Asp Asn Ala Leu Gln Ser
145                 150             155                 160

Gly Asn Ser Gln Glu Ser Val Thr Glu Gln Asp Ser Lys Asp Ser Thr
            165             170             175

Tyr Ser Leu Ser Ser Thr Leu Thr Leu Ser Lys Ala Asp Tyr Glu Lys
        180             185             190

His Lys Val Tyr Ala Cys Glu Val Thr His Gln Gly Leu Ser Ser Pro
        195             200             205

Val Thr Lys Ser Phe Asn Arg Gly Glu Cys
    210             215
```

```
<210> SEQ ID NO 921
<211> LENGTH: 637
<212> TYPE: PRT
<213> ORGANISM: Artificial sequence
<220> FEATURE:
<223> OTHER INFORMATION: an artificially synthesized sequence

<400> SEQUENCE: 921

Gln Val Gln Leu Gln Gln Ser Gly Ala Glu Leu Val Arg Pro Gly Thr
1               5               10              15

Ser Val Lys Val Ser Cys Lys Ala Ser Gly Tyr Ala Phe Thr Asn Tyr
            20              25              30

Leu Ile Glu Trp Val Lys Gln Arg Pro Gly Gln Gly Leu Glu Trp Ile
        35              40              45

Gly Val Ile Asn Pro Gly Ser Gly Gly Thr Asn Tyr Asn Glu Lys Phe
    50              55              60

Lys Gly Lys Ala Thr Leu Thr Ala Asp Lys Ser Ser Ser Thr Ala Tyr
65              70              75              80

Met Gln Leu Ser Ser Leu Thr Ser Asp Asp Ser Ala Val Tyr Phe Cys
            85              90              95

Ala Arg Trp Arg Gly Asp Gly Tyr Tyr Ala Tyr Phe Asp Val Trp Gly
        100             105             110

Ala Gly Thr Thr Val Thr Val Ser Ser Gly Gly Gly Ser Gly Gly Gly
        115             120             125

Ser Gly Gly Gly Ser Ala Ser Thr Lys Gly Pro Ser Val Phe Pro Leu
    130             135             140

Ala Pro Ser Ser Lys Ser Thr Ser Gly Gly Thr Ala Ala Leu Gly Cys
145             150             155             160

Leu Val Lys Asp Tyr Phe Pro Glu Pro Val Thr Val Ser Trp Asn Ser
            165             170             175

Gly Ala Leu Thr Ser Gly Val His Thr Phe Pro Ala Val Leu Gln Ser
            180             185             190

Ser Gly Leu Tyr Ser Leu Ser Ser Val Val Thr Val Pro Ser Ser Ser
        195             200             205

Leu Gly Thr Gln Thr Tyr Ile Cys Asn Val Asn His Lys Pro Ser Asn
    210             215             220

Thr Lys Val Asp Lys Arg Val Glu Pro Lys Ser Cys Asp Lys Thr His
225             230             235             240

Thr Gly Gly Gly Gly Ser Gly Gly Gly Gly Ser Cys Pro Pro Cys Pro
            245             250             255
```

-continued

```
Ala Pro Glu Leu Arg Arg Gly Pro Ser Val Phe Leu Phe Pro Pro Lys
            260             265             270

Pro Lys Asp Thr Leu Met Ile Ser Arg Thr Pro Glu Val Thr Cys Val
        275             280             285

Val Val Asp Val Ser His Glu Asp Pro Glu Val Lys Phe Asn Trp Tyr
    290             295             300

Val Asp Gly Val Glu Val His Asn Ala Lys Thr Lys Pro Arg Glu Glu
305             310             315             320

Gln Tyr Asn Ser Thr Tyr Arg Val Val Ser Val Leu Thr Val Leu His
            325             330             335

Gln Asp Trp Leu Asn Gly Lys Glu Tyr Lys Cys Lys Val Ser Asn Lys
        340             345             350

Gly Leu Pro Ser Ser Ile Glu Lys Thr Ile Ser Lys Ala Lys Gly Gln
        355             360             365

Pro Arg Glu Pro Gln Val Tyr Thr Leu Pro Pro Ser Arg Glu Glu Met
    370             375             380

Thr Lys Asn Gln Val Ser Leu Thr Cys Leu Val Lys Gly Phe Tyr Pro
385             390             395             400

Ser Asp Ile Ala Val Glu Trp Glu Ser Asn Gly Gln Pro Glu Asn Asn
            405             410             415

Tyr Lys Thr Thr Pro Pro Val Leu Asp Ser Asp Gly Ser Phe Phe Leu
            420             425             430

Tyr Ser Lys Leu Thr Val Asp Lys Ser Arg Trp Gln Glu Gly Asn Val
        435             440             445

Phe Ser Cys Ser Val Met His Glu Ala Leu His Asn His Tyr Thr Gln
    450             455             460

Lys Ser Leu Ser Leu Ser Pro Gly Gly Gly Gly Ser Gly Gly Gly Gly
465             470             475             480

Ser Gly Gly Gly Gly Ser Gly Gly Gly Gly Ser Gly Gly Gly Gly Ser
            485             490             495

Ala Pro Thr Ser Ser Ser Thr Lys Lys Thr Gln Leu Gln Leu Glu His
        500             505             510

Leu Leu Leu Asp Leu Gln Met Ile Leu Asn Gly Ile Asn Asn Tyr Lys
        515             520             525

Asn Pro Lys Leu Thr Arg Met Leu Thr Phe Lys Phe Tyr Met Pro Lys
    530             535             540

Lys Ala Thr Glu Leu Lys His Leu Gln Cys Leu Glu Glu Glu Leu Lys
545             550             555             560

Pro Leu Glu Glu Val Leu Asn Leu Ala Gln Ser Lys Asn Phe His Leu
            565             570             575

Arg Pro Arg Asp Leu Ile Ser Asp Ile Asn Val Ile Val Leu Glu Leu
        580             585             590

Lys Gly Ser Glu Thr Thr Phe Met Cys Glu Tyr Ala Asp Glu Thr Ala
        595             600             605

Thr Ile Val Glu Phe Leu Asn Arg Trp Ile Thr Phe Ala Gln Ser Ile
    610             615             620

Ile Ser Thr Leu Thr His His His His His His
625             630             635
```

<210> SEQ ID NO 922
<211> LENGTH: 635
<212> TYPE: PRT
<213> ORGANISM: Artificial sequence
<220> FEATURE:
<223> OTHER INFORMATION: an artificially synthesized sequence -continued

```
<400> SEQUENCE: 922

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Ala Met Asn Trp Val Arg Gln Ala Pro Gly Lys Gly Leu Glu Trp Val
            35                  40                  45

Thr Leu Ile Ser Tyr Asp Gly Ser Gln Lys Tyr Tyr Ala Asp Ser Val
        50                  55                  60

Lys Gly Arg Phe Thr Thr Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Thr Thr Leu Gly Ala Phe Asp Val Trp Gly Gln Gly
            100                 105                 110

Thr Met Val Thr Val Ser Ser Thr Ser Thr Ser Gly Arg Ser Ala Asn
        115                 120                 125

Pro Arg Gly Ala Ser Thr Lys Gly Pro Ser Val Phe Pro Leu Ala Pro
        130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
            195                 200                 205

Thr Gln Thr Tyr Ile Cys Asn Val Asn His Lys Pro Ser Asn Thr Lys
        210                 215                 220

Val Asp Lys Arg Val Glu Pro Lys Ser Cys Asp Lys Thr His Thr Gly
225                 230                 235                 240

Gly Gly Gly Ser Gly Gly Gly Gly Ser Cys Pro Pro Cys Pro Ala Pro
                245                 250                 255

Glu Leu Arg Arg Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
            355                 360                 365

Glu Pro Gln Val Tyr Thr Leu Pro Pro Ser Arg Glu Glu Met Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
```

-continued

```
                    405              410              415
Thr Thr Pro Pro Val Leu Asp Ser Asp Gly Ser Phe Phe Leu Tyr Ser
            420              425              430
Lys Leu Thr Val Asp Lys Ser Arg Trp Gln Glu Gly Asn Val Phe Ser
        435              440              445
Cys Ser Val Met His Glu Ala Leu His Asn His Tyr Thr Gln Lys Ser
    450              455              460
Leu Ser Leu Ser Pro Gly Gly Gly Gly Ser Gly Gly Gly Gly Ser Gly
465              470              475              480
Gly Gly Ser Gly Gly Gly Gly Ser Gly Gly Gly Gly Ser Ala Pro
            485              490              495
Thr Ser Ser Ser Thr Lys Lys Thr Gln Leu Gln Leu Glu His Leu Leu
        500              505              510
Leu Asp Leu Gln Met Ile Leu Asn Gly Ile Asn Asn Tyr Lys Asn Pro
        515              520              525
Lys Leu Thr Arg Met Leu Thr Phe Lys Phe Tyr Met Pro Lys Lys Ala
        530              535              540
Thr Glu Leu Lys His Leu Gln Cys Leu Glu Glu Glu Leu Lys Pro Leu
545              550              555              560
Glu Glu Val Leu Asn Leu Ala Gln Ser Lys Asn Phe His Leu Arg Pro
            565              570              575
Arg Asp Leu Ile Ser Asp Ile Asn Val Ile Val Leu Glu Leu Lys Gly
            580              585              590
Ser Glu Thr Thr Phe Met Cys Glu Tyr Ala Asp Glu Thr Ala Thr Ile
        595              600              605
Val Glu Phe Leu Asn Arg Trp Ile Thr Phe Ala Gln Ser Ile Ile Ser
    610              615              620
Thr Leu Thr His His His His His His His
625              630              635
```

```
<210> SEQ ID NO 923
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 923

Ser Tyr Glu Leu Thr Gln Pro Pro Ser Leu Ser Val Ser Pro Gly Gln
1               5               10              15
Thr Ala Thr Ile Ser Cys Ser Gly Asp Ala Phe Pro Arg Lys Phe Ala
            20              25              30
Tyr Trp Tyr Gln Gln Lys Ser Gly Gln Ala Pro Val Leu Val Ile Tyr
        35              40              45
Glu Asp Thr Arg Arg Pro Ser Gly Ile Pro Glu Arg Phe Ser Gly Ser
    50              55              60
Ser Ser Gly Thr Met Ala Thr Leu Thr Ile Ser Gly Ala Gln Val Glu
65              70              75              80
Asp Glu Ala Asp Tyr Phe Cys Tyr Ser Thr Asp Thr Thr Gly Thr His
            85              90              95
Arg Val Phe Gly Gly Gly Thr Lys Leu Thr Val Leu Gly Gln Pro Lys
            100             105             110
Ala Ala Pro Ser Val Thr Leu Phe Pro Pro Ser Ser Glu Glu Leu Gln
        115             120             125
Ala Asn Lys Ala Thr Leu Val Cys Leu Ile Ser Asp Phe Tyr Pro Gly
```

```
        130              135              140
Ala Val Thr Val Ala Trp Lys Ala Asp Ser Ser Pro Val Lys Ala Gly
145              150              155              160

Val Glu Thr Thr Thr Pro Ser Lys Gln Ser Asn Asn Lys Tyr Ala Ala
                165              170              175

Ser Ser Tyr Leu Ser Leu Thr Pro Glu Gln Trp Lys Ser His Arg Ser
            180              185              190

Tyr Ser Cys Gln Val Thr His Glu Gly Ser Thr Val Glu Lys Thr Val
            195              200              205

Ala Pro Thr Glu Cys Ser
    210

<210> SEQ ID NO 924
<211> LENGTH: 635
<212> TYPE: PRT
<213> ORGANISM: Artificial sequence
<220> FEATURE:
<223> OTHER INFORMATION: an artificially synthesized sequence

<400> SEQUENCE: 924

Gln Val Gln Leu Val Gln Ser Gly Gly Gly Val Val Gln Pro Gly Arg
1               5               10              15

Ser Leu Arg Leu Ser Cys Ala Ala Ser Gly Phe Thr Phe Ser Asn Tyr
            20              25              30

Ala Met Asn Trp Val Arg Gln Ala Pro Gly Lys Gly Leu Glu Trp Val
            35              40              45

Thr Leu Ile Ser Tyr Asp Gly Ser Gln Lys Tyr Tyr Ala Asp Ser Val
    50              55              60

Lys Gly Arg Phe Thr Thr Ser Arg Asp Asn Ser Lys Asn Thr Leu Tyr
65              70              75              80

Leu Gln Met Asn Ser Leu Arg Ala Glu Asp Thr Ala Val Tyr Tyr Cys
            85              90              95

Ala Arg Asp Ser Thr Thr Leu Gly Ala Phe Asp Val Trp Gly Gln Gly
            100             105             110

Thr Met Val Thr Val Ser Ser Gly Gly Gly Ser Gly Gly Gly Ser Gly
            115             120             125

Gly Gly Ser Ala Ser Thr Lys Gly Pro Ser Val Phe Pro Leu Ala Pro
    130             135             140

Ser Ser Lys Ser Thr Ser Gly Gly Thr Ala Ala Leu Gly Cys Leu Val
145             150             155             160

Lys Asp Tyr Phe Pro Glu Pro Val Thr Val Ser Trp Asn Ser Gly Ala
            165             170             175

Leu Thr Ser Gly Val His Thr Phe Pro Ala Val Leu Gln Ser Ser Gly
            180             185             190

Leu Tyr Ser Leu Ser Ser Val Val Thr Val Pro Ser Ser Ser Leu Gly
            195             200             205

Thr Gln Thr Tyr Ile Cys Asn Val Asn His Lys Pro Ser Asn Thr Lys
    210             215             220

Val Asp Lys Arg Val Glu Pro Lys Ser Cys Asp Lys Thr His Thr Gly
225             230             235             240

Gly Gly Gly Ser Gly Gly Gly Gly Ser Cys Pro Pro Cys Pro Ala Pro
            245             250             255

Glu Leu Arg Arg Gly Pro Ser Val Phe Leu Phe Pro Pro Lys Pro Lys
            260             265             270

Asp Thr Leu Met Ile Ser Arg Thr Pro Glu Val Thr Cys Val Val Val
```

-continued

```
              275               280               285

Asp Val Ser His Glu Asp Pro Glu Val Lys Phe Asn Trp Tyr Val Asp
    290               295               300

Gly Val Glu Val His Asn Ala Lys Thr Lys Pro Arg Glu Glu Gln Tyr
305               310               315               320

Asn Ser Thr Tyr Arg Val Val Ser Val Leu Thr Val Leu His Gln Asp
              325               330               335

Trp Leu Asn Gly Lys Glu Tyr Lys Cys Lys Val Ser Asn Lys Gly Leu
              340               345               350

Pro Ser Ser Ile Glu Lys Thr Ile Ser Lys Ala Lys Gly Gln Pro Arg
              355               360               365

Glu Pro Gln Val Tyr Thr Leu Pro Pro Ser Arg Glu Glu Met Thr Lys
    370               375               380

Asn Gln Val Ser Leu Thr Cys Leu Val Lys Gly Phe Tyr Pro Ser Asp
385               390               395               400

Ile Ala Val Glu Trp Glu Ser Asn Gly Gln Pro Glu Asn Asn Tyr Lys
              405               410               415

Thr Thr Pro Pro Val Leu Asp Ser Asp Gly Ser Phe Phe Leu Tyr Ser
              420               425               430

Lys Leu Thr Val Asp Lys Ser Arg Trp Gln Glu Gly Asn Val Phe Ser
              435               440               445

Cys Ser Val Met His Glu Ala Leu His Asn His Tyr Thr Gln Lys Ser
    450               455               460

Leu Ser Leu Ser Pro Gly Gly Gly Gly Ser Gly Gly Gly Gly Ser Gly
465               470               475               480

Gly Gly Gly Ser Gly Gly Gly Gly Ser Gly Gly Gly Gly Ser Ala Pro
              485               490               495

Thr Ser Ser Ser Thr Lys Lys Thr Gln Leu Gln Leu Glu His Leu Leu
              500               505               510

Leu Asp Leu Gln Met Ile Leu Asn Gly Ile Asn Asn Tyr Lys Asn Pro
              515               520               525

Lys Leu Thr Arg Met Leu Thr Phe Lys Phe Tyr Met Pro Lys Lys Ala
    530               535               540

Thr Glu Leu Lys His Leu Gln Cys Leu Glu Glu Glu Leu Lys Pro Leu
545               550               555               560

Glu Glu Val Leu Asn Leu Ala Gln Ser Lys Asn Phe His Leu Arg Pro
              565               570               575

Arg Asp Leu Ile Ser Asp Ile Asn Val Ile Val Leu Glu Leu Lys Gly
              580               585               590

Ser Glu Thr Thr Phe Met Cys Glu Tyr Ala Asp Glu Thr Ala Thr Ile
              595               600               605

Val Glu Phe Leu Asn Arg Trp Ile Thr Phe Ala Gln Ser Ile Ile Ser
    610               615               620

Thr Leu Thr His His His His His His His
625               630               635
```

<210> SEQ ID NO 925
<211> LENGTH: 632
<212> TYPE: PRT
<213> ORGANISM: Artificial sequence
<220> FEATURE:
<223> OTHER INFORMATION: an artificially synthesized sequence

<400> SEQUENCE: 925

Gln Val Gln Leu Gln Gln Ser Gly Pro Gln Leu Val Arg Pro Gly Ala

-continued

```
1                  5                 10                15
Ser Val Lys Ile Ser Cys Lys Ala Ser Gly Tyr Ser Phe Thr Ser Tyr
                20                25                30

Trp Met His Trp Val Asn Gln Arg Pro Gly Gln Gly Leu Glu Trp Ile
                35                40                45

Gly Met Ile Asp Pro Ser Tyr Ser Glu Thr Arg Leu Asn Gln Lys Phe
                50                55                60

Lys Asp Lys Ala Thr Leu Thr Val Asp Lys Ser Ser Ser Thr Ala Tyr
65                70                75                80

Met Gln Leu Ser Ser Pro Thr Ser Glu Asp Ser Ala Val Tyr Tyr Cys
                85                90                95

Ala Leu Tyr Gly Asn Tyr Phe Asp Tyr Trp Gly Gln Gly Thr Thr Leu
                100               105               110

Thr Val Ser Ser Gly Gly Gly Ser Gly Gly Gly Ser Gly Gly Gly Ser
                115               120               125

Ala Ser Thr Lys Gly Pro Ser Val Phe Pro Leu Ala Pro Ser Ser Lys
                130               135               140

Ser Thr Ser Gly Gly Thr Ala Ala Leu Gly Cys Leu Val Lys Asp Tyr
145               150               155               160

Phe Pro Glu Pro Val Thr Val Ser Trp Asn Ser Gly Ala Leu Thr Ser
                165               170               175

Gly Val His Thr Phe Pro Ala Val Leu Gln Ser Ser Gly Leu Tyr Ser
                180               185               190

Leu Ser Ser Val Val Thr Val Pro Ser Ser Ser Leu Gly Thr Gln Thr
                195               200               205

Tyr Ile Cys Asn Val Asn His Lys Pro Ser Asn Thr Lys Val Asp Lys
                210               215               220

Arg Val Glu Pro Lys Ser Cys Asp Lys Thr His Thr Gly Gly Gly Gly
225               230               235               240

Ser Gly Gly Gly Gly Ser Cys Pro Pro Cys Pro Ala Pro Glu Leu Arg
                245               250               255

Arg Gly Pro Ser Val Phe Leu Phe Pro Pro Lys Pro Lys Asp Thr Leu
                260               265               270

Met Ile Ser Arg Thr Pro Glu Val Thr Cys Val Val Val Asp Val Ser
                275               280               285

His Glu Asp Pro Glu Val Lys Phe Asn Trp Tyr Val Asp Gly Val Glu
                290               295               300

Val His Asn Ala Lys Thr Lys Pro Arg Glu Glu Gln Tyr Asn Ser Thr
305               310               315               320

Tyr Arg Val Val Ser Val Leu Thr Val Leu His Gln Asp Trp Leu Asn
                325               330               335

Gly Lys Glu Tyr Lys Cys Lys Val Ser Asn Lys Gly Leu Pro Ser Ser
                340               345               350

Ile Glu Lys Thr Ile Ser Lys Ala Lys Gly Gln Pro Arg Glu Pro Gln
                355               360               365

Val Tyr Thr Leu Pro Pro Ser Arg Glu Glu Met Thr Lys Asn Gln Val
                370               375               380

Ser Leu Thr Cys Leu Val Lys Gly Phe Tyr Pro Ser Asp Ile Ala Val
385               390               395               400

Glu Trp Glu Ser Asn Gly Gln Pro Glu Asn Asn Tyr Lys Thr Thr Pro
                405               410               415

Pro Val Leu Asp Ser Asp Gly Ser Phe Phe Leu Tyr Ser Lys Leu Thr
                420               425               430
```

```
Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Gly Gly Gly Ser Gly Gly Gly Ser Gly Gly Gly Gly
465                 470                 475                 480

Ser Gly Gly Gly Gly Ser Gly Gly Gly Gly Ser Ala Pro Thr Ser Ser
                485                 490                 495

Ser Thr Lys Lys Thr Gln Leu Gln Leu Glu His Leu Leu Leu Asp Leu
            500                 505                 510

Gln Met Ile Leu Asn Gly Ile Asn Asn Tyr Lys Asn Pro Lys Leu Thr
        515                 520                 525

Arg Met Leu Thr Phe Lys Phe Tyr Met Pro Lys Lys Ala Thr Glu Leu
    530                 535                 540

Lys His Leu Gln Cys Leu Glu Glu Glu Leu Lys Pro Leu Glu Glu Val
545                 550                 555                 560

Leu Asn Leu Ala Gln Ser Lys Asn Phe His Leu Arg Pro Arg Asp Leu
                565                 570                 575

Ile Ser Asp Ile Asn Val Ile Val Leu Glu Leu Lys Gly Ser Glu Thr
            580                 585                 590

Thr Phe Met Cys Glu Tyr Ala Asp Glu Thr Ala Thr Ile Val Glu Phe
        595                 600                 605

Leu Asn Arg Trp Ile Thr Phe Ala Gln Ser Ile Ile Ser Thr Leu Thr
    610                 615                 620

His His His His His His His His
625                 630
```

```
<210> SEQ ID NO 926
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 926

Asp Ile Gln Met Thr Gln Ser Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Tyr
                85                  90                  95

Thr Phe Gly Gly Gly Thr Lys Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

-continued

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 927
<211> LENGTH: 25
<212> TYPE: PRT
<213> ORGANISM: Artificial sequence
<220> FEATURE:
<223> OTHER INFORMATION: an artificially synthesized sequence

<400> SEQUENCE: 927

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 928
<211> LENGTH: 12
<212> TYPE: PRT
<213> ORGANISM: Artificial sequence
<220> FEATURE:
<223> OTHER INFORMATION: an artificially synthesized sequence

<400> SEQUENCE: 928

Gly Gly Gly Ser Gly Gly Gly Ser Gly Gly Gly Ser
1               5                   10

<210> SEQ ID NO 929
<211> LENGTH: 635
<212> TYPE: PRT
<213> ORGANISM: Artificial sequence
<220> FEATURE:
<223> OTHER INFORMATION: an artificially synthesized sequence

<400> SEQUENCE: 929

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Gly Met Asn Trp Val Arg Gln Ala Pro Gly Lys Gly Leu Glu Trp Val
            35                  40                  45

Ser Gly Val Asn Trp Asn Gly Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Gly Trp Tyr Ser Gly Ala Ala Trp Asn Met Gly Tyr Trp Gly
            100                 105                 110

Arg Gly Thr Leu Val Thr Val Ser Ser Thr Ser Thr Ser Gly Arg Ser
            115                 120                 125

Ala Asn Pro Arg Gly Ala Ser Thr Lys Gly Pro Ser Val Phe Pro Leu
    130                 135                 140
```

-continued

```
Ala Pro Ser Ser Lys Ser Thr Ser Gly Gly Thr Ala Ala Leu Gly Cys
145             150              155              160

Leu Val Lys Asp Tyr Phe Pro Glu Pro Val Thr Val Ser Trp Asn Ser
                165          170              175

Gly Ala Leu Thr Ser Gly Val His Thr Phe Pro Ala Val Leu Gln Ser
            180              185              190

Ser Gly Leu Tyr Ser Leu Ser Ser Val Val Thr Val Pro Ser Ser Ser
            195              200              205

Leu Gly Thr Gln Thr Tyr Ile Cys Asn Val Asn His Lys Pro Ser Asn
            210              215              220

Thr Lys Val Asp Lys Arg Val Glu Pro Lys Ser Cys Gly Gly Gly Gly
225              230              235              240

Ser Gly Gly Gly Gly Ser Asp Lys Thr His Thr Cys Pro Pro Cys Pro
                245              250              255

Ala Pro Glu Leu Arg Arg Gly Pro Ser Val Phe Leu Phe Pro Pro Lys
            260              265              270

Pro Lys Asp Thr Leu Met Ile Ser Arg Thr Pro Glu Val Thr Cys Val
            275              280              285

Val Val Asp Val Ser His Glu Asp Pro Glu Val Lys Phe Asn Trp Tyr
    290              295              300

Val Asp Gly Val Glu Val His Asn Ala Lys Thr Lys Pro Arg Glu Glu
305              310              315              320

Gln Tyr Asn Ser Thr Tyr Arg Val Val Ser Val Leu Thr Val Leu His
            325              330              335

Gln Asp Trp Leu Asn Gly Lys Glu Tyr Lys Cys Lys Val Ser Asn Lys
            340              345              350

Ala Leu Pro Ala Pro Ile Glu Lys Thr Ile Ser Lys Ala Lys Gly Gln
            355              360              365

Pro Arg Glu Pro Gln Val Tyr Thr Leu Pro Pro Ser Arg Glu Glu Met
    370              375              380

Thr Lys Asn Gln Val Ser Leu Thr Cys Leu Val Lys Gly Phe Tyr Pro
385              390              395              400

Ser Asp Ile Ala Val Glu Trp Glu Ser Asn Gly Gln Pro Glu Asn Asn
            405              410              415

Tyr Lys Thr Thr Pro Pro Val Leu Asp Ser Asp Gly Ser Phe Phe Leu
            420              425              430

Tyr Ser Lys Leu Thr Val Asp Lys Ser Arg Trp Gln Gln Gly Asn Val
            435              440              445

Phe Ser Cys Ser Val Met His Glu Ala Leu His Asn His Tyr Thr Gln
    450              455              460

Lys Ser Leu Ser Leu Ser Pro Gly Gly Ser Thr Ser Thr Ser Gly Arg
465              470              475              480

Ser Ala Asn Pro Arg Gly Gly Gly Ser Ala Pro Ile Ser Ser His Cys
            485              490              495

Arg Leu Asp Lys Ser Asn Phe Gln Gln Pro Tyr Ile Thr Asn Arg Thr
            500              505              510

Phe Met Leu Ala Lys Glu Ala Ser Leu Ala Asp Asn Asn Thr Asp Val
            515              520              525

Arg Leu Ile Gly Glu Lys Leu Phe His Gly Val Ser Met Ser Glu Arg
    530              535              540

Cys Tyr Leu Met Lys Gln Val Leu Asn Phe Thr Leu Glu Glu Val Leu
545              550              555              560

Phe Pro Gln Ser Asp Arg Phe Gln Pro Tyr Met Gln Glu Val Val Pro
```

-continued

```
                      565                 570                 575

Phe Leu Ala Arg Leu Ser Asn Arg Leu Ser Thr Cys His Ile Glu Gly
            580                 585                 590

Asp Asp Leu His Ile Gln Arg Asn Val Gln Lys Leu Lys Asp Thr Val
            595                 600                 605

Lys Lys Leu Gly Glu Ser Gly Glu Ile Lys Ala Ile Gly Glu Leu Asp
            610                 615                 620

Leu Leu Phe Met Ser Leu Arg Asn Ala Cys Ile
625                 630                 635

<210> SEQ ID NO 930
<211> LENGTH: 635
<212> TYPE: PRT
<213> ORGANISM: Artificial sequence
<220> FEATURE:
<223> OTHER INFORMATION: an artificially synthesized sequence

<400> SEQUENCE: 930

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
            35                  40                  45

Ser Gly Val Asn Trp Asn Gly Gly Thr Arg Asp Tyr Ala Ala Ser Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Gly Trp Tyr Ser Gly Ala Ala Trp Asn Met Gly Tyr Trp Gly
            100                 105                 110

Arg Gly Thr Leu Val Thr Val Ser Ser Thr Ser Thr Ser Gly Arg Ser
            115                 120                 125

Ala Asn Pro Arg Gly Ala Ser Thr Lys Gly Pro Ser Val Phe Pro Leu
            130                 135                 140

Ala Pro Cys Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
            195                 200                 205

Leu Gly Thr Gln Thr Tyr Ile Cys Asn Val Asn His Lys Pro Ser Asn
            210                 215                 220

Thr Lys Val Asp Lys Arg Val Gly Gly Gly Ser Gly Gly Gly Gly
225                 230                 235                 240

Ser Glu Pro Lys Ser Ser Asp Lys Thr His Thr Cys Pro Pro Cys Pro
                245                 250                 255

Ala Pro Glu Leu Arg Arg Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
```

-continued

```
          290               295                300

Val Asp Gly Val Glu Val His Asn Ala Lys Thr Lys Pro Arg Glu Glu
305               310                315                320

Gln Tyr Asn Ser Thr Tyr Arg Val Val Ser Val Leu Thr Val Leu His
              325                330                335

Gln Asp Trp Leu Asn Gly Lys Glu Tyr Lys Cys Lys Val Ser Asn Lys
              340                345                350

Ala Leu Pro Ala Pro Ile Glu Lys Thr Ile Ser Lys Ala Lys Gly Gln
          355                360                365

Pro Arg Glu Pro Gln Val Tyr Thr Leu Pro Pro Ser Arg Glu Glu Met
          370                375                380

Thr Lys Asn Gln Val Ser Leu Thr Cys Leu Val Lys Gly Phe Tyr Pro
385                390                395                400

Ser Asp Ile Ala Val Glu Trp Glu Ser Asn Gly Gln Pro Glu Asn Asn
              405                410                415

Tyr Lys Thr Thr Pro Pro Val Leu Asp Ser Asp Gly Ser Phe Phe Leu
              420                425                430

Tyr Ser Lys Leu Thr Val Asp Lys Ser Arg Trp Gln Gln Gly Asn Val
              435                440                445

Phe Ser Cys Ser Val Met His Glu Ala Leu His Asn His Tyr Thr Gln
          450                455                460

Lys Ser Leu Ser Leu Ser Pro Gly Gly Ser Thr Ser Thr Ser Gly Arg
465                470                475                480

Ser Ala Asn Pro Arg Gly Gly Gly Ser Ala Pro Ile Ser Ser His Cys
              485                490                495

Arg Leu Asp Lys Ser Asn Phe Gln Gln Pro Tyr Ile Thr Asn Arg Thr
              500                505                510

Phe Met Leu Ala Lys Glu Ala Ser Leu Ala Asp Asn Asn Thr Asp Val
              515                520                525

Arg Leu Ile Gly Glu Lys Leu Phe His Gly Val Ser Met Ser Glu Arg
          530                535                540

Cys Tyr Leu Met Lys Gln Val Leu Asn Phe Thr Leu Glu Glu Val Leu
545                550                555                560

Phe Pro Gln Ser Asp Arg Phe Gln Pro Tyr Met Gln Glu Val Val Pro
              565                570                575

Phe Leu Ala Arg Leu Ser Asn Arg Leu Ser Thr Cys His Ile Glu Gly
              580                585                590

Asp Asp Leu His Ile Gln Arg Asn Val Gln Lys Leu Lys Asp Thr Val
              595                600                605

Lys Lys Leu Gly Glu Ser Gly Glu Ile Lys Ala Ile Gly Glu Leu Asp
          610                615                620

Leu Leu Phe Met Ser Leu Arg Asn Ala Cys Ile
625                630                635
```

```
<210> SEQ ID NO 931
<211> LENGTH: 121
<212> TYPE: PRT
<213> ORGANISM: Artificial sequence
<220> FEATURE:
<223> OTHER INFORMATION: an artificially synthesized sequence

<400> SEQUENCE: 931

Gln Val Gln Leu Gln Gln Ser Gly Ala Glu Leu Val Arg Pro Gly Thr
1               5                10                15

Ser Val Lys Val Ser Cys Lys Ala Ser Gly Tyr Ala Phe Thr Asn Tyr
```

-continued

```
                20              25              30
Leu Ile Glu Trp Val Lys Gln Arg Pro Gly Gln Gly Leu Glu Trp Ile
            35              40              45
Gly Val Ile Asn Pro Gly Ser Gly Gly Thr Asn Tyr Asn Glu Lys Phe
        50              55              60
Lys Gly Lys Ala Thr Leu Thr Ala Asp Lys Ser Ser Ser Thr Ala Tyr
65              70              75              80
Met Gln Leu Ser Ser Leu Thr Ser Asp Asp Ser Ala Val Tyr Phe Cys
                85              90              95
Ala Arg Trp Arg Gly Asp Gly Tyr Tyr Ala Tyr Phe Asp Val Trp Gly
            100             105             110
Ala Gly Thr Thr Val Thr Val Ser Ser
        115             120

<210> SEQ ID NO 932
<211> LENGTH: 338
<212> TYPE: PRT
<213> ORGANISM: Artificial sequence
<220> FEATURE:
<223> OTHER INFORMATION: an artificially synthesized sequence

<400> SEQUENCE: 932

Ala Ser Thr Lys Gly Pro Ser Val Phe Pro Leu Ala Pro Ser Ser Lys
1               5               10              15
Ser Thr Ser Gly Gly Thr Ala Ala Leu Gly Cys Leu Val Lys Asp Tyr
            20              25              30
Phe Pro Glu Pro Val Thr Val Ser Trp Asn Ser Gly Ala Leu Thr Ser
            35              40              45
Gly Val His Thr Phe Pro Ala Val Leu Gln Ser Ser Gly Leu Tyr Ser
        50              55              60
Leu Ser Ser Val Val Thr Val Pro Ser Ser Ser Leu Gly Thr Gln Thr
65              70              75              80
Tyr Ile Cys Asn Val Asn His Lys Pro Ser Asn Thr Lys Val Asp Lys
                85              90              95
Arg Val Glu Pro Lys Ser Cys Asp Lys Thr His Thr Gly Gly Gly Gly
            100             105             110
Ser Gly Gly Gly Gly Ser Cys Pro Pro Cys Pro Ala Pro Glu Leu Arg
        115             120             125
Arg Gly Pro Ser Val Phe Leu Phe Pro Pro Lys Pro Lys Asp Thr Leu
        130             135             140
Met Ile Ser Arg Thr Pro Glu Val Thr Cys Val Val Val Asp Val Ser
145             150             155             160
His Glu Asp Pro Glu Val Lys Phe Asn Trp Tyr Val Asp Gly Val Glu
            165             170             175
Val His Asn Ala Lys Thr Lys Pro Arg Glu Glu Gln Tyr Asn Ser Thr
            180             185             190
Tyr Arg Val Val Ser Val Leu Thr Val Leu His Gln Asp Trp Leu Asn
            195             200             205
Gly Lys Glu Tyr Lys Cys Lys Val Ser Asn Lys Gly Leu Pro Ser Ser
        210             215             220
Ile Glu Lys Thr Ile Ser Lys Ala Lys Gly Gln Pro Arg Glu Pro Gln
225             230             235             240
Val Tyr Thr Leu Pro Pro Ser Arg Glu Glu Met Thr Lys Asn Gln Val
            245             250             255
Ser Leu Thr Cys Leu Val Lys Gly Phe Tyr Pro Ser Asp Ile Ala Val
```

-continued

```
                260                 265                 270
Glu Trp Glu Ser Asn Gly Gln Pro Glu Asn Asn Tyr Lys Thr Thr Pro
            275                 280                 285

Pro Val Leu Asp Ser Asp Gly Ser Phe Phe Leu Tyr Ser Lys Leu Thr
        290                 295                 300

Val Asp Lys Ser Arg Trp Gln Glu Gly Asn Val Phe Ser Cys Ser Val
305                 310                 315                 320

Met His Glu Ala Leu His Asn His Tyr Thr Gln Lys Ser Leu Ser Leu
                325                 330                 335

Ser Pro

<210> SEQ ID NO 933
<211> LENGTH: 119
<212> TYPE: PRT
<213> ORGANISM: Artificial sequence
<220> FEATURE:
<223> OTHER INFORMATION: an artificially synthesized sequence

<400> SEQUENCE: 933

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Ala Pro Gly Lys Gly Leu Glu Trp Val
        35                  40                  45

Thr Leu Ile Ser Tyr Asp Gly Ser Gln Lys Tyr Tyr Ala Asp Ser Val
    50                  55                  60

Lys Gly Arg Phe Thr Thr Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Thr Thr Leu Gly Ala Phe Asp Val Trp Gly Gln Gly
            100                 105                 110

Thr Met Val Thr Val Ser Ser
        115

<210> SEQ ID NO 934
<211> LENGTH: 116
<212> TYPE: PRT
<213> ORGANISM: Artificial sequence
<220> FEATURE:
<223> OTHER INFORMATION: an artificially synthesized sequence

<400> SEQUENCE: 934

Gln Val Gln Leu Gln Gln Ser Gly Pro Gln Leu Val Arg Pro Gly Ala
1               5                   10                  15

Ser Val Lys Ile Ser Cys Lys Ala Ser Gly Tyr Ser Phe Thr Ser Tyr
            20                  25                  30

Trp Met His Trp Val Asn Gln Arg Pro Gly Gln Gly Leu Glu Trp Ile
        35                  40                  45

Gly Met Ile Asp Pro Ser Tyr Ser Glu Thr Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Leu Tyr Gly Asn Tyr Phe Asp Tyr Trp Gly Gln Gly Thr Thr Leu
```

-continued

```
                    100                 105                 110

Thr Val Ser Ser
        115

<210> SEQ ID NO 935
<211> LENGTH: 25
<212> TYPE: PRT
<213> ORGANISM: Artificial Sequence
<220> FEATURE:
<223> OTHER INFORMATION: an artificially synthesized sequence

<400> SEQUENCE: 935

Glu Pro Lys Ser Cys Gly Gly Gly Gly Ser Gly Gly Gly Gly Ser Asp
1               5                   10                  15

Lys Thr His Thr Cys Pro Pro Cys Pro
            20                  25

<210> SEQ ID NO 936
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 936

Glu Pro Lys Ser Cys
1               5

<210> SEQ ID NO 937
<211> LENGTH: 25
<212> TYPE: PRT
<213> ORGANISM: Artificial Sequence
<220> FEATURE:
<223> OTHER INFORMATION: an artificially synthesized sequence

<400> SEQUENCE: 937

Gly Gly Gly Gly Ser Gly Gly Gly Gly Ser Glu Pro Lys Ser Cys Asp
1               5                   10                  15

Lys Thr His Thr Cys Pro Pro Cys Pro
            20                  25

<210> SEQ ID NO 938
<211> LENGTH: 25
<212> TYPE: PRT
<213> ORGANISM: Artificial Sequence
<220> FEATURE:
<223> OTHER INFORMATION: an artificially synthesized sequence

<400> SEQUENCE: 938

Glu Pro Lys Ser Cys Asp Lys Thr His Thr Gly Gly Gly Gly Ser Gly
1               5                   10                  15

Gly Gly Gly Ser Cys Pro Pro Cys Pro
            20                  25
```

LIGAND-BINDING FUSION PROTEINS

CROSS-REFERENCE TO RELATED APPLICATIONS

This application is a U.S. National Phase of PCT Application No. PCT/JP2021/001758, filed Jan. 20, 2021, which claims the benefit of Japanese Patent Application No. 2020-006806, filed Jan. 20, 2020, and Japanese Patent Application No. 2020-182089, filed Oct. 30, 2020, each of which is incorporated herein by reference in its entirety.

REFERENCE TO SEQUENCE LISTING SUBMITTED ELECTRONICALLY

The content of the electronically submitted sequence listing (Name: 6663_0209 Sequence_Listing.txt; Size: 398 KB; and Date of Creation: Jul. 15, 2022) filed with the application is incorporated herein by reference in its entirety.

The present invention relates to fusion proteins in which a ligand moiety is connected via a peptide linker with a ligand-binding moiety that binds to the ligand moiety. The present invention also relates to their methods of production, their uses, and pharmaceutical compositions comprising such a fusion protein.

BACKGROUND ART

Antibodies have received attention as drugs because of being highly stable in plasma and causing few adverse reactions. Among them, many IgG-type antibody drugs have been launched, and a large number of antibody drugs are currently under development (NPLs 1 and 2).

Rituxan against CD20, cetuximab against EGFR, Herceptin against HER2, and the like have been approved so far as therapeutic drugs for cancer using antibody drugs (NPL 3). These antibody molecules bind to their antigens expressed on cancer cells and thereby exert cytotoxic activity against the cancer cells through ADCC, signal inhibition, etc.

A method for delivering a ligand having physiological activity, such as a cytokine, to solid cancer by an immunocytokine containing the ligand fused with an antibody molecule binding to a cancer antigen highly expressed on cancer cells is also known. The cytokine delivered to solid cancer by the immunocytokine activates immunity and thereby exerts an antitumor effect. Since cytokines including IL-2, IL-12, and TNF have strong toxicity, it is expected for the local action of these cytokines on cancer that the local delivery to the cancer by an antibody strengthens their effects while alleviating adverse reactions (NPLs 4, 5, and 6). However, all of these cytokines have not yet been approved as drugs because of their problems that, for example: they do not clinically exhibit a sufficient effect by systemic administration; their therapeutic windows are narrow; and they cannot be systemically administered due to strong toxicity.

This is largely because cytokines including immunocytokines, when systemically administered, are exposed to the whole bodies and are therefore capable of exhibiting toxicity by systemic action, or the cytokines can be administered only at very low doses in order to circumvent the toxicity. It has also been reported that an antitumor effect did not vary between an immunocytokine containing IL-2 fused with an antibody binding to a cancer antigen and an immunocytokine containing IL-2 fused with an antibody that does not bind to the cancer antigen (NPL 7).

A molecule containing a cytokine and a cytokine receptor connected via a linker that is cleaved by protease highly expressed in cancer has been reported as a method for circumventing the problems described above. The cytokine is inhibited by the cytokine receptor connected therewith via the linker, while the cytokine is liberated from the cytokine receptor by the protease cleavage of the linker and thereby becomes an active form. As an example, a molecule containing TNF-alpha and TNF-R connected via a linker that is cleaved by uPA (NPL 8) has been reported, and a molecule containing IL-2 and IL-2R connected via a linker that is cleaved by MMP-2 (NPL 9) has been reported. However, the cytokines in these molecules are active even before cleavage of the linker, and the cleavage of the linker improves the activity by only approximately 10 times. Meanwhile, molecules containing a cytokine connected with an anti-cytokine scFv, instead of a cytokine receptor, via a linker that is cleaved by an MMP (NPLs 9 and 10) have also been reported. Some other documents (e.g., PTLs 1 to 6) also relate to fusion polypeptides containing a cleavable portion.

CITATION LIST

Patent Literature

[PTL 1] WO 2009/025846
[PTL 2] WO 2011/123683
[PTL 3] WO 2018/097307
[PTL 4] WO 2019/107380
[PTL 5] WO 2019/010219
[PTL 6] WO 2019/010224

Non Patent Literature

[NPL 1] Monoclonal antibody successes in the clinic. Janice M Reichert, Clark J Rosensweig, Laura B Faden & Matthew C Dewitz, Nat. Biotechnol.
[NPL 2] The therapeutic antibodies market to 2008. Pavlou A K, Belsey M J., Eur. J. Pharm. Biopharm. (2005) 59 (3), 389-396
[NPL 3] Monoclonal antibodies: versatile platforms for cancer immunotherapy. Weiner L M, Surana R, Wang S., Nat. Rev. Immunol. (2010) 10 (5), 317-327
[NPL 4] Cyclophosphamide and tucotuzumab (huKS-IL2) following first-line chemotherapy in responding patients with extensive-disease small-cell lung cancer. Gladkov O, Ramlau R, Serwatowski P, Milanowski J, Tomeczko J, Komarnitsky P B, Kramer D, Krzakowski M J. Anticancer Drugs. 2015 November; 26 (10): 1061-8.
[NPL 5] Defining the Pharmacodynamic Profile and Therapeutic Index of NHS-IL12 Immunocytokine in Dogs with Malignant Melanoma. Paoloni M, Mazcko C, Selting K, Lana S, Barber L, Phillips J, Skorupski K, Vail D, Wilson H, Biller B, Avery A, Kiupel M, LeBlanc A, Bernhardt A, Brunkhorst B, Tighe R, Khanna C. PLoS One. 2015 Jun. 19; 10 (6): e0129954.
[NPL 6] Isolated limb perfusion with the tumor-targeting human monoclonal antibody-cytokine fusion protein L19-TNF plus melphalan and mild hyperthermia in patients with locally advanced extremity melanoma. Papadia F, Basso V, Patuzzo R, Maurichi A, Di Florio A, Zardi L, Ventura E, Gonzalez-Iglesias R, Lovato V, Giovannoni L, Tasciotti A, Neri D, Santinami M, Menssen H D, De Cian F. J Surg Oncol. 2013 February; 107 (2): 173-9.
[NPL 7] Antigen specificity can be irrelevant to immunocytokine efficacy and biodistribution. Tzeng A, Kwan B H, Opel C F, Navaratna T, Wittrup K D. Proc Natl Acad Sci USA. 2015 Mar. 17; 112 (11): 3320-5.

[NPL 8] Cancer Immunol Immunother. 2006 December; 55 (12): 1590-600. Epub 2006 Apr. 25. Target-selective activation of a TNF prodrug by urokinase-type plasminogen activator (uPA) mediated proteolytic processing at the cell surface. Gerspach J1, Nemeth J, Munkel S, Wajant H, Pfizenmaier K.

[NPL 9] Immunology. 2011 June; 133 (2): 206-20. doi: 10.1111/j.1365-2567.2011.03428.x. Epub 2011 Mar. 23. Development of an attenuated interleukin-2 fusion protein that can be activated by tumour-expressed proteases. Puskas J1, Skrombolas D, Sedlacek A, Lord E, Sullivan M, Frelinger J.

[NPL 10] Development of an Interleukin-12 Fusion Protein That Is Activated by Cleavage with Matrix Metalloproteinase 9. Skrombolas D, Sullivan M, Frelinger J G. J Interferon Cytokine Res. 2019 April; 39(4):233-245.

SUMMARY OF INVENTION

Technical Problem

The present invention has been made in light of these circumstances. An object of the present invention is to provide a fusion protein that can activate its ligand moiety such as a cytokine or a chemokine selectively in a target tissue, its methods of production, uses, and pharmaceutical compositions comprising the fusion protein.

Solution to Problem

The present inventors have conducted diligent studies to attain the object and consequently developed fusion proteins in which a ligand moiety (e.g. cytokine or chemokine) is connected via a peptide linker with a ligand-binding moiety, wherein the ligand-binding moiety binds to the ligand moiety but is capable of releasing the ligand moiety in the presence of a protease. The present inventors have also found that such a fusion protein or a pharmaceutical composition comprising the fusion protein is useful in the treatment of a disease using the ligand and also found that the fusion protein or the pharmaceutical composition is useful in the treatment of a disease which involves administering the fusion protein; and the fusion protein is useful in the production of a drug for the treatment of a disease. The present inventors have also developed a method for producing the fusion protein, completing the present invention.

The molecular formats of the fusion proteins of the present invention are advantageous over the other molecular formats already known in the prior art in that they may allow higher expression levels and higher activity.

The present invention is based on these findings and specifically encompasses exemplary embodiments described below.

[1] A fusion protein, comprising:
(a) a ligand-binding moiety comprising a ligand-binding domain and at least one first protease cleavage site;
(b) at least one ligand moiety; and
(c) at least one peptide linker connecting the at least one ligand moiety to a C-terminal region of the ligand-binding moiety;
wherein the ligand-binding domain binds to the at least one ligand moiety, and is capable of releasing the at least one ligand moiety in the presence of a protease.

[2] The fusion protein of [1], wherein the at least one peptide linker comprises no protease cleavage site.

[3] The fusion protein of [1], wherein the at least one peptide linker comprises a second protease cleavage site.

[4] The fusion protein of any one of [1] to [3], wherein the ligand-binding domain comprises an antibody variable region.

[5] The fusion protein of [4], wherein the ligand-binding domain comprises a VH region and a VL region associating with each other.

[6] The fusion protein of [4] or [5], wherein the ligand-binding moiety further comprises a CH1 region and a CL region.

[7] The fusion protein of [6], wherein at least one of the at least one first protease cleavage site is located near the boundary between the VH or VL region and the CH1 or CL region.

[8] The fusion protein of any one of [4] to [7], wherein the ligand-binding moiety further comprises an Fc region.

[8-1] The fusion protein of [8], which comprises a constant region comprising a linker.

[8-2] The fusion protein of [8-1], which comprises a constant region comprising the sequence of SEQ ID NO: 901 (C1).

[8-3] The fusion protein of [8-1], which comprises a constant region comprising the sequence of SEQ ID NO: 905 (C2) or 932 (C5).

[8-4] The fusion protein of [8-1], which comprises a heavy chain and a light chain, wherein the linker is positioned in a hinge region so that disulfide bond formation between Cys at position 220 (C220) (EU numbering) of the heavy chain and Cys at position 214 (C214) (EU numbering) of the light chain is promoted.

[8-5] The fusion protein of [8-4], wherein the hinge region comprises the following amino acid sequence from position 216 (EU numbering): EPKSCGGGGSGGGGSDKTHTCPPCP (SEQ ID NO: 935).

[8-6] The fusion protein of [8-1], wherein the ligand-binding moiety comprises a heavy chain and a light chain, wherein amino acid residues in the heavy chain and the light chain are modified so that no disulfide bond is formed between position 220 (EU numbering) of the heavy chain and position 214 (EU numbering) of the light chain.

[8-7] The fusion protein of [8-6], wherein the light chain comprises C214S (EU numbering) modification and the heavy chain comprises C220S (EU numbering) modification.

[8-8] The fusion protein of [8-1], which comprises a constant region comprising the sequence of SEQ ID NO: 908 (C3).

[8-9] The fusion protein of [8-1], wherein the ligand-binding moiety comprises a heavy chain and a light chain, wherein the heavy chain is modified to allow disulfide bond formation between position 131 (EU numbering) of the heavy chain and position 214 (EU numbering) of the light chain.

[8-10] The fusion protein of [8-9], wherein the heavy chain comprises S131C (EU numbering) and C220S (EU numbering) modifications.

[8-11] The fusion protein of [8-1], which comprises a constant region comprising the sequence of SEQ ID NO: 910 (C4).

[9] The fusion protein of [8], wherein the ligand-binding moiety comprises a full-length antibody.

[10] The fusion protein of [9], wherein the full-length antibody is an IgG antibody.

[11] The fusion protein of [9] or [10], wherein the at least one ligand moiety comprises two ligand moieties, and the at least one peptide linker comprises two peptide linkers, wherein each ligand moiety is connected to the C-terminal region of the ligand-binding moiety via each peptide linker.

[12] The fusion protein of any one of [8] to [11], wherein the at least one ligand moiety is connected to an amino acid residue exposed on the surface of the CH3 region of the Fc region via the at least one peptide linker.

[13] The fusion protein of any one of [1] to [12], wherein the at least one ligand moiety is connected to the C-terminal amino acid residue of the ligand-binding moiety via the at least one peptide linker.

[14] The fusion protein of any one of [1] to [13], which further comprises a cleavable linker comprising a third protease cleavage site, wherein the at least one ligand moiety is connected to an N-terminal region of the ligand-binding moiety via the cleavable linker.

[15] The fusion protein of any one of [8] to [13], which further comprises a cleavable linker comprising a third protease cleavage site, wherein the at least one ligand moiety is connected to one of the 1st to 230th amino acid residues from the N-terminus of the ligand-binding moiety via the cleavable linker.

[16] The fusion protein of [14] or [15], wherein the at least one ligand moiety is connected to the N-terminal amino acid residue of the ligand-binding moiety via the cleavable linker.

[17] The fusion protein of any one of [1] to [16], wherein the at least one ligand moiety is biologically active, wherein binding of the ligand-binding domain to the ligand moiety inhibits the biological activity of the ligand moiety.

[18] The fusion protein of [17], wherein the at least one ligand moiety comprises a biologically active protein or polypeptide.

[19] The fusion protein of [18], wherein the at least one ligand moiety comprises a cytokine or chemokine.

[20] The fusion protein of [18], wherein the at least one ligand moiety comprises a ligand protein or polypeptide selected from the group consisting of CXCL10, IL-2, IL-12, IL-22, PD-1, or IL-6R.

[21] The fusion protein of any one of [1] to [20], wherein the at least one ligand moiety comprises IL-12, and the fusion protein comprises antibody heavy and light chains selected from the group consisting of:

(a) a light chain comprising the amino acid sequence of SEQ ID NO: 874, and a heavy chain comprising the amino acid sequence of SEQ ID NO: 875;

(b) a light chain comprising the amino acid sequence of SEQ ID NO: 876, and a heavy chain comprising the amino acid sequence of SEQ ID NO: 880;

(c) a light chain comprising the amino acid sequence of SEQ ID NO: 876, and a heavy chain comprising the amino acid sequence of SEQ ID NO: 881;

(d) a light chain comprising the amino acid sequence of SEQ ID NO: 874, and a heavy chain comprising the amino acid sequence of SEQ ID NO: 884;

(e) a light chain comprising the amino acid sequence of SEQ ID NO: 876, and a heavy chain comprising the amino acid sequence of SEQ ID NO: 885;

(f) a light chain comprising the amino acid sequence of SEQ ID NO: 876, and a heavy chain comprising the amino acid sequence of SEQ ID NO: 886;

(g) a light chain comprising the amino acid sequence of SEQ ID NO: 887, and a heavy chain comprising the amino acid sequence of SEQ ID NO: 888;

(h) a light chain comprising the amino acid sequence of SEQ ID NO: 890, and a heavy chain comprising the amino acid sequence of SEQ ID NO: 891

(i) a light chain comprising the amino acid sequence of SEQ ID NO: 876, and a heavy chain comprising the amino acid sequence of SEQ ID NO: 904;

(j) a light chain comprising the amino acid sequence of SEQ ID NO: 906, and a heavy chain comprising the amino acid sequence of SEQ ID NO: 907;

(k) a light chain comprising the amino acid sequence of SEQ ID NO: 876, and a heavy chain comprising the amino acid sequence of SEQ ID NO: 909; and (1) antibody heavy and light chains that compete with the antibody heavy chain and the antibody light chain described in (a) to (k).

[21-a] The fusion protein of any one of [1] to [20], wherein the at least one ligand moiety comprises IL-12, and the ligand-binding moiety comprises an antibody variable region comprising any one of the combinations of H-chain CDR1, CDR2, and CDR3 and L-chain CDR1, CDR2, and CDR3 selected from (a) to (1) below, or any one of the combinations of H-chain CDR1, CDR2, and CDR3 and L-chain CDR1, CDR2, and CDR3 of antibody variable regions functionally equivalent thereto:

(a) H-chain CDR1, CDR2, and CDR3 comprised in the antibody variable region are identical to the amino acid sequences of the CDR1, CDR2, and CDR3 regions comprised in SEQ ID NO: 875; and L-chain CDR1, CDR2, and CDR3 comprised in the antibody variable region are identical to the amino acid sequences of the CDR1, CDR2, and CDR3 regions comprised in SEQ ID NO: 874;

(b) H-chain CDR1, CDR2, and CDR3 comprised in the antibody variable region are identical to the amino acid sequences of the CDR1, CDR2, and CDR3 regions comprised in SEQ ID NO: 880; and L-chain CDR1, CDR2, and CDR3 comprised in the antibody variable region are identical to the amino acid sequences of the CDR1, CDR2, and CDR3 regions comprised in SEQ ID NO: 876;

(c) H-chain CDR1, CDR2, and CDR3 comprised in the antibody variable region are identical to the amino acid sequences of the CDR1, CDR2, and CDR3 regions comprised in SEQ ID NO: 881; and L-chain CDR1, CDR2, and CDR3 comprised in the antibody variable region are identical to the amino acid sequences of the CDR1, CDR2, and CDR3 regions comprised in SEQ ID NO: 876;

(d) H-chain CDR1, CDR2, and CDR3 comprised in the antibody variable region are identical to the amino acid sequences of the CDR1, CDR2, and CDR3 regions comprised in SEQ ID NO: 884; and L-chain CDR1, CDR2, and CDR3 comprised in the antibody variable region are identical to the amino acid sequences of the CDR1, CDR2, and CDR3 regions comprised in SEQ ID NO: 874;

(e) H-chain CDR1, CDR2, and CDR3 comprised in the antibody variable region are identical to the amino acid sequences of the CDR1, CDR2, and CDR3 regions comprised in SEQ ID NO: 885; and L-chain CDR1, CDR2, and CDR3 comprised in the antibody variable region are identical to the amino acid sequences of the CDR1, CDR2, and CDR3 regions comprised in SEQ ID NO: 876;

(f) H-chain CDR1, CDR2, and CDR3 comprised in the antibody variable region are identical to the amino acid sequences of the CDR1, CDR2, and CDR3 regions comprised in SEQ ID NO: 886; and L-chain CDR1, CDR2, and CDR3 comprised in the antibody variable region are identical to the amino acid sequences of the CDR1, CDR2, and CDR3 regions comprised in SEQ ID NO: 876;

(g) H-chain CDR1, CDR2, and CDR3 comprised in the antibody variable region are identical to the amino acid sequences of the CDR1, CDR2, and CDR3 regions comprised in SEQ ID NO: 888; and L-chain CDR1, CDR2, and CDR3 comprised in the antibody variable region are identical to the amino acid sequences of the CDR1, CDR2, and CDR3 regions comprised in SEQ ID NO: 887;

(h) H-chain CDR1, CDR2, and CDR3 comprised in the antibody variable region are identical to the amino acid sequences of the CDR1, CDR2, and CDR3 regions comprised in SEQ ID NO: 891; and L-chain CDR1, CDR2, and CDR3 comprised in the antibody variable region are identical to the amino acid sequences of the CDR1, CDR2, and CDR3 regions comprised in SEQ ID NO: 890;

(i) H-chain CDR1, CDR2, and CDR3 comprised in the antibody variable region are identical to the amino acid sequences of the CDR1, CDR2, and CDR3 regions comprised in SEQ ID NO: 904; and L-chain CDR1, CDR2, and CDR3 comprised in the antibody variable region are identical to the amino acid sequences of the CDR1, CDR2, and CDR3 regions comprised in SEQ ID NO: 876;

(j) H-chain CDR1, CDR2, and CDR3 comprised in the antibody variable region are identical to the amino acid sequences of the CDR1, CDR2, and CDR3 regions comprised in SEQ ID NO: 907; and L-chain CDR1, CDR2, and CDR3 comprised in the antibody variable region are identical to the amino acid sequences of the CDR1, CDR2, and CDR3 regions comprised in SEQ ID NO: 906;

(k) H-chain CDR1, CDR2, and CDR3 comprised in the antibody variable region are identical to the amino acid sequences of the CDR1, CDR2, and CDR3 regions comprised in SEQ ID NO: 909; and L-chain CDR1, CDR2, and CDR3 comprised in the antibody variable region are identical to the amino acid sequences of the CDR1, CDR2, and CDR3 regions comprised in SEQ ID NO: 876; and (l) H-chain and L-chain CDR1, CDR2 and CDR3 comprised in antibody variable regions that compete with the antibody heavy chain variable region and the antibody light chain variable region described in (a) to (k).

[21-b] The fusion protein of any one of [1] to [20], wherein the at least one ligand moiety comprises IL-12, and the ligand-binding moiety comprises any one of the combinations of heavy-chain variable region (VH) and light-chain variable region (VL) selected from (a) to (l) below:

(a) a VH comprised in SEQ ID NO: 875; and a VL comprised in SEQ ID NO: 874;
(b) a VH comprised in SEQ ID NO: 880; and a VL comprised in SEQ ID NO: 876;
(c) a VH comprised in SEQ ID NO: 881; and a VL comprised in SEQ ID NO: 876;
(d) a VH comprised in SEQ ID NO: 884; and a VL comprised in SEQ ID NO: 874;
(e) a VH comprised in SEQ ID NO: 885; and a VL comprised in SEQ ID NO: 876;
(f) a VH comprised in SEQ ID NO: 886; and a VL comprised in SEQ ID NO: 876;
(g) a VH comprised in SEQ ID NO: 888; and a VL comprised in SEQ ID NO: 887;

(h) a VH comprised in SEQ ID NO: 891; and a VL comprised in SEQ ID NO: 890;
(i) a VH comprised in SEQ ID NO: 904; and a VL comprised in SEQ ID NO: 876;
(j) a VH comprised in SEQ ID NO: 907; and a VL comprised in SEQ ID NO: 906;
(k) a VH comprised in SEQ ID NO: 909; and a VL comprised in SEQ ID NO: 876; and
(l) a VH and a VL that compete with the VH and the VL described in (a) to (k).

[21-c] The fusion protein of any one of [1] to [20], wherein the at least one ligand moiety comprises IL-12, wherein the fusion protein comprises any one of the combinations selected from (a) to (d) below:

(a) a first light chain comprising the sequence of SEQ ID NO: 876, a first heavy chain comprising the sequence of SEQ ID NO: 881, a second light chain comprising the sequence of SEQ ID NO: 882, and a second heavy chain comprising the sequence of SEQ ID NO: 883;
(b) a first light chain comprising the sequence of SEQ ID NO: 876, a first heavy chain comprising the sequence of SEQ ID NO: 886, a second light chain comprising the sequence of SEQ ID NO: 882, and a second heavy chain comprising the sequence of SEQ ID NO: 883;
(c) a first light chain comprising the sequence of SEQ ID NO: 887, a first heavy chain comprising the sequence of SEQ ID NO: 888, a second light chain comprising the sequence of SEQ ID NO: 882, and a second heavy chain comprising the sequence of SEQ ID NO: 883; and
(d) a first light chain comprising the sequence of SEQ ID NO: 890, a first heavy chain comprising the sequence of SEQ ID NO: 891, a second light chain comprising the sequence of SEQ ID NO: 882, and a second heavy chain comprising the sequence of SEQ ID NO: 883.

[21-2] The fusion protein of any one of [1] to [20], wherein the at least one ligand moiety comprises IL-22, and the fusion protein comprises antibody heavy and light chains selected from the group consisting of:

(a) a light chain comprising the amino acid sequence of SEQ ID NO: 912, and a heavy chain comprising the amino acid sequence of SEQ ID NO: 913;
(b) a light chain comprising the amino acid sequence of SEQ ID NO: 915, and a heavy chain comprising the amino acid sequence of SEQ ID NO: 916;
(c) a light chain comprising the amino acid sequence of SEQ ID NO: 912, and a heavy chain comprising the amino acid sequence of SEQ ID NO: 929;
(d) a light chain comprising the amino acid sequence of SEQ ID NO: 912, and a heavy chain comprising the amino acid sequence of SEQ ID NO: 930; and
(e) antibody heavy and light chains that compete with the antibody heavy chain and the antibody light chain described in (a) to (d).

[21-2a] The fusion protein of any one of [1] to [20], wherein the at least one ligand moiety comprises IL-22 and the ligand-binding moiety comprises an antibody variable region comprising any one of the combinations of H-chain CDR1, CDR2, and CDR3 and L-chain CDR1, CDR2, and CDR3 selected from (a) to (e) below, or any one of the combinations of H-chain CDR1, CDR2, and CDR3 and L-chain CDR1, CDR2, and CDR3 of antibody variable regions functionally equivalent thereto:

(a) H-chain CDR1, CDR2, and CDR3 comprised in the antibody variable region are identical to the amino acid sequences of the CDR1, CDR2, and CDR3 regions comprised in SEQ ID NO: 913; and L-chain CDR1, CDR2, and CDR3 comprised in the antibody variable region are identical to the amino acid sequences of the CDR1, CDR2, and CDR3 regions comprised in SEQ ID NO: 912;

(b) H-chain CDR1, CDR2, and CDR3 comprised in the antibody variable region are identical to the amino acid sequences of the CDR1, CDR2, and CDR3 regions comprised in SEQ ID NO: 916; and L-chain CDR1, CDR2, and CDR3 comprised in the antibody variable region are identical to the amino acid sequences of the CDR1, CDR2, and CDR3 regions comprised in SEQ ID NO: 915;

(c) H-chain CDR1, CDR2, and CDR3 comprised in the antibody variable region are identical to the amino acid sequences of the CDR1, CDR2, and CDR3 regions comprised in SEQ ID NO: 929; and L-chain CDR1, CDR2, and CDR3 comprised in the antibody variable region are identical to the amino acid sequences of the CDR1, CDR2, and CDR3 regions comprised in SEQ ID NO: 912;

(d) H-chain CDR1, CDR2, and CDR3 comprised in the antibody variable region are identical to the amino acid sequences of the CDR1, CDR2, and CDR3 regions comprised in SEQ ID NO: 930; and L-chain CDR1, CDR2, and CDR3 comprised in the antibody variable region are identical to the amino acid sequences of the CDR1, CDR2, and CDR3 regions comprised in SEQ ID NO: 912; and (e) H-chain and L-chain CDR1, CDR2 and CDR3 comprised in antibody variable regions that compete with the antibody heavy chain variable region and the antibody light chain variable region described in (a) to (d).

[21-2b] The fusion protein of any one of [1] to [20], wherein the at least one ligand moiety comprises IL-22, and the ligand-binding moiety comprises any one of the combinations of heavy-chain variable region (VH) and light-chain variable region (VL) selected from (a) to (e) below:

(a) a VH comprised in SEQ ID NO: 913; and a VL comprised in SEQ ID NO: 912;

(b) a VH comprised in SEQ ID NO: 916; and a VL comprised in SEQ ID NO: 915;

(c) a VH comprised in SEQ ID NO: 929; and a VL comprised in SEQ ID NO: 912;

(d) a VH comprised in SEQ ID NO: 930; and a VL comprised in SEQ ID NO: 912; and (e) a VH and a VL that compete with the VH and the VL described in (a) to (d).

[21-3] The fusion protein of any one of [1] to [20], wherein the at least one ligand moiety comprises IL-2, and the fusion protein comprises antibody heavy and light chains selected from the group consisting of:

(a) a light chain comprising the amino acid sequence of SEQ ID NO: 920, and a heavy chain comprising the amino acid sequence of SEQ ID NO: 919;

(b) a light chain comprising the amino acid sequence of SEQ ID NO: 923, and a heavy chain comprising the amino acid sequence of SEQ ID NO: 922; and (c) antibody heavy and light chains that compete with the antibody heavy chain and the antibody light chain described in (a) to (b).

[21-3a] The fusion protein of any one of [1] to [20], wherein the at least one ligand moiety comprises IL-2 and the ligand-binding moiety comprises an antibody variable region comprising any one of the combinations of H-chain CDR1, CDR2, and CDR3 and L-chain CDR1, CDR2, and CDR3 selected from (a) to (e) below, or any one of the combinations of H-chain CDR1, CDR2, and CDR3 and L-chain CDR1, CDR2, and CDR3 of antibody variable regions functionally equivalent thereto:

(a) H-chain CDR1, CDR2, and CDR3 comprised in the antibody variable region are identical to the amino acid sequences of the CDR1, CDR2, and CDR3 regions comprised in SEQ ID NO: 919; and L-chain CDR1, CDR2, and CDR3 comprised in the antibody variable region are identical to the amino acid sequences of the CDR1, CDR2, and CDR3 regions comprised in SEQ ID NO: 920;

(b) H-chain CDR1, CDR2, and CDR3 comprised in the antibody variable region are identical to the amino acid sequences of the CDR1, CDR2, and CDR3 regions comprised in SEQ ID NO: 922; and L-chain CDR1, CDR2, and CDR3 comprised in the antibody variable region are identical to the amino acid sequences of the CDR1, CDR2, and CDR3 regions comprised in SEQ ID NO: 923; and (c) H-chain and L-chain CDR1, CDR2 and CDR3 comprised in antibody variable regions that compete with the antibody heavy chain variable region and the antibody light chain variable region described in (a) to (b).

[21-3b] The fusion protein of any one of [1] to [20], wherein the at least one ligand moiety comprises IL-2, and the ligand-binding moiety comprises any one of the combinations of heavy-chain variable region (VH) and light-chain variable region (VL) selected from (a) to (c) below:

(a) a VH comprised in SEQ ID NO: 919; and a VL comprised in SEQ ID NO: 920;

(b) a VH comprised in SEQ ID NO: 922; and a VL comprised in SEQ ID NO: 923; and (c) a VH and a VL that compete with the VH and the VL described in (a) to (b).

[22] The fusion protein of any one of [1] to [21-2], wherein each protease cleavage site is independently cleavable by a protease specific to a target tissue.

[23] The fusion protein of [22], wherein the target tissue is a cancer tissue.

[24] The fusion protein of [23], wherein each protease cleavage site is independently cleavable by a protease selected from the group consisting of matriptase, urokinase-type plasminogen activator (uPA), and metalloprotease.

[25] The fusion protein of any one of [1] to [24], wherein each protease cleavage site independently comprises a protease cleavage sequence selected from the group consisting of SEQ ID NOs: 2-135 and 160-870.

[26] The fusion protein of any one of [1] to [25], wherein each protease cleavage site is cleavable by the same protease.

[27] The fusion protein of any one of [1] to [26], wherein each protease cleavage site comprises the same protease cleavage sequence.

[28] The fusion protein of [27], wherein each protease cleavage site comprises the amino acid sequence of SEQ ID NO: 873.

[29] The fusion protein of [1], wherein the ligand-binding moiety further comprises a first flexible linker attached to one end of the at least one first protease cleavage site.

[30] The fusion protein of [29], wherein the ligand-binding domain further comprises a second flexible linker attached to the other end of the at least one first protease cleavage site.

[31] The fusion protein of [29] or [30], wherein the first flexible linker consists of a glycine-serine polymer.

[32] The fusion protein of [30] or [31], wherein the second flexible linker consists of a glycine-serine polymer.

[33] The fusion protein of [2], wherein the at least one peptide linker comprises a flexible linker.

[34] The fusion protein of [33], wherein the flexible linker consists of a glycine-serine polymer.

[35] The fusion protein of [3], wherein the at least one peptide linker further comprises a third flexible linker attached to one end of the second protease cleavage site.

[36] The fusion protein of [35], wherein the at least one peptide linker further comprises a fourth flexible linker attached to the other end of the second protease cleavage site.

[37] The fusion protein of [35] or [36], wherein the third flexible linker consists of a glycine-serine polymer.

[38] The fusion protein of [36] or [37], wherein the fourth flexible linker consists of a glycine-serine polymer.

[39] The fusion protein of [15], wherein the cleavable linker further comprises a fifth flexible linker attached to one end of the third protease cleavage site.

[40] The fusion protein of [39], wherein the cleavable linker further comprises a sixth flexible linker attached to the other end of the third protease cleavage site.

[41] The fusion protein of [39] or [40], wherein the fifth flexible linker consists of a glycine-serine polymer.

[42] The fusion protein of [40] or [41], wherein the sixth flexible linker consists of a glycine-serine polymer.

[43] The fusion protein of any one of [31], [32], [34], [37], [38], [41], and [42], wherein the glycine-serine polymer is selected from the group consisting of:

```
Ser;

Gly Ser (GS);

Ser Gly (SG);

Gly Gly Ser (GGS);

Gly Ser Gly (GSG);

Ser Gly Gly (SGG);

Gly Ser Ser (GSS);

Ser Ser Gly (SSG);

Ser Gly Ser (SGS);

Gly Gly Gly Ser (GGGS, SEQ ID NO: 136);

Gly Gly Ser Gly (GGSG, SEQ ID NO: 137);

Gly Ser Gly Gly (GSGG, SEQ ID NO: 138);

Ser Gly Gly Gly (SGGG, SEQ ID NO: 139);

Gly Ser Ser Gly (GSSG, SEQ ID NO: 140);

Gly Gly Gly Gly Ser (GGGGS, SEQ ID NO: 141);

Gly Gly Gly Ser Gly (GGGSG, SEQ ID NO: 142);

Gly Gly Ser Gly Gly (GGSGG, SEQ ID NO: 143);

Gly Ser Gly Gly Gly (GSGGG, SEQ ID NO: 144);

Gly Ser Gly Gly Ser (GSGGS, SEQ ID NO: 145);

Ser Gly Gly Gly Gly (SGGGG, SEQ ID NO: 146);

Gly Ser Ser Gly Gly (GSSGG, SEQ ID NO: 147);

Gly Ser Gly Ser Gly (GSGSG, SEQ ID NO: 148);

Ser Gly Gly Ser Gly (SGGSG, SEQ ID NO: 149);
```

-continued

```
Gly Ser Ser Ser Gly (GSSSG, SEQ ID NO: 150);

Gly Gly Gly Gly Gly Ser (GGGGGS, SEQ ID NO: 151);

Ser Gly Gly Gly Gly Gly (SGGGGG, SEQ ID NO: 152);

Gly Gly Gly Gly Gly Gly Ser (GGGGGGS, SEQ ID NO: 153);

Ser Gly Gly Gly Gly Gly Gly (SGGGGGG, SEQ ID NO: 154);

(Gly Gly Gly Gly Ser (GGGGS, SEQ ID NO: 141))n;
and (Ser Gly Gly Gly Gly (SGGGG, SEQ ID NO: 146))n;
``` wherein n is an integer of 1 or larger.

[44] The fusion protein of any one of [1] to [3], wherein the ligand-binding domain comprises a non-antibody protein or polypeptide.

[45] The fusion protein of [44], wherein the non-antibody protein or polypeptide is selected from the group consisting of a scaffold peptide, a peptide aptamer and IL-12 receptor.

[46] A pharmaceutical composition comprising the fusion protein of any one of [1] to [45].

[47] The pharmaceutical composition of [46], which is for use in treating cancer.

[48] Use of the fusion protein of any one of [1] to [45] for the production of a pharmaceutical composition for the treatment of cancer.

[49] A method for producing the fusion protein of any one of [1] to [45], comprising: providing:

(a) an ligand-binding molecule comprising an ligand binding domain and at least one first protease cleavage site, (b) at least one ligand molecule, and (c) at least one peptide linker; and connecting the at least one ligand molecule to a C-terminal region of the ligand-binding molecule via the at least one peptide linker;

wherein the ligand-binding domain binds to the ligand molecule, wherein the ligand-binding domain is capable of releasing the ligand molecule in the presence of a protease.

[50] The method of [49], which further comprises connecting the at least one ligand molecule to a N-terminal region of the ligand-binding molecule via a cleavable linker.

[51] A method for treating cancer, comprising administering the fusion protein of any one of [1] to [41] or the pharmaceutical composition of [46] or [47] to a subject.

[52] A polynucleotide encoding the fusion protein of any one of [1] to [45].

[53] A vector comprising the polynucleotide of [52].

[54] A host cell comprising the polynucleotide of [52] or the vector of [53].

[55] A method for producing the fusion protein of any one of [1] to [45], comprising culturing the host cell of [54].

[101] A fusion protein which comprises a ligand-binding moiety and is represented by general formula (I):

$$[\text{Ligand-binding domain}]\text{-}[Lx]\text{-}[Cx]\text{-}[Ly]\text{-}[\text{Ligand moiety}] \quad (I)$$

wherein:

Lx represents a first peptide linker optionally comprising a first protease cleavage site, or Lx is absent;

Cx represents a constant region comprising a second peptide linker and optionally one or more amino acid residues which are modified from or to cysteine;

Ly represents a third peptide linker, wherein the ligand-binding domain binds to the ligand moiety, and is capable of releasing the ligand moiety in the presence of a protease.

[101-1] The fusion protein of [101], which comprises two sets of the ligand-binding domain, ligand moiety, first peptide linker, constant region, and third peptide linker.

[101-2] The fusion protein of [101], which is represented by general formula (II):

$$[\text{Ligand-binding domain}]\text{-}[\text{Lx}]\text{-}[\text{Cx}]\text{-}[\text{Ly}]\text{-}[\text{Ligand moiety}]//[\text{Non-ligand-binding domain}]\text{-}[\text{Lz}]\text{-}[\text{Cz}] \quad (\text{II})$$

wherein:

Lx, Cx, and Ly are as defined in [101];

Lz represents a fourth peptide linker optionally comprising a first protease cleavage site, or Lz is absent;

Cz represents a second constant region comprising optionally a fifth peptide linker and optionally one or more amino acid residues which are modified from or to cysteine.

[101-3] The fusion protein of any one of [101] or [101-2], wherein the ligand moiety comprises CXCL10, IL-2, IL-12, IL-22, PD-1, or IL-6R.

[101-11] The fusion protein of any one of [101] to [101-3], wherein the first (or fourth) peptide linker (Lx (or Lz)) is a linker comprising the sequence of SEQ ID NO: 873 (L1).

[101-12] The fusion protein of any one of [101] to [101-3], wherein the constant region (or second constant region) comprises the sequence of SEQ ID NO: 901 (C1).

[101-13] The fusion protein of any one of [101] to [101-3], wherein the third peptide linker (Ly) is a linker comprising the sequence of SEQ ID NO: 903 (L4) or SEQ ID NO: 873 or 879 (L3) or SEQ ID NO: 927 (L5).

[101-14] The fusion protein of any one of [101], [101-1], and [101-3], which is a homo-dimer (Mab80-L1-C1-L4-IL12) comprising a light chain of SEQ ID NO: 876 and a heavy chain of SEQ ID NO: 885.

[101-15] The fusion protein of any one of [101], [101-1], and [101-3], which is a homo-dimer (087B03-L1-C1-L3-IL22) comprising a light chain of SEQ ID NO: 912 and a heavy chain of SEQ ID NO: 913.

[101-21] The fusion protein of any one of any one of [101] to [101-3], wherein the constant region (or second constant region) comprises the sequence of SEQ ID NO: 905 (C2) or 932 (C5).

[101-22] The fusion protein of any one of [101] to [101-3], which comprises a heavy chain, a light chain, wherein the second linker is positioned in a hinge region so that disulfide bond formation between Cys at position 220 (C220) (EU numbering) of the heavy chain and Cys at position 214 (C214) (EU numbering) of the light chain is promoted.

[101-23] The fusion protein of [101-22], wherein the hinge region comprises the following amino acid sequence from position 216 (EU numbering): EPKSCGGGGSGGGGSDKTHTCPPCP (SEQ ID NO: 935).

[101-24] The fusion protein of any one of [101], [101-1], and [101-3], which is a homo-dimer (Mab80-L1-C2-L4-IL12) comprising a light chain of SEQ ID NO: 876 and a heavy chain of SEQ ID NO: 904.

[101-25] The fusion protein of any one of [101], [101-1], and [101-3], which is a homo-dimer (087B03-L1-C2-L3-IL22) comprising a light chain of SEQ ID NO: 912 and a heavy chain of SEQ ID NO: 929.

[101-26] The fusion protein of any one of [101], [101-1], and [101-3], which is a homo-dimer (Cx-L1-C5-L5-IL2.N88D) comprising a light chain of SEQ ID NO: 920 and a heavy chain of SEQ ID NO: 919.

[101-27] The fusion protein of any one of [101], [101-1], and [101-3], which is a homo-dimer (16C3-L1-C5-L5-IL2.N88D) comprising a light chain of SEQ ID NO: 923 and a heavy chain of SEQ ID NO: 922.

[101-31] The fusion protein of any one of [101] to [101-3], wherein the ligand-binding moiety comprises a heavy chain and a light chain, wherein amino acid residues in the heavy chain and the light chain are modified so that no disulfide bond is formed between position 220 (EU numbering) of the heavy chain and position 214 (EU numbering) of the light chain.

[101-32] The fusion protein of [101-31], wherein the light chain comprises C214S (EU numbering) modification and the heavy chain comprises C220S (EU numbering) modification.

[101-33] The fusion protein of any one of [101] to [101-3], wherein the constant region (or second constant region) comprises the sequence of SEQ ID NO: 908 (C3).

[101-34] The fusion protein of any one of [101], [101-1], and [101-3], which is a homo-dimer (Mab80-L1-C3-L4-IL12) comprising a light chain of SEQ ID NO: 906 and heavy chain of SEQ ID NO: 907.

[101-35] The fusion protein of any one of [101], [101-1], and [101-3], which is a homo-dimer (087B03-L1-C3-L3-IL22) comprising a light chain of SEQ ID NO: 915 and a heavy chain of SEQ ID NO: 916.

[101-41] The fusion protein of any one of [101] to [101-3], wherein the ligand-binding moiety comprises a heavy chain and a light chain, wherein the heavy chain is modified to allow disulfide bond formation between position 131 (EU numbering) of the heavy chain and position 214 (EU numbering) of the light chain.

[101-42] The fusion protein of [101-41], wherein the heavy chain comprises S131C (EU numbering) and C220S (EU numbering) modifications.

[101-43] The fusion protein of any one of [101] to [101-3], wherein the constant region (or second constant region) comprises the sequence of SEQ ID NO: 910 (C4).

[101-44] The fusion protein of any one of [101], [101-1], and [101-3], which is a homo-dimer (Mab80-L1-C4-L4-IL12) comprising a light chain of SEQ ID NO: 876 and a heavy chain of SEQ ID NO: 909.

[101-45] The fusion protein of any one of [101], [101-1], and [101-3], which is a homo-dimer (087B03-L1-C4-L3-IL22) comprising a light chain of SEQ ID NO: 912 and a heavy chain of SEQ ID NO: 930.

[102] The fusion protein of any one of [101] to [101-3], wherein at least one peptide linker comprises no protease cleavage site.

[102-1] The fusion protein of any one of [101] to [101-3], wherein Cx and/or Ly comprises no protease cleavage site.

[103] The fusion protein of any one of [101] to [101-3], wherein at least one peptide linker comprises a second protease cleavage site.

[103-1] The fusion protein of any one of [101] to [101-3], wherein Ly comprises a second protease cleavage site.

[104] The fusion protein of any one of [101] to [103-1], wherein the ligand-binding domain comprises an antibody variable region.

[105] The fusion protein of [104], wherein the ligand-binding domain comprises a VH region and a VL region associating with each other.

[106] The fusion protein of [104] or [105], wherein Cx comprises a CH1 region and a CL region.

[107] The fusion protein of [106], wherein at least one protease cleavage site is located near the boundary between the VH or VL region and the CH1 or CL region.

[107-1] The fusion protein of [106], wherein Lx comprises at least one protease cleavage site which is located near the boundary between the VH or VL region and the CH1 or CL region.

[108] The fusion protein of any one of [104] to [107-1], wherein the fusion protein comprises an Fc region.

[109] The fusion protein of [108], wherein the fusion protein comprises a full-length antibody.

[110] The fusion protein of [109], wherein the full-length antibody is an IgG antibody.

[111] The fusion protein of [109] or [110], wherein the fusion protein comprises two ligand moieties and two peptide linkers, wherein each ligand moiety is connected to the C-terminal region of the ligand-binding moiety via each peptide linker.

[111-1] The fusion protein of [109] or [110], wherein the fusion protein comprises two ligand moieties and two peptide linkers, wherein each ligand moiety is connected to the C-terminal region of Cx via Ly.

[112] The fusion protein of any one of [108] to [111-2], wherein at least one ligand moiety is connected to an amino acid residue exposed on the surface of the CH3 region of the Fc region via the at least one peptide linker.

[112-1] The fusion protein of any one of [108] to [111-1], wherein at least one ligand moiety is connected to an amino acid residue exposed on the surface of the CH3 region of the Fc region via Ly.

[113] The fusion protein of any one of [101] to [112-1], wherein at least one ligand moiety is connected to the C-terminal amino acid residue of the ligand-binding moiety via the at least one peptide linker.

[113-1] The fusion protein of any one of [101] to [112-1], wherein at least one ligand moiety is connected to the C-terminal amino acid residue of the Cx via Ly.

[114] The fusion protein of any one of [101] to [113-1], which further comprises a cleavable linker comprising a third protease cleavage site, wherein at least one ligand moiety is connected to an N-terminal region of the ligand-binding moiety (domain) via the cleavable linker.

[115] The fusion protein of any one of [108] to [113-1], which further comprises a cleavable linker comprising a third protease cleavage site, wherein at least one ligand moiety is connected to one of the 1st to 230th amino acid residues from the N-terminus of the ligand-binding moiety (domain) via the cleavable linker.

[116] The fusion protein of [114] or [115], wherein the at least one ligand moiety is connected to the N-terminal amino acid residue of the ligand-binding moiety (domain) via the cleavable linker.

[117] The fusion protein of any one of [101] to [116], wherein at least one ligand moiety is biologically active, wherein binding of the ligand-binding domain to the ligand moiety inhibits the biological activity of the ligand moiety.

[118] The fusion protein of [117], wherein the at least one ligand moiety comprises a biologically active protein or polypeptide.

[119] The fusion protein of [118], wherein the at least one ligand moiety comprises a cytokine or chemokine.

[120] The fusion protein of [118], wherein the at least one ligand moiety comprises a ligand protein or polypeptide selected from the group consisting of CXCL10, IL-2, IL-12, IL-22, PD-1, or IL-6R.

[121] The fusion protein of any one of [101] to [120], wherein at least one ligand moiety comprises IL-12, and the fusion protein comprises antibody heavy and light chains selected from the group consisting of:

(a) a light chain comprising the amino acid sequence of SEQ ID NO: 874, and a heavy chain comprising the amino acid sequence of SEQ ID NO: 875;

(b) a light chain comprising the amino acid sequence of SEQ ID NO: 876, and a heavy chain comprising the amino acid sequence of SEQ ID NO: 880;

(c) a light chain comprising the amino acid sequence of SEQ ID NO: 876, and a heavy chain comprising the amino acid sequence of SEQ ID NO: 881;

(d) a light chain comprising the amino acid sequence of SEQ ID NO: 874, and a heavy chain comprising the amino acid sequence of SEQ ID NO: 884;

(e) a light chain comprising the amino acid sequence of SEQ ID NO: 876, and a heavy chain comprising the amino acid sequence of SEQ ID NO: 885;

(f) a light chain comprising the amino acid sequence of SEQ ID NO: 876, and a heavy chain comprising the amino acid sequence of SEQ ID NO: 886;

(g) a light chain comprising the amino acid sequence of SEQ ID NO: 887, and a heavy chain comprising the amino acid sequence of SEQ ID NO: 888;

(h) a light chain comprising the amino acid sequence of SEQ ID NO: 890, and a heavy chain comprising the amino acid sequence of SEQ ID NO: 891;

(i) a light chain comprising the amino acid sequence of SEQ ID NO: 876, and a heavy chain comprising the amino acid sequence of SEQ ID NO: 904;

(j) a light chain comprising the amino acid sequence of SEQ ID NO: 906, and a heavy chain comprising the amino acid sequence of SEQ ID NO: 907;

(k) a light chain comprising the amino acid sequence of SEQ ID NO: 876, and a heavy chain comprising the amino acid sequence of SEQ ID NO: 909; and (l) antibody heavy and light chains that compete with the antibody heavy chain and the antibody light chain described in (a) to (k).

[121-a] The fusion protein of any one of [101] to [120], wherein the at least one ligand moiety comprises IL-12, and the ligand-binding moiety comprises an antibody variable region comprising any one of the combinations of H-chain CDR1, CDR2, and CDR3 and L-chain CDR1, CDR2, and CDR3 selected from (a) to (l) below, or any one of the combinations of H-chain CDR1, CDR2, and CDR3 and L-chain CDR1, CDR2, and CDR3 of antibody variable regions functionally equivalent thereto:

(a) H-chain CDR1, CDR2, and CDR3 comprised in the antibody variable region are identical to the amino acid sequences of the CDR1, CDR2, and CDR3 regions comprised in SEQ ID NO: 875; and L-chain CDR1, CDR2, and CDR3 comprised in the antibody variable region are identical to the amino acid sequences of the CDR1, CDR2, and CDR3 regions comprised in SEQ ID NO: 874;

(b) H-chain CDR1, CDR2, and CDR3 comprised in the antibody variable region are identical to the amino acid sequences of the CDR1, CDR2, and CDR3 regions comprised in SEQ ID NO: 880; and L-chain CDR1, CDR2, and CDR3 comprised in the antibody variable region are identical to the amino acid sequences of the CDR1, CDR2, and CDR3 regions comprised in SEQ ID NO: 876;

(c) H-chain CDR1, CDR2, and CDR3 comprised in the antibody variable region are identical to the amino acid sequences of the CDR1, CDR2, and CDR3 regions comprised in SEQ ID NO: 881; and L-chain CDR1, CDR2, and CDR3 comprised in the antibody variable region are identical to the amino acid sequences of the CDR1, CDR2, and CDR3 regions comprised in SEQ ID NO: 876;

(d) H-chain CDR1, CDR2, and CDR3 comprised in the antibody variable region are identical to the amino acid sequences of the CDR1, CDR2, and CDR3 regions comprised in SEQ ID NO: 884; and L-chain CDR1, CDR2, and CDR3 comprised in the antibody variable region are identical to the amino acid sequences of the CDR1, CDR2, and CDR3 regions comprised in SEQ ID NO: 874;

(e) H-chain CDR1, CDR2, and CDR3 comprised in the antibody variable region are identical to the amino acid sequences of the CDR1, CDR2, and CDR3 regions comprised in SEQ ID NO: 885; and L-chain CDR1, CDR2, and CDR3 comprised in the antibody variable region are identical to the amino acid sequences of the CDR1, CDR2, and CDR3 regions comprised in SEQ ID NO: 876;

(f) H-chain CDR1, CDR2, and CDR3 comprised in the antibody variable region are identical to the amino acid sequences of the CDR1, CDR2, and CDR3 regions comprised in SEQ ID NO: 886; and L-chain CDR1, CDR2, and CDR3 comprised in the antibody variable region are identical to the amino acid sequences of the CDR1, CDR2, and CDR3 regions comprised in SEQ ID NO: 876;

(g) H-chain CDR1, CDR2, and CDR3 comprised in the antibody variable region are identical to the amino acid sequences of the CDR1, CDR2, and CDR3 regions comprised in SEQ ID NO: 888; and L-chain CDR1, CDR2, and CDR3 comprised in the antibody variable region are identical to the amino acid sequences of the CDR1, CDR2, and CDR3 regions comprised in SEQ ID NO: 887;

(h) H-chain CDR1, CDR2, and CDR3 comprised in the antibody variable region are identical to the amino acid sequences of the CDR1, CDR2, and CDR3 regions comprised in SEQ ID NO: 891; and L-chain CDR1, CDR2, and CDR3 comprised in the antibody variable region are identical to the amino acid sequences of the CDR1, CDR2, and CDR3 regions comprised in SEQ ID NO: 890;

(i) H-chain CDR1, CDR2, and CDR3 comprised in the antibody variable region are identical to the amino acid sequences of the CDR1, CDR2, and CDR3 regions comprised in SEQ ID NO: 904; and L-chain CDR1, CDR2, and CDR3 comprised in the antibody variable region are identical to the amino acid sequences of the CDR1, CDR2, and CDR3 regions comprised in SEQ ID NO: 876;

(j) H-chain CDR1, CDR2, and CDR3 comprised in the antibody variable region are identical to the amino acid sequences of the CDR1, CDR2, and CDR3 regions comprised in SEQ ID NO: 907; and L-chain CDR1, CDR2, and CDR3 comprised in the antibody variable region are identical to the amino acid sequences of the CDR1, CDR2, and CDR3 regions comprised in SEQ ID NO: 906;

(k) H-chain CDR1, CDR2, and CDR3 comprised in the antibody variable region are identical to the amino acid sequences of the CDR1, CDR2, and CDR3 regions comprised in SEQ ID NO: 909; and L-chain CDR1, CDR2, and CDR3 comprised in the antibody variable region are identical to the amino acid sequences of the CDR1, CDR2, and CDR3 regions comprised in SEQ ID NO: 876; and (l) H-chain and L-chain CDR1, CDR2 and CDR3 comprised in antibody variable regions that compete with the antibody heavy chain variable region and the antibody light chain variable region described in (a) to (k).

[121-b] The fusion protein of any one of [101] to [120], wherein the at least one ligand moiety comprises IL-12, and the ligand-binding moiety comprises any one of the combinations of heavy-chain variable region (VH) and light-chain variable region (VL) selected from (a) to (l) below:

(a) a VH comprised in SEQ ID NO: 875; and a VL comprised in SEQ ID NO: 874;

(b) a VH comprised in SEQ ID NO: 880; and a VL comprised in SEQ ID NO: 876;

(c) a VH comprised in SEQ ID NO: 881; and a VL comprised in SEQ ID NO: 876;

(d) a VH comprised in SEQ ID NO: 884; and a VL comprised in SEQ ID NO: 874;

(e) a VH comprised in SEQ ID NO: 885; and a VL comprised in SEQ ID NO: 876;

(f) a VH comprised in SEQ ID NO: 886; and a VL comprised in SEQ ID NO: 876;

(g) a VH comprised in SEQ ID NO: 888; and a VL comprised in SEQ ID NO: 887;

(h) a VH comprised in SEQ ID NO: 891; and a VL comprised in SEQ ID NO: 890;

(i) a VH comprised in SEQ ID NO: 904; and a VL comprised in SEQ ID NO: 876;

(j) a VH comprised in SEQ ID NO: 907; and a VL comprised in SEQ ID NO: 906;

(k) a VH comprised in SEQ ID NO: 909; and a VL comprised in SEQ ID NO: 876; and (l) a VH and a VL that compete with the VH and the VL described in (a) to (k).

[121-c] The fusion protein of any one of [101] to [120], wherein the at least one ligand moiety comprises IL-12, wherein the fusion protein comprises any one of the combinations selected from (a) to (d) below:

(a) a first light chain comprising the sequence of SEQ ID NO: 876, a first heavy chain comprising the sequence of SEQ ID NO: 881, a second light chain comprising the sequence of SEQ ID NO: 882, and a second heavy chain comprising the sequence of SEQ ID NO: 883;

(b) a first light chain comprising the sequence of SEQ ID NO: 876, a first heavy chain comprising the sequence of SEQ ID NO: 886, a second light chain comprising the sequence of SEQ ID NO: 882, and a second heavy chain comprising the sequence of SEQ ID NO: 883;

(c) a first light chain comprising the sequence of SEQ ID NO: 887, a first heavy chain comprising the sequence of SEQ ID NO: 888, a second light chain comprising the sequence of SEQ ID NO: 882, and a second heavy chain comprising the sequence of SEQ ID NO: 883; and (d) a first light chain comprising the sequence of SEQ ID NO: 890, a first heavy chain comprising the sequence of SEQ ID NO: 891, a second light chain comprising the sequence of SEQ ID NO: 882, and a second heavy chain comprising the sequence of SEQ ID NO: 883.

[121-2] The fusion protein of any one of [101] to [120], wherein at least one ligand moiety comprises IL-22, and the fusion protein comprises antibody heavy and light chains selected from the group consisting of:

(a) a light chain comprising the amino acid sequence of SEQ ID NO: 912, and a heavy chain comprising the amino acid sequence of SEQ ID NO: 913;

(b) a light chain comprising the amino acid sequence of SEQ ID NO: 915, and a heavy chain comprising the amino acid sequence of SEQ ID NO: 916;

(c) a light chain comprising the amino acid sequence of SEQ ID NO: 912, and a heavy chain comprising the amino acid sequence of SEQ ID NO: 929;

(d) a light chain comprising the amino acid sequence of SEQ ID NO: 912, and a heavy chain comprising the amino acid sequence of SEQ ID NO: 930; and (e) antibody heavy and light chains that compete with the antibody heavy chain and the antibody light chain described in (a) to (d).

[121-2a] The fusion protein of any one of [101] to [120], wherein the at least one ligand moiety comprises IL-22 and the ligand-binding moiety comprises an antibody variable region comprising any one of the combinations of H-chain CDR1, CDR2, and CDR3 and L-chain CDR1, CDR2, and CDR3 selected from (a) to (e) below, or any one of the combinations of H-chain CDR1, CDR2, and CDR3 and L-chain CDR1, CDR2, and CDR3 of antibody variable regions functionally equivalent thereto:

(a) H-chain CDR1, CDR2, and CDR3 comprised in the antibody variable region are identical to the amino acid sequences of the CDR1, CDR2, and CDR3 regions comprised in SEQ ID NO: 913; and L-chain CDR1, CDR2, and CDR3 comprised in the antibody variable region are identical to the amino acid sequences of the CDR1, CDR2, and CDR3 regions comprised in SEQ ID NO: 912;

(b) H-chain CDR1, CDR2, and CDR3 comprised in the antibody variable region are identical to the amino acid sequences of the CDR1, CDR2, and CDR3 regions comprised in SEQ ID NO: 916; and L-chain CDR1, CDR2, and CDR3 comprised in the antibody variable region are identical to the amino acid sequences of the CDR1, CDR2, and CDR3 regions comprised in SEQ ID NO: 915;

(c) H-chain CDR1, CDR2, and CDR3 comprised in the antibody variable region are identical to the amino acid sequences of the CDR1, CDR2, and CDR3 regions comprised in SEQ ID NO: 929; and L-chain CDR1, CDR2, and CDR3 comprised in the antibody variable region are identical to the amino acid sequences of the CDR1, CDR2, and CDR3 regions comprised in SEQ ID NO: 912;

(d) H-chain CDR1, CDR2, and CDR3 comprised in the antibody variable region are identical to the amino acid sequences of the CDR1, CDR2, and CDR3 regions comprised in SEQ ID NO: 930; and L-chain CDR1, CDR2, and CDR3 comprised in the antibody variable region are identical to the amino acid sequences of the CDR1, CDR2, and CDR3 regions comprised in SEQ ID NO: 912; and (e) H-chain and L-chain CDR1, CDR2 and CDR3 comprised in antibody variable regions that compete with the antibody heavy chain variable region and the antibody light chain variable region described in (a) to (d).

[121-2b] The fusion protein of any one of [101] to [120], wherein the at least one ligand moiety comprises IL-22, and the ligand-binding moiety comprises any one of the combinations of heavy-chain variable region (VH) and light-chain variable region (VL) selected from (a) to (e) below:

(a) a VH comprised in SEQ ID NO: 913; and a VL comprised in SEQ ID NO: 912;

(b) a VH comprised in SEQ ID NO: 916; and a VL comprised in SEQ ID NO: 915;

(c) a VH comprised in SEQ ID NO: 929; and a VL comprised in SEQ ID NO: 912;

(d) a VH comprised in SEQ ID NO: 930; and a VL comprised in SEQ ID NO: 912; and (e) a VH and a VL that compete with the VH and the VL described in (a) to (d).

[121-3] The fusion protein of any one of [101] to [120], wherein the at least one ligand moiety comprises IL-2, and the fusion protein comprises antibody heavy and light chains selected from the group consisting of:

(a) a light chain comprising the amino acid sequence of SEQ ID NO: 920, and a heavy chain comprising the amino acid sequence of SEQ ID NO: 919;

(b) a light chain comprising the amino acid sequence of SEQ ID NO: 923, and a heavy chain comprising the amino acid sequence of SEQ ID NO: 922; and (c) antibody heavy and light chains that compete with the antibody heavy chain and the antibody light chain described in (a) to (b).

[121-3a] The fusion protein of any one of [101] to [120], wherein the at least one ligand moiety comprises IL-2 and the ligand-binding moiety comprises an antibody variable region comprising any one of the combinations of H-chain CDR1, CDR2, and CDR3 and L-chain CDR1, CDR2, and CDR3 selected from (a) to (e) below, or any one of the combinations of H-chain CDR1, CDR2, and CDR3 and L-chain CDR1, CDR2, and CDR3 of antibody variable regions functionally equivalent thereto:

(a) H-chain CDR1, CDR2, and CDR3 comprised in the antibody variable region are identical to the amino acid sequences of the CDR1, CDR2, and CDR3 regions comprised in SEQ ID NO: 919; and L-chain CDR1, CDR2, and CDR3 comprised in the antibody variable region are identical to the amino acid sequences of the CDR1, CDR2, and CDR3 regions comprised in SEQ ID NO: 920;

(b) H-chain CDR1, CDR2, and CDR3 comprised in the antibody variable region are identical to the amino acid sequences of the CDR1, CDR2, and CDR3 regions comprised in SEQ ID NO: 922; and L-chain CDR1, CDR2, and CDR3 comprised in the antibody variable region are identical to the amino acid sequences of the CDR1, CDR2, and CDR3 regions comprised in SEQ ID NO: 923; and (c) H-chain and L-chain CDR1, CDR2 and CDR3 comprised in antibody variable regions that compete with the antibody heavy chain variable region and the antibody light chain variable region described in (a) to (b).

[121-3b] The fusion protein of any one of [101] to [120], wherein the at least one ligand moiety comprises IL-2, and the ligand-binding moiety comprises any one of the combinations of heavy-chain variable region (VH) and light-chain variable region (VL) selected from (a) to (c) below:

(a) a VH comprised in SEQ ID NO: 919; and a VL comprised in SEQ ID NO: 920;

(b) a VH comprised in SEQ ID NO: 922; and a VL comprised in SEQ ID NO: 923; and (c) a VH and a VL that compete with the VH and the VL described in (a) to (b).

[122] The fusion protein of any one of [101] to [121-3b], wherein each protease cleavage site is independently cleavable by a protease specific to a target tissue.

[123] The fusion protein of [122], wherein the target tissue is a cancer tissue.

[124] The fusion protein of [123], wherein each protease cleavage site is independently cleavable by a protease selected from the group consisting of matriptase, urokinase-type plasminogen activator (uPA), and metalloprotease.

[125] The fusion protein of any one of [101] to [124], wherein each protease cleavage site independently comprises a protease cleavage sequence selected from the group consisting of SEQ ID NOs: 2-135 and 160-870.

[126] The fusion protein of any one of [101] to [125], wherein each protease cleavage site is cleavable by the same protease.

[127] The fusion protein of any one of [101] to [126], wherein each protease cleavage site comprises the same protease cleavage sequence.

[128] The fusion protein of [127], wherein each protease cleavage site comprises the amino acid sequence of SEQ ID NO: 873.

[129] The fusion protein of any one of [101] to [101-3], wherein the ligand-binding moiety further comprises a first flexible linker attached to one end of the first protease cleavage site.

[130] The fusion protein of [129], wherein the ligand-binding domain further comprises a second flexible linker attached to the other end of the first protease cleavage site.

[131] The fusion protein of [129] or [130], wherein the first flexible linker consists of a glycine-serine polymer.

[132] The fusion protein of [130] or [131], wherein the second flexible linker consists of a glycine-serine polymer.

[133] The fusion protein of [102], wherein at least one peptide linker comprises a flexible linker.

[134] The fusion protein of [133], wherein the flexible linker consists of a glycine-serine polymer.

[135] The fusion protein of [103], wherein at least one peptide linker further comprises a third flexible linker attached to one end of the second protease cleavage site.

[136] The fusion protein of [135], wherein the at least one peptide linker further comprises a fourth flexible linker attached to the other end of the second protease cleavage site.

[137] The fusion protein of [135] or [136], wherein the third flexible linker consists of a glycine-serine polymer.

[138] The fusion protein of [136] or [137], wherein the fourth flexible linker consists of a glycine-serine polymer.

[139] The fusion protein of [115], wherein the cleavable linker further comprises a fifth flexible linker attached to one end of the third protease cleavage site.

[140] The fusion protein of [139], wherein the cleavable linker further comprises a sixth flexible linker attached to the other end of the third protease cleavage site.

[141] The fusion protein of [139] or [140], wherein the fifth flexible linker consists of a glycine-serine polymer.

[142] The fusion protein of [140] or [141], wherein the sixth flexible linker consists of a glycine-serine polymer.

[143] The fusion protein of any one of [131], [132], [134],

[137], [138], [141], and [142], wherein the glycine-serine polymer is selected from the group consisting of:

```
Ser;

Gly Ser (GS);

Ser Gly (SG);

Gly Gly Ser (GGS);

Gly Ser Gly (GSG);

Ser Gly Gly (SGG);

Gly SerSer(GSS);

Ser Ser Gly (SSG);

Ser Gly Ser (SGS);

Gly Gly Gly Ser (GGGS, SEQ ID NO: 136);

Gly Gly Ser Gly (GGSG, SEQ ID NO: 137);

Gly Ser Gly Gly (GSGG, SEQ ID NO: 138);

Ser Gly Gly Gly (SGGG, SEQ ID NO: 139);

Gly Ser Ser Gly (GSSG, SEQ ID NO: 140);

Gly Gly Gly Gly Ser (GGGGS, SEQ ID NO: 141);

Gly Gly Gly Ser Gly (GGGSG, SEQ ID NO: 142);

Gly Gly Ser Gly Gly (GGSGG, SEQ ID NO: 143);

Gly Ser Gly Gly Gly (GSGGG, SEQ ID NO: 144);

Gly Ser Gly Gly Ser (GSGGS, SEQ ID NO: 145);

Ser Gly Gly Gly Gly (SGGGG, SEQ ID NO: 146);

Gly Ser Ser Gly Gly (GSSGG, SEQ ID NO: 147);

Gly Ser Gly Ser Gly (GSGSG, SEQ ID NO: 148);

Ser Gly Gly Ser Gly (SGGSG, SEQ ID NO: 149);

Gly Ser Ser Ser Gly (GSSSG, SEQ ID NO: 150);

Gly Gly Gly Gly Gly Ser
(GGGGGS, SEQ ID NO: 151);

Ser Gly Gly Gly Gly Gly
(SGGGGG, SEQ ID NO: 152);

Gly Gly Gly Gly Gly Gly
Ser (GGGGGGS, SEQ ID NO: 153);

Ser Gly Gly Gly Gly Gly Gly (SGGGGGG, SEQ ID NO: 154);

(Gly Gly Gly Gly Ser (GGGGS, SEQ ID NO: 141))n;
and (Ser Gly Gly Gly Gly (SGGGG, SEQ ID NO: 146))n;
``` wherein n is an integer of 1 or larger.

[144] The fusion protein of any one of [101] to [103], wherein the ligand-binding domain comprises a non-antibody protein or polypeptide.

[145] The fusion protein of [144], wherein the non-antibody protein or polypeptide is selected from the group consisting of a scaffold peptide, a peptide aptamer and IL-12 receptor.

[146] A pharmaceutical composition comprising the fusion protein of any one of [101] to [145].

[147] The pharmaceutical composition of [146], which is for use in treating cancer.

[148] Use of the fusion protein of any one of [101] to [145] for the production of a pharmaceutical composition for the treatment of cancer.

[149] A method for producing the fusion protein of any one of [101] to [145], comprising:

providing:

(a) an ligand-binding molecule comprising an ligand binding domain and at least one protease cleavage site, (b) at least one ligand moiety, and (c) at least one peptide linker; and connecting the at least one ligand moiety to a C-terminal region of the ligand-binding molecule via the at least one peptide linker;

wherein the ligand-binding domain binds to the ligand moiety, wherein the ligand-binding domain is capable of releasing the ligand moiety in the presence of a protease.

[150] The method of [149], which further comprises connecting the at least one ligand moiety to a N-terminal region of the ligand-binding molecule via a cleavable linker.

[151] A method for treating cancer, comprising administering the fusion protein of any one of [101] to [141] or the pharmaceutical composition of [146] or [147] to a subject.

[152] A polynucleotide encoding the fusion protein of any one of [101] to [145].

[153] A vector comprising the polynucleotide of [152].

[154] A host cell comprising the polynucleotide of [152] or the vector of [153].

[155] A method for producing the fusion protein of any one of [101] to [145], comprising culturing the host cell of [154].

BRIEF DESCRIPTION OF DRAWINGS

FIG. 3C shows the SDS-PAGE for cleaved products obtained after MTSP1 digestion of IL-12 release type molecules.

FIG. 5 shows IL-12 bioactivity of intact and MTSP1-cleaved IL-12 release type antibodies.

FIG. 6 shows IL-12 bioactivity of intact and MTSP1-cleaved IL-12 fusion type antibodies.

FIG. 7A shows the results of SDS-PAGE under reducing and non-reducing conditions for Mab80-L1-C1-L4-IL12 (F4 bivalent IL-12 fusion Mab80).

FIG. 9 is a diagram showing IL-22 fused antibodies in which IL-22 is fused to the C-terminus of Fc via cleavable (A) or non-cleavable (B) linkers. Cleavable linkers are indicated by black triangles, and if cleaved by protease, active IL-22 molecules are released.

FIG. 12 shows the SDS-PAGE analysis for IL-22 releasing antibodies with improved homogeneity.

FIG. 15 shows IL-22 bioactivity of uPA-cleaved and intact IL-22 release type molecules 087B03-L1-C2-L3-IL22 and 087B03-L1-C4-L3-IL22.

FIG. 16 shows a schematic diagram of exemplary IL-2 N88D fused antibodies, with and without protease cleavage sites, to illustrate the cleavage by protease.

FIG. 17 shows VH release from the antibody Cx-L1-C5-L5-IL2.N88D and 16C3-L1-C5-L5-IL2.N88D as a result of protease digestion.

DESCRIPTION OF EMBODIMENTS

Figure 1A:
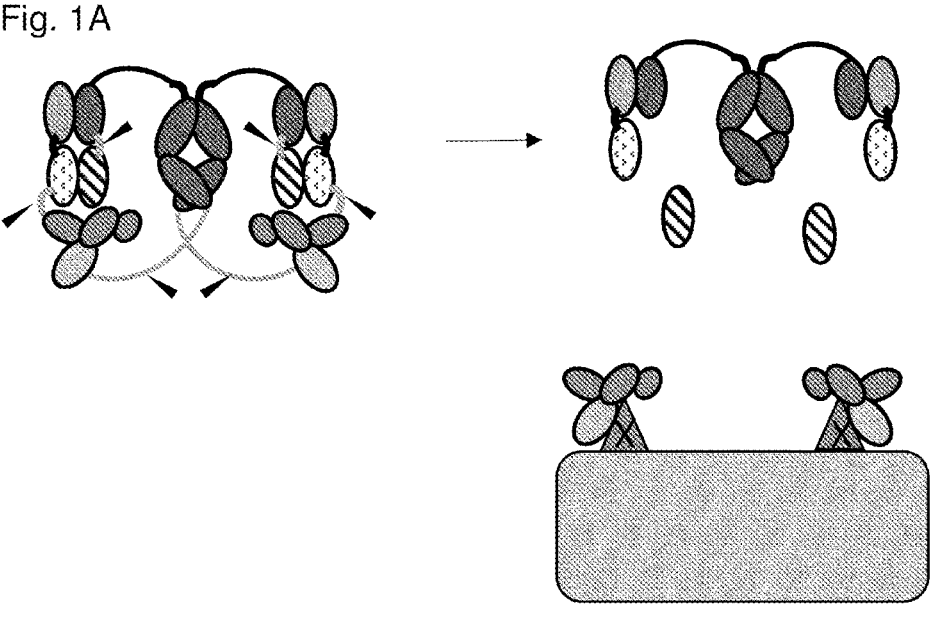
FIG. 1A is a diagram showing a fusion protein of an IgG antibody and IL-12 in which antibody and IL-12 molecules are fused via cleavable linkers. Cleavable linkers indicated by black triangles are cleaved by proteases and active free IL-12 molecules are released after cleavage.

As used herein, the term "polypeptide" or "protein" usually refers to a peptide having a length on the order of 4 amino acids or longer. Also, a polypeptide or protein herein is typically a polypeptide consisting of an artificially designed sequence, but is not limited thereto. For example, a polypeptide or protein may be of biological origin. Alternatively, a polypeptide or protein herein may be any of a natural polypeptide, a synthetic polypeptide, a recombinant polypeptide, and the like. Furthermore, fragments of such polypeptides or proteins are also included in the term "polypeptide" or "protein" as used herein.

Herein, each amino acid is indicated by one-letter code or three-letter code, or both, as represented by, for example, Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I, or Val/V.

Herein, alteration of amino acids is mentioned Amino acid alteration means any of substitution, deletion, addition, and insertion, or a combination thereof. In the present disclosure, amino acid alteration may be rephrased as amino acid mutation or amino acid modification. For amino acid alteration in the amino acid sequence of an antigen-binding molecule, known methods such as site-directed mutagenesis methods (Kunkel et al. (Proc. Natl. Acad. Sci. USA (1985) 82, 488-492)) and overlap extension PCR may be appropriately employed. Furthermore, several known methods may also be employed as amino acid alteration methods for substitution to non-natural amino acids (Annu Rev. Biophys. Biomol. Struct. (2006) 35, 225-249; and Proc. Natl. Acad. Sci. U.S.A. (2003) 100 (11), 6353-6357). For example, it is suitable to use a cell-free translation system (Clover Direct (Protein Express)) containing a tRNA which has a non-natural amino acid bound to a complementary amber suppressor tRNA of one of the stop codons, the UAG codon (amber codon).

Herein, the term "and/or" used to refer to amino acid alteration sites is meant to include all combinations of amino acid alteration sites appropriately combined with "and" and "or". Specifically, for example, the phrase "amino acids at positions 37, 45, and/or 47 are substituted" includes the following variations of amino acid alteration: (a) position 37, (b) position 45, (c) position 47, (d) positions 37 and 45, (e) positions 37 and 47, (f) positions 45 and 47, and (g) positions 37, 45 and 47.

Herein, where appropriate, amino acid alteration may be denoted by a number representing a particular position preceded and followed by the one-letter codes or three-letter codes of amino acids before and after alteration, respectively. For example, an alteration F37V or Phe37Val used for substituting an amino acid contained in an antibody variable region represents the substitution of Phe at position 37 defined by the Kabat numbering by Val. Specifically, the number represents an amino acid position defined by the Kabat numbering; the one-letter code or three-letter code of the amino acid previous to the number represents the amino acid before the substitution; and the one-letter code or three-letter code of the amino acid next to the number represents the amino acid after the substitution. Likewise, an alteration P238A or Pro238Ala used for substituting an amino acid in a Fc region contained in an antibody constant region represents the substitution of Pro at position 238 defined by the EU numbering by Ala. Specifically, the number represents an amino acid position defined by the EU numbering; the one-letter code or three-letter code of the amino acid previous to the number represents the amino acid before the substitution; and the one-letter code or three-letter code of the amino acid next to the number represents the amino acid after the substitution.

In one aspect, the present invention relates to a fusion protein, comprising:

(a) a ligand-binding moiety comprising a ligand-binding domain and at least one first protease cleavage site;

(b) at least one ligand moiety; and (c) at least one peptide linker connecting the at least one ligand moiety to a C-terminal region of the ligand-binding moiety;

wherein the ligand-binding domain binds to the at least one ligand moiety, and is capable of releasing the at least one ligand moiety in the presence of a protease.

As used herein, the term "ligand-binding moiety" or "ligand-binding molecule" refers to a moiety or molecule that is capable of binding to a ligand (e.g., a ligand moiety within the fusion protein of the present invention), and particularly refers to a moiety or molecule that is capable of binding to a ligand when the moiety or molecule is in the uncleaved state. In this context, the "binding" usually refers to binding through interaction based mainly on a noncovalent bond such as electrostatic force, van der Waals' force, or a hydrogen bond. Preferred examples of the binding mode of the ligand-binding moiety or molecule include, but are not limited to, antigen-antibody reaction through which an antigen-binding domain, an antigen-binding molecule, an antibody, an antibody fragment, or the like binds to the antigen. In certain embodiments, the ligand-binding moiety or molecule includes, but is not limited to, antibody fragments, antibodies, and molecules formed from antibody fragments (e.g. diabodies, chimeric antigen receptors (CARs)), including multispecific binding molecules (e.g. bispecific diabodies and bispecific antibodies).

The phrase "capable of binding to a ligand" means that the ligand-binding domain in the ligand-binding moiety or molecule is capable of binding to the ligand even if the ligand-binding moiety/molecule and the ligand are separate molecules, instead of being bound to each other in a single molecule. That is, the ligand-binding moiety/molecule and the ligand may be or may not be connected through a covalent bond. For example, the phrase "capable of binding to a ligand" may not necessarily mean that the ligand and the ligand-binding moiety/molecule are connected through a covalent bond via a linker. Also, the phrase "ligand binding is attenuated" means that the capability of binding (i.e., binding capacity of the ligand-binding domain) described above is attenuated. For example, when the ligand and the ligand-binding molecule are connected through a covalent bond via a linker, cleavage of the linker does not mean attenuation of the ligand binding. In the present invention, the ligand-binding moiety/molecule is connected with the ligand moiety/molecule via a peptide linker in a manner that allows the ligand-binding domain to bind to the ligand moiety/molecule.

As used herein, the term "ligand-binding domain" refers to a portion of a ligand-binding moiety or molecule which binds only to a portion of a ligand (epitope) when the ligand-binding moiety/molecule binds to the ligand. In the present invention, the ligand-binding domain is limited only by the fact that the domain binds to a ligand when the ligand-binding moiety/molecule is in the uncleaved state, and may have any structure as long as the domain can bind to a ligand of interest when the ligand-binding moiety/molecule is in the uncleaved state. Examples of the ligand-binding domain include, but are not limited to, an antibody heavy chain variable region (VH), an antibody light chain variable region (VL), an antibody Fv region, a single-domain antibody (sdAb), a scaffold peptide, a peptide aptamer (Reverdatto S. et al., Curr Top Med Chem. 2015; 15(12): 1082-1101), IL-12 receptor, a module called A domain of approximately 35 amino acids contained in an in vivo cell membrane protein avimer (WO2004/044011 and WO2005/040229), adnectin containing a 10Fn3 domain serving as a protein binding domain derived from a glyco-protein fibronectin expressed on cell membranes (WO2002/032925), Affibody containing an IgG binding domain scaffold constituting a three-helix bundle composed of 58 amino acids of protein A (WO1995/001937), DARPins (designed ankyrin repeat proteins) which are molecular surface-exposed regions of ankyrin repeats (AR) each having a 33-amino acid residue structure folded into a subunit of a turn, two antiparallel helices, and a loop (WO2002/020565), anticalin having four loop regions connecting eight antiparallel strands bent toward the central axis in one end of a barrel structure highly conserved in lipocalin molecules such as neutrophil gelatinase-associated lipocalin (NGAL) (WO2003/029462), and a depressed region in the internal parallel sheet structure of a horseshoe-shaped fold composed of repeated leucine-rich-repeat (LRR) modules of an immu-noglobulin structure-free variable lymphocyte receptor (VLR) as seen in the acquired immune systems of jawless vertebrates such as lamprey or hagfish (WO2008/016854).

In the present specification, the term "antibody" is used in the broadest sense and encompasses various antibody structures including, but are not limited to, a monoclonal antibody, a polyclonal antibody, a multispecific antibody (e.g., a bispecific antibody), and an antibody fragment as long as the antibody exhibits the desired antigen binding activity.

A method for preparing an antibody having desired binding activity is known to those skilled in the art. Hereinafter, a method for preparing an antibody binding to IL-6R (anti-IL-6R antibody) will be given as an example. Antibodies binding to antigens other than IL-6R can also be appropriately prepared according to the example given below.

The anti-IL-6R antibody can be obtained as a polyclonal or monoclonal antibody by use of an approach known in the art. A mammal-derived monoclonal antibody can be preferably prepared as the anti-IL-6R antibody. The mammal-derived monoclonal antibody includes, for example, those produced by hybridomas and those produced by host cells transformed with an expression vector containing an antibody gene by a genetic engineering approach. The antibody described in the present application includes a "humanized antibody" and a "chimeric antibody".

The monoclonal antibody-producing hybridomas can be prepared by use of a technique known in the art, for example, as follows: mammals are immunized with IL-6R protein used as a sensitizing antigen according to a usual immunization method Immunocytes thus obtained are fused with parental cells known in the art by a usual cell fusion method. Next, cells producing a monoclonal antibody can be screened for by a usual screening method to select hybridomas producing the anti-IL-6R antibody.

Specifically, the monoclonal antibody is prepared, for example, as follows: first, the IL-6R gene can be expressed to obtain the IL-6R protein which is used as a sensitizing antigen for antibody obtainment. Specifically, a gene sequence encoding IL-6R is inserted into an expression vector known in the art, with which appropriate host cells are then transformed. The desired human IL-6R protein is purified from the host cells or from a culture supernatant thereof by a method known in the art. In order to obtain soluble IL-6R from the culture supernatant, for example, soluble IL-6R as described by Mullberg et al. (J. Immunol. (1994) 152 (10), 4958-4968) is expressed. Alternatively, purified natural IL-6R protein can also be used as a sensitizing antigen.

The purified IL-6R protein can be used as the sensitizing antigen for use in the immunization of mammals. A partial peptide of IL-6R can also be used as the sensitizing antigen. This partial peptide may be obtained by chemical synthesis from the amino acid sequence of human IL-6R. Alternatively, the partial peptide may be obtained by the integration of a portion of the IL-6R gene to an expression vector followed by its expression. Furthermore, the partial peptide can also be obtained by the degradation of the IL-6R protein with a proteolytic enzyme. The region and size of the IL-6R peptide for use as such a partial peptide are not particularly limited by specific embodiments. The number of amino acids constituting the peptide as the sensitizing antigen is preferably at least 5 or more, for example, 6 or more or 7 or more. More specifically, a peptide of 8 to 50, preferably 10 to 30 residues can be used as the sensitizing antigen.

Also, a fusion protein of a desired partial polypeptide or peptide of the IL-6R protein fused with a different polypeptide can be used as the sensitizing antigen. For example, an antibody Fc fragment or a peptide tag can be preferably used for producing the fusion protein for use as the sensitizing antigen. A vector for the expression of the fusion protein can be prepared by fusing in frame genes encoding two or more types of the desired polypeptide fragments, and inserting the fusion gene into an expression vector as described above. The method for preparing the fusion protein is described in Molecular Cloning 2nd ed. (Sambrook, J. et al., Molecular Cloning 2nd ed., 9.47-9.58 (1989), Cold Spring Harbor Lab. Press). The method for obtaining IL-6R for use as the sensitizing antigen and the immunization method using this sensitizing antigen are also specifically described in WO2003/000883, WO2004/022754, WO2006/006693, etc.

The mammals to be immunized with the sensitizing antigen are not limited to particular animals. The mammals to be immunized are preferably selected in consideration of compatibility with the parental cells for use in cell fusion. In general, rodents (e.g., mice, rats, and hamsters), rabbits, monkeys, or the like are preferably used.

These animals are immunized with the sensitizing antigen according to a method known in the art. For example, a general immunization method involves administering the sensitizing antigen to the mammals by intraperitoneal or subcutaneous injection. Specifically, the sensitizing antigen diluted with PBS (phosphate-buffered saline), physiological saline, or the like at an appropriate dilution ratio is mixed, if desired, with a usual adjuvant, for example, a Freund's complete adjuvant and emulsified. Then, the resulting sensitizing antigen is administered to the mammals several times at 4- to 21-day intervals. Also, an appropriate carrier can be used in the immunization with the sensitizing antigen. Particularly, in the case of using a partial peptide having a small molecular weight as the sensitizing antigen, immunization with the sensitizing antigen peptide bound with a carrier protein such as albumin or keyhole limpet hemocyanin may be desirable in some cases.

Alternatively, the hybridomas producing the desired antibody can also be prepared as described below by use of DNA immunization. The DNA immunization is an immunization method which involves immunostimulating immunized animals by expressing in vivo the sensitizing antigen in the immunized animals given vector DNA that has been constructed in a form capable of expressing the gene encoding the antigenic protein in the immunized animals. The DNA immunization can be expected to be superior to the general immunization method using the administration of the protein antigen to animals to be immunized as follows:

the DNA immunization can provide immunostimulation with the structure of a membrane protein (e.g., IL-6R) maintained; and the DNA immunization eliminates the need of purifying the immunizing antigen.

In order to obtain the monoclonal antibody of the present invention by the DNA immunization, first, DNA for IL-6R protein expression is administered to animals to be immunized. The DNA encoding IL-6R can be synthesized by a method known in the art such as PCR. The obtained DNA is inserted into an appropriate expression vector, and then administered to the animals to be immunized. For example, a commercially available expression vector such as pcDNA3.1 can be preferably used as the expression vector. The vector can be administered to the organisms by a method generally used. For example, animal individuals are DNA-immunized by introducing into their cells gold particles with the expression vector adsorbed thereon using a gene gun. Furthermore, the antibody recognizing IL-6R can also be prepared by use of a method described in WO 2003/104453.

A rise in the titer of the antibody binding to IL-6R is confirmed in the serum of the mammals thus immunized. Then, immunocytes are collected from the mammals and subjected to cell fusion. Particularly, spleen cells can be used as preferred immunocytes.

Mammalian myeloma cells are used in the cell fusion with the immunocytes. The myeloma cells preferably have an appropriate selection marker for screening. The selection marker refers to a trait that can survive (or cannot survive) under particular culture conditions. For example, hypoxanthine-guanine phosphoribosyltransferase deficiency (hereinafter, referred to as HGPRT deficiency) or thymidine kinase deficiency (hereinafter, referred to as TK deficiency) is known in the art as the selection marker. Cells having the HGPRT or TK deficiency are sensitive to hypoxanthine-aminopterin-thymidine (hereinafter, referred to as HAT-sensitive). The HAT-sensitive cells are killed in a HAT selective medium because the cells fail to synthesize DNA.

By contrast, these cells, when fused with normal cells, become able to grow even in the HAT selective medium because the fused cells can continue DNA synthesis through the use of the salvage pathway of the normal cells.

The cells having the HGPRT or TK deficiency can be selected in a medium containing 6-thioguanine or 8-azaguanine (hereinafter, abbreviated to 8AG) for the HGPRT deficiency or 5'-bromodeoxyuridine for the TK deficiency. The normal cells are killed by incorporating these pyrimidine analogs into their DNAs. By contrast, the cells deficient in these enzymes can survive in the selective medium because the cells cannot incorporate the pyrimidine analogs therein. In addition, a selection marker called G418 resistance confers resistance to a 2-deoxystreptamine antibiotic (gentamicin analog) through a neomycin resistance gene. Various myeloma cells suitable for cell fusion are known in the art.

For example, P3 (P3x63Ag8.653) (J. Immunol. (1979) 123 (4), 1548-1550), P3x63Ag8U.1 (Current Topics in Microbiology and Immunology (1978) 81, 1-7), NS-1 (C. Eur. J. Immunol. (1976) 6 (7), 511-519), MPC-11 (Cell (1976) 8 (3), 405-415), SP2/0 (Nature (1978) 276 (5685), 269-270), FO (J. Immunol. Methods (1980) 35 (1-2), 1-21), S194/5.XXO.BU.1 (J. Exp. Med. (1978) 148 (1), 313-323), and R210 (Nature (1979) 277 (5692), 131-133) can be preferably used as such myeloma cells.

Basically, the cell fusion of the immunocytes with the myeloma cells is performed according to a method known in the art, for example, the method of Kohler and Milstein et al. (Methods Enzymol. (1981) 73, 3-46).

More specifically, the cell fusion can be carried out, for example, in a usual nutrient medium in the presence of a cell fusion promoter. For example, polyethylene glycol (PEG) or hemagglutinating virus of Japan (HVJ) is used as the fusion promoter. In addition, an auxiliary such as dimethyl sulfoxide is added thereto for use, if desired, for enhancing fusion efficiency.

The ratio between the immunocytes and the myeloma cells used can be arbitrarily set. For example, the amount of the immunocytes is preferably set to 1 to 10 times the amount of the myeloma cells. For example, an RPMI1640 medium or a MEM medium suitable for the growth of the myeloma cell line as well as a usual medium for use in this kind of cell culture is used as the medium in the cell fusion. Preferably, a solution supplemented with serum (e.g., fetal calf serum (FCS)) can be further added to the medium.

For the cell fusion, the immunocytes and the myeloma cells are well mixed in the predetermined amounts in the medium. A PEG solution (e.g., average molecular weight of PEG: on the order of 1000 to 6000) preheated to approximately 37 degrees Celsius (C) is usually added thereto at a concentration of 30 to 60% (w/v). The mixed solution is gently mixed so that the desired fusion cells (hybridomas) are formed. Subsequently, the appropriate medium listed above is sequentially added to the cell cultures, and its supernatant is removed by centrifugation. This operation can be repeated to remove the cell fusion agents or the like unfavorable for hybridoma growth.

The hybridomas thus obtained can be cultured in a usual selective medium, for example, a HAT medium (medium containing hypoxanthine, aminopterin, and thymidine), for selection. The culture using the HAT medium can be continued for a time long enough to kill cells (non-fused cells) other than the desired hybridomas (usually, the time long enough is several days to several weeks). Subsequently, the hybridomas producing the desired antibody are screened for and single-cell cloned by a usual limiting dilution method.

The hybridomas thus obtained can be selected through the use of a selective medium appropriate for the selection marker of the myeloma cells used in the cell fusion. For example, the cells having the HGPRT or TK deficiency can be selected by culture in a HAT medium (medium containing hypoxanthine, aminopterin, and thymidine). Specifically, in the case of using HAT-sensitive myeloma cells in the cell fusion, only cells successfully fused with normal cells can be grown selectively in the HAT medium. The culture using the HAT medium is continued for a time long enough to kill cells (non-fused cells) other than the desired hybridomas. Specifically, the culture can generally be performed for several days to several weeks to select the desired hybridomas. Subsequently, the hybridomas producing the desired antibody can be screened for and single-cell cloned by a usual limiting dilution method.

The screening of the desired antibody and the single-cell cloning can be preferably carried out by a screening method based on antigen-antibody reaction known in the art. For example, a monoclonal antibody binding to IL-6R can bind to IL-6R expressed on cell surface. Such a monoclonal antibody can be screened for by, for example, FACS (fluorescence activated cell sorting). FACS is a system capable of measuring the binding of an antibody to cell surface by analyzing cells contacted with a fluorescent antibody using laser beam, and measuring the fluorescence emitted from the individual cells.

In order to screen for hybridomas producing a monoclonal antibody of interest by FACS, first, IL-6R-expressing cells are prepared. Cells preferred for screening are mammalian cells forced to express IL-6R. Untransformed, host mammalian cells can be used as a control to selectively detect the binding activity of an antibody against IL-6R on cell surface. Specifically, hybridomas producing an antibody that does not bind to the control host cells but binds to the cells forced to express IL-6R are selected to obtain hybridomas producing a monoclonal antibody against IL-6R.

Alternatively, the antibody can be evaluated for its binding activity against immobilized IL-6R-expressing cells on the basis of the principle of ELISA. The IL-6R-expressing cells are immobilized onto each well of, for example, an ELISA plate. The hybridoma culture supernatant is contacted with the immobilized cells in the well to detect an antibody binding to the immobilized cells. When the monoclonal antibody is derived from a mouse, the antibody bound with the cell can be detected using an anti-mouse immunoglobulin antibody. Hybridomas selected by these screening methods, which produce a desired antibody capable of binding to the antigen, can be cloned by limiting dilution method or other methods.

The monoclonal antibody-producing hybridomas thus prepared can be subcultured in a usual medium. The hybridomas can also be preserved over a long period in liquid nitrogen.

The hybridomas are cultured according to a usual method, and the desired monoclonal antibody can be obtained from the culture supernatant thereof. Alternatively, the hybridomas may be administered to mammals compatible therewith and grown, and the monoclonal antibody can be obtained from the ascitic fluids thereof. The former method is suitable for obtaining highly pure antibodies.

An antibody encoded by an antibody gene cloned from the antibody-producing cells such as hybridomas can also be preferably used. The cloned antibody gene is integrated to an appropriate vector, which is then transfected into hosts so that the antibody encoded by the gene is expressed. Methods for the isolation of the antibody gene, the integration to a vector, and the transformation of host cells have already been established by, for example, Vandamme et al. (Eur. J. Biochem. (1990) 192 (3), 767-775). A method for producing a recombinant antibody as mentioned below is also known in the art.

For example, cDNA encoding the variable region (V region) of an anti-IL-6R antibody is obtained from a hybridoma cell producing the anti-IL-6R antibody. For this purpose, usually, total RNA is first extracted from the hybridoma. For example, mRNA can be extracted from the cell using any of the following methods:
a guanidine ultracentrifugation method (Biochemistry (1979) 18 (24), 5294-5299), and
an AGPC method (Anal. Biochem. (1987) 162 (1), 156-159).

The extracted mRNA can be purified using mRNA Purification Kit (manufactured by GE Healthcare Bio-Sciences Corp.) or the like. Alternatively, a kit for directly extracting total mRNA from cells is also commercially available, such as QuickPrep mRNA Purification Kit (manufactured by GE Healthcare Bio-Sciences Corp.). The mRNA can be obtained from the hybridomas using such a kit. From the obtained mRNA, the cDNA encoding the antibody V region can be synthesized using reverse transcriptase. The cDNA can be synthesized using, for example, AMV Reverse Transcriptase First-strand cDNA Synthesis Kit (manufactured by Seikagaku Corp.). Alternatively, a 5'-RACE method (Proc. Natl. Acad. Sci. USA (1988) 85 (23), 8998-9002; and Nucleic Acids Res. (1989) 17 (8), 2919-2932) using SMART RACE cDNA amplification kit (manufactured by Clontech Laboratories, Inc.) and PCR can be appropriately used for the cDNA synthesis and amplification. In the course of such cDNA synthesis, appropriate restriction sites mentioned later can be further introduced to both ends of the cDNA.

The cDNA fragment of interest is purified from the obtained PCR product and subsequently ligated with vector DNA. The recombinant vector thus prepared is transfected into E. coli or the like. After colony selection, the desired recombinant vector can be prepared from the E. coli that has formed the colony. Then, whether or not the recombinant vector has the nucleotide sequence of the cDNA of interest is confirmed by a method known in the art, for example, a dideoxynucleotide chain termination method.

The 5'-RACE method using primers for variable region gene amplification is conveniently used for obtaining the gene encoding the variable region. First, a 5'-RACE cDNA library is obtained by cDNA synthesis with RNAs extracted from the hybridoma cells as templates. A commercially available kit such as SMART RACE cDNA amplification kit is appropriately used in the synthesis of the 5'-RACE cDNA library.

The antibody gene is amplified by PCR with the obtained 5'-RACE cDNA library as a template. Primers for mouse antibody gene amplification can be designed on the basis of an antibody gene sequence known in the art. These primers have nucleotide sequences differing depending on immunoglobulin subclasses. Thus, the subclass is desirably determined in advance using a commercially available kit such as Iso Strip mouse monoclonal antibody isotyping kit (Roche Diagnostics K.K.).

Specifically, primers capable of amplifying genes encoding gamma 1, gamma 2a, gamma 2b, and gamma 3 heavy chains and kappa and lambda light chains can be used, for example, for the purpose of obtaining a gene encoding mouse IgG. In order to amplify an IgG variable region gene, a primer that anneals to a moiety corresponding to a constant region close to the variable region is generally used as a 3' primer. On the other hand, a primer attached to the 5' RACE cDNA library preparation kit is used as a 5' primer.

The PCR products thus obtained by amplification can be used to reconstruct immunoglobulins composed of heavy and light chains in combination. The reconstructed immunoglobulins can be screened for binding activity to IL-6R to obtain a desired antibody. More preferably, the binding of the antibody to IL-6R is specific, for example, for the purpose of obtaining the antibody against IL-6R. An antibody binding to IL-6R can be screened for, for example, by the following steps:

(1) contacting an antibody containing the V region encoded by the cDNA obtained from a hybridoma, with IL-6R-expressing cells;

(2) detecting the binding of the antibody to the IL-6R-expressing cells; and (3) selecting the antibody binding to the IL-6R-expressing cells.

A method for detecting the binding of the antibody to the IL-6R-expressing cells is known in the art. Specifically, the binding of the antibody to the IL-6R-expressing cells can be detected by an approach such as FACS mentioned above. A fixed preparation of IL-6R-expressing cells can be appropriately used for evaluating the binding activity of the antibody.

A panning method using phage vectors is also preferably used as a method for screening for the antibody with binding activity as an index. When antibody genes are obtained as libraries of heavy chain and light chain subclasses from a polyclonal antibody-expressing cell population, a screening method using phage vectors is advantageous. Genes encoding heavy chain and light chain variable regions can be linked via an appropriate linker sequence to form a gene encoding single-chain Fv (scFv). The gene encoding scFv can be inserted into phage vectors to obtain phages expressing scFv on their surface. After contact of the phages with the desired antigen, phages bound with the antigen can be recovered to recover DNA encoding scFv having the binding activity of interest. This operation can be repeated, if necessary, to enrich scFvs having the desired binding activity.

After the obtainment of the cDNA encoding the V region of the anti-IL-6R antibody of interest, this cDNA is digested with restriction enzymes that recognize the restriction sites inserted at both ends of the cDNA. The restriction enzymes preferably recognize and digest a nucleotide sequence that appears low frequently in the nucleotide sequence constituting the antibody gene. The insertion of sites for restriction enzymes that provide cohesive ends is preferred for inserting one copy of the digested fragment in the correct orientation into a vector. The thus-digested cDNA encoding the V region of the anti-IL-6R antibody can be inserted into an appropriate expression vector to obtain an antibody expression vector. In this case, a gene encoding an antibody constant region (C region) and the gene encoding the V region are fused in frame to obtain a chimeric antibody. In this context, the "chimeric antibody" refers to an antibody having constant and variable regions of different origins. Thus, heterogeneous (e.g., mouse-human) chimeric antibodies as well as human-human homogeneous chimeric antibodies are also included in the chimeric antibody according to the present invention. The V region gene can be inserted into an expression vector preliminarily having a constant region gene to construct a chimeric antibody expression vector. Specifically, for example, recognition sequences for restriction enzymes digesting the V region gene can be appropriately placed on the 5' side of an expression vector carrying the DNA encoding the desired antibody constant region (C region). This expression vector having the C region gene and the V region gene are digested with the same combination of restriction enzymes and fused in frame to construct a chimeric antibody expression vector.

In order to produce the anti-IL-6R monoclonal antibody, the antibody gene is integrated to an expression vector such that the antibody gene is expressed under the control of expression control regions. The expression control regions for antibody expression include, for example, an enhancer and a promoter. Also, an appropriate signal sequence can be added to the amino terminus such that the expressed antibody is extracellularly secreted. For example, a peptide having an amino acid sequence MGWSCIILFL-VATATGVHS (SEQ ID NO: 1) can be used as the signal sequence. Any of other suitable signal sequences may be added thereto. The expressed polypeptide is cleaved at the carboxyl-terminal moiety of this sequence. The cleaved polypeptide can be extracellularly secreted as a mature polypeptide. Subsequently, appropriate host cells can be transformed with this expression vector to obtain recombinant cells expressing the DNA encoding the anti-IL-6R antibody.

The "antibody fragment" refers to a molecule, other than full-length antibody, containing a portion of the full-length antibody and binding to an antigen to which the full-length antibody binds. Examples of the antibody fragment include, but are not limited to, Fv, Fab, Fab', Fab'-SH, F(ab')2, diabody, linear antibodies, single-chain antibody molecules (e.g., scFv), and multispecific antibodies formed from antibody fragments.

The terms "full-length antibody", "complete antibody", and "whole antibody" are used interchangeably with each other in the present specification and refer to an antibody having a structure substantially similar to a natural antibody structure, or having heavy chains containing a Fc region defined in the present specification.

The term "variable region" or "variable domain" refers to a region or a domain of an antibody heavy chain or light chain involved in the binding of the antibody to its antigen. Usually, antibody heavy chain and light chain variable domains (VH and VL, respectively) are structurally similar and each contain 4 conserved framework regions (FRs) and 3 complementarity determining regions (CDRs) (see e.g., Kindt et al., Kuby Immunology, 6th ed., W.H. Freeman and Co., page 91 (2007)). One VH or VL domain may suffice for conferring antigen binding specificity.

The term "complementarity determining region" or "CDR" used in the present specification is hypervariable in the sequence, and/or forms a structurally determined loop ("hypervariable loop"), and/or refers to antigen contact residues ("antigen contacts") or each region of an antibody variable domain. Usually, an antibody contains 6 CDRs: three in VH (H1, H2, and H3), and three in VL (L1, L2, and L3). In the present specification, exemplary CDRs include the following:

(a) hypervariable loops formed at amino acid residues 26 to 32 (L1), 50 to 52 (L2), 91 to 96 (L3), 26 to 32 (H1), 53 to 55 (H2), and 96 to 101 (H3) (Chothia and Lesk, J. Mol. Biol. 196: 901-917 (1987));

(b) CDRs formed at amino acid residues 24 to 34 (L1), 50 to 56 (L2), 89 to 97 (L3), 31 to 35b (H1), 50 to 65 (H2), and 95 to 102 (H3) (Kabat et al., Sequences of Proteins of Immunological Interest, 5th Ed. Public Health Service, National Institutes of Health, Bethesda, MD (1991));

(c) antigen contacts formed at amino acid residues 27c to 36 (L1), 46 to 55 (L2), 89 to 96 (L3), 30 to 35b (H1), 47 to 58 (H2), and 93 to 101 (H3) (MacCallum et al., J. Mol. Biol. 262: 732-745 (1996)); and (d) a combination of (a), (b), and/or (c) containing HVR amino acid residues 46 to 56 (L2), 47 to 56 (L2), 48 to 56 (L2), 49 to 56 (L2), 26 to 35 (H1), 26 to 35b (H1), 49 to 65 (H2), 93 to 102 (H3), and 94 to 102 (H3).

In the present specification, CDR residues and other residues (e.g., FR residues) in a variable domain are numbered according to Kabat et al. (supra), unless otherwise specified.

The term "framework" or "FR" refers to variable domain residues other than complementarity determining region (CDR) residues. FRs in a variable domain consist of 4 FR domains: FR1, FR2, FR3, and 1-R4. Accordingly, the sequences of CDRs and FRs usually appear in VH (or VL) in the following order: 1-R1-H1 (L1)-FR2-H2 (L2)-FR3-H3 (L3)-FR4.

In the present specification, the term "constant region" or "constant domain" refers to a region or a domain other than variable regions in an antibody. For example, an IgG antibody is a heterotetrameric glycoprotein of approximately 150,000 Da constituted by two identical light chains and two identical heavy chains connected through disulfide bonds. Each heavy chain has a variable region (VH) also called variable heavy chain domain or heavy chain variable domain, followed by a heavy chain constant region (CH) containing a CH1 domain, a hinge region, a CH2 domain, and a CH3 domain, from the N terminus toward the C terminus. Likewise, each light chain has a variable region (VL) also called variable light chain domain or light chain variable domain, followed by a constant light chain (CL) domain, from the N terminus toward the C terminus. The light chains of natural antibodies may be attributed to one of two types called kappa and lambda on the basis of the amino acid sequences of their constant domains.

The "class" of an antibody refers to the type of a constant domain or a constant region carried by the heavy chain of the antibody. Antibodies have 5 major classes: IgA, IgD, IgE, IgG, and IgM. Some of these classes may be further divided into subclasses (isotypes), for example, IgG1, IgG2, IgG3, IgG4, IgA1, and IgA2. Heavy chain constant domains corresponding to immunoglobulins of different classes are called alpha, delta, epsilon, gamma, and mu, respectively.

In the present specification, the term "Fc region" is used for defining the C-terminal region of immunoglobulin heavy chains, including at least a portion of constant regions. This term includes a Fc region having a natural sequence and a mutant Fc region. In one aspect, the heavy chain Fc region of human IgG1 spans from Cys226 or Pro230 to the carboxyl terminus of the heavy chain. However, the C-terminal lysine (Lys447) or glycine-lysine (Gly446-Lys447) of the Fc region may be present or absent. In the present specification, amino acid residues in a Fc region or a constant region are numbered according to the EU numbering system (also called EU index) described in Kabat et al., Sequences of Proteins of Immunological Interest, 5th Ed. Public Health Service, National Institutes of Health, Bethesda, MD 1991, unless otherwise specified.

In the present invention, the ligand binding moiety or molecule comprises at least one protease cleavage site. The protease cleavage site may be placed anywhere within the ligand-binding moiety/molecule as long as the ligand binding domain of the ligand-binding moiety/molecule is capable of releasing the ligand moiety/molecule in the presense of a protease. For example, a protease cleavage site may be placed even within the ligand-binding domain in the ligand-binding moiety/molecule. Herein, the phrase "release/releasing the ligand moiety/molecule" or "the ligand moiety/molecule is released" means that the ligand moiety/molecule becomes able to exert and/or increase its biological activity through interacting with a binding partner thereof compared with the the biological activity of the ligand moiety/molecule bound with the uncleaved ligand binding moiety/molecule, but does not refer to any particular level of release or any particular mode of action by which the ligand moiety/molecule is released. In some embodiments, in the presense of a protease, a ligand moiety/molecule may be released from the ligand-binding domain in the ligand-binding moiety/molecule, due to the cleavage at a protease cleavage site placed within or near the ligand-binding domain in the ligand-binding moiety/molecule. In this case, even after cleavage, the ligand moiety/molecule may still be linked to the C-terminal region (e.g., Fc region/domain) of the ligand-binding moiety/molecule. In some embodiments, in the presense of a protease, a ligand moiety/molecule may be released from the (entire) ligand-binding moiety/molecule, due to the cleavage at a protease cleavage site placed between the ligand moiety/molecule and the C-terminal region (e.g., Fc region/domain) of the ligand-binding moiety/molecule. In this case, after cleavage, the ligand moiety/molecule is no longer linked to the C-terminal region (e.g., Fc region/domain) of the ligand-binding moiety/molecule.

In one embodiment, the ligand-binding moiety or molecule binds to the ligand or ligand moiety more weakly (i.e., ligand binding is attenuated) in a cleaved state compared with an uncleaved state. In an embodiment in which the ligand-binding moiety/molecule binds to the ligand or ligand moiety by antigen-antibody reaction, the attenuation of the ligand binding can be evaluated on the basis of the ligand binding activity of the ligand-binding moiety/molecule.

The ligand binding activity of the ligand binding moiety/molecule can be confirmed by a well-known method such as FACS, an ELISA format, a BIACORE method using ALPHA (amplified luminescent proximity homogeneous assay) screening or surface plasmon resonance (SPR) phenomena, or BLI (bio-layer interferometry) (Octet) (Proc. Natl. Acad. Sci. USA (2006) 103 (11), 4005-4010).

The ALPHA screening is carried out on the basis of the following principle according to ALPHA technology using two beads, a donor and an acceptor. Luminescence signals are detected only when these two beads are located in proximity through the interaction between a molecule bound with the donor bead and a molecule bound with the acceptor bead. A laser-excited photosensitizer in the donor bead converts ambient oxygen to singlet oxygen in an excited state. The singlet oxygen diffuses around the donor bead and reaches the acceptor bead located in proximity thereto to thereby cause chemiluminescent reaction in the bead, which finally emits light. In the absence of the interaction between the molecule bound with the donor bead and the molecule bound with the acceptor bead, no chemiluminescent reaction occurs because singlet oxygen produced by the donor bead does not reach the acceptor bead.

For example, a biotin-labeled ligand binding molecule is bound to the donor bead, while a glutathione S transferase (GST)-tagged ligand is bound to the acceptor bead. In the absence of an untagged competitor ligand binding molecule, the ligand binding molecule interacts with the ligand to generate signals of 520 to 620 nm. The untagged ligand binding molecule competes with the tagged ligand binding molecule for the interaction with the ligand. Decrease in fluorescence resulting from the competition can be quantified to determine relative binding affinity. The biotinylation of the ligand binding molecule such as an antibody using sulfo-NHS-biotin or the like is known in the art. A method which involves, for example: fusing a polynucleotide encoding the ligand in flame with a polynucleotide encoding GST; expressing a GST-fused ligand from cells or the like carrying a vector that permits expression of the resulting fusion gene; and purifying the GST-fused ligand using a glutathione column can be appropriately adopted as a method for tagging the ligand with GST. The obtained signals are preferably analyzed using, for example, software GRAPH-PAD PRISM (GraphPad Software, Inc., San Diego) adapted to a one-site competition model based on nonlinear regression analysis.

One (ligand) of the substances between which the interaction is to be observed is immobilized onto a thin gold film of a sensor chip. The sensor chip is irradiated with light from the back such that total reflection occurs at the interface between the thin gold film and glass. As a result, a site having a drop in reflection intensity (SPR signal) is formed in a portion of reflected light. The other (analyte) of the substances between which the interaction is to be observed is flowed on the surface of the sensor chip and bound to the ligand so that the mass of the immobilized ligand molecule is increased to change the refractive index of the solvent on the sensor chip surface. This change in the refractive index shifts the position of the SPR signal (on the contrary, the dissociation of the bound molecules gets the signal back to the original position). The Biacore system plots on the ordinate the amount of the shift, i.e., change in mass on the sensor chip surface, and displays time-dependent change in mass as assay data (sensorgram). Kinetics: an association rate constant (ka) and a dissociation rate constant (kd) are determined from the curve of the sensorgram, and a dissociation constant (KD) is determined from the ratio between these constants. Inhibition assay or equilibrium analysis is also preferably used in the BIACORE method. Examples of the inhibition assay are described in Proc. Natl. Acad. Sci. USA (2006) 103 (11), 4005-4010, and examples of the equilibrium analysis are described in Methods Enzymol. 2000; 323: 325-40.

The phrase "ligand binding function of the ligand binding molecule is attenuated" means that the amount of a test ligand binding molecule bound with the ligand is, for example, 90% or less, 80% or less, 70% or less, 60% or less, 50% or less, preferably 45% or less, 40% or less, 35% or less, 30% or less, 20% or less, or 15% or less, particularly preferably 10% or less, 9% or less, 8% or less, 7% or less, 6% or less, 5% or less, 4% or less, 3% or less, 2% or less, or 1% or less, of the amount of a control ligand binding molecule bound with the ligand on the basis of the measurement method described above. The desired index may be appropriately used as an index for binding activity. For example, a dissociation constant (KD) may be used. In the case of using a dissociation constant (KD) as an index for evaluating binding activity, a larger dissociation constant (KD) of the test ligand binding molecule for the ligand than that of a control ligand binding molecule for the ligand means that the test ligand binding molecule has weaker binding activity against the ligand than that of the control ligand binding molecule. The phrase "ligand binding function is attenuated" means that the dissociation constant (KD) of the test ligand binding molecule for the ligand is, for example, at least 2 times, preferably at least 5 times or at least 10 times, particularly preferably at least 100 times the dissociation constant (KD) of the control ligand binding molecule for the ligand.

Examples of the control ligand binding molecule include an uncleaved form of the ligand binding molecule.

In the fusion protein of the present invention, the ligand moiety or molecule is connected with a C-terminal region of the ligand-binding moiety or molecule via a peptide linker. As used herein, the term "C-terminal region" refers to a region of a polypeptide that extends from an internal amino acid residue in the polypeptide to the C-terminal amino acid residue of the polypeptide. In certain embodiments where the ligand-binding moiety/molecule is, for example, in the form of an antibody or in the form of an antibody fragment that contains an Fc region, the C-terminal region of the ligand-binding moiety/molecule typically refers to a region of the 1st to 250th amino acid residues from the C-terminus of the ligand binding moiety/molecule. In a preferred embodiment, the ligand-binding moiety/molecule is linked with an amino acid residue exposed on the surface of the CH3 region of the antibody Fc region via a peptide linker. In another preferred embodiment, the ligand moiety/molecule is connected with the C-terminal amino acid residue of the ligand-binding moiety/molecule via a peptide linker. The peptide linker may be attached to the ligand moiety/molecule and to the C-terminal region of the ligand-binding moiety/molecule by any covalent bonds such as peptide bonds. The length of the peptide linker is not particularly limited as long as it allows the ligand moiety/molecule to bind to the ligand-binding domain in the ligand-binding moiety/molecule. The above-mentioned peptide linker may or may not contain a protease cleavage site.

In one embodiment, the ligand moiety/molecule of the present invention is IL-12 and the IL-12 is connected with C-terminal amino acid residue of the ligand-binding moiety/molecule via a peptide linker attached to p35 subunit of IL-12 or p40 subunit of IL-12.

In one embodiment, the ligand moiety/molecule of the present invention is IL-12 and the IL-12 is connected with C-terminal amino acid residue of the ligand-binding moiety/molecule via a peptide linker attached to the N-terminus of p35 subunit of IL-12 or p40 subunit of IL-12.

In one embodiment, the ligand-binding domain of the present invention is connected to a hinge region comprised in the ligand-binding moiety via a peptide linker. In a preferred embodiment, the ligand-binding moiety of the present invention may further comprise a CH1 region which is connected to a hinge region via a peptide linker. The peptide linker can be inserted between CH1 and hinge on either side of the linker.

In some embodiments, the fusion protein (or ligand-binding moiety) of the invention comprises a constant region comprising a peptide linker. In some embodiments, the constant region comprises a hinge region comprising a peptide linker. The peptide linker may be comprised at any position before/within the hinge region. The peptide linker may be comprised between CH1 and the hinge region, i.e., before the amino acid sequence EPKSC (SEQ ID NO: 936) in the hinge region (note: the initial residue (E) is at position 216 (EU numbering)). The peptide linker may be comprised after the amino acid sequence EPKSC (SEQ ID NO: 936) in the hinge region. Examples of the position of the peptide linker include, but are not limited to, the following:

[Peptide linker]EPKSCDKTHTCPPCP (see SEQ ID NO: 901; examples include "C1" type);

EPKSC[Peptide linker]DKTHTCPPCP (see SEQ ID NO: 905; examples include "C2" type); and

[Peptide linker]EPKSSDKTHTCPPCP (see SEQ ID NOs: 908 and 910; examples include "C3" and "C4" types); and EPKSCDKTHT[Peptide linker]CPPCP (see SEQ ID NO: 932; examples include "C5" type).

In some embodiments, the peptide linker ([Peptide linker] indicated above) is a GS linker mentioned herein, such as $(GS)_2$, $(GGGGS: SEQ\ ID\ NO: 141)_2$.

The suitable peptide linker above may be readily selected and can be preferably selected from among different lengths such as 1 amino acid (Gly, etc.) to 300 amino acids, 2 amino acids to 200 amino acids, or 3 amino acids to 100 amino acids including 4 amino acids to 100 amino acids, 5 amino acids to 100 amino acids, 5 amino acids to 50 amino acids, 5 amino acids to 30 amino acids, 5 amino acids to 25 amino acids, or 5 amino acids to 20 amino acids.

Examples of the peptide linker include, but are not limited to, glycine polymers (G)n, glycine-serine polymers (including e.g., (GS)n, (GGGGS: SEQ ID NO: 141)n and (GGGS: SEQ ID NO: 136)n, wherein n is an integer of at least 1), glycine-alanine polymers, alanine-serine polymers, and other flexible linkers well known in conventional techniques.

Examples of the peptide linker consisting can include, but are not limited to,

```
                                (GGGGS, SEQ ID NO: 141)
Gly Gly Gly Gly Ser (Gly Gly Gly Gly Ser (GGGGS, SEQ ID NO: 141))n (GGGGA, SEQ ID NO: 893)
Gly Gly Gly Gly Ala (GGGGE, SEQ ID NO: 894)
Gly Gly Gly Gly Glu (GGGS, SEQ ID NO: 136)
Gly Gly Gly Ser (Gly Gly Gly Ser (GGGS, SEQ ID NO: 136))n (GGGA, SEQ ID NO: 895)
Gly Gly Gly Ala (GGGE, SEQ ID NO: 896)
Gly Gly Gly Glu (QQQG, SEQ ID NO: 897)
Gln Gln Gln Gly (QQQQG, SEQ ID NO: 898)
Gln Gln Gln Gln Gly (SSSG, SEQ ID NO: 899)
Ser Ser Ser Gly (SSSSG, SEQ ID NO: 900)
Ser Ser Ser Ser Gly
``` wherein n is an integer of 1 or larger.

However, the length and sequence of the peptide linker can be appropriately selected by those skilled in the art according to the purpose.

The presence of a linker (such as the GS linker) in the hinge region between the Fab and Fc may result in heterogeneity in the disulphide bond formation between HC (heavy-chain constant region) and LC (light-chain constant region). In some embodiments, a fusion protein of the invention is a homo-dimer of a light chain and heavy chain. The heavy chain comprises a linker such as a cleavable linker ("L1", e.g., SEQ ID NO: 873) introduced into the elbow hinge region between the heavy-chain variable region and Constant Region 1 ("C1", e.g., SEQ ID NO: 901). A single-chain ligand (such as IL-12 and IL-22) may be attached to the C-terminus of Fc domain via a linker such as the GS linker ("L4", e.g., SEQ ID NO: 903); alternatively, the linker may be a cleavable linker ("L3", e.g., SEQ ID NO: 879).

This type of fusion protein may be called "C1" variant. In some embodiments, the variant is Mab80-L1-C1-L4-IL12 (F4 bivalent IL-12 fusion Mab80) which is a homo-dimer comprising a light chain of SEQ ID NO: 876 and a heavy chain of SEQ ID NO: 885. In some embodiments, the variant is 087B03-L1-C1-L3-IL22 which is a homo-dimer comprising a light chain of SEQ ID NO: 912 and a heavy chain of SEQ ID NO: 913. In some embodiments, the variant is 087B03-C1-L4-IL22 which is a homo-dimer comprising a light chain of SEQ ID NO: 912 and a heavy chain of SEQ ID NO: 917.

To promote homogeneity, improved forms (further variants) may be generated as follows.

In some embodiments, a "C2" variant is used. The heavy chain of this variant may comprise a linker such as a cleavable linker ("L1", e.g., SEQ ID NO: 873) introduced into the elbow hinge region between the heavy-chain variable region and Constant Region 2 ("C2", e.g., SEQ ID NO: 905). In the Constant Region 2, a non-limiting example of the positional shift of a linker (e.g., the GS linker $(GGGGSGGGGS\ (SEQ\ ID\ NO: 141)_2)$ present in the hinge region) is shown below: from [GGGGSGGGGSEPKSCDKTHTCPPCP] (SEQ ID NO: 937) to [EPKSCGGGGSGGGGSDKTHTCPPCP] (SEQ ID NO: 935) (the initial residue (E) is at position 216 (EU numbering)). The shifted position of the linker may be can be appropriately selected or designed by those skilled in the art according to the purpose, i.e., to promote homogeneity. The positional shift of the linker can promote or facilitate disulfide (cysteine-cysteine (Cys-Cys)) bond formation between Cys at position 220 (C220) (EU numbering) of the heavy chain and Cys at position 214 (C214) (EU numbering) of the light chain. A single-chain ligand (such as IL-12 and IL-22) may be attached to the C-terminus of Fc domain via a linker such as the GS linker ("L4", e.g., SEQ ID NO: 903); alternatively, the linker may be a cleavable linker ("L3", e.g., SEQ ID NO: 879).

In some embodiments, the variant is Mab80-L1-C2-L4-IL12 which is a homo-dimer comprising a light chain of SEQ ID NO: 876 and a heavy chain of SEQ ID NO: 904.

In some embodiments, the variant is 087B03-L1-C2-L3-IL22 which is a homo-dimer of a light chain (SEQ ID NO: 912) and heavy chain (SEQ ID NO: 929).

In some embodiments, a "C3" variant is used. In this variant, the light chain may comprise C214S (EU numbering) modification and the heavy chain may comprise C220S (EU numbering) modification which result in no disulfide bond formation between the heavy chain and light chain, i.e., between position 220 (EU numbering) of the heavy chain and position 214 (EU numbering) of the light chain. The heavy chain of this variant may comprise a linker such as a cleavable linker ("L1", e.g., SEQ ID NO: 873) introduced into the elbow hinge region between the heavy-chain variable region and and Constant Region 3 ("C3", e.g., SEQ ID NO: 908). A single-chain ligand (such as IL-12 and IL-22) may be attached to the C-terminus of Fc domain via a linker such as the GS linker ("L4", e.g., SEQ ID NO: 903); alternatively, the linker may be a cleavable linker ("L3", e.g., SEQ ID NO: 879).

In some embodiments, the variant is Mab80-L1-C3-L4-IL12 which is a homo-dimer comprising a light chain of SEQ ID NO: 906 and heavy chain of SEQ ID NO: 907. In some embodiments, the variant is 087B03-L1-C3-L3-IL22 which is a homo-dimer comprising a light chain of SEQ ID NO: 915 and a heavy chain of SEQ ID NO: 916.

In some embodiments, a "C4" variant is used. In this variant, the light chain may not comprise the above-mentioned modification, while the heavy chain may comprise S131C (EU numbering) and C220S (EU numbering) modifications which result in disulfide bond formation between the heavy chain and light chain, i.e., between Cys at position 131 (C131) (EU numbering) of the heavy chain and Cys at position 214 (C214) (EU numbering) of the light chain. The heavy chain of this variant may comprise a linker such as a cleavable linker ("L1", e.g., SEQ ID NO: 873) introduced into the elbow hinge region between the heavy-chain variable region and Constant Region 4 ("C4", e.g., SEQ ID NO: 910). A single-chain ligand (such as IL-12 and IL-22) may be attached to the C-terminus of Fc domain via a linker such as the GS linker (L4, e.g., SEQ ID NO: 903); alternatively, the linker may be a cleavable linker ("L3", e.g., SEQ ID NO: 879).

In some embodiments, the variant is Mab80-L1-C4-L4-IL12 which is a homo-dimer comprising a light chain of SEQ ID NO: 876 and a heavy chain of SEQ ID NO: 909.

In some embodiments, the variant is 087B03-L1-C4-L3-IL22 which is a homo-dimer of a light chain (SEQ ID NO: 912) and heavy chain (SEQ ID NO: 930).

In some embodiments, a "C5" variant is used. The heavy chain of this variant may comprise a linker such as a cleavable linker ("L1", e.g., SEQ ID NO: 873) introduced into the elbow hinge region between the heavy-chain variable region and Constant Region 5 ("C5", e.g., SEQ ID NO: 932). In the Constant Region 5, a non-limiting example of the positional shift of a linker (e.g., the GS linker $(GGGGSGGGGS$ (SEQ ID NO: 141)$_2$) present in the hinge region) is shown below: from [GGGGSGGGGSEPKSCDKTHTCPPCP] (SEQ ID NO: 937) to [EPKSCDKTHTGGGGSGGGGSCPPCP] (SEQ ID NO: 938) (the initial residue (E) is at position 216 (EU numbering)). The shifted position of the linker may be can be appropriately selected or designed by those skilled in the art according to the purpose, i.e., to promote homogeneity. The positional shift of the linker can promote or facilitate disulfide (cysteine-cysteine (Cys-Cys)) bond formation between Cys at position 220 (C220) (EU numbering) of the heavy chain and Cys at position 214 (C214) (EU numbering) of the light chain. A single-chain ligand (such as IL-2) may be attached to the C-terminus of Fc domain via a linker such as the GS linker ("L5", e.g., SEQ ID NO: 927).

In some embodiments, the variant is Cx-L1-C5-L5-IL2.N88D which is a homo-dimer of a heavy chain (SEQ ID NO: 919) and light chain (SEQ ID NO: 920). In some embodiments, the variant is 16C3-L1-C5-L5-IL2.N88D which is a homo-dimer of a heavy chain (SEQ ID NO: 922) and light chain (SEQ ID NO: 923).

In some aspects, a fusion protein of the present invention comprises a ligand-binding moiety comprising (i) a ligand-binding domain, (ii) a first peptide linker, and (iii) a constant region comprising a second peptide linker, and a third peptide linker, and a ligand moiety. The fusion protein is represented by the following general formula (I):

$$\text{[Ligand-binding domain]-[Lx]-[Cx]-[Ly]-[Ligand moiety]} \quad \text{(I)}$$

wherein:

Lx represents a first peptide linker optionally comprising a protease cleavage site, or Lx is absent;

Cx represents a constant region comprising a second peptide linker and optionally one or more amino acid residues which are modified from or to cysteine;

Ly represents a third peptide linker, wherein the ligand-binding domain binds to the ligand moiety, and is capable of releasing the ligand moiety from the ligand-binding domain in the presence of a protease.

In some embodiments, the fusion protein is a bivalent ligand-binding fusion protein which comprises two sets (e.g., two identical sets) of the ligand-binding domain, the ligand moiety, the first peptide linker, the constant (or Fc) region (comprising the second peptide linker), and the third peptide linker. When the fusion protein comprises two Fc regions, the regions dimerize with each other to form a ligand-binding moiety. In this case, in some embodiments, the fusion protein may be an IgG-type protein, e.g., IgG-type antibody, comprising two Fc regions that dimerize.

In some embodiments, the fusion protein comprises an Fc region, e.g., the protein comprises at least one (i.e., one, two, or more than two) Fc region(s).

Each of the first peptide linker, second peptide linker, and third peptide linker may be any linker disclosed herein. In some embodiments, each linker may be a cleavable or non-cleavable linker which can be or cannot be cleaved by any protease.

Alternatively, in some aspects, a fusion protein of the present invention comprises a ligand-binding moiety comprising (i) a ligand-binding domain, (ii) a first peptide linker, and (iii) a first constant region comprising a second peptide linker, and a third peptide linker, and a ligand moiety; and a non-ligand-binding domain, a fourth peptide linker, and a second constant region comprising a fifth peptide linker. The fusion protein is represented by the following general formula (II):

$$\text{[Ligand-binding domain]-[Lx]-[Cx]-[Ly]-[Ligand moiety]//[Non-ligand-binding domain]-[Lz]-[Cz]} \quad \text{(II)}$$

wherein:

Lx, Cx, and Ly are as defined for formula (I) above;

Lz represents a fourth peptide linker optionally comprising a protease cleavage site, or Lz is absent;

Cz represents a second constant region comprising optionally a fifth peptide linker and optionally one or more amino acid residues which are modified from or to cysteine.

In some embodiments, the fusion protein is a monovalent ligand-binding fusion protein which comprises one set of the ligand-binding domain, the ligand moiety, the first peptide linker, the first constant region (comprising the second peptide linker), and the third peptide linker; and one set of the non-ligand-binding domain, the fourth peptide linker, the second constant region (comprising the fifth peptide linker).

Each of the first peptide linker, second peptide linker, third peptide linker, fourth peptide linker, and fifth peptide linker may be any linker disclosed herein. In some embodiments, each linker may be a cleavable or non-cleavable linker which can be or cannot be cleaved by any protease.

Possible variations of the fusion protein of the present invention may include fusion proteins having a structure in which the ligand moiety attached to the peptide linker is inserted into the C-terminal region of the ligand-binding molecule so as to split the ligand-binding molecule into two parts. It is understood that such fusion proteins are also included in the scope of the present invention as long as the ligand moiety is linked to the C-terminal amino acid residue of the part containing the ligand-binding domain (which serves as the ligand-binding moiety in the present invention) via the peptide linker.

In further embodiments of the present invention, the ligand moiety or molecule is further connected with a N-terminal region of the ligand-binding moiety or molecule via a cleavable linker. As used herein, the term "N-terminal region" refers to a region of a polypeptide that extends from the N-terminus of the polypeptide to an internal amino acid residue in the polypeptide. In certain embodiments where the ligand-binding moiety/molecule is, for example, in the form of an antibody or in the form of an antibody fragment, the N-terminal region of the ligand-binding moiety/molecule typically refers to a region of the 1st to 230th amino acid residues from the N-terminus of the ligand binding moiety/molecule. In a preferred embodiment, the ligand moiety/molecule is connected with the N-terminal amino acid residue of the ligand-binding moiety/molecule via a cleavable linker. The cleavable linker may be attached to the ligand moiety/molecule and to the N-terminal region of the ligand-binding moiety/molecule by any covalent bonds such as peptide bonds. The length of the cleavable linker is not particularly limited as long as it allows the ligand moiety/molecule to bind to the ligand-binding domain in the ligand-binding moiety/molecule. The above-mentioned cleavable linker may contain a protease cleavage site and can be cleaved by a protease.

Possible variations of the present invention may include fusion proteins having a structure in which the ligand moiety attached to the cleavable linker is inserted into the N-terminal region of the ligand-binding molecule so as to split the ligand-binding molecule into two parts. It is understood that such fusion proteins are also included in the scope of the present invention as long as the ligand moiety is linked to the N-terminal amino acid residue of the part containing the ligand-binding domain (which serves as the ligand-binding moiety in the present invention) via the cleavable linker.

In one embodiment of the present invention, the ligand moiety is released from the ligand-binding domain of the ligand-binding moiety by protease cleavage of the fusion protein. In this context, when the ligand moiety is connected with the C-terminal region of the ligand binding moiety via a peptide linker having a protease cleavage site, the ligand moiety may be completely released from the fusion protein (see e.g., FIGS. 1A to 1C). Herein, this type of fusion protein is referred to as "release type". On the other hand, when the ligand moiety is connected with the C-terminal region of the ligand binding moiety via a peptide linker having no protease cleavage site, the ligand moiety may be released from the ligand-binding domain while remaining fused to the C-terminal region of the ligand binding moiety via the peptide linker (see e.g., FIGS. 2A to 2E). Herein, this type of fusion protein is referred to as "fusion type".

A method for detecting release of the ligand moiety or molecule from the ligand-binding domain by cleavage of the protease cleavage site(s) includes a method of detecting the ligand using, for example, an antibody for ligand detection that recognizes the ligand. When the ligand binding moiety/molecule is an antibody fragment, the antibody for ligand detection preferably binds to the same epitope as that for the ligand binding domain. The ligand detected using the antibody for ligand detection can be confirmed by a well-known method such as FACS, an ELISA format, a BIACORE method using ALPHA (amplified luminescent proximity homogeneous assay) screening or surface plasmon resonance (SPR) phenomena, or BLI (bio-layer interferometry) (Octet) (Proc. Natl. Acad. Sci. USA (2006) 103 (11), 4005-4010).

In the case of detecting the release of the ligand using, for example, Octet, the antibody for ligand detection that recognizes the ligand is biotinylated and contacted with a biosensor. Then, binding to the ligand in a sample can be measured to detect the release of the ligand. Specifically, the amount of the ligand is measured in a sample containing the ligand binding molecule before protease treatment or after protease treatment and the ligand, using the antibody for ligand detection. The amount of the ligand detected in the sample can be compared between before and after protease treatment to detect the release of the ligand. Alternatively, the amount of the ligand is measured in a sample containing protease, the ligand binding molecule, and the ligand and a sample containing the ligand binding molecule and the ligand without containing protease, using the antibody for ligand detection. The amount of the ligand detected in the sample can be compared between the presence and absence of protease to detect the release of the ligand. More specifically, the release of the ligand can be detected by a method described in Examples of the present application. When the ligand binding molecule is fused with the ligand to form a fusion protein, the amount of the ligand is measured in a sample containing the fusion protein before protease treatment or after protease treatment, using the antibody for ligand detection. The amount of the ligand detected in the sample can be compared between before and after protease treatment to detect the release of the ligand. Alternatively, the amount of the ligand is measured in a sample containing protease and the fusion protein and a sample containing the fusion protein without containing protease, using the antibody for ligand detection. The amount of the ligand detected in the sample can be compared between the presence and absence of protease to detect the release of the ligand. More specifically, the release of the ligand can be detected by a method described in Examples of the present application.

In an embodiment in which the physiological activity of the ligand is inhibited upon binding to the ligand-binding domain, the release from the ligand binding molecule can be detected by a method of measuring the physiological activity of the ligand in a sample. Specifically, the physiological activity of the ligand can be measured in a sample containing the ligand binding molecule before protease treatment or after protease treatment and the ligand and compared between before and after protease treatment to detect the release of the ligand. Alternatively, the physiological activity of the ligand can be measured in a sample containing protease, the ligand binding molecule, and the ligand and a sample containing the ligand binding molecule and the ligand without containing protease and compared between these samples to detect the release of the ligand. When the ligand binding molecule is fused with the ligand to form a fusion protein, the physiological activity of the ligand can be measured in a sample containing the fusion protein before protease treatment or after protease treatment and compared between before and after protease treatment to detect the release of the ligand. Alternatively, the physiological activity of the ligand can be measured in a sample containing protease and the fusion protein and a sample containing the fusion protein without containing protease and compared between these samples to detect the release of the ligand.

In the present invention, the protease cleavage site(s) comprises a protease cleavage sequence and is cleaved by a protease. In certain embodiments where the fusion protein of the present invention has a plurality of protease cleavage sites, those protease cleavage sites may have the same protease cleavage sequence or different protease cleavage sequences. When the protease cleavage sites have different protease cleavage sequences, those different protease cleavage sequences may be cleaved by the same protease or different proteases. In some embodiments of the present invention, the protease cleavage sites(s) may also comprise one or more amino acid residues at one or both ends of the protease cleavage sequence as long as those residues do not inhibit recognition and cleavage of the protease cleavage sequence by the protease.

In the present specification, the term "protease" refers to an enzyme such as endopeptidase or exopeptidase which hydrolyzes a peptide bond, and typically refers to endopeptidase. The protease used in the present invention is limited only by its capability of cleaving a protease cleavage sequence, and is not limited to any particular type of protease. In some embodiments, target tissue specific protease is used. The target tissue specific protease can refer to, for example, any of (1) protease that is expressed at a higher level in the target tissue than in normal tissues, (2) protease that has higher activity in the target tissue than in normal tissues, (3) protease that is expressed at a higher level in the target cells than in normal cells, and (4) protease that has higher activity in the target cells than in normal cells.

In a more specific embodiment, a cancer tissue specific protease or an inflammatory tissue specific protease is used.

In the present specification, the term "target tissue" means a tissue containing at least one target cell. In some embodiments of the present invention, the target tissue is a cancer tissue. In some embodiments of the present invention, the target tissue is an inflammatory tissue.

The term "cancer tissue" means a tissue containing at least one cancer cell. Thus, considering that, for example, the cancer tissue contains cancer cells and vascular vessels, every cell type that contributes to the formation of tumor mass containing cancer cells and endothelial cells is included in the scope of the present invention. In the present specification, the tumor mass refers to a foci of tumor tissue. The term "tumor" is generally used to mean benign neoplasm or malignant neoplasm.

In the present specification, examples of the "inflammatory tissue" include the following:

a joint tissue in rheumatoid arthritis or osteoarthritis, a lung (alveolus) tissue in bronchial asthma or COPD, a digestive organ tissue in inflammatory bowel disease, Crohn disease, or ulcerative colitis, a fibrotic tissue in fibrosis in the liver, the kidney, or the lung, a tissue under rejection of organ transplantation, a vascular vessel or heart (cardiac muscle) tissue in arteriosclerosis or heart failure, a visceral fat tissue in metabolic syndrome, a skin tissue in atopic dermatitis and other dermatitides, and a spinal nerve tissue in disk herniation or chronic lumbago.

any tissue that is infiltrated with immune cells

Specifically expressed or specifically activated protease, or protease considered to be related to the disease condition of a target tissue (target tissue specific protease) is known for some types of target tissues. For example, International Publication Nos. WO2013/128194, WO2010/081173, and WO2009/025846 disclose protease specifically expressed in a cancer tissue. Also, J Inflamm (Lond). 2010; 7: 45, Nat Rev Immunol. 2006 July; 6 (7): 541-50, Nat Rev Drug Discov. 2014 December; 13 (12): 904-27, Respir Res. 2016 Mar. 4; 17: 23, Dis Model Mech. 2014 February; 7 (2): 193-203, and Biochim Biophys Acta. 2012 January; 1824 (1): 133-45 disclose protease considered to be related to inflammation.

In addition to the protease specifically expressed in a target tissue, there also exists protease specifically activated in a target tissue. For example, protease may be expressed in an inactive form and then converted to an active form. Many tissues contain a substance inhibiting active protease and control the activity by the process of activation and the presence of the inhibitor (Nat Rev Cancer. 2003 July; 3 (7): 489-501). In a target tissue, the active protease may be specifically activated by escaping inhibition.

The active protease can be measured by use of a method using an antibody recognizing the active protease (PNAS 2013 Jan. 2; 110 (1): 93-98) or a method of fluorescently labeling a peptide recognizable by protease so that the fluorescence is quenched before cleavage, but emitted after cleavage (Nat Rev Drug Discov. 2010 September; 9 (9): 690-701. doi: 10.1038/nrd3053).

From one viewpoint, the term "target tissue specific protease" can refer to any of (i) protease that is expressed at a higher level in the target tissue than in normal tissues, (ii) protease that has higher activity in the target tissue than in normal tissues, (iii) protease that is expressed at a higher level in the target cells than in normal cells, and (iv) protease that has higher activity in the target cells than in normal cells.

Specific examples of the protease include, but are not limited to, cysteine protease (including cathepsin families B, L, S, etc.), aspartyl protease (cathepsins D, E, K, O, etc.), serine protease (including matriptase (including MT-SP1), cathepsins A and G, thrombin, plasmin, urokinase-type plasminogen activator (uPA), tissue plasminogen activator (tPA), elastase, proteinase 3, thrombin, kallikrein, tryptase, and chymase), metalloproteinase (metalloproteinase (MMP1-28) including both membrane-bound forms (MMP14-17 and MMP24-25) and secreted forms (MMP1-13, MMP18-23 and MMP26-28), A disintegrin and metalloproteinase (ADAM), A disintegrin and metalloproteinase with thrombospondin motifs (ADAMTS), meprin (meprin alpha and meprin beta), CD10 (CALLA), prostate-specific antigen (PSA), legumain, TMPRSS3, TMPRSS4, human neutrophil elastase (HNE), beta secretase (BACE), fibroblast activation protein alpha (FAP), granzyme B, guanidinobenzoatase (GB), hepsin, neprilysin, NS3/4A, HCV-NS3/4, calpain, ADAMDEC1, renin, cathepsin C, cathepsin V/L2, cathepsin X/Z/P, cruzipain, otubain 2, kallikrein-related peptidases (KLKs (KLK3, KLK4, KLKS, KLK6, KLK7, KLK8, KLK10, KLK11, KLK13, and KLK14)), bone morphogenetic protein 1 (BMP-1), activated protein C, blood coagulation-related protease (Factor VIIa, Factor IXa, Factor Xa, Factor XIa, and Factor XIIa), HtrA1, lactoferrin, marapsin, PACE4, DESC1, dipeptidyl peptidase 4 (DPP-4), TMPRSS2, cathepsin F, cathepsin H, cathepsin L2, cathepsin 0, cathepsin S, granzyme A, Gepsin calpain 2, glutamate carboxypeptidase 2, AMSH-like proteases, AMSH, gamma secretase, antiplasmin cleaving enzyme (APCE), decysin 1, N-acetylated alpha-linked acidic dipeptidase-like 1 (NAALADL1), and furin.

From another viewpoint, the target tissue specific protease can refer to cancer tissue specific protease or inflammatory tissue specific protease.

Examples of the cancer tissue specific protease include protease specifically expressed in a cancer tissue disclosed in International Publication Nos. WO2013/128194, WO2010/081173, and WO2009/025846.

As for the type of the cancer tissue specific protease, the protease having higher expression specificity in the cancer tissue to be treated is more effective for reducing adverse reactions. Preferable cancer tissue specific protease has a concentration in the cancer tissue at least 5 times, more preferably at least 10 times, further preferably at least 100 times, particularly preferably at least 500 times, most preferably at least 1000 times higher than its concentration in normal tissues. Also, preferable cancer tissue specific protease has activity in the cancer tissue at least 2 times, more preferably at least 3 times, at least 4 times, at least 5 times, or at least 10 times, further preferably at least 100 times, particularly preferably at least 500 times, most preferably at least 1000 times higher than its activity in normal tissues.

The cancer tissue specific protease may be in a form bound with a cancer cell membrane or may be in a form secreted extracellularly without being bound with a cell membrane. When the cancer tissue specific protease is not bound with a cancer cell membrane, it is preferred that the cancer tissue specific protease should exist within or in the vicinity of the cancer tissue. In the present specification, the "vicinity of the cancer tissue" means to fall within the scope of location where the protease cleavage sequence specific for the cancer tissue is cleaved so that the effect of reducing the ligand binding activity is exerted.

From an alternative viewpoint, cancer tissue specific protease is any of (i) protease that is expressed at a higher level in the cancer tissue than in normal tissues, (ii) protease that has higher activity in the cancer tissue than in normal tissues, (iii) protease that is expressed at a higher level in the cancer cells than in normal cells, and (iv) protease that has higher activity in the cancer cells than in normal cells.

One type of cancer tissue specific protease may be used alone, or two or more types of cancer tissue specific proteases may be combined. The number of types of the cancer tissue specific protease can be appropriately set by those skilled in the art in consideration of the cancer type to be treated.

From these viewpoints, the cancer tissue specific protease is preferably serine protease or metalloproteinase, more preferably matriptase (including MT-SP1), urokinase-type plasminogen activator (uPA), or metalloproteinase, further preferably MT-SP1, uPA, MMP-2, or MMP-9, among the proteases listed above, particular preferably MMP-2, or MMP-9, among the proteases listed above.

As for the type of inflammatory tissue specific protease, the protease having higher expression specificity in the inflammatory tissue to be treated is more effective for reducing adverse reactions. Preferable inflammatory tissue specific protease has a concentration in the inflammatory tissue at least 5 times, more preferably at least 10 times, further preferably at least 100 times, particularly preferably at least 500 times, most preferably at least 1000 times higher than its concentration in normal tissues. Also, preferable inflammatory tissue specific protease has activity in the inflammatory tissues at least 2 times, more preferably at least 3 times, at least 4 times, at least 5 times, or at least 10 times, further preferably at least 100 times, particularly preferably at least 500 times, most preferably at least 1000 times higher than its activity in normal tissues.

The inflammatory tissue specific protease may be in a form bound with an inflammatory cell membrane or may be in a form secreted extracellularly without being bound with a cell membrane. When the inflammatory tissue specific protease is not bound with an inflammatory cell membrane, it is preferred that the inflammatory tissue specific protease should exist within or in the vicinity of the inflammatory tissue. In the present specification, the "vicinity of the inflammatory tissue" means to fall within the scope of location where the protease cleavage sequence specific for the inflammatory tissue is cleaved so that the effect of reducing the ligand binding activity is exerted.

From an alternative viewpoint, inflammatory tissue specific protease is any of (i) protease that is expressed at a higher level in the inflammatory tissue than in normal tissues, (ii) protease that has higher activity in the inflammatory tissue than in normal tissues, (iii) protease that is expressed at a higher level in the inflammatory cells than in normal cells, and (iv) protease that has higher activity in the inflammatory cells than in normal cells.

One type of inflammatory tissue specific protease may be used alone, or two or more types of inflammatory tissue specific proteases may be combined. The number of types of the inflammatory tissue specific protease can be appropriately set by those skilled in the art in consideration of the pathological condition to be treated.

From these viewpoints, the inflammatory tissue specific protease is preferably metalloproteinase among the proteases listed above. The metalloproteinase is more preferably ADAMTS5, MMP-1, MMP-2, MMP-3, MMP-7, MMP-9, MMP11, or MMP-13.

The protease cleavage sequence is a particular amino acid sequence that is specifically recognized by target tissue specific protease when the polypeptide is hydrolyzed by the target tissue specific protease in an aqueous solution.

The protease cleavage sequence is preferably an amino acid sequence that is hydrolyzed with high specificity by target tissue specific protease more specifically expressed in the target tissue or cells to be treated or more specifically activated in the target tissue/cells to be treated, from the viewpoint of reduction in adverse reactions.

Specific examples of the protease cleavage sequence include target sequences that are specifically hydrolyzed by the above-listed protease specifically expressed in a cancer tissue disclosed in International Publication Nos. WO2013/128194, WO2010/081173, and WO2009/025846, the inflammatory tissue specific protease, and the like. A sequence artificially altered by, for example, appropriately introducing an amino acid mutation to a target sequence that is specifically hydrolyzed by known protease can also be used. Alternatively, a protease cleavage sequence identified by a method known to those skilled in the art as described in Nature Biotechnology 19, 661-667 (2001) may be used.

Furthermore, a naturally occurring protease cleavage sequence may be used. For example, TGF beta is converted to a latent form by protease cleavage. Likewise, a protease cleavage sequence in a protein that changes its molecular form by protease cleavage can also be used.

Examples of the protease cleavage sequence that can be used include, but are not limited to, sequences disclosed in WO2015/116933, WO2015/048329, WO2016/118629, WO2016/179257, WO2016/179285, WO2016/179335, WO2016/179003, WO2016/046778, WO2016/014974, U.S. Patent Publication No. US2016/0289324, U.S. Patent Publication No. US2016/0311903, PNAS (2000) 97: 7754-7759, Biochemical Journal (2010) 426: 219-228, and Beilstein J Nanotechnol. (2016) 7: 364-373.

The protease cleavage sequence is more preferably an amino acid sequence that is specifically hydrolyzed by suitable target tissue specific protease as mentioned above. The amino acid sequence that is specifically hydrolyzed by target tissue specific protease is preferably any of the following amino acid sequences:

LSGRSDNH (SEQ ID NO: 2, cleavable by MT-SP1 or uPA),

PLGLAG (SEQ ID NO: 3, cleavable by MMP-2 or MMP-9), and

VPLSLTMG (SEQ ID NO: 4, cleavable by MMP-7).

Any of the following sequences can also be used as the protease cleavage sequence:

```
                          (SEQ ID NO: 5, cleavable by MT-SP1 or uPA)
TSTSGRSANPRG, (SEQ ID NO: 6, cleavable by MT-SP1 or uPA)
ISSGLLSGRSDNH, (SEQ ID NO: 7, cleavable by MT-SP1 or uPA)
AVGLLAPPGGLSGRSDNH, (SEQ ID NO: 8, cleavable by MMP-1)
GAGVPMSMRGGAG, (SEQ ID NO: 9, cleavable by MMP-2)
GAGIPVSLRSGAG, (SEQ ID NO: 10, cleavable by MMP-2)
GPLGIAGQ, (SEQ ID NO: 11, cleavable by MMP-2)
GGPLGMLSQS, (SEQ ID NO: 12, cleavable by MMP-2)
PLGLWA, (SEQ ID NO: 13, cleavable by MMP-3)
GAGRPFSMIMGAG, (SEQ ID NO: 14, cleavable by MMP-7)
GAGVPLSLTMGAG, (SEQ ID NO: 15, cleavable by MMP-9)
GAGVPLSLYSGAG, (SEQ ID NO: 16, cleavable by MMP-11)
AANLRN, (SEQ ID NO: 17, cleavable by MMP-11)
AQAYVK, (SEQ ID NO: 18, cleavable by MMP-11)
AANYMR, (SEQ ID NO: 19, cleavable by MMP-11)
AAALTR, (SEQ ID NO: 20, cleavable by MMP-11)
AQNLMR, (SEQ ID NO: 21, cleavable by MMP-11)
AANYTK, (SEQ ID NO: 22, cleavable by MMP-13)
GAGPQGLAGQRGIVAG, (SEQ ID NO: 23, cleavable by pro-urokinase)
PRFKIIGG, (SEQ ID NO: 24, cleavable by pro-urokinase)
PRFRIIGG, (SEQ ID NO: 25, cleavable by uPA)
GAGSGRSAG, (SEQ ID NO: 26, cleavable by uPA)
SGRSA, (SEQ ID NO: 27, cleavable by uPA)
GSGRSA,
```

-continued (SEQ ID NO: 28, cleavable by uPA)
SGKSA, (SEQ ID NO: 29, cleavable by uPA)
SGRSS, (SEQ ID NO: 30, cleavable by uPA)
SGRRA, (SEQ ID NO: 31, cleavable by uPA)
SGRNA, (SEQ ID NO: 32, cleavable by uPA)
SGRKA, (SEQ ID NO: 33, cleavable by tPA)
QRGRSA, (SEQ ID NO: 34, cleavable by cathepsin B)
GAGSLLKSRMVPNFNAG (SEQ ID NO: 35, cleavable by cathepsin B)
TQGAAA, (SEQ ID NO: 36, cleavable by cathepsin B)
GAAAAA, (SEQ ID NO: 37, cleavable by cathepsin B)
GAGAAG, (SEQ ID NO: 38, cleavable by cathepsin B)
AAAAAG, (SEQ ID NO: 39, cleavable by cathepsin B)
LCGAAI, (SEQ ID NO: 40, cleavable by cathepsin B)
FAQALG, (SEQ ID NO: 41, cleavable by cathepsin B)
LLQANP, (SEQ ID NO: 42, cleavable by cathepsin B)
LAAANP, (SEQ ID NO: 43, cleavable by cathepsin B)
LYGAQF, (SEQ ID NO: 44, cleavable by cathepsin B)
LSQAQG, (SEQ ID NO: 45, cleavable by cathepsin B)
ASAASG, (SEQ ID NO: 46, cleavable by cathepsin B)
FLGASL, (SEQ ID NO: 47, cleavable by cathepsin B)
AYGATG, (SEQ ID NO: 48, cleavable by cathepsin B)
LAQATG, (SEQ ID NO: 49, cleavable by cathepsin L)
GAGSGVVIATVIVITAG, (SEQ ID NO: 50, cleavable by meprin alpha or meprin beta)
APMAEGGG, (SEQ ID NO: 51, cleavable by meprin alpha or meprin beta)
EAQGDKII, (SEQ ID NO: 52, cleavable by meprin alpha or meprin beta)
LAFSDAGP, (SEQ ID NO: 53, cleavable by meprin alpha or meprin beta)
YVADAPK, (SEQ ID NO: 54, cleavable by furin)
RRRRR, -continued

```
                         (SEQ ID NO: 55, cleavable by furin)
RRRRRR, (SEQ ID NO: 56, cleavable by furin)
GQSSRHRRAL, (SEQ ID NO: 57)
SSRHRRALD, (SEQ ID NO: 58, cleavable by plasminogen)
RKSSIIIRMRDVVL, (SEQ ID NO: 59, cleavable by staphylokinase)
SSSFDKGKYKKGDDA, (SEQ ID NO: 60, cleavable by staphylokinase)
SSSFDKGKYKRGDDA, (SEQ ID NO: 61, cleavable by Factor IXa)
IEGR, (SEQ ID NO: 62, cleavable by Factor IXa)
IDGR, (SEQ ID NO: 63, cleavable by Factor IXa)
GGSIDGR, (SEQ ID NO: 64, cleavable by collagenase)
GPQGIAGQ, (SEQ ID NO: 65, cleavable by collagenase)
GPQGLLGA, (SEQ ID NO: 66, cleavable by collagenase)
GIAGQ, (SEQ ID NO: 67, cleavable by collagenase)
GPLGIAG, (SEQ ID NO: 68, cleavable by collagenase)
GPEGLRVG, (SEQ ID NO: 69, cleavable by collagenase)
YGAGLGVV, (SEQ ID NO: 70, cleavable by collagenase)
AGLGVVER, (SEQ ID NO: 71, cleavable by collagenase)
AGLGISST, (SEQ ID NO: 72, cleavable by collagenase)
EPQALAMS, (SEQ ID NO: 73, cleavable by collagenase)
QALAMSAI, (SEQ ID NO: 74, cleavable by collagenase)
AAYHLVSQ, (SEQ ID NO: 75, cleavable by collagenase)
MDAFLESS, (SEQ ID NO: 76, cleavable by collagenase)
ESLPVVAV, (SEQ ID NO: 77, cleavable by collagenase)
SAPAVESE, (SEQ ID NO: 78, cleavable by collagenase)
DVAQFVLT, (SEQ ID NO: 79, cleavable by collagenase)
VAQFVLTE, (SEQ ID NO: 80, cleavable by collagenase)
AQFVLTEG, (SEQ ID NO: 81, cleavable by collagenase)
PVQPIGPQ,
```

-continued
(SEQ ID NO: 82, cleavable by thrombin)
LVPRGS,

```
                                        (SEQ ID NO: 83)
TSTSGRSANPRG, (SEQ ID NO: 84)
TSTSGRSANPRG, (SEQ ID NO: 85)
TSGSGRSANARG (SEQ ID NO: 86)
TSQSGRSANQRG (SEQ ID NO: 87)
TSPSGRSAYPRG (SEQ ID NO: 88)
TSGSGRSATPRG (SEQ ID NO: 89)
TSQSGRSATPRG (SEQ ID NO: 90)
TSASGRSATPRG (SEQ ID NO: 91)
TSYSGRSAVPRG (SEQ ID NO: 92)
TSYSGRSANFRG (SEQ ID NO: 93)
TSSSGRSATPRG (SEQ ID NO: 94)
TSTTGRSASPRG (SEQ ID NO: 95)
TSTSGRSANPRG.
```

The sequences shown in Table 1 may also be used as protease cleavage sequences.

TABLE 1

Protease cleavage sequences (cleavable by uPA and MT-SP1)

| SEQ ID NO | Cleavage sequence |
|---|---|
| 160 | TSASGRSANPRG |
| 161 | TSESGRSANPRG |
| 162 | TSFSGRSANPRG |
| 163 | TSGSGRSANPRG |
| 164 | TSHSGRSANPRG |
| 165 | TSKSGRSANPRG |
| 166 | TSMSGRSANPRG |
| 167 | TSNSGRSANPRG |
| 168 | TSPSGRSANPRG |
| 169 | TSQSGRSANPRG |
| 170 | TSWSGRSANPRG |
| 171 | TSYSGRSANPRG |
| 172 | TSTAGRSANPRG |
| 173 | TSTDGRSANPRG |

TABLE 1-continued

Protease cleavage sequences (cleavable by uPA and MT-SP1)

| SEQ ID NO | Cleavage sequence |
|---|---|
| 174 | TSTEGRSANPRG |
| 175 | TSTFGRSANPRG |
| 176 | TSTLGRSANPRG |
| 177 | TSTMGRSANPRG |
| 178 | TSTPGRSANPRG |
| 179 | TSTQGRSANPRG |
| 180 | TSTVGRSANPRG |
| 181 | TSTWGRSANPRG |
| 182 | TSTSARSANPRG |
| 183 | TSTSERSANPRG |
| 184 | TSTSFRSANPRG |
| 185 | TSTSHRSANPRG |
| 186 | TSTSIRSANPRG |
| 187 | TSTSKRSANPRG |
| 188 | TSTSLRSANPRG |

57

TABLE 1-continued

Protease cleavage sequences (cleavable
by uPA and MT-SP1)

| SEQ ID NO | Cleavage sequence |
|-----------|-------------------|
| 189 | TSTSMRSANPRG |
| 190 | TSTSNRSANPRG |
| 191 | TSTSPRSANPRG |
| 192 | TSTSQRSANPRG |
| 193 | TSTSRRSANPRG |
| 194 | TSTSTRSANPRG |
| 195 | TSTSVRSANPRG |
| 196 | TSTSWRSANPRG |
| 197 | TSTSYRSANPRG |
| 198 | TSTSGRAANPRG |
| 199 | TSTSGRDANPRG |
| 200 | TSTSGREANPRG |
| 201 | TSTSGRGANPRG |
| 202 | TSTSGRHANPRG |
| 203 | TSTSGRIANPRG |
| 204 | TSTSGRKANPRG |
| 205 | TSTSGREANPRG |
| 206 | TSTSGRMANPRG |
| 207 | TSTSGRNANPRG |
| 208 | TSTSGRPANPRG |
| 209 | TSTSGRQANPRG |
| 210 | TSTSGRRANPRG |
| 211 | TSTSGRTANPRG |
| 212 | TSTSGRVANPRG |
| 213 | TSTSGRWANPRG |
| 214 | TSTSGRYANPRG |
| 215 | TSTSGRSENPRG |
| 216 | TSTSGRSFNPRG |
| 217 | TSTSGRSKNPRG |
| 218 | TSTSGRSMNPRG |
| 219 | TSTSGRSNNPRG |
| 220 | TSTSGRSPNPRG |
| 221 | TSTSGRSQNPRG |
| 222 | TSTSGRSRNPRG |
| 223 | TSTSGRSSNPRG |
| 224 | TSTSGRSWNPRG |
| 225 | TSTSGRSYNPRG |

58

TABLE 1-continued

Protease cleavage sequences (cleavable
by uPA and MT-SP1)

| SEQ ID NO | Cleavage sequence |
|-----------|-------------------|
| 226 | TSTSGRSAAPRG |
| 227 | TSTSGRSADPRG |
| 228 | TSTSGRSAEPRG |
| 229 | TSTSGRSAFPRG |
| 230 | TSTSGRSAGPRG |
| 231 | TSTSGRSAKPRG |
| 232 | TSTSGRSALPRG |
| 233 | TSTSGRSAMPRG |
| 234 | TSTSGRSAPPRG |
| 235 | TSTSGRSAQPRG |
| 236 | TSTSGRSAVPRG |
| 237 | TSTSGRSAWPRG |
| 238 | TSTSGRSAYPRG |
| 239 | TSTSGRSANARG |
| 240 | TSTSGRSANDRG |
| 241 | TSTSGRSANERG |
| 242 | TSTSGRSANFRG |
| 243 | TSTSGRSANGRG |
| 244 | TSTSGRSANIRG |
| 245 | TSTSGRSANERG |
| 246 | TSTSGRSANNRG |
| 247 | TSTSGRSANQRG |
| 248 | TSTSGRSANSRG |
| 249 | TSTSGRSANTRG |
| 250 | TSTSGRSANWRG |
| 251 | TSDSGRSANPRG |
| 252 | TSISGRSANPRG |
| 253 | TSSSGRSANPRG |
| 254 | TSTHGRSANPRG |
| 255 | TSTKGRSANPRG |
| 256 | TSTTGRSANPRG |
| 257 | TSTYGRSANPRG |
| 258 | TSTSDRSANPRG |
| 259 | TSTSSRSANPRG |
| 260 | TSTSGRFANPRG |
| 261 | TSTSGRSDNPRG |
| 262 | TSTSGRSHNPRG |
| 263 | TSTSGRSINPRG |

59

TABLE 1-continued

| SEQ ID NO | Cleavage sequence |
|-----------|-------------------|

Protease cleavage sequences (cleavable by uPA and MT-SP1)

| SEQ ID NO | Cleavage sequence |
|-----------|-------------------|
| 264 | TSTSGRSLNPRG |
| 265 | TSTSGRSTNPRG |
| 266 | TSTSGRSVNPRG |
| 267 | TSTSGRSAHPRG |
| 268 | TSTSGRSAIPRG |
| 269 | TSTSGRSARPRG |
| 270 | TSTSGRSASPRG |
| 271 | TSTSGRSATPRG |
| 272 | TSTSGRSANHRG |
| 273 | TSTSGRSANLRG |
| 274 | TSTSGRSANMRG |
| 275 | TSTSGRSANRRG |
| 276 | TSTSGRSANVRG |
| 277 | TSTSGRSANYRG |
| 278 | TSGSGRSAVPRG |
| 279 | TSGSGRSAYPRG |
| 280 | TSGSGRSANQRG |
| 281 | TSGSGRSANIRG |
| 282 | TSGSGRSANFRG |
| 283 | TSGSGRSANSRG |
| 284 | TSQSGRSAVPRG |
| 285 | TSQSGRSAYPRG |
| 286 | TSQSGRSANARG |
| 287 | TSQSGRSANIRG |
| 288 | TSQSGRSANFRG |
| 289 | TSQSGRSANSRG |
| 290 | TSPSGRSAVPRG |
| 291 | TSPSGRSANQRG |
| 292 | TSPSGRSANARG |
| 293 | TSPSGRSANIRG |
| 294 | TSPSGRSANFRG |
| 295 | TSPSGRSANSRG |
| 296 | TSASGRSAVPRG |
| 297 | TSASGRSAYPRG |
| 298 | TSASGRSANQRG |
| 299 | TSASGRSANARG |
| 300 | TSASGRSANIRG |

60

TABLE 1-continued

Protease cleavage sequences (cleavable by uPA and MT-SP1)

| SEQ ID NO | Cleavage sequence |
|-----------|-------------------|
| 301 | TSASGRSANFRG |
| 302 | TSASGRSANSRG |
| 303 | TSYSGRSENPRG |
| 304 | TSGSGRSENPRG |
| 305 | TSQSGRSENPRG |
| 306 | TSPSGRSENPRG |
| 307 | TSASGRSENPRG |
| 308 | TSHSGRSENPRG |
| 309 | TSTSGRSENQRG |
| 310 | TSTSGRSENARG |
| 311 | TSTSGRSENIRG |
| 312 | TSTSGRSENFRG |
| 313 | TSTSGRSENSRG |
| 314 | TSYSGRSAEPRG |
| 315 | TSGSGRSAEPRG |
| 316 | TSQSGRSAEPRG |
| 317 | TSPSGRSAEPRG |
| 318 | TSASGRSAEPRG |
| 319 | TSHSGRSAEPRG |
| 320 | TSTSGRSAEQRG |
| 321 | TSTSGRSAEARG |
| 322 | TSTSGRSAEIRG |
| 323 | TSTSGRSAEFRG |
| 324 | TSTSGRSAESRG |
| 325 | TSGTGRSANPRG |
| 326 | TSGKGRSANPRG |
| 327 | TSGSGRSAIPRG |
| 328 | TSGSGRSASPRG |
| 329 | TSGSGRSAHPRG |
| 330 | TSGSGRSANYRG |
| 331 | TSGSGRSANVRG |
| 332 | TSGSGRSANHRG |
| 333 | TSQTGRSANPRG |
| 334 | TSQKGRSANPRG |
| 335 | TSQSGRSAIPRG |
| 336 | TSQSGRSASPRG |
| 337 | TSQSGRSAHPRG |
| 338 | TSQSGRSANYRG |

TABLE 1-continued

| Protease cleavage sequences (cleavable by uPA and MT-SP1) | |
| --- | --- |
| SEQ ID NO | Cleavage sequence |
| 339 | TSQSGRSANVRG |
| 340 | TSQSGRSANHRG |
| 341 | TSPTGRSANPRG |
| 342 | TSPKGRSANPRG |
| 343 | TSPSGRSAIPRG |
| 344 | TSPSGRSATPRG |
| 345 | TSPSGRSASPRG |
| 346 | TSPSGRSAHPRG |
| 347 | TSPSGRSANYRG |
| 348 | TSPSGRSANVRG |
| 349 | TSPSGRSANHRG |
| 350 | TSATGRSANPRG |
| 351 | TSAKGRSANPRG |
| 352 | TSASGRSAIPRG |
| 353 | TSASGRSASPRG |
| 354 | TSASGRSAHPRG |
| 355 | TSASGRSANYRG |
| 356 | TSASGRSANVRG |
| 357 | TSASGRSANHRG |
| 358 | TSYTGRSANPRG |
| 359 | TSYKGRSANPRG |
| 360 | TSYSGRSAIPRG |
| 361 | TSYSGRSATPRG |
| 362 | TSYSGRSASPRG |
| 363 | TSYSGRSAHPRG |
| 364 | TSYSGRSANARG |
| 365 | TSYSGRSANYRG |
| 366 | TSYSGRSANVRG |
| 367 | TSYSGRSANHRG |
| 368 | TSSTGRSANPRG |
| 369 | TSSKGRSANPRG |
| 370 | TSSSGRSAVPRG |
| 371 | TSSSGRSAIPRG |
| 372 | TSSSGRSASPRG |
| 373 | TSSSGRSAHPRG |
| 374 | TSSSGRSANARG |
| 375 | TSSSGRSANFRG |

TABLE 1-continued

| Protease cleavage sequences (cleavable by uPA and MT-SP1) | |
| --- | --- |
| SEQ ID NO | Cleavage sequence |
| 376 | TSSSGRSANYRG |
| 377 | TSSSGRSANVRG |
| 378 | TSSSGRSANHRG |
| 379 | TSITGRSANPRG |
| 380 | TSIKGRSANPRG |
| 381 | TSISGRSAVPRG |
| 382 | TSISGRSAIPRG |
| 383 | TSISGRSATPRG |
| 384 | TSISGRSASPRG |
| 385 | TSISGRSAHPRG |
| 386 | TSISGRSANARG |
| 387 | TSISGRSANFRG |
| 388 | TSISGRSANYRG |
| 389 | TSISGRSANYRG |
| 390 | TSISGRSANHRG |
| 391 | TSTTGRSAVPRG |
| 392 | TSTTGRSAIPRG |
| 393 | TSTTGRSATPRG |
| 394 | TSTTGRSAHPRG |
| 395 | TSTTGRSANARG |
| 396 | TSTTGRSANFRG |
| 397 | TSTTGRSANYRG |
| 398 | TSTTGRSANVRG |
| 399 | TSTTGRSANHRG |
| 400 | TSTKGRSAVPRG |
| 401 | TSTKGRSAIPRG |
| 402 | TSTKGRSATPRG |
| 403 | TSTKGRSASPRG |
| 404 | TSTKGRSAHPRG |
| 405 | TSTKGRSANARG |
| 406 | TSTKGRSANFRG |
| 407 | TSTKGRSANYRG |
| 408 | TSTKGRSANVRG |
| 409 | TSTKGRSANHRG |
| 410 | TSTSGRSAVYRG |
| 411 | TSTSGRSAVVRG |
| 412 | TSTSGRSAVHRG |
| 413 | TSTSGRSAIYRG |

TABLE 1-continued

| SEQ ID NO | Cleavage sequence |
|-----------|-------------------|
| | Protease cleavage sequences (cleavable by uPA and MT-SP1) |
| 414 | TSTSGRSAIVRG |
| 415 | TSTSGRSAIHRG |
| 416 | TSTSGRSASYRG |
| 417 | TSTSGRSASVRG |
| 418 | TSTSGRSASHRG |
| 419 | TSTSGRSAHYRG |
| 420 | TSTSGRSAHVRG |
| 421 | TSTSGRSAHHRG |
| 422 | TSPSGRSEVPRG |
| 423 | TSPSGRSAEPRG |
| 424 | TSPSGRSAGPRG |
| 425 | TSASGRSENARG |
| 426 | TSASGRSAEARG |
| 427 | TSASGRSAGARG |
| 428 | TSGTGRSATPRG |
| 429 | TSGSGRSATYRG |
| 430 | TSGSGRSATVRG |
| 431 | TSGSGRSATHRG |
| 432 | TSGTGRSATYRG |
| 433 | TSGTGRSATVRG |
| 434 | TSGTGRSATHRG |
| 435 | TSGSGRSETPRG |
| 436 | TSGTGRSETPRG |
| 437 | TSGSGRSETYRG |
| 438 | TSGSGRSETVRG |
| 439 | TSGSGRSETHRG |
| 440 | TSYTGRSAVPRG |
| 441 | TSYSGRSAVYRG |
| 442 | TSYSGRSAVVRG |
| 443 | TSYSGRSAVHRG |
| 444 | TSYTGRSAVYRG |
| 445 | TSYTGRSAVVRG |
| 446 | TSYTGRSAVHRG |
| 447 | TSYSGRSEVPRG |
| 448 | TSYTGRSEVPRG |
| 449 | TSYSGRSEVYRG |
| 450 | TSYSGRSEVVRG |

TABLE 1-continued

| SEQ ID NO | Cleavage sequence |
|-----------|-------------------|
| | Protease cleavage sequences (cleavable by uPA and MT-SP1) |
| 451 | TSYSGRSEVHRG |
| 452 | TSYTGRSAVPGG |
| 453 | TSYSGRSAVYGG |
| 454 | TSYSGRSAVVGG |
| 455 | TSYSGRSAVHGG |
| 456 | TSYTGRSAVYGG |
| 457 | TSYTGRSAVVGG |
| 458 | TSYTGRSAVHGG |
| 459 | ASGRSANP |
| 460 | ESGRSANP |
| 461 | FSGRSANP |
| 462 | GSGRSANP |
| 463 | HSGRSANP |
| 464 | KSGRSANP |
| 465 | MSGRSANP |
| 466 | NSGRSANP |
| 467 | PSGRSANP |
| 468 | QSGRSANP |
| 469 | WSGRSANP |
| 470 | YSGRSANP |
| 471 | TAGRSANP |
| 472 | TDGRSANP |
| 473 | TEGRSANP |
| 474 | TFGRSANP |
| 475 | TLGRSANP |
| 476 | TMGRSANP |
| 477 | TPGRSANP |
| 478 | TQGRSANP |
| 479 | TVGRSANP |
| 480 | TWGRSANP |
| 481 | TSARSANP |
| 482 | TSERSANP |
| 483 | TSFRSANP |
| 484 | TSHRSANP |
| 485 | TSIRSANP |
| 486 | TSKRSANP |
| 487 | TSLRSANP |
| 488 | TSMRSANP |

TABLE 1-continued

| Protease cleavage sequences (cleavable by uPA and MT-SP1) | |
| --- | --- |
| SEQ ID NO | Cleavage sequence |
| 489 | TSNRSANP |
| 490 | TSPRSANP |
| 491 | TSQRSANP |
| 492 | TSRRSANP |
| 493 | TSTRSANP |
| 494 | TSVRSANP |
| 495 | TSWRSANP |
| 496 | TSYRSANP |
| 497 | TSGRAANP |
| 498 | TSGRDANP |
| 499 | TSGREANP |
| 500 | TSGRGANP |
| 501 | TSGRHANP |
| 502 | TSGRIANP |
| 503 | TSGRKANP |
| 504 | TSGRLANP |
| 505 | TSGRMANP |
| 506 | TSGRNANP |
| 507 | TSGRPANP |
| 508 | TSGRQANP |
| 509 | TSGRRANP |
| 510 | TSGRTANP |
| 511 | TSGRVANP |
| 512 | TSGRWANP |
| 513 | TSGRYANP |
| 514 | TSGRSENP |
| 515 | TSGRSFNP |
| 516 | TSGRSKNP |
| 517 | TSGRSMNP |
| 518 | TSGRSNNP |
| 519 | TSGRSPNP |
| 520 | TSGRSQNP |
| 521 | TSGRSRNP |
| 522 | TSGRSSNP |
| 523 | TSGRSWNP |
| 524 | TSGRSYNP |
| 525 | TSGRSAAP |

TABLE 1-continued

| Protease cleavage sequences (cleavable by uPA and MT-SP1) | |
| --- | --- |
| SEQ ID NO | Cleavage sequence |
| 526 | TSGRSADP |
| 527 | TSGRSAEP |
| 528 | TSGRSAFP |
| 529 | TSGRSAGP |
| 530 | TSGRSAKP |
| 531 | TSGRSALP |
| 532 | TSGRSAMP |
| 533 | TSGRSAPP |
| 534 | TSGRSAQP |
| 535 | TSGRSAVP |
| 536 | TSGRSAWP |
| 537 | TSGRSAYP |
| 538 | TSGRSANA |
| 539 | TSGRSAND |
| 540 | TSGRSANE |
| 541 | TSGRSANF |
| 542 | TSGRSANG |
| 543 | TSGRSANI |
| 544 | TSGRSANK |
| 545 | TSGRSANN |
| 546 | TSGRSANQ |
| 547 | TSGRSANS |
| 548 | TSGRSANT |
| 549 | TSGRSANW |
| 550 | DSGRSANP |
| 551 | ISGRSANP |
| 552 | SSGRSANP |
| 553 | THGRSANP |
| 554 | TKGRSANP |
| 555 | TTGRSANP |
| 556 | TYGRSANP |
| 557 | TSDRSANP |
| 558 | TSSRSANP |
| 559 | TSGRFANP |
| 560 | TSGRSDNP |
| 561 | TSGRSHNP |
| 562 | TSGRSINP |
| 563 | TSGRSLNP |

TABLE 1-continued

| Protease cleavage sequences (cleavable by uPA and MT-SP1) | |
|---|---|
| SEQ ID NO | Cleavage sequence |
| 564 | TSGRSTNP |
| 565 | TSGRSVNP |
| 566 | TSGRSAHP |
| 567 | TSGRSAIP |
| 568 | TSGRSARP |
| 569 | TSGRSASP |
| 570 | TSGRSATP |
| 571 | TSGRSANH |
| 572 | TSGRSANL |
| 573 | TSGRSANM |
| 574 | TSGRSANR |
| 575 | TSGRSANV |
| 576 | TSGRSANY |
| 577 | GSGRSAVP |
| 578 | GSGRSAYP |
| 579 | GSGRSANQ |
| 580 | GSGRSANA |
| 581 | GSGRSANI |
| 582 | GSGRSANF |
| 583 | GSGRSANS |
| 584 | QSGRSAVP |
| 585 | QSGRSAYP |
| 586 | QSGRSANQ |
| 587 | QSGRSANA |
| 588 | QSGRSANI |
| 589 | QSGRSANF |
| 590 | QSGRSANS |
| 591 | PSGRSAVP |
| 592 | PSGRSAYP |
| 593 | PSGRSANQ |
| 594 | PSGRSANA |
| 595 | PSGRSANI |
| 596 | PSGRSANF |
| 597 | PSGRSANS |
| 598 | ASGRSAVP |
| 599 | ASGRSAYP |
| 600 | ASGRSANQ |

TABLE 1-continued

| Protease cleavage sequences (cleavable by uPA and MT-SP1) | |
|---|---|
| SEQ ID NO | Cleavage sequence |
| 601 | ASGRSANA |
| 602 | ASGRSANI |
| 603 | ASGRSANF |
| 604 | ASGRSANS |
| 605 | YSGRSENP |
| 606 | GSGRSENP |
| 607 | QSGRSENP |
| 608 | PSGRSENP |
| 609 | ASGRSENP |
| 610 | HSGRSENP |
| 611 | TSGRSENQ |
| 612 | TSGRSENA |
| 613 | TSGRSENI |
| 614 | TSGRSENF |
| 615 | TSGRSENS |
| 616 | YSGRSAEP |
| 617 | GSGRSAEP |
| 618 | QSGRSAEP |
| 619 | PSGRSAEP |
| 620 | ASGRSAEP |
| 621 | HSGRSAEP |
| 622 | TSGRSAEQ |
| 623 | TSGRSAEA |
| 624 | TSGRSAEI |
| 625 | TSGRSAEF |
| 626 | TSGRSAES |
| 627 | GTGRSANP |
| 628 | GKGRSANP |
| 629 | GSGRSAIP |
| 630 | GSGRSATP |
| 631 | GSGRSASP |
| 632 | GSGRSAHP |
| 633 | GSGRSANY |
| 634 | GSGRSANV |
| 635 | GSGRSANH |
| 636 | QTGRSANP |
| 637 | QKGRSANP |
| 638 | QSGRSAIP |

TABLE 1-continued

| Protease cleavage sequences (cleavable by uPA and MT-SP1) | |
|---|---|
| SEQ ID NO | Cleavage sequence |
| 639 | QSGRSATP |
| 640 | QSGRSASP |
| 641 | QSGRSAHP |
| 642 | QSGRSANY |
| 643 | QSGRSANV |
| 644 | QSGRSANH |
| 645 | PTGRSANP |
| 646 | PKGRSANP |
| 647 | PSGRSAIP |
| 648 | PSGRSATP |
| 649 | PSGRSASP |
| 650 | PSGRSAHP |
| 651 | PSGRSANY |
| 652 | PSGRSANV |
| 653 | PSGRSANH |
| 654 | ATGRSANP |
| 655 | AKGRSANP |
| 656 | ASGRSAIP |
| 657 | ASGRSAEP |
| 658 | ASGRSASP |
| 659 | ASGRSAHP |
| 660 | ASGRSANY |
| 661 | ASGRSANV |
| 662 | ASGRSANH |
| 663 | YTGRSANP |
| 664 | YKGRSANP |
| 665 | YSGRSAVP |
| 666 | YSGRSAIP |
| 667 | YSGRSATP |
| 668 | YSGRSASP |
| 669 | YSGRSAHP |
| 670 | YSGRSANA |
| 671 | YSGRSANF |
| 672 | YSGRSANY |
| 673 | YSGRSANV |
| 674 | YSGRSANH |
| 675 | STGRSANP |

TABLE 1-continued

| Protease cleavage sequences (cleavable by uPA and MT-SP1) | |
|---|---|
| SEQ ID NO | Cleavage sequence |
| 676 | SKGRSANP |
| 677 | SSGRSAVP |
| 678 | SSGRSAIP |
| 679 | SSGRSATP |
| 680 | SSGRSASP |
| 681 | SSGRSAHP |
| 682 | SSGRSANA |
| 683 | SSGRSANF |
| 684 | SSGRSANY |
| 685 | SSGRSANV |
| 686 | SSGRSANH |
| 687 | ITGRSANP |
| 688 | IKGRSANP |
| 689 | ISGRSAVP |
| 690 | ISGRSAIP |
| 691 | ISGRSATP |
| 692 | ISGRSASP |
| 693 | ISGRSAHP |
| 694 | ISGRSANA |
| 695 | ISGRSANF |
| 696 | ISGRSANY |
| 697 | ISGRSANV |
| 698 | ISGRSANH |
| 699 | TTGRSAVP |
| 700 | TTGRSAIP |
| 701 | TTGRSATP |
| 702 | TTGRSASP |
| 703 | TTGRSAHP |
| 704 | TTGRSANA |
| 705 | TTGRSANF |
| 706 | TTGRSANY |
| 707 | TTGRSANV |
| 708 | TTGRSANH |
| 709 | TKGRSAVP |
| 710 | TKGRSAIP |
| 711 | TKGRSATP |
| 712 | TKGRSASP |
| 713 | TKGRSAHP |

TABLE 1-continued

| Protease cleavage sequences (cleavable by uPA and MT-SP1) | |
|---|---|
| SEQ ID NO | Cleavage sequence |
| 714 | TKGRSANA |
| 715 | TKGRSANF |
| 716 | TKGRSANY |
| 717 | TKGRSANV |
| 718 | TKGRSANH |
| 719 | TSGRSAVY |
| 720 | TSGRSAVV |
| 721 | TSGRSAVH |
| 722 | TSGRSAIY |
| 723 | TSGRSAIV |
| 724 | TSGRSAIH |
| 725 | TSGRSASY |
| 726 | TSGRSASV |
| 727 | TSGRSASH |
| 728 | TSGRSAHY |
| 729 | TSGRSAHV |
| 730 | TSGRSAHH |
| 731 | PSGRSEVP |
| 732 | PSGRSAEP |
| 733 | PSGRSAGP |
| 734 | ASGRSENA |
| 735 | ASGRSAEA |
| 736 | ASGRSAGA |
| 737 | GTGRSATP |
| 738 | GSGRSATY |
| 739 | GSGRSATV |
| 740 | GSGRSATH |
| 741 | GTGRSATY |
| 742 | GTGRSATV |
| 743 | GTGRSATH |
| 744 | GSGRSETP |
| 745 | GTGRSETP |
| 746 | GSGRSETY |
| 747 | GSGRSETV |
| 748 | GSGRSETH |
| 749 | YTGRSAVP |
| 750 | YSGRSAVY |

TABLE 1-continued

| Protease cleavage sequences (cleavable by uPA and MT-SP1) | |
|---|---|
| SEQ ID NO | Cleavage sequence |
| 751 | YSGRSAVV |
| 752 | YSGRSAVH |
| 753 | YTGRSAVY |
| 754 | YTGRSAVV |
| 755 | YTGRSAVH |
| 756 | YSGRSEVP |
| 757 | YTGRSEVP |
| 758 | YSGRSEVY |
| 759 | YSGRSEVV |
| 760 | YSGRSEVH |
| 761 | YTGRSAVP |
| 762 | YSGRSAVY |
| 763 | YSGRSAVV |
| 764 | YSGRSAVH |
| 765 | YTGRSAVY |
| 766 | YTGRSAVV |
| 767 | YTGRSAVH |
| 768 | TSTSGRSANPRG |
| 769 | TSTSGRSANPAG |
| 770 | TSTSGRSANPHG |
| 771 | TSTSGRSANPIG |
| 772 | TSTSGRSANPLG |
| 773 | TSTSGRSANPSG |
| 774 | ISTSGRSANPIG |
| 775 | YSTSGRSANPIG |
| 776 | TSYSGRSAVPAG |
| 777 | TSPSGRSANIAG |
| 778 | TSPSGRSANFAG |
| 779 | TSPTGRSANPAG |
| 780 | TSPSGRSAIPAG |
| 781 | TSYTGRSANPAG |
| 782 | TSYSGRSAIPAG |
| 783 | TSISGRSANYAG |
| 784 | TSPSGRSAGPAG |
| 785 | TSYTGRSAVPAG |
| 786 | TSYTGRSAVYAG |
| 787 | TSYTGRSAVVAG |
| 788 | TSYTGRSAVHAG |

TABLE 1-continued

Protease cleavage sequences (cleavable
by uPA and MT-SP1)

| SEQ ID NO | Cleavage sequence |
|-----------|-------------------|
| 789 | TSYSGRSAVPHG |
| 790 | TSPSGRSANIHG |
| 791 | TSPSGRSANFHG |
| 792 | TSPTGRSANPHG |
| 793 | TSPSGRSAIPHG |
| 794 | TSYTGRSANPHG |
| 795 | TSYSGRSAIPHG |
| 796 | TSISGRSANYHG |
| 797 | TSPSGRSAGPHG |
| 798 | TSYTGRSAVPHG |
| 799 | TSYTGRSAVYHG |
| 800 | TSYTGRSAVVHG |
| 801 | TSYTGRSAVHHG |
| 802 | TSYSGRSAVPIG |
| 803 | TSPSGRSANIIG |
| 804 | TSPSGRSANFIG |
| 805 | TSPTGRSANPIG |
| 806 | TSPSGRSAIPIG |
| 807 | TSYTGRSANPIG |
| 808 | TSYSGRSAIPIG |
| 809 | TSISGRSANYIG |
| 810 | TSPSGRSAGPIG |
| 811 | TSYTGRSAVPIG |
| 812 | TSYTGRSAVYIG |
| 813 | TSYTGRSAVVIG |
| 814 | TSYTGRSAVHIG |
| 815 | TSYSGRSAVPLG |
| 816 | TSPSGRSANILG |
| 817 | TSPSGRSANFLG |
| 818 | TSPTGRSANPLG |
| 819 | TSPSGRSAIPLG |
| 820 | TSYTGRSANPLG |
| 821 | TSYSGRSAIPLG |
| 822 | TSISGRSANYLG |
| 823 | TSPSGRSAGPLG |
| 824 | TSYTGRSAVPLG |
| 825 | TSYTGRSAVYLG |

TABLE 1-continued

Protease cleavage sequences (cleavable
by uPA and MT-SP1)

| SEQ ID NO | Cleavage sequence |
|-----------|-------------------|
| 826 | TSYTGRSAVVLG |
| 827 | TSYTGRSAVHLG |
| 828 | TSYSGRSAVPSG |
| 829 | TSPSGRSANISG |
| 830 | TSPSGRSANFSG |
| 831 | TSPTGRSANPSG |
| 832 | TSPSGRSAIPSG |
| 833 | TSYTGRSANPSG |
| 834 | TSYSGRSAIPSG |
| 835 | TSISGRSANYSG |
| 836 | TSPSGRSAGPSG |
| 837 | TSYTGRSAVPSG |
| 838 | TSYTGRSAVYSG |
| 839 | TSYTGRSAVVSG |
| 840 | TSYTGRSAVHSG |
| 841 | ISYSGRSAVPIG |
| 842 | ISPSGRSANIIG |
| 843 | ISPSGRSANFIG |
| 844 | ISPTGRSANPIG |
| 845 | ISPSGRSAIPIG |
| 846 | ISYTGRSANPIG |
| 847 | ISYSGRSAIPIG |
| 848 | ISISGRSANYIG |
| 849 | ISPSGRSAGPIG |
| 850 | ISYTGRSAVPIG |
| 851 | ISYTGRSAVYIG |
| 852 | ISYTGRSAVVIG |
| 853 | ISYTGRSAVHIG |
| 854 | YSYSGRSAVPIG |
| 855 | YSPSGRSANIIG |
| 856 | YSPSGRSANFIG |
| 857 | YSPTGRSANPIG |
| 858 | YSPSGRSAIPIG |
| 859 | YSYTGRSANPIG |
| 860 | YSYSGRSAIPIG |
| 861 | YSISGRSANYIG |
| 862 | YSPSGRSAGPIG |
| 863 | YSYTGRSAVPIG |

TABLE 1-continued

| Protease cleavage sequences (cleavable by uPA and MT-SP1) | |
|---|---|
| SEQ ID NO | Cleavage sequence |
| 864 | YSYTGRSAVYIG |
| 865 | YSYTGRSAVVIG |
| 866 | YSYTGRSAVHIG |
| 867 | TSYTGRSAVPRG |
| 868 | TSYSGRSAVVRG |
| 869 | TSYTGRSAVYRG |
| 870 | TSYTGRSAVHRG |

The following sequence may also be used as a protease cleavage sequence:

(SEQ ID NO: 96)
X1-X2-X3-X4-X5-X6-X7-X8 wherein, X1 to X8 each represent a single amino acid, X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; and X8 is an amino acid selected from A, D, E, F, G, H, I, K, L, M, N, P, Q, R, S, T, V, W and Y.

The following sequence may also be used as a protease cleavage sequence:

(SEQ ID NO: 97)
X1-X2-X3-X4-X5-X6-X7-X8 wherein, X1 to X8 each represent a single amino acid, X1 is an amino acid selected from A, E, F, G, H, K, M, N, P, Q, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y.

The following sequence may also be used as a protease cleavage sequence:

(SEQ ID NO: 98)
X1-X2-X3-X4-X5-X6-X7-X8 wherein, X1 to X8 each represent a single amino acid, X1 is an amino acid selected from A, D, E, F, G, H, I, K, M, N, P, Q, S, T, W and Y; X2 is an amino acid selected from A, D, F, L, M, P, Q, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y.

The following sequence may also be used as a protease cleavage sequence:

(SEQ ID NO: 99)
X1-X2-X3-X4-X5-X6-X7-X8 wherein, X1 to X8 each represent a single amino acid, X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, E, F, H, I, K, L, M, N, P, Q, R, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y.

The following sequence may also be used as a protease cleavage sequence:

(SEQ ID NO: 100)
X1-X2-X3-X4-X5-X6-X7-X8 wherein, X1 to X8 each represent a single amino acid, X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, G, H, I, K, L, M, N, Q, R, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y.

The following sequence may also be used as a protease cleavage sequence:

(SEQ ID NO: 101)
X1-X2-X3-X4-X5-X6-X7-X8 wherein, X1 to X8 each represent a single amino acid, X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from E, F, K, M, N, P, Q, R, S and W; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y.

The following sequence may also be used as a protease cleavage sequence:

(SEQ ID NO: 102)
X1-X2-X3-X4-X5-X6-X7-X8 wherein, X1 to X8 each represent a single amino acid, X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, F, G, L, M, P, Q, V and W; X8 is an amino acid selected from A, D, E, F, G, H, I, K, L, M, N, P, Q, R, S, T, V, W and Y.

The following sequence may also be used as a protease cleavage sequence:

(SEQ ID NO: 103)
X1-X2-X3-X4-X5-X6-X7-X8 wherein, X1 to X8 each represent a single amino acid, X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, I, K, N, T and W.

The following sequence may also be used as a protease cleavage sequence:

(SEQ ID NO: 104)
X1-X2-X3-X4-X5-X6-X7-X8 wherein, X1 to X8 each represent a single amino acid, X1 is an amino acid selected from A, G, I, P, Q, S and Y; X2 is an amino acid selected from K or T; X3 is G; X4 is R; X5 is S; X6 is A; X7 is an amino acid selected from H, I and V; X8 is an amino acid selected from H, V and Y.

The following sequence may also be used as a protease cleavage sequence:

(SEQ ID NO: 105)
X1-X2-X3-X4-X5-X6-X7-X8 wherein, X1 to X8 each represent a single amino acid, X1 is Y; X2 is an amino acid selected from S and T; X3 is G; X4 is R; X5 is S; X6 is an amino acid selected from A and E; X7 is an amino acid selected from N and V; X8 is an amino acid selected from H, P, V and Y.

The following sequence may also be used as a protease cleavage sequence:

(SEQ ID NO: 106)
X1-X2-X3-X4-X5-X6-X7-X8-X9 wherein, X1 to X9 each represent a single amino acid, X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y; X9 is an amino acid selected from A, G, H, I, L and R.

The following sequence may also be used as a protease cleavage sequence:

(SEQ ID NO: 107)
X1-X2-X3-X4-X5-X6-X7-X8-X9 wherein, X1 to X9 each represent a single amino acid, X1 is an amino acid selected from A, E, F, G, H, K, M, N, P, Q, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y; X9 is an amino acid selected from A, G, H, I, L and R.

The following sequence may also be used as a protease cleavage sequence:

(SEQ ID NO: 108)
X1-X2-X3-X4-X5-X6-X7-X8-X9 wherein, X1 to X9 each represent a single amino acid, X1 is an amino acid selected from A, D, E, F, G, H, I, K, M, N, P, Q, S, T, W and Y; X2 is an amino acid selected from A, D, F, L, M, P, Q, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y; X9 is an amino acid selected from A, G, H, I, L and R.

The following sequence may also be used as a protease cleavage sequence:

(SEQ ID NO: 109)
X1-X2-X3-X4-X5-X6-X7-X8-X9 wherein, X1 to X9 each represent a single amino acid, X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, E, F, H, I, K, L, M, N, P, Q, R, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y;

X8 is an amino acid selected from A, D, E, F, G, H, I, K, L, M, N, P, Q, R, S, T, V, W and Y; X9 is an amino acid selected from A, G, H, I, L and R.

The following sequence may also be used as a protease cleavage sequence:

(SEQ ID NO: 110)

X1-X2-X3-X4-X5-X6-X7-X8-X9 wherein, X1 to X9 each represent a single amino acid, X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, G, H, I, K, L, M, N, Q, R, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y; X9 is an amino acid selected from A, G, H, I, L and R.

The following sequence may also be used as a protease cleavage sequence:

(SEQ ID NO: 111)

X1-X2-X3-X4-X5-X6-X7-X8-X9 wherein, X1 to X9 each represent a single amino acid, X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from E, F, K, M, N, P, Q, R, S and W; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y; X9 is an amino acid selected from A, G, H, I, L and R.

The following sequence may also be used as a protease cleavage sequence:

(SEQ ID NO: 112)

X1-X2-X3-X4-X5-X6-X7-X8-X9 wherein, X1 to X9 each represent a single amino acid, X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, F, G, L, M, P, Q, V and W; X8 is an amino acid selected from A, D, E, F, G, H, I, K, L, M, N, P, Q, R, S, T, V, W and Y; X9 is an amino acid selected from A, G, H, I, L and R.

The following sequence may also be used as a protease cleavage sequence:

(SEQ ID NO: 113)

X1-X2-X3-X4-X5-X6-X7-X8-X9 wherein, X1 to X9 each represent a single amino acid, X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, I, K, N, T and W; X9 is an amino acid selected from A, G, H, I, L and R.

The following sequence may also be used as a protease cleavage sequence:

(SEQ ID NO: 114)

X1-X2-X3-X4-X5-X6-X7-X8-X9 wherein, X1 to X9 each represent a single amino acid, X1 is an amino acid selected from A, G, I, P, Q, S and Y; X2 is an amino acid selected from K or T; X3 is G; X4 is R; X5 is S; X6 is A; X7 is an amino acid selected from H, I and V; X8 is an amino acid selected from H, V and Y; X9 is an amino acid selected from A, G, H, I, L and R.

The following sequence may also be used as a protease cleavage sequence:

(SEQ ID NO: 115)

X1-X2-X3-X4-X5-X6-X7-X8-X9 wherein, X1 to X9 each represent a single amino acid, X1 is Y; X2 is an amino acid selected from S and T; X3 is G; X4 is R; X5 is S; X6 is an amino acid selected from A and E; X7 is an amino acid selected from N and V; X8 is an amino acid selected from H, P, V and Y; X9 is an amino acid selected from A, G, H, I, L and R.

The following sequence may also be used as a protease cleavage sequence:

(SEQ ID NO: 116)

X10-X11-X1-X2-X3-X4-X5-X6-X7-X8 wherein, X1 to X11 each represent a single amino acid, X10 is an amino acid selected from I, T and Y; X11 is S; X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y.

The following sequence may also be used as a protease cleavage sequence:

(SEQ ID NO: 117)
X10-X11-X1-X2-X3-X4-X5-X6-X7-X8 wherein, X1 to X11 each represent a single amino acid, X10 is an amino acid selected from I, T and Y; X11 is S; X1 is an amino acid selected from A, E, F, G, H, K, M, N, P, Q, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y.

The following sequence may also be used as a protease cleavage sequence:

(SEQ ID NO: 118)
X10-X11-X1-X2-X3-X4-X5-X6-X7-X8 wherein, X1 to X11 each represent a single amino acid, X10 is an amino acid selected from I, T and Y; X11 is S; X1 is an amino acid selected from A, D, E, F, G, H, I, K, M, N, P, Q, S, T, W and Y; X2 is an amino acid selected from A, D, F, L, M, P, Q, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y.

The following sequence may also be used as a protease cleavage sequence:

(SEQ ID NO: 119)
X10-X11-X1-X2-X3-X4-X5-X6-X7-X8 wherein, X1 to X11 each represent a single amino acid, X10 is an amino acid selected from I, T and Y; X11 is S; X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, E, F, H, I, K, L, M, N, P, Q, R, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y.

The following sequence may also be used as a protease cleavage sequence:

(SEQ ID NO: 120)
X10-X11-X1-X2-X3-X4-X5-X6-X7-X8 wherein, X1 to X11 each represent a single amino acid, X10 is an amino acid selected from I, T and Y; X11 is S; X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, G, H, I, K, L, M, N, Q, R, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y.

The following sequence may also be used as a protease cleavage sequence:

(SEQ ID NO: 121)
X10-X11-X1-X2-X3-X4-X5-X6-X7-X8 wherein, X1 to X11 each represent a single amino acid, X10 is an amino acid selected from I, T and Y; X11 is S; X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from E, F, K, M, N, P, Q, R, S and W; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y.

The following sequence may also be used as a protease cleavage sequence:

(SEQ ID NO: 122)
X10-X11-X1-X2-X3-X4-X5-X6-X7-X8 wherein, X1 to X11 each represent a single amino acid, X10 is an amino acid selected from I, T and Y; X11 is S; X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, F, G, L, M, P, Q, V and W; X8 is an amino acid selected from A, D, E, F, G, H, I, K, L, M, N, P, Q, R, S, T, V, W and Y.

The following sequence may also be used as a protease cleavage sequence:

(SEQ ID NO: 123)
X10-X11-X1-X2-X3-X4-X5-X6-X7-X8 wherein, X1 to X11 each represent a single amino acid, X10 is an amino acid selected from I, T and Y; X11 is S; X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, I, K, N, T and W.

The following sequence may also be used as a protease cleavage sequence:

```
                                          (SEQ ID NO: 124)
        X10-X11-X1-X2-X3-X4-X5-X6-X7-X8
``` wherein, X1 to X11 each represent a single amino acid, X10 is an amino acid selected from I, T and Y; X11 is S; X1 is an amino acid selected from A, G, I, P, Q, S and Y; X2 is an amino acid selected from K or T; X3 is G; X4 is R; X5 is S; X6 is A; X7 is an amino acid selected from H, I and V; X8 is an amino acid selected from H, V and Y.

The following sequence may also be used as a protease cleavage sequence:

```
                                          (SEQ ID NO: 125)
        X10-X11-X1-X2-X3-X4-X5-X6-X7-X8
``` wherein, X1 to X11 each represent a single amino acid, X10 is an amino acid selected from I, T and Y; X11 is S; X1 is Y; X2 is an amino acid selected from S and T; X3 is G; X4 is R; X5 is S; X6 is an amino acid selected from A and E; X7 is an amino acid selected from N and V; X8 is an amino acid selected from H, P, V and Y.

The following sequence may also be used as a protease cleavage sequence:

```
                                          (SEQ ID NO: 126)
        X10-X11-X1-X2-X3-X4-X5-X6-X7-X8-X9
``` wherein, X1 to X11 each represent a single amino acid, X10 is an amino acid selected from I, T and Y; X11 is S; X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y; X9 is an amino acid selected from A, G, H, I, L and R.

The following sequence may also be used as a protease cleavage sequence:

```
                                          (SEQ ID NO: 127)
        X10-X11-X1-X2-X3-X4-X5-X6-X7-X8-X9
``` wherein, X1 to X11 each represent a single amino acid, X10 is an amino acid selected from I, T and Y; X11 is S; X1 is an amino acid selected from A, E, F, G, H, K, M, N, P, Q, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y; X9 is an amino acid selected from A, G, H, I, L and R.

The following sequence may also be used as a protease cleavage sequence:

```
                                          (SEQ ID NO: 128)
        X10-X11-X1-X2-X3-X4-X5-X6-X7-X8-X9
``` wherein, X1 to X11 each represent a single amino acid, X10 is an amino acid selected from I, T and Y; X11 is S; X1 is an amino acid selected from A, D, E, F, G, H, I, K, M, N, P, Q, S, T, W and Y; X2 is an amino acid selected from A, D, F, L, M, P, Q, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y; X9 is an amino acid selected from A, G, H, I, L and R.

The following sequence may also be used as a protease cleavage sequence:

```
                                          (SEQ ID NO: 129)
        X10-X11-X1-X2-X3-X4-X5-X6-X7-X8-X9
``` wherein, X1 to X11 each represent a single amino acid, X10 is an amino acid selected from I, T and Y; X11 is S; X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, E, F, H, I, K, L, M, N, P, Q, R, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y; X9 is an amino acid selected from A, G, H, I, L and R.

The following sequence may also be used as a protease cleavage sequence:

```
                                          (SEQ ID NO: 130)
        X10-X11-X1-X2-X3-X4-X5-X6-X7-X8-X9
``` wherein, X1 to X11 each represent a single amino acid, X10 is an amino acid selected from I, T and Y; X11 is S; X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, G, H, I, K, L, M, N, Q, R, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y; X9 is an amino acid selected from A, G, H, I, L and R.

The following sequence may also be used as a protease cleavage sequence:

(SEQ ID NO: 131)

X10-X11-X1-X2-X3-X4-X5-X6-X7-X8-X9 wherein, X1 to X11 each represent a single amino acid, X10 is an amino acid selected from I, T and Y; X11 is S; X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from E, F, K, M, N, P, Q, R, S and W; X7 is an amino acid selected from A, D, E, F, G, H, I, K, L, M, N, P, Q, R, S, T, V, W and Y; X8 is an amino acid selected from A, D, E, F, G, H, I, K, L, M, N, P, Q, R, S, T, V, W and Y; X9 is an amino acid selected from A, G, H, I, L and R.

The following sequence may also be used as a protease cleavage sequence:

(SEQ ID NO: 132)

X10-X11-X1-X2-X3-X4-X5-X6-X7-X8-X9 wherein, X1 to X11 each represent a single amino acid, X10 is an amino acid selected from I, T and Y; X11 is S; X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, F, G, L, M, P, Q, V and W; X8 is an amino acid selected from A, D, E, F, G, H, I, K, L, M, N, P, Q, R, S, T, V, W and Y; X9 is an amino acid selected from A, G, H, I, L and R.

The following sequence may also be used as a protease cleavage sequence:

(SEQ ID NO: 133)

X10-X11-X1-X2-X3-X4-X5-X6-X7-X8-X9 wherein, X1 to X11 each represent a single amino acid, X10 is an amino acid selected from I, T and Y; X11 is S; X1 is an amino acid selected from A, D, E, F, G, H, I, K, M, N, P, Q, S, T, W and Y; X2 is an amino acid selected from A, D, E, F, H, K, L, M, P, Q, S, T, V, W and Y; X3 is an amino acid selected from A, D, E, F, G, H, I, K, L, M, N, P, Q, R, S, T, V, W and Y; X4 is R; X5 is an amino acid selected from A, D, E, F, G, H, I, K, L, M, N, P, Q, R, S, T, V, W and Y; X6 is an amino acid selected from A, D, E, F, H, I, K, L, M, N, P, Q, R, S, T, V, W and Y; X7 is an amino acid selected from A, D, E, F, G, H, I, K, L, M, N, P, Q, R, S, T, V, W and Y; X8 is an amino acid selected from A, D, E, F, G, I, K, N, T and W; X9 is an amino acid selected from A, G, H, I, L and R.

The following sequence may also be used as a protease cleavage sequence:

(SEQ ID NO: 134)

X10-X11-X1-X2-X3-X4-X5-X6-X7-X8-X9 wherein, X1 to X11 each represent a single amino acid, X10 is an amino acid selected from I, T and Y; X11 is S; X1 is an amino acid selected from A, G, I, P, Q, S and Y; X2 is an amino acid selected from K or T; X3 is G; X4 is R; X5 is S; X6 is A; X7 is an amino acid selected from H, I and V; X8 is an amino acid selected from H, V and Y; X9 is an amino acid selected from A, G, H, I, L and R.

The following sequence may also be used as a protease cleavage sequence:

(SEQ ID NO: 135)

X10-X11-X1-X2-X3-X4-X5-X6-X7-X8-X9 wherein, X1 to X11 each represent a single amino acid, X10 is an amino acid selected from I, T and Y; X11 is S; X1 is Y; X2 is an amino acid selected from S and T; X3 is G; X4 is R; X5 is S; X6 is an amino acid selected from A and E; X7 is an amino acid selected from N and V; X8 is an amino acid selected from H, P, V and Y; X9 is an amino acid selected from A, G, H, I, L and R.

In addition to using the above-mentioned protease cleavage sequences, novel protease cleavage sequences may also be obtained by screening. For example, based on the result of crystal structure analysis of a known protease cleavage sequence, novel protease cleavage sequences can be explored by changing the interaction of active residues/recognition residues of the cleavage sequence and the enzyme. Novel protease cleavage sequences can also be explored by altering amino acids in a known protease cleavage sequence and examining interaction between the altered sequence and the protease. As an another example, protease cleavage sequences can be explored by examining interaction of the protease with a library of peptides displayed using an in vitro display method such as phage display and ribosome display, or with an array of peptides immobilized on a chip or beads.

Interaction between a protease cleavage sequence and a protease can be examined by testing cleavage of the sequence by the protease in vitro or in vivo.

Cleavage fragments after protease treatment can be separated by electrophoresis such as SDS-PAGE and quantified to evaluate the protease cleavage sequence, the activity of the protease, and the cleavage ratio of a molecule into which the protease cleavage sequence has been introduced. A non-limiting embodiment of the method of evaluating the cleavage ratio of a molecule into which a protease cleavage sequence has been introduced includes the following method: For example, when the cleavage ratio of an antibody variant into which a protease cleavage sequence has been introduced is evaluated using recombinant human u-Plasminogen Activator/Urokinase (human uPA, huPA) (R&D Systems; 1310-SE-010) or recombinant human Matriptase/ST14 Catalytic Domain (human MT-SP1, hMT-SP1) (R&D Systems; 3946-SE-010), 100 microgram/mL of the antibody variant is reacted with 40 nM huPA or 3 nM hMT-SP1 in PBS at 37 degrees C. for one hour, and then subjected to capillary electrophoresis immunoassay. Capillary electrophoresis immunoassay can be performed using Wes (Protein Simple), but the present method is not limited thereto. As an alternative to capillary electrophoresis immunoassay, SDS-PAGE and such may be performed for separation, followed by detection with Western blotting. The present method is not limited to these methods. Before and after cleavage, the light chain can be detected using anti-human lambda chain HRP-labeled antibody (abcam; ab9007), but any antibody that can detect cleavage fragments may be used. The area of each peak obtained after protease treatment is output using software for Wes (Compass for SW; Protein Simple), and the cleavage ratio (%) of the antibody variant can be determined with the following formula:

$$\text{(Peak area of cleaved light chain)} \times 100/\text{(Peak area of cleaved light chain+Peak area of uncleaved light chain)}$$

Cleavage ratios can be determined if protein fragments are detectable before and after protease treatment. Cleavage ratios can be determined not only for antibody variants but also for various protein molecules into which a protease cleavage sequence has been introduced.

The in vivo cleavage ratio of a molecule into which a protease cleavage sequence has been introduced can be determined by administering the molecule into animals and detecting the administered molecule in blood samples. For example, an antibody variant into which a protease cleavage sequence has been introduced is administered to mice, and plasma is collected from their blood samples. The antibody is purified from the plasma by a method known to those skilled in the art using Dynabeads Protein A (Thermo; 10001D), and then subjected to capillary electrophoresis immunoassay to evaluate the protease cleavage ratio of the antibody variant. Capillary electrophoresis immunoassay can be performed using Wes (Protein Simple), but the present method is not limited thereto. As an alternative to capillary electrophoresis immunoassay, SDS-PAGE and such may be performed for separation, followed by detection with Western blotting. The present method is not limited to these methods. The light chain of the antibody variant collected from mice can be detected using anti-human lambda chain HRP-labeled antibody (abcam; ab9007), but any antibody that can detect cleavage fragments may be used. Once the area of each peak obtained by capillary electrophoresis immunoassay is output using software for Wes (Compass for SW; Protein Simple), the ratio of the remaining light chain can be calculated as [Peak area of light chain]/[Peak area of heavy chain] to determine the ratio of the full-length light chain that remain uncleaved in the mouse body. In vivo cleavage efficiencies can be determined if protein fragments collected from a living organism are detectable. Cleavage ratios can be determined not only for antibody variants but also for various protein molecules into which a protease cleavage sequence has been introduced. Calculation of cleavage ratios by the above-mentioned methods enables, for example, comparison of the in vivo cleavage ratios of antibody variants into which different cleavage sequences have been introduced, and comparison of the cleavage ratio of a single antibody variant between different animal models such as a normal mouse model and a tumor-grafted mouse model.

For example, the protease cleavage sequences shown in Table 1 have all been disclosed in WO2019/107384 Polypeptides containing these protease cleavage sequences are all useful as protease substrates which are hydrolyzed by the action of proteases. Thus, the present invention provides protease substrates comprising a sequence selected from SEQ ID NOs: 96-135, and the sequences listed in Table 1. The protease substrates of the present invention can be utilized as, for example, a library from which one with properties that suit the purpose can be selected to incorporate into a ligand-binding moiety or molecule. Specifically, in order to cleave the ligand-binding moiety/molecule selectively by a protease localized in the lesion, the substrates can be evaluated for sensitivity to that protease. When a ligand-binding moiety/molecule connected with a ligand moiety/molecule is administered in vivo, the molecule may come in contact with various proteases before reaching the lesion. Therefore, the molecule should preferably have sensitivity to the protease localized to the lesion and also as high resistance as possible to the other proteases. In order to select a desired protease cleavage sequence depending on the purpose, each protease substrate can be analyzed in advance for sensitivity to various proteases exhaustively to find its protease resistance. Based on the obtained protease resistance spectra, it is possible to find a protease cleavage sequence with necessary sensitivity and resistance.

Alternatively, a ligand-binding molecule into which a protease cleavage sequence has been incorporated undergoes not only enzymatic actions by proteases but also various environmental stresses such as pH changes, temperature, and oxidative/reductive stress, before reaching the lesion. Resistance to these external factors can also be compared among the protease substrates, and this comparative information can be used to select a protease cleavage sequence with desired properties depending on the purpose.

In one embodiment of the present invention, a flexible linker is further attached to one end or both ends of each protease cleavage site. The flexible linker attached to one end of the first protease cleavage site is referred to as "first flexible linker", and the flexible linker attached to the other end as "second flexible linker". When the fusion protein of the present invention contains two or more protease cleavage sites, similarly, the flexible linkers attached to the second protease cleavage site are referred to as "third flexible linker" and "fourth flexible linker, and the flexible linkers attached to the third protease cleavage site are referred to as "fifth flexible linker" and "sixth flexible linker, and so on. The descriptions below are provided to explain the first and second flexible linkers attached to the first protease cleavage site, but also similarly apply to the third and subsequent flexible linkers attached to the second and subsequent protease cleavage sites.

In a particular embodiment, the protease cleavage site and the flexible linker have any of the following formulas:

(protease cleavage site),
    (first flexible linker)-(protease cleavage site),
    (protease cleavage site)-(second flexible linker), and
    (first flexible linker)-(protease cleavage site)-(second flexible linker).

The flexible linker according to the present embodiment is preferably a peptide linker. The first flexible linker and the second flexible linker each independently and arbitrarily exist and are identical or different flexible linkers each containing at least one flexible amino acid (Gly, etc.). The flexible linker contains, for example, a sufficient number of residues (amino acids arbitrarily selected from Arg, Ile, Gln, Glu, Cys, Tyr, Trp, Thr, Val, His, Phe, Pro, Met, Lys, Gly, Ser, Asp, Asn, Ala, etc., particularly Gly, Ser, Asp, Asn, and Ala, in particular, Gly and Ser, especially Gly, etc.) for the protease cleavage sequence to obtain the desired protease accessibility.

The flexible linker suitable for use at both ends of the protease cleavage sequence is usually a flexible linker that improves the access of protease to the protease cleavage sequence and elevates the cleavage efficiency of the protease. A suitable flexible linker may be readily selected and can be preferably selected from among different lengths such as 1 amino acid (Gly, etc.) to 20 amino acids, 2 amino acids to 15 amino acids, or 3 amino acids to 12 amino acids including 4 amino acids to 10 amino acids, 5 amino acids to 9 amino acids, 6 amino acids to 8 amino acids, or 7 amino acids to 8 amino acids. In some embodiments of the present invention, the flexible linker is a peptide linker of 1 to 7 amino acids.

Examples of the flexible linker include, but are not limited to, glycine polymers (G)n, glycine-serine polymers (including e.g., (GS)n, (GSGGS: SEQ ID NO: 145)n and (GGGS: SEQ ID NO: 136)n, wherein n is an integer of at least 1), glycine-alanine polymers, alanine-serine polymers, and other flexible linkers well known in conventional techniques.

Among them, glycine and glycine-serine polymers are receiving attention because these amino acids are relatively unstructured and easily function as neutral tethers between components.

Examples of the flexible linker consisting of the glycine-serine polymer can include, but are not limited to,

```
Ser

Gly Ser (GS)

Ser Gly (SG)

Gly Ser (GGS)

Gly Ser Gly (GSG)

Ser Gly Gly (SGG)

Gly Ser Ser (GSS)

Ser Ser Gly (SSG)

Ser Gly Ser (SGS)

(GGGS, SEQ ID NO: 136)
Gly Gly Gly Ser (GGSG, SEQ ID NO: 137)
Gly Gly Ser Gly (GSGG, SEQ ID NO: 138)
Gly Ser Gly Gly (SGGG, SEQ ID NO: 139)
Ser Gly Gly Gly (GSSG, SEQ ID NO: 140)
Gly Ser Ser Gly (GGGGS, SEQ ID NO: 141)
Gly Gly Gly Gly Ser (GGGSG, SEQ ID NO: 142)
Gly Gly Gly Ser Gly (GGSGG, SEQ ID NO: 143)
Gly Gly Ser Gly Gly (GSGGG, SEQ ID NO: 144)
Gly Ser Gly Gly Gly (GSGGS, SEQ ID NO: 145)
Gly Ser Gly Gly Ser (SGGGG, SEQ ID NO: 146)
Ser Gly Gly Gly Gly
```

-continued

```
                              (GSSGG, SEQ ID NO: 147)
Gly Ser Ser Gly Gly (GSGSG, SEQ ID NO: 148)
Gly Ser Gly Ser Gly (SGGSG, SEQ ID NO: 149)
Ser Gly Gly Ser Gly (GSSSG, SEQ ID NO: 150)
Gly Ser Ser Ser Gly (GGGGGS, SEQ ID NO: 151)
Gly Gly Gly Gly Gly Ser (SGGGGG, SEQ ID NO: 152)
Ser Gly Gly Gly Gly Gly (GGGGGGS, SEQ ID NO: 153)
Gly Gly Gly Gly Gly Gly Ser (SGGGGGG, SEQ ID NO: 154)
Ser Gly Gly Gly Gly Gly Gly (Gly Gly Gly Gly Ser (GGGGS, SEQ ID NO: 141))n (Ser Gly Gly Gly Gly (SGGGG, SEQ ID NO: 146))n
``` wherein n is an integer of 1 or larger.

However, the length and sequence of the peptide linker can be appropriately selected by those skilled in the art according to the purpose.

In some embodiments of the present invention, the ligand binding moiety or molecule comprises an ligand-binding domain comprising antibody VH and antibody VL. Examples of the ligand binding moiety/molecule comprising VH and VL include, but are not limited to, Fv, scFv, Fab, Fab', Fab'-SH, F(ab')$_2$, and full-length antibodies.

In some embodiments of the present invention, the ligand binding moiety or molecule contains a Fc region. In the case of using an IgG antibody Fc region, its type is not limited, and, for example, IgG1, IgG2, IgG3, or IgG4 Fc region may be used. In the case of using an IgG antibody Fc region, its type is not limited, and, for example, IgG1, IgG2, or IgG4 Fc region may be used. For example, a Fc region containing one sequence selected from the amino acid sequences represented by SEQ ID NOs: 155, 156, 157, and 158, or a Fc region mutant prepared by adding an alteration to the Fc region may be used. In some embodiments of the present invention, the ligand binding moiety/molecule comprises an antibody constant region.

For instance, the heavy chain constant region of human IgG1, human IgG2, human IgG3, and human IgG4 are shown in SEQ ID NOs: 153 to 158, respectively. For instance, the Fc region of human IgG1, human IgG2, human IgG3, and human IgG4 are shown as a partial sequence of SEQ ID NOs: 153 to 158.

In some more specific embodiments of the present invention, the ligand binding moiety or molecule is an antibody. In the case of using an antibody as the ligand binding moiety/molecule, the binding to the ligand is achieved by a variable region. In some further specific embodiments, the ligand binding moiety/molecule is an IgG antibody. In the case of using an IgG antibody as the ligand binding moiety/molecule, its type is not limited, and IgG1, IgG2, IgG3, IgG4, or the like can be used. In the case of using an IgG antibody as the ligand binding moiety/molecule, its type is not limited, and IgG1, IgG2, IgG4, or the like can be used. In the case of using an IgG antibody as the ligand binding moiety/molecule, the binding to the ligand is also achieved by a variable region. One or both of the two variable regions of the IgG antibody can achieve the binding to the ligand. In the above-mentioned embodiments, the fusion protein of the present invention preferably comprises one ligand moiety (monovalent) or two ligand moieties (bivalent) which are connected with the C-terminal region of the antibody moiety via one or two peptide linkers. In some embodiments where the antibody is a bispecific antibody in which only one of the two variable regions binds to a ligand of interest, the fusion protein preferably comprises only one ligand moiety.

In some embodiments of the present invention, a domain having ligand binding activity is separated from the ligand binding moiety/molecule by the cleavage of the protease cleavage site or the protease cleavage sequence in the ligand binding moiety/molecule so that the binding to the ligand is attenuated. In an embodiment using an IgG antibody as the ligand binding moiety/molecule, for example, one of the variable regions of the antibody is provided with a protease cleavage site or a protease cleavage sequence so that the antibody cannot form the full-length antibody variable region in a cleaved state, and thereby the binding to the ligand is attenuated.

In the present specification, the "association" can refer to, for example, a state where two or more polypeptide regions interact with each other. In general, a hydrophobic bond, a hydrogen bond, an ionic bond, or the like is formed between the intended polypeptide regions to form an associate. As one example of common association, an antibody typified by a natural antibody is known to retain a paired structure of a heavy chain variable region (VH) and a light chain variable region (VL) through a noncovalent bond or the like therebetween.

In some embodiments of the present invention, VH and VL contained in the ligand binding domain associate with each other. The association between the antibody VH and the antibody VL may be canceled, for example, by the cleavage of the cleavage site or the protease cleavage sequence. The cancelation of the association can be used interchangeably with, for example, the whole or partial cancelation of the state where two or more polypeptide regions interact with each other. For the cancelation of the association between the VH and the VL, the interaction between the VH and the VL may be wholly canceled, or the interaction between the VH and the VL may be partially canceled.

The ligand binding domain in the present invention encompasses a ligand binding moiety or molecule in which the association between antibody VL or a portion thereof and antibody VH or a portion thereof is canceled by the cleavage of the protease cleavage site or canceled by the cleavage of the protease cleavage sequence.

In some embodiments of the present invention, the ligand binding moiety or molecule comprises a ligand binding domain comprising antibody VH and antibody VL, and the antibody VH and the antibody VL in the ligand binding moiety/molecule are associated with each other in a state where the protease cleavage site or the protease cleavage sequence of the ligand binding moiety/molecule is uncleaved, whereas the association between the antibody VH and the antibody VL in the ligand binding moiety/molecule is canceled by the cleavage of the cleavage site or the protease cleavage sequence. The cleavage site or the protease cleavage sequence in the ligand binding moiety/molecule may be placed at any position in the ligand binding moiety/molecule as long as the ligand binding of the ligand binding moiety/molecule can be attenuated by the cleavage of the cleavage site or the protease cleavage sequence.

In some embodiments of the present invention, the ligand binding moiety or molecule comprises a ligand-binding domain comprising antibody VH, antibody VL, and an antibody constant region.

As mentioned by Rothlisberger et al. (J Mol Biol. 2005 Apr. 8; 347 (4): 773-89), it is known that the VH and VL domains or the CH and CL domains of an antibody interact with each other via many amino acid side chains. VH-CH1 and VL-CL are known to be capable of forming a stable structure as a Fab domain. As previously reported, amino acid side chains generally interact between VH and VL with a dissociation constant in the range of $10^{-5}$ M to $10^{-8}$ M. When only VH and VL domains exist, only a small proportion may form an associated state.

In some embodiments of the present invention, the fusion protein is designed such that the protease cleavage site or protease cleavage sequence is provided in the ligand binding moiety or molecule comprising a ligand-binding domain comprising antibody VH and antibody VL, and whereas the two peptides in the Fab structure have entire heavy chain-light chain interaction with each other before cleavage, the cleavage of the protease cleavage site or protease cleavage sequence results in attenuation of the interaction between the peptide containing the VH (or a portion of the VH) and the peptide containing the VL (or a portion of the VL), eliminating the association between the VH and the VL.

In one embodiment of the present invention, the protease cleavage site or the protease cleavage sequence is located within the antibody constant region. In a more specific embodiment, the protease cleavage site or the protease cleavage sequence is located on the variable region side with respect to amino acid position 140 (EU numbering) in an antibody heavy chain constant region, preferably on the variable region side with respect to amino acid position 122 (EU numbering) in an antibody heavy chain constant region. In some specific embodiments, the cleavage site or the protease cleavage sequence is introduced at any position in a sequence from antibody heavy chain constant region amino acid position 118 (EU numbering) to antibody heavy chain constant region amino acid position 140 (EU numbering). In another more specific embodiment, the cleavage site or the protease cleavage sequence is located on the variable region side with respect to amino acid position 130 (EU numbering) (Kabat numbering position 130) in an antibody light chain constant region, preferably on the variable region side with respect to amino acid position 113 (EU numbering) (Kabat numbering position 113) in an antibody light chain constant region or on the variable region side with respect to amino acid position 112 (EU numbering) (Kabat numbering position 112) in an antibody light chain constant region. In some specific embodiments, the cleavage site or the protease cleavage sequence is introduced at any position in a sequence from antibody light chain constant region amino acid position 108 (EU numbering) (Kabat numbering position 108) to antibody light chain constant region amino acid position 131 (EU numbering) (Kabat numbering position 131).

In one embodiment of the present invention, the protease cleavage site or the protease cleavage sequence is located within the antibody VH or within the antibody VL. In a more specific embodiment, the cleavage site or the protease cleavage sequence is located on the antibody constant region side with respect to amino acid position 7 (Kabat numbering) of the antibody VH, preferably on the antibody constant region side with respect to amino acid position 40 (Kabat numbering) of the antibody VH, more preferably on the antibody constant region side with respect to amino acid position 101

(Kabat numbering) of the antibody VH, further preferably on the antibody constant region side with respect to amino acid position 109 (Kabat numbering) of the antibody VH or on the antibody constant region side with respect to amino acid position 111 (Kabat numbering) of the antibody VH. In a more specific embodiment, the cleavage site or the protease cleavage sequence is located on the antibody constant region side with respect to amino acid position 7 (Kabat numbering) of the antibody VL, preferably on the antibody constant region side with respect to amino acid position 39 (Kabat numbering) of the antibody VL, more preferably on the antibody constant region side with respect to amino acid position 96 (Kabat numbering) of the antibody VL, further preferably on the antibody constant region side with respect to amino acid position 104 (Kabat numbering) of the antibody VL or on the antibody constant region side with respect to amino acid position 105 (Kabat numbering) of the antibody VL.

In some more specific embodiments, the protease cleavage site or the protease cleavage sequence is introduced at a position of residues constituting a loop structure in the antibody VH or the antibody VL, and residues close to the loop structure. The loop structure in the antibody VH or the antibody VL refers to a moiety that does not form a secondary structure such as alpha-helix or beta-sheet, in the antibody VH or the antibody VL. Specifically, the position of the residues constituting the loop structure and the residues close to the loop structure can refer to the range of amino acid position 7 (Kabat numbering) to amino acid position 16 (Kabat numbering), amino acid position 40 (Kabat numbering) to amino acid position 47 (Kabat numbering), amino acid position 55 (Kabat numbering) to amino acid position 69 (Kabat numbering), amino acid position 73 (Kabat numbering) to amino acid position 79 (Kabat numbering), amino acid position 83 (Kabat numbering) to amino acid position 89 (Kabat numbering), amino acid position 95 (Kabat numbering) to amino acid position 99 (Kabat numbering), or amino acid position 101 (Kabat numbering) to amino acid position 113 (Kabat numbering) of the antibody VH, or amino acid position 7 (Kabat numbering) to amino acid position 19 (Kabat numbering), amino acid position 39 (Kabat numbering) to amino acid position 46 (Kabat numbering), amino acid position 49 (Kabat numbering) to amino acid position 62 (Kabat numbering), or amino acid position 96 (Kabat numbering) to amino acid position 107 (Kabat numbering) of the antibody VL.

In some more specific embodiments, the cleavage site or the protease cleavage sequence is introduced at any position in a sequence from amino acid position 7 (Kabat numbering) to amino acid position 16 (Kabat numbering), from amino acid position 40 (Kabat numbering) to amino acid position 47 (Kabat numbering), from amino acid position 55 (Kabat numbering) to amino acid position 69 (Kabat numbering), from amino acid position 73 (Kabat numbering) to amino acid position 79 (Kabat numbering), from amino acid position 83 (Kabat numbering) to amino acid position 89 (Kabat numbering), from amino acid position 95 (Kabat numbering) to amino acid position 99 (Kabat numbering), or from amino acid position 101 (Kabat numbering) to amino acid position 113 (Kabat numbering) of the antibody VH.

In some more specific embodiments, the cleavage site or the protease cleavage sequence is introduced at any position in a sequence from amino acid position 7 (Kabat numbering) to amino acid position 19 (Kabat numbering), from amino acid position 39 (Kabat numbering) to amino acid position 46 (Kabat numbering), from amino acid position 49 (Kabat numbering) to amino acid position 62 (Kabat numbering), or from amino acid position 96 (Kabat numbering) to amino acid position 107 (Kabat numbering) of the antibody VL.

In one embodiment of the present invention, the protease cleavage site or the protease cleavage sequence is located near the boundary between the antibody VH and the antibody constant region. The phrase "near the boundary between the antibody VH and the antibody heavy chain constant region" can refer to between amino acid position 101 (Kabat numbering) of the antibody VH and amino acid position 140 (EU numbering) of the antibody heavy chain constant region and can preferably refer to between amino acid position 109 (Kabat numbering) of the antibody VH and amino acid position 122 (EU numbering) of the antibody heavy chain constant region, or between amino acid position 111 (Kabat numbering) of the antibody VH and amino acid position 122 (EU numbering) of the antibody heavy chain constant region. When antibody VH is fused with an antibody light chain constant region, the phrase "near the boundary between the antibody VH and the antibody light chain constant region" can refer to between amino acid position 101 (Kabat numbering) of the antibody VH and amino acid position 130 (EU numbering) (Kabat numbering position 130) of the antibody light chain constant region and can preferably refer to between amino acid position 109 (Kabat numbering) of the antibody VH and amino acid position 113 (EU numbering) (Kabat numbering position 113) of the antibody light chain constant region, or between amino acid position 111 (Kabat numbering) of the antibody VH and amino acid position 112 (EU numbering) (Kabat numbering position 112) of the antibody light chain constant region.

In one embodiment, the cleavage site or the protease cleavage sequence is located near the boundary between the antibody VL and the antibody constant region. The phrase "near the boundary between the antibody VL and the antibody light chain constant region" can refer to between amino acid position 96 (Kabat numbering) of the antibody VL and amino acid position 130 (EU numbering) (Kabat numbering position 130) of the antibody light chain constant region and can preferably refer to between amino acid position 104 (Kabat numbering) of the antibody VL and amino acid position 113 (EU numbering) (Kabat numbering position 113) of the antibody light chain constant region, or between amino acid position 105 (Kabat numbering) of the antibody VL and amino acid position 112 (EU numbering) (Kabat numbering position 112) of the antibody light chain constant region. When antibody VL is fused with an antibody heavy chain constant region, the phrase "near the boundary between the antibody VL and the antibody heavy chain constant region" can refer to between amino acid position 96 (Kabat numbering) of the antibody VL and amino acid position 140 (EU numbering) of the antibody heavy chain constant region and can preferably refer to between amino acid position 104 (Kabat numbering) of the antibody VL and amino acid position 122 (EU numbering) of the antibody heavy chain constant region, or between amino acid position 105 (Kabat numbering) of the antibody VL and amino acid position 122 (EU numbering) of the antibody heavy chain constant region.

The ligand binding moiety/molecule can be provided with a protease cleavage site or protease cleavage sequence at a plurality of positions selected from, for example, within the antibody constant region, within the antibody VH, within the antibody VL, near the boundary between the antibody VH and the antibody constant region, and near the boundary between antibody VL and the antibody constant region. Those skilled in the art with reference to the present invention can change the form of a molecule comprising antibody VH, antibody VL, and an antibody constant region, for example, by swapping the antibody VH with the antibody VL. Such a molecular form is included in the scope of the present invention.

In the present specification, the term "ligand moiety" or "ligand molecule" refers to a moiety or molecule having biological activity. Herein, the "ligand moiety" and "ligand molecule" may be simply referred to as "ligand". The molecule having biological activity usually functions by interacting with a receptor on cell surface and thereby performing biological stimulation, inhibition, or modulation in other modes. These functions are usually thought to participate in the intracellular signaling pathways of cells carrying the receptor.

In the present specification, the ligand encompasses the desired molecule that exerts biological activity through interaction with a biomolecule. For example, the ligand not only means a molecule that interacts with a receptor but also includes a molecule that exerts biological activity through interaction with the molecule, for example, a receptor that interacts with the molecule, or a binding fragment thereof. For example, a ligand binding site of a protein known as a receptor, and a protein containing an interaction site of the receptor with another molecule are included in the ligand according to the present invention. Specifically, for example, a soluble receptor, a soluble fragment of a receptor, an extracellular domain of a transmembrane receptor, and polypeptides containing them are included in the ligand according to the present invention.

The ligand of the present invention can usually exert desirable biological activity by binding to one or more binding partners. The binding partner of the ligand can be an extracellular, intracellular, or transmembrane protein. In one embodiment, the binding partner of the ligand is an extracellular protein, for example, a soluble receptor. In another embodiment, the binding partner of the ligand is a membrane-bound receptor.

The ligand of the present invention can specifically bind to the binding partner with a dissociation constant (KD) of 10 micromolar (micro M), 1 micromolar, 100 nM, 50 nM, 10 nM, 5 nM, 1 nM, 500 pM, 400 pM, 350 pM, 300 pM, 250 pM, 200 pM, 150 pM, 100 pM, 50 pM, 25 pM, 10 pM, 5 pM, 1 pM, 0.5 pM, or 0.1 pM or less.

Examples of the molecule having biological activity include, but are not limited to, cytokines, chemokines, polypeptide hormones, growth factors, apoptosis inducing factors, PAMPs, DAMPs, nucleic acids, and fragments thereof. In a specific embodiment, an interleukin, an interferon, a hematopoietic factor, a member of the TNF superfamily, a chemokine, a cell growth factor, a member of the TGF-beta family, a myokine, an adipokine, or a neurotrophic factor can be used as the ligand. In a more specific embodiment, CXCL9, CXCL10, CXCL11, IL-2, IL-7, IL-12, IL-15, IL-18, IL-21, IL-22, IFN-alpha, IFN-beta, IFN-g, MIG, I-TAC, RANTES, MIP-1a, MIP-1b, IL-1R1 (Interleukin-1 receptor, type I), IL-1R2 (Interleukin-1 receptor, type II), IL-1RAcP (Interleukin-1 receptor accessory protein), or IL-1Ra (Protein Accession No. NP_776214, mRNA Accession No. NM_173842.2) can be used as the ligand. There is no limitations on the ligand used in the present disclosure. In some embodiments, the ligand may be a wild-type (or naturally-occurring) ligand or a mutant ligand with any mutation(s). In the case of IL-12 which is a heterodimeric cytokine, in some embodiments, the ligand, IL-12, may be wild-type (or naturally-occurring) IL-12 or a mutant IL-12 with any mutation(s). In some embodiments, IL-12 may be a single-chain IL-12 in which p35 and p40 are linked to be contained in a single chain.

In some embodiments of the present invention, the ligand is a cytokine.

Cytokines are a secreted cell signaling protein family involved in immunomodulatory and inflammatory processes. These cytokines are secreted by glial cells of the nervous system and by many cells of the immune system. The cytokines can be classified into proteins, peptides and glycoproteins and encompass large diverse regulator families. The cytokines can induce intracellular signal transduction through binding to their cell surface receptors, thereby causing the regulation of enzyme activity, upregulation or downregulation of some genes and transcriptional factors thereof, or feedback inhibition, etc.

In some embodiments, the cytokine of the present invention includes immunomodulatory factors such as interleukins (IL) and interferons (IFN). A suitable cytokine can contain a protein derived from one or more of the following types: four alpha-helix bundle families (which include the IL-2 subfamily, the IFN subfamily and IL-10 subfamily); the IL-1 family (which includes IL-1 and IL-8); and the IL-17 family. The cytokine can also include those classified into type 1 cytokines (e.g., IFN-gamma and TGF-beta) which enhance cellular immune response, or type 2 cytokines (e.g., IL-4, IL-10, and IL-13) which work advantageously for antibody reaction.

Interleukin 12 (IL-12) is a heterodimeric cytokine consisting of disulfide-linked glycosylated polypeptide chains of 30 and 40 kD. Cytokines are synthesized and then secreted by dendritic cells, monocytes, macrophages, B cells, Langerhans cells and keratinocytes, and antigen-presenting cells including natural killer (NK) cells. IL-12 mediates various biological processes and has been mentioned as a NK cell stimulatory factor (NKSF), a T cell stimulatory factor, a cytotoxic T lymphocyte maturation factor and an EBV-transformed B cell line factor.

Interleukin 12 can bind to an IL-12 receptor expressed on the cytoplasmic membranes of cells (e.g., T cells and NK cells) and thereby change (e.g., start or block) a biological process. For example, the binding of IL-12 to an IL-12 receptor stimulates the growth of preactivated T cells and NK cells, promotes the cytolytic activity of cytotoxic T cells (CTL), NK cells and LAK (lymphokine-activated killer) cells, induces the production of gamma interferon (IFN-gamma) by T cells and NK cells, and induces the differentiation of naive Th0 cells into Th1 cells producing IFN-gamma and IL-2. In particular, IL-12 is absolutely necessary for setting the production and cellular immune response (e.g., Th1 cell-mediated immune response) of cytolytic cells (e.g., NK and CTL). Thus, IL-12 is absolutely necessary for generating and regulating both protective immunity (e.g., eradication of infectious disease) and pathological immune response (e.g., autoimmunity).

Examples of the method for measuring the physiological activity of IL-12 include a method of measuring the cell growth activity of IL-12, STAT4 reporter assay, a method of measuring cell activation (cell surface marker expression, cytokine production, etc.) by IL-12, and a method of measuring the promotion of cell differentiation by IL-12.

Interleukin 22 (IL-22) is a member of the IL-10 family of cytokines. It is secreted by immune cells such as T-cells, NKT-cells, type 3 innate lymphoid cells (ILC3), and to a lesser extent by neutrophils and macrophages. IL-22 binds to its receptor IL-22R, which is a heterodimer composed of IL-22R1 and IL-10R2. IL22R is mainly expressed on nonhematopoetic cells such as epithelial cells and stromal cells. IL-22 activity is regulated by IL-22 binding protein (IL-22BP, also known as IL22RA2), which is a secreted protein with high structural homology to IL-22R1. IL-22BP binds to IL-22 with high affinity, blocking it from interacting with IL-22R1.

Binding of IL-22 to IL-22 receptor leads to activation of JAK1 and TYK2 kinases, which in turn leads to activation of STAT3 signaling. IL-22 plays an important role in epithelial cell function. For example, in the gut, IL-22 promotes the integrity of the intestinal barrier by stimulating proliferation of gut epithelial cells, mucus secretion and antimicrobial peptide secretion. In the liver, IL-22 acts as a survival factor for hepatocytes during liver injury, and also stimulates hepatocytes to proliferate for liver regeneration.

Examples of the method for measuring the physiological activity of IL-22 include a method of measuring the cell growth activity of IL-22, STAT3 reporter assay, and a method of measuring cell activation (cell surface marker expression, cytokine production, etc.) by IL-22.

Interleukin 2 (IL-2) is monomeric cytokine and mainly secreted by activated CD4 T and CD8 T cells. IL-2 binds to its receptor (IL-2R), which consists of 3 subunits, alpha, beta, and gamma. IL-2R beta and gamma are involved in signal transduction and IL-2R alpha and beta are involved in binding. All three subunits are important for high affinity cytokine-receptor complex. IL-2 is essential for both promoting and regulating immune responses since it binds and activates both effector T cells and regulatory T cells.

Examples of the method for measuring the physiological activity of IL-2 include a method of measuring the cell growth activity of IL-2, a method of measuring cell activation (cell surface marker expression, cytokine production, etc.) by IL-2, and a method of measuring the promotion of cell differentiation by IL-2.

In some embodiments of the present invention, the ligand is a chemokine. Chemokines generally act as chemoattractants that mobilize immune effector cells to chemokine expression sites. This is considered beneficial for expressing a particular chemokine gene, for example, together with a cytokine gene, for the purpose of mobilizing other immune system components to a treatment site. Such chemokines include CXCL10, RANTES, MCAF, MIP1-alpha, and MIP1-beta. Those skilled in the art should know that certain cytokines also have a chemoattractive effect and acknowledge that such cytokines can be classified by the term "chemokine".

Chemokines are a homogeneous serum protein family of 7 to 16 kDa originally characterized by their ability to induce leukocyte migration. Most of chemokines have four characteristic cysteines (Cys) and are classified into CXC or alpha, CC or beta, C or gamma and CX3C or delta chemokine classes according to motifs formed by the first two cysteines. Two disulfide bonds are formed between the first and third cysteines and between the second and fourth cysteines. In general, the disulfide bridges are considered necessary. Clark-Lewis and collaborators have reported that the disulfide bonds are crucial for the chemokine activity of at least CXCL10 (Clark-Lewis et al., J. Biol. Chem. 269: 16075-16081, 1994). The only one exception to having four cysteines is lymphotactin, which has only two cysteine residues. Thus, lymphotactin narrowly maintains its functional structure by only one disulfide bond.

Subfamilies of CXC or alpha are further classified, according to the presence of an ELR motif (Glu-Leu-Arg) preceding the first cysteine, into two groups: ELR-CXC chemokines and non-ELR-CXC chemokines (see e.g., Clark-Lewis, supra; and Belperio et al., "CXC Chemokines in Angiogenesis", J. Leukoc. Biol. 68: 1-8, 2000).

Interferon-inducible protein-10 (IP-10 or CXCL10) is induced by interferon-gamma and TNF-alpha and produced by keratinocytes, endothelial cells, fibroblasts and monocytes. IP-10 is considered to play a role in mobilizing activated T cells to an inflammatory site of a tissue (Dufour, et al., "IFN-gamma-inducible protein 10 (IP-10; CXCL10)-deficient mice reveal a role for IP-10 in effector T cell generation and trafficking", J Immunol., 168: 3195-204, 2002). Furthermore, there is a possibility that IP-10 plays a role in hypersensitive reaction. There is a possibility that IP-10 also plays a role in the occurrence of inflammatory demyelinating neuropathies (Kieseier, et al., "Chemokines and chemokine receptors in inflammatory demyelinating neuropathies: a central role for IP-10", Brain 125: 823-34, 2002).

Research indicates the possibility that IP-10 is useful in the engraftment of stem cells following transplantation (Nagasawa, T., Int. J. Hematol. 72: 408-11, 2000), the mobilization of stem cells (Gazitt, Y., J. Hematother Stem Cell Res 10: 229-36, 2001; and Hattori et al., Blood 97: 3354-59, 2001) and antitumor hyperimmunity (Nomura et al., Int. J. Cancer 91: 597-606, 2001; and Mach and Dranoff, Curr. Opin. Immunol. 12: 571-75, 2000). For example, previous reports known to those skilled in the art discuss the biological activity of chemokine (Bruce, L. et al., "Radio-labeled Chemokine binding assays", Methods in Molecular Biology (2000) vol. 138, pp. 129-134; Raphaele, B. et al., "Calcium Mobilization", Methods in Molecular Biology (2000) vol. 138, pp. 143-148; and Paul D. Ponath et al., "Transwell Chemotaxis", Methods in Molecular Biology (2000) vol. 138, pp. 113-120 Humana Press. Totowa, New Jersey).

Examples of the biological activity of CXCL10 include binding to a CXCL10 receptor (CXCR3), CXCL10-induced calcium flux, CXCL10-induced cell chemotaxis, binding of CXCL10 to glycosaminoglycan and CXCL10 oligomerization.

Examples of the method for measuring the physiological activity of CXCL10 include a method of measuring the cell chemotactic activity of CXCL10, reporter assay using a cell line stably expressing CXCR3 (see PLoS One. 2010 Sep. 13; 5 (9): e12700), and PathHunter™ beta-Arrestin recruitment assay using B-arrestin recruitment induced at the early stage of GPCR signal transduction.

Programmed death 1 (PD-1) protein is an inhibitory member of the CD28 family of receptors. The CD28 family also includes CD28, CTLA-4, ICOS and BTLA. PD-1 is expressed on activated B cells, T cells and bone marrow cells (Okazaki et al., (2002) Curr. Opin. Immunol. 14: 391779-82; and Bennett et al., (2003) J Immunol 170: 711-8). CD28 and ICOS, the initial members of the family, were discovered on the basis of functional influence on the elevation of T cell growth after monoclonal antibody addition (Hutloff et al., (1999) Nature 397: 263-266; and Hansen et al., (1980) Immunogenics 10: 247-260). PD-1 was discovered by screening for differential expression in apoptotic cells (Ishida et al., (1992) EMBO J 11: 3887-95). CTLA-4 and BTLA, the other members of the family, were discovered by screening for differential expression in cytotoxic T lymphocytes and TH1 cells, respectively. CD28, ICOS and CTLA-4 all have an unpaired cysteine residue which permits homodimerization. In contrast, PD-1 is considered to exist as a monomer and lacks the unpaired cysteine residue characteristic of other members of the CD28 family.

The PD-1 gene encodes a 55 kDa type I transmembrane protein which is part of the Ig superfamily PD-1 contains a membrane-proximal immunoreceptor tyrosine inhibitory motif (ITIM) and a membrane-distal tyrosine-based switch motif (ITSM). PD-1 is structurally similar to CTLA-4, but lacks a MYPPPY motif (SEQ ID NO: 159) important for B7-1 and B7-2 binding. Two ligands, PD-L1 and PD-L2, for PD-1 have been identified and have been shown to negatively regulate T-cell activation upon binding to PD-1 (Freeman et al., (2000) J Exp Med 192: 1027-34; Latchman et al., (2001) Nat Immunol 2: 261-8; and Carter et al., (2002) Eur J Immunol 32: 634-43). Both PD-L1 and PD-L2 are B7 homologs that bind to PD-1, but do not bind to the other members of the CD28 family PD-L1, one of the PD-1 ligands, is abundant in various human cancers (Dong et al., (2002) Nat. Med. 8: 787-9). The interaction between PD-1 and PD-L1 results in decrease in tumor-infiltrating lymphocytes, reduction in T cell receptor-mediated growth, and immune evasion by the cancerous cells (Dong et al., (2003) J. Mol. Med. 81: 281-7; Blank et al., (2005) Cancer Immunol. Immunother. 54: 307-314; and Konishi et al., (2004) Clin. Cancer Res. 10: 5094-100) Immunosuppression can be reversed by inhibiting the local interaction of PD-1 with PD-L1, and this effect is additive when the interaction of PD-2 with PD-L2 is also inhibited (Iwai et al., (2002) Proc. Natl. Acad. Sci. USA 99: 12293-7; and Brown et al., (2003) J. Immunol. 170: 1257-66).

PD-1 is an inhibitory member of the CD28 family expressed on activated B cells, T-cells, and bone marrow cells. Animals deficient in PD-1 develop various autoimmune phenotypes, including autoimmune cardiomyopathy and lupus-like syndrome with arthritis and nephritis (Nishimura et al., (1999) Immunity 11: 141-51; and Nishimura et al., (2001) Science 291: 319-22). PD-1 has been further found to play an important role in autoimmune encephalomyelitis, systemic lupus erythematosus, graft-versus-host disease (GVHD), type I diabetes mellitus, and rheumatoid arthritis (Salama et al., (2003) J Exp Med 198: 71-78; Prokunia and Alarcon-Riquelme (2004) Hum Mol Genet 13: R143; and Nielsen et al., (2004) Lupus 13: 510). In a mouse B cell tumor line, the ITSM of PD-1 has been shown to be essential for inhibiting BCR-mediated $Ca^{2+}$ flux and tyrosine phosphorylation of downstream effector molecules (Okazaki et al., (2001) PNAS 98: 13866-71).

In some embodiments of the present invention, a cytokine variant, a chemokine variant, or the like (e.g., Annu Rev Immunol. 2015; 33: 139-67) or a fusion protein containing the variants (e.g., Stem Cells Transl Med. 2015 January; 4 (1): 66-73) can be used as the ligand.

In some embodiments of the present invention, the ligand is selected from CXCL9, CXCL10, CXCL11, PD-1, IL-2, IL-12, IL-22, IL-6R, IL-1R1, IL-1R2, IL-1RAcP, and IL-1Ra. The CXCL10, PD-1, IL-2, IL-12, IL-22, IL-6R, IL-1R1, IL-1R2, IL-1RAcP, and IL-1Ra may have the same sequences as those of naturally occurring CXCL10, PD-1, IL-2, IL-12, IL-22, IL-6R, IL-1R1, IL-1R2, IL-1RAcP, and IL-1Ra, respectively, or may be a ligand variant that differs in sequence from naturally occurring CXCL9, CXCL10, CXCL11, PD-1, IL-2, IL-12, IL-22, IL-6R, IL-1R1, IL-1R2, IL-1RAcP, and IL-1Ra, but retains the physiological activity of the corresponding natural ligand. In order to obtain the ligand variant, an alteration may be artificially added to the ligand sequence for various purposes. Preferably, an alteration to resist protease cleavage (protease resistance alteration) is added thereto to obtain a ligand variant.

In some embodiments of the present invention, the biological activity of the ligand moiety or molecule is inhibited by binding to the ligand binding domain of the uncleaved ligand binding moiety or molecule. Examples of the embodiments in which the biological activity of the ligand is inhibited include, but are not limited to, embodiments in which the binding of the ligand moiety/molecule to the ligand binding domain of the uncleaved ligand binding moiety/molecule substantially or significantly interferes or competes with the binding of the ligand to its binding partner. In the case of using an antibody or a fragment thereof having ligand neutralizing activity as the ligand binding moiety/molecule, the ligand binding moiety/molecule bound with the ligand is capable of inhibiting the biological activity of the ligand by exerting its neutralizing activity.

In one embodiment of the present invention, preferably, the uncleaved ligand binding moiety or molecule can sufficiently neutralize the biological activity of the ligand moiety or molecule by binding to the ligand moiety/molecule. Specifically, the biological activity of the ligand moiety/molecule bound with the uncleaved ligand binding moiety/molecule is preferably lower than that of the ligand moiety/molecule unbound with the uncleaved ligand binding moiety/molecule. The biological activity of the ligand bound with the uncleaved ligand binding molecule can be, for example, 90% or less, preferably 80% or less, 70% or less, 60% or less, 50% or less, 40% or less, or 30% or less, particularly preferably 20% or less, 10% or less, 9% or less, 8% or less, 7% or less, 6% or less, 5% or less, 4% or less, 3% or less, 2% or less, or 1% or less, of the biological activity of the ligand unbound with the uncleaved ligand binding molecule, though not limited thereto. The administration of the ligand binding molecule, which sufficiently neutralizes the biological activity of the ligand, can be expected to prevent the ligand from exerting its biological activity before arriving at a target tissue.

Alternatively, the present invention provides methods for neutralizing the biological activity of a ligand. The methods of the present invention comprise the steps of contacting a ligand-binding molecule of the present invention with a ligand whose biological activity should be neutralized, and collecting the product of binding of the two molecules. Cleavage of the ligand-binding molecule in the collected binding product can restore the neutralized biological activity of the ligand. Thus, the methods for neutralizing the biological activity of a ligand according to the present invention may further comprise the step of restoring the biological activity of the ligand by cleaving the ligand-binding molecule in the binding product which consists of the ligand and the ligand-binding molecule (in other words, cancelling the neutralizing activity of the ligand-binding molecule).

In one embodiment of the present invention, the binding activity of the cleaved ligand binding moiety or molecule against the ligand moiety or molecule is preferably lower than that of an in vivo natural ligand binding partner (e.g., natural receptor for the ligand) against the ligand. The binding activity of the cleaved ligand binding moiety/molecule against the ligand moiety/molecule exhibits, for example, 90% or less, preferably 80% or less, 70% or less, 60% or less, 50% or less, 40% or less, or 30% or less, particularly preferably 20% or less, 10% or less, 9% or less, 8% or less, 7% or less, 6% or less, 5% or less, 4% or less, 3% or less, 2% or less, or 1% or less, of the amount of the ligand bound with the in vivo natural binding partner (per unit binding partner), though not limited thereto. The desired index may be appropriately used as an index for binding activity. For example, a dissociation constant (1(D) may be used. In the case of using a dissociation constant (KD) as an index for evaluating binding activity, a larger dissociation constant (KD) of the cleaved ligand binding moiety/molecule for the ligand than that of the in vivo natural binding partner for the ligand means that the cleaved ligand binding molecule has weaker binding activity against the ligand than that of the in vivo natural binding partner. The dissociation constant (KD) of the cleaved ligand binding molecule for the ligand is, for example, at least 1.1 times, preferably at least 1.5 times, at least 2 times, at least 5 times, or at least 10 times, particularly preferably at least 100 times the dissociation constant (KD) of the in vivo natural binding partner for the ligand. The ligand binding molecule having only low binding activity against the ligand or hardly having binding activity against the ligand after cleavage guarantees that the ligand is released by the cleavage of the ligand binding molecule, and can be expected to be prevented from binding to another ligand molecule again.

The ligand desirably restores the suppressed biological activity after cleavage of the ligand binding molecule. Desirably, the ligand binding of the cleaved ligand binding molecule is attenuated so that the ligand biological activity-inhibiting function of the ligand binding molecule is also attenuated. Those skilled in the art can confirm the biological activity of the ligand by a known method, for example, a method of detecting the binding of the ligand to its binding partner.

In some embodiments of the present invention, the uncleaved ligand binding molecule forms a complex with the ligand through antigen-antibody binding. In a more specific embodiment, the complex of the ligand binding molecule and the ligand is formed through a noncovalent bond, for example, antigen-antibody binding, between the ligand binding molecule and the ligand.

In the present invention, an uncleaved ligand binding molecule is fused with a ligand molecule to form a fusion protein. The ligand binding domain of the ligand binding moiety and the ligand moiety in the fusion protein further interact with each other through antigen-antibody binding. The ligand binding molecule and the ligand can be fused via a peptide linker. Even when the ligand binding molecule and the ligand in the fusion protein are fused via a peptide linker, the noncovalent bond still exists between the ligand binding domain of the ligand binding moiety and the ligand moiety. In other words, even in the embodiments in which the ligand binding molecule is fused with the ligand, the noncovalent bond between the ligand binding domain of the ligand binding moiety and the ligand moiety is similar to that in the case where the ligand binding molecule is not fused with the ligand. The noncovalent bond is attenuated by the cleavage of the ligand binding moiety/molecule. In short, the ligand binding of the ligand binding moiety/molecule is attenuated.

In the present invention, the ligand binding moiety or molecule and the ligand moiety or molecule are fused via a peptide linker. For example, an arbitrary peptide linker that can be introduced by genetic engineering, or a linker disclosed as a synthetic compound linker (see e.g., Protein Engineering, 9 (3), 299-305, 1996) can be used as the linker in the fusion of the ligand binding molecule with the ligand. The length of the peptide linker is not particularly limited and may be appropriately selected by those skilled in the art according to the purpose. Examples of the peptide linker can include, but are not limited to:

Ser

Gly Ser (GS)

Ser Gly (SG)

Gly Ser (GGS)

Gly Ser Gly (GSG)

Ser Gly Gly (SGG)

Gly Ser Ser (GSS)

Ser Ser Gly (SSG)

Ser Gly Ser (SGS)

Gly Gly Gly Ser (GGGS, SEQ ID NO: 136)

Gly Gly Ser Gly (GGSG, SEQ ID NO: 137)

Gly Ser Gly Gly (GSGG, SEQ ID NO: 138)

Ser Gly Gly Gly (SGGG, SEQ ID NO: 139)

Gly Ser Ser Gly (GSSG, SEQ ID NO: 140)

Gly Gly Gly Gly Ser (GGGGS, SEQ ID NO: 141)

Gly Gly Gly Ser Gly (GGGSG, SEQ ID NO: 142)

Gly Gly Ser Gly Gly (GGSGG, SEQ ID NO: 143)

Gly Ser Gly Gly Gly (GSGGG, SEQ ID NO: 144)

Gly Ser Gly Gly Ser (GSGGS, SEQ ID NO: 145)

Ser Gly Gly Gly Gly (SGGGG, SEQ ID NO: 146)

Gly Ser Ser Gly Gly (GSSGG, SEQ ID NO: 147)

Gly Ser Gly Ser Gly (GSGSG, SEQ ID NO: 148)

Ser Gly Gly Ser Gly (SGGSG, SEQ ID NO: 149)

Gly Ser Ser Ser Gly (GSSSG, SEQ ID NO: 150)

Gly Gly Gly Gly Gly Ser (GGGGGS, SEQ ID NO: 151)

Ser Gly Gly Gly Gly Gly (SGGGGG, SEQ ID NO: 152)

Gly Gly Gly Gly Gly Gly Ser (GGGGGGS, SEQ ID NO: 153)

Ser Gly Gly Gly Gly Gly Gly (SGGGGGG, SEQ ID NO: 154)

(Gly Gly Gly Gly Ser (GGGGS, SEQ ID NO: 141))n (Ser Gly Gly Gly Gly (SGGGG, SEQ ID NO: 146))n wherein n is an integer of 1 or larger.

However, the length and sequence of the peptide linker can be appropriately selected by those skilled in the art according to the purpose.

The synthetic compound linker (chemical cross-linking agent) is a cross-linking agent usually used in peptide cross-linking, for example, N-hydroxysuccinimide (NHS), disuccinimidyl suberate (DSS), bis(sulfosuccinimidyl) suberate (BS3), dithiobis(succinimidyl propionate) (DSP), dithiobis(sulfosuccinimidyl propionate) (DTSSP), ethylene glycol bis(succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-(succinimidoxycarbonyloxy)ethyl]sulfone (BSOCOES), or bis[2-(sulfosuccinimidoxycarbonyloxy)ethyl]sulfone (sulfo-BSOCOES). These cross-linking agents are commercially available.

In some embodiments of the present application, the ligand moiety comprises IL-12 and the ligand-binding moiety (or fusion protein) comprises antibody heavy and light chains selected from the group consisting of:

(a) a light chain comprising the amino acid sequence of SEQ ID NO: 874, and a heavy chain comprising the amino acid sequence of SEQ ID NO: 875;

(b) a light chain comprising the amino acid sequence of SEQ ID NO: 876, and a heavy chain comprising the amino acid sequence of SEQ ID NO: 880;

(c) a light chain comprising the amino acid sequence of SEQ ID NO: 876, and a heavy chain comprising the amino acid sequence of SEQ ID NO: 881;

(d) a light chain comprising the amino acid sequence of SEQ ID NO: 874, and a heavy chain comprising the amino acid sequence of SEQ ID NO: 884;

(e) a light chain comprising the amino acid sequence of SEQ ID NO: 876, and a heavy chain comprising the amino acid sequence of SEQ ID NO: 885;

(f) a light chain comprising the amino acid sequence of SEQ ID NO: 876, and a heavy chain comprising the amino acid sequence of SEQ ID NO: 886;

(g) a light chain comprising the amino acid sequence of SEQ ID NO: 887, and a heavy chain comprising the amino acid sequence of SEQ ID NO: 888;

(h) a light chain comprising the amino acid sequence of SEQ ID NO: 890, and a heavy chain comprising the amino acid sequence of SEQ ID NO: 891;

(i) a light chain comprising the amino acid sequence of SEQ ID NO: 876, and a heavy chain comprising the amino acid sequence of SEQ ID NO: 904;

(j) a light chain comprising the amino acid sequence of SEQ ID NO: 906, and a heavy chain comprising the amino acid sequence of SEQ ID NO: 907;

(k) a light chain comprising the amino acid sequence of SEQ ID NO: 876, and a heavy chain comprising the amino acid sequence of SEQ ID NO: 909; and (l) antibody heavy and light chains that compete with the antibody heavy chain and the antibody light chain described in (a) to (k).

In some embodiments of the present application, the ligand moiety comprises IL-12 and the ligand-binding moiety comprises an antibody variable region comprising any one of the combinations of H-chain CDR1, CDR2, and CDR3 and L-chain CDR1, CDR2, and CDR3 selected from (a) to (l) below, or any one of the combinations of H-chain CDR1, CDR2, and CDR3 and L-chain CDR1, CDR2, and CDR3 of antibody variable regions functionally equivalent thereto:

(a) H-chain CDR1, CDR2, and CDR3 comprised in the antibody variable region are identical to the amino acid sequences of the CDR1, CDR2, and CDR3 regions comprised in SEQ ID NO: 875; and L-chain CDR1, CDR2, and CDR3 comprised in the antibody variable region are identical to the amino acid sequences of the CDR1, CDR2, and CDR3 regions comprised in SEQ ID NO: 874;

(b) H-chain CDR1, CDR2, and CDR3 comprised in the antibody variable region are identical to the amino acid sequences of the CDR1, CDR2, and CDR3 regions comprised in SEQ ID NO: 880; and L-chain CDR1, CDR2, and CDR3 comprised in the antibody variable region are identical to the amino acid sequences of the CDR1, CDR2, and CDR3 regions comprised in SEQ ID NO: 876;

(c) H-chain CDR1, CDR2, and CDR3 comprised in the antibody variable region are identical to the amino acid sequences of the CDR1, CDR2, and CDR3 regions comprised in SEQ ID NO: 881; and L-chain CDR1, CDR2, and CDR3 comprised in the antibody variable region are identical to the amino acid sequences of the CDR1, CDR2, and CDR3 regions comprised in SEQ ID NO: 876;

(d) H-chain CDR1, CDR2, and CDR3 comprised in the antibody variable region are identical to the amino acid sequences of the CDR1, CDR2, and CDR3 regions comprised in SEQ ID NO: 884; and L-chain CDR1, CDR2, and CDR3 comprised in the antibody variable region are identical to the amino acid sequences of the CDR1, CDR2, and CDR3 regions comprised in SEQ ID NO: 874;

(e) H-chain CDR1, CDR2, and CDR3 comprised in the antibody variable region are identical to the amino acid sequences of the CDR1, CDR2, and CDR3 regions comprised in SEQ ID NO: 885; and L-chain CDR1, CDR2, and CDR3 comprised in the antibody variable region are identical to the amino acid sequences of the CDR1, CDR2, and CDR3 regions comprised in SEQ ID NO: 876;

(f) H-chain CDR1, CDR2, and CDR3 comprised in the antibody variable region are identical to the amino acid sequences of the CDR1, CDR2, and CDR3 regions comprised in SEQ ID NO: 886; and L-chain CDR1, CDR2, and CDR3 comprised in the antibody variable region are identical to the amino acid sequences of the CDR1, CDR2, and CDR3 regions comprised in SEQ ID NO: 876;

(g) H-chain CDR1, CDR2, and CDR3 comprised in the antibody variable region are identical to the amino acid sequences of the CDR1, CDR2, and CDR3 regions comprised in SEQ ID NO: 888; and L-chain CDR1, CDR2, and CDR3 comprised in the antibody variable region are identical to the amino acid sequences of the CDR1, CDR2, and CDR3 regions comprised in SEQ ID NO: 887;

(h) H-chain CDR1, CDR2, and CDR3 comprised in the antibody variable region are identical to the amino acid sequences of the CDR1, CDR2, and CDR3 regions comprised in SEQ ID NO: 891; and L-chain CDR1, CDR2, and CDR3 comprised in the antibody variable region are identical to the amino acid sequences of the CDR1, CDR2, and CDR3 regions comprised in SEQ ID NO: 890;

(i) H-chain CDR1, CDR2, and CDR3 comprised in the antibody variable region are identical to the amino acid sequences of the CDR1, CDR2, and CDR3 regions comprised in SEQ ID NO: 904; and L-chain CDR1, CDR2, and CDR3 comprised in the antibody variable region are identical to the amino acid sequences of the CDR1, CDR2, and CDR3 regions comprised in SEQ ID NO: 876;

(j) H-chain CDR1, CDR2, and CDR3 comprised in the antibody variable region are identical to the amino acid sequences of the CDR1, CDR2, and CDR3 regions comprised in SEQ ID NO: 907; and L-chain CDR1, CDR2, and CDR3 comprised in the antibody variable region are identical to the amino acid sequences of the CDR1, CDR2, and CDR3 regions comprised in SEQ ID NO: 906;

(k) H-chain CDR1, CDR2, and CDR3 comprised in the antibody variable region are identical to the amino acid sequences of the CDR1, CDR2, and CDR3 regions comprised in SEQ ID NO: 909; and L-chain CDR1, CDR2, and CDR3 comprised in the antibody variable region are identical to the amino acid sequences of the CDR1, CDR2, and CDR3 regions comprised in SEQ ID NO: 876; and (l) H-chain and L-chain CDR1, CDR2 and CDR3 comprised in antibody variable regions that compete with the antibody heavy chain variable region and the antibody light chain variable region described in (a) to (k).

In some embodiments of the present application, the ligand moiety comprises IL-12 and the ligand-binding moiety comprises any one of the combinations of heavy-chain variable region (VH) and light-chain variable region (VL) selected from (a) to (1) below:

(a) a VH comprised in SEQ ID NO: 875; and a VL comprised in SEQ ID NO: 874;

(b) a VH comprised in SEQ ID NO: 880; and a VL comprised in SEQ ID NO: 876;

(c) a VH comprised in SEQ ID NO: 881; and a VL comprised in SEQ ID NO: 876;

(d) a VH comprised in SEQ ID NO: 884; and a VL comprised in SEQ ID NO: 874;

(e) a VH comprised in SEQ ID NO: 885; and a VL comprised in SEQ ID NO: 876;

(f) a VH comprised in SEQ ID NO: 886; and a VL comprised in SEQ ID NO: 876;

(g) a VH comprised in SEQ ID NO: 888; and a VL comprised in SEQ ID NO: 887;

(h) a VH comprised in SEQ ID NO: 891; and a VL comprised in SEQ ID NO: 890;

(i) a VH comprised in SEQ ID NO: 904; and a VL comprised in SEQ ID NO: 876;

(j) a VH comprised in SEQ ID NO: 907; and a VL comprised in SEQ ID NO: 906;

(k) a VH comprised in SEQ ID NO: 909; and a VL comprised in SEQ ID NO: 876; and (l) a VH and a VL that compete with the VH and the VL described in (a) to (k).

In some embodiments, as shown in Tables 2 and 3 herein, the ligand moiety comprises IL-12, and the fusion protein comprises any one of the combinations selected from (a) to (d) below:

(a) a first light chain comprising the sequence of SEQ ID NO: 876, a first heavy chain comprising the sequence of SEQ ID NO: 881, a second light chain comprising the sequence of SEQ ID NO: 882, and a second heavy chain comprising the sequence of SEQ ID NO: 883;

(b) a first light chain comprising the sequence of SEQ ID NO: 876, a first heavy chain comprising the sequence of SEQ ID NO: 886, a second light chain comprising the sequence of SEQ ID NO: 882, and a second heavy chain comprising the sequence of SEQ ID NO: 883;

(c) a first light chain comprising the sequence of SEQ ID NO: 887, a first heavy chain comprising the sequence of SEQ ID NO: 888, a second light chain comprising the sequence of SEQ ID NO: 882, and a second heavy chain comprising the sequence of SEQ ID NO: 883; and (d) a first light chain comprising the sequence of SEQ ID NO: 890, a first heavy chain comprising the sequence of SEQ ID NO: 891, a second light chain comprising the sequence of SEQ ID NO: 882, and a second heavy chain comprising the sequence of SEQ ID NO: 883.

In some embodiments of the present application, the ligand moiety comprises IL-22 and the ligand-binding moiety (or fusion protein) comprises antibody heavy and light chains selected from the group consisting of:

(a) a light chain comprising the amino acid sequence of SEQ ID NO: 912, and a heavy chain comprising the amino acid sequence of SEQ ID NO: 913;

(b) a light chain comprising the amino acid sequence of SEQ ID NO: 915, and a heavy chain comprising the amino acid sequence of SEQ ID NO: 916; and (c) a light chain comprising the amino acid sequence of SEQ ID NO: 912, and a heavy chain comprising the amino acid sequence of SEQ ID NO: 929;

(d) a light chain comprising the amino acid sequence of SEQ ID NO: 912, and a heavy chain comprising the amino acid sequence of SEQ ID NO: 930; and (e) antibody heavy and light chains that compete with the antibody heavy chain and the antibody light chain described in (a) to (d).

In some embodiments of the present application, the ligand moiety comprises IL-22 and the ligand-binding moiety comprises an antibody variable region comprising any one of the combinations of H-chain CDR1, CDR2, and CDR3 and L-chain CDR1, CDR2, and CDR3 selected from (a) to (e) below, or any one of the combinations of H-chain CDR1, CDR2, and CDR3 and L-chain CDR1, CDR2, and CDR3 of antibody variable regions functionally equivalent thereto:

(a) H-chain CDR1, CDR2, and CDR3 comprised in the antibody variable region are identical to the amino acid sequences of the CDR1, CDR2, and CDR3 regions comprised in SEQ ID NO: 913; and L-chain CDR1, CDR2, and CDR3 comprised in the antibody variable region are identical to the amino acid sequences of the CDR1, CDR2, and CDR3 regions comprised in SEQ ID NO: 912;

(b) H-chain CDR1, CDR2, and CDR3 comprised in the antibody variable region are identical to the amino acid sequences of the CDR1, CDR2, and CDR3 regions comprised in SEQ ID NO: 916; and L-chain CDR1, CDR2, and CDR3 comprised in the antibody variable region are identical to the amino acid sequences of the CDR1, CDR2, and CDR3 regions comprised in SEQ ID NO: 915;

(c) H-chain CDR1, CDR2, and CDR3 comprised in the antibody variable region are identical to the amino acid sequences of the CDR1, CDR2, and CDR3 regions comprised in SEQ ID NO: 929; and L-chain CDR1, CDR2, and CDR3 comprised in the antibody variable region are identical to the amino acid sequences of the CDR1, CDR2, and CDR3 regions comprised in SEQ ID NO: 912;

(d) H-chain CDR1, CDR2, and CDR3 comprised in the antibody variable region are identical to the amino acid sequences of the CDR1, CDR2, and CDR3 regions comprised in SEQ ID NO: 930; and L-chain CDR1, CDR2, and CDR3 comprised in the antibody variable region are identical to the amino acid sequences of the CDR1, CDR2, and CDR3 regions comprised in SEQ ID NO: 912; and (e) H-chain and L-chain CDR1, CDR2 and CDR3 comprised in antibody variable regions that compete with the antibody heavy chain variable region and the antibody light chain variable region described in (a) to (d).

In some embodiments of the present application, the ligand moiety comprises IL-22 and the ligand-binding moiety comprises any one of the combinations of heavy-chain variable region (VH) and light-chain variable region (VL) selected from (a) to (e) below:

(a) a VH comprised in SEQ ID NO: 913; and a VL comprised in SEQ ID NO: 912;

(b) a VH comprised in SEQ ID NO: 916; and a VL comprised in SEQ ID NO: 915;

(c) a VH comprised in SEQ ID NO: 929; and a VL comprised in SEQ ID NO: 912;

(d) a VH comprised in SEQ ID NO: 930; and a VL comprised in SEQ ID NO: 912; and (e) a VH and a VL that compete with the VH and the VL described in (a) to (d).

In some embodiments of the present application, the ligand moiety comprises IL-2 and the ligand-binding moiety (or fusion protein) comprises antibody heavy and light chains selected from the group consisting of:

(a) a light chain comprising the amino acid sequence of SEQ ID NO: 920, and a heavy chain comprising the amino acid sequence of SEQ ID NO: 919;

(b) a light chain comprising the amino acid sequence of SEQ ID NO: 923, and a heavy chain comprising the amino acid sequence of SEQ ID NO: 922; and (c) antibody heavy and light chains that compete with the antibody heavy chain and the antibody light chain described in (a) to (b).

In some embodiments of the present application, the ligand moiety comprises IL-2 and the ligand-binding moiety comprises an antibody variable region comprising any one of the combinations of H-chain CDR1, CDR2, and CDR3 and L-chain CDR1, CDR2, and CDR3 selected from (a) to (c) below, or any one of the combinations of H-chain CDR1, CDR2, and CDR3 and L-chain CDR1, CDR2, and CDR3 of antibody variable regions functionally equivalent thereto:

(a) H-chain CDR1, CDR2, and CDR3 comprised in the antibody variable region are identical to the amino acid sequences of the CDR1, CDR2, and CDR3 regions comprised in SEQ ID NO: 919; and L-chain CDR1, CDR2, and CDR3 comprised in the antibody variable region are identical to the amino acid sequences of the CDR1, CDR2, and CDR3 regions comprised in SEQ ID NO: 920;

(b) H-chain CDR1, CDR2, and CDR3 comprised in the antibody variable region are identical to the amino acid sequences of the CDR1, CDR2, and CDR3 regions comprised in SEQ ID NO: 922; and L-chain CDR1, CDR2, and CDR3 comprised in the antibody variable region are identical to the amino acid sequences of the CDR1, CDR2, and CDR3 regions comprised in SEQ ID NO: 923; and (c) H-chain and L-chain CDR1, CDR2 and CDR3 comprised in antibody variable regions that compete with the antibody heavy chain variable region and the antibody light chain variable region described in (a) to (b).

In some embodiments of the present application, the ligand moiety comprises IL-2 and the ligand-binding moiety comprises any one of the combinations of heavy-chain variable region (VH) and light-chain variable region (VL) selected from (a) to (c) below:

(a) a VH comprised in SEQ ID NO: 919; and a VL comprised in SEQ ID NO: 920;

(b) a VH comprised in SEQ ID NO: 922; and a VL comprised in SEQ ID NO: 923; and (c) a VH and a VL that compete with the VH and the VL described in (a) to (b).

The present invention also relates to a pharmaceutical composition (drug) comprising the fusion protein of the present invention and a pharmaceutically acceptable carrier.

In certain embodiments, the pharmaceutical composition of the disclosure is cell growth-suppressing agent. In certain embodiments, the pharmaceutical composition of the disclosure is a pharmaceutical composition used for treatment and/or prevention of cancers or malignancies.

In certain embodiments, the pharmaceutical composition of the disclosure is a pharmaceutical composition used for treatment and/or prevention of inflammatory diseases. In certain embodiments, the pharmaceutical composition of the disclosure is a pharmaceutical composition used for treatment and/or prevention of gut or liver inflammatory diseases. In certain embodiments, the pharmaceutical composition of the disclosure is a pharmaceutical composition used for treatment and/or prevention of inflammatory bowel disease, alcoholic fatty liver disease, or non-alcoholic fatty liver disease. In certain embodiments, the pharmaceutical composition of the disclosure is a pharmaceutical composition used for treatment and/or prevention of Ulcerative Colitis or Crohn's Disease.

In certain embodiments, the pharmaceutical composition of the disclosure is a pharmaceutical composition used for treatment and/or prevention of autoimmune diseases. In certain embodiments, the pharmaceutical composition of the disclosure is a pharmaceutical composition used for treatment and/or prevention of rheumatoid arthritis, type 1 diabetes, and SLE.

The "treatment" (and its grammatically derived words, for example, "treat" and "treating") used in the present specification means clinical intervention that intends to alter the natural course of an individual to be treated and can be carried out both for prevention and during the course of a clinical pathological condition. The desirable effect of the treatment includes, but is not limited to, the prevention of the development or recurrence of a disease, the alleviation of symptoms, the attenuation of any direct or indirect pathological influence of the disease, the prevention of metastasis, reduction in the rate of progression of the disease, recovery from or alleviation of a disease condition, and ameliorated or improved prognosis. In some embodiments, the ligand binding molecule of the present invention can control the biological activity of the ligand and is used for delaying the onset of a disease or delaying the progression of the disease.

In the present invention, the pharmaceutical composition usually refers to a drug for the treatment or prevention of a disease or for examination or diagnosis.

In the present invention, the term "pharmaceutical composition comprising the fusion protein" may be used interchangeably with a "method for treating a disease, comprising administering the fusion protein to a subject to be treated" and may be used interchangeably with "use of the fusion protein for the production of a drug for the treatment of a disease". Also, the term "pharmaceutical composition comprising the fusion protein" may be used interchangeably with "use of the fusion protein for treating a disease".

In some embodiments of the present invention, the fusion protein of the present invention can be administered to an individual. The noncovalent bond still exists between the ligand binding domain of the ligand binding moiety and the ligand moiety. In the case of administering the fusion protein of the present invention to an individual, the fusion protein is transported in vivo. The ligand binding moiety in the fusion protein is cleaved in a target tissue so that the noncovalent bond of the ligand binding domain of the ligand binding molecule moiety to the ligand is attenuated to release the ligand and a portion of the ligand binding molecule from the fusion protein. The released ligand and the released portion of the ligand binding molecule can exert the biological activity of the ligand in the target tissue and treat a disease caused by the target tissue. In the embodiments in which the ligand binding moiety suppresses the biological activity of the ligand moiety when the ligand binding domain is bound with the ligand, and the ligand binding moiety is cleaved specifically in a target tissue, the ligand in the fusion protein does not exert biological activity during transport and exerts biological activity only when the fusion protein is cleaved in the target tissue. As a result, the disease can be treated with less systemic adverse reactions.

The pharmaceutical composition of the present invention can be formulated by use of a method known to those skilled in the art. For example, the pharmaceutical composition can be parenterally used in an injection form of a sterile solution or suspension with water or any of other pharmaceutically acceptable liquids. The pharmaceutical composition can be formulated, for example, by appropriately combining the polypeptide with a pharmacologically acceptable carrier or medium, specifically, sterile water or physiological saline, a plant oil, an emulsifier, a suspending agent, a surfactant, a stabilizer, a flavoring agent, an excipient, a vehicle, an antiseptic, a binder, etc. and mixing them into a unit dosage form required for generally accepted pharmaceutical practice. The amount of the active ingredient in these formulations is set so as to give an appropriate volume in a prescribed range.

A sterile composition for injection can be formulated according to usual pharmaceutical practice using a vehicle such as injectable distilled water. Examples of the injectable aqueous solution include isotonic solutions containing physiological saline, glucose, or other adjuvants (e.g., D-sorbitol, D-mannose, D-mannitol, and sodium chloride). The aqueous solution can be used in combination with an appropriate solubilizer, for example, an alcohol (ethanol, etc.), a polyalcohol (propylene glycol, polyethylene glycol, etc.), or a nonionic surfactant (Polysorbate 80™, HCO-50, etc.).

Examples of the oil solution include sesame oil and soybean oil. The oil solution can also be used in combination with benzyl benzoate and/or benzyl alcohol as a solubilizer. The oil solution can be supplemented with a buffer (e.g., a phosphate buffer solution and a sodium acetate buffer solution), a soothing agent (e.g., procaine hydrochloride), a stabilizer (e.g., benzyl alcohol and phenol), and an antioxidant. The prepared injection solution is usually filled into an appropriate ampule.

The pharmaceutical composition of the present invention is preferably administered through a parenteral route. For example, a composition having an injection, transnasal, transpulmonary, or percutaneous dosage form is administered. The pharmaceutical composition can be administered systemically or locally by, for example, intravenous injection, intramuscular injection, intraperitoneal injection, or subcutaneous injection.

The administration method can be appropriately selected according to the age and symptoms of a patient. The dose of the pharmaceutical composition containing the ligand binding molecule can be set to the range of, for example, 0.0001 mg to 1000 mg per kg body weight per dose. Alternatively, the dose of the pharmaceutical composition containing the polypeptide can be set to a dose of, for example, 0.001 to 100000 mg per patient. However, the present invention is not necessarily limited by these numerical values. Although the dose and the administration method vary depending on the body weight, age, symptoms, etc. of a patient, those skilled in the art can set an appropriate dose and administration method in consideration of these conditions.

The present invention also relates to a method for producing the fusion protein of the present invention. In one embodiment, the present invention provides a method for producing the fusion protein, comprising:

providing:
(a) an ligand-binding molecule comprising an ligand binding domain and at least one first protease cleavage site,
(b) at least one ligand molecule, and
(c) at least one peptide linker; and
connecting the at least one ligand molecule to a C-terminal region of the ligand-binding molecule via the at least one peptide linker.

Examples of the method for introducing a protease cleavage sequence into a molecule capable of binding to a ligand include a method of inserting the protease cleavage sequence into the amino acid sequence of a polypeptide capable of binding to the ligand, and a method of replacing a portion of the amino acid sequence of a polypeptide capable of binding to the ligand with the protease cleavage sequence.

To "insert" amino acid sequence A into amino acid sequence B refers to splitting amino acid sequence B into two parts without deletion, and linking the two parts with amino acid sequence A (that is, producing such an amino acid sequence as "first half of amino acid sequence B-amino acid sequence A-second half of amino acid sequence B"). To "introduce" amino acid sequence A into amino acid sequence B refers to splitting amino acid sequence B into two parts and linking the two parts with amino acid sequence A. This encompasses not only "inserting" amino acid sequence A into amino acid sequence B as mentioned above, but also linking the two parts with amino acid sequence A after deleting one or more amino acid residues of amino acid sequence B including those adjacent to amino acid sequence A (that is, replacing a portion of amino acid sequence B with amino acid sequence A).

Examples of the method for obtaining the molecule capable of binding to a ligand include a method of obtaining a ligand binding region having the ability to bind to the ligand. The ligand binding region is obtained by a method using, for example, an antibody preparation method known in the art.

The antibody obtained by the preparation method may be used directly in the fusion protein, or only a Fv region in the obtained antibody may be used. When the Fv region in a single-chain (also referred to as "sc") form is capable of recognizing the antigen, only the single chain may be used. Alternatively, a Fab region containing the Fv region may be used.

The specific antibody preparation method is well known to those skilled in the art. For example, monoclonal antibodies may be produced by a hybridoma method (Kohler and Milstein, Nature 256: 495 (1975)) or a recombination method (U.S. Pat. No. 4,816,567). Alternatively, the monoclonal antibodies may be isolated from phage-displayed antibody libraries (Clackson et al., Nature 352: 624-628 (1991); and Marks et al., J. Mol. Biol. 222: 581-597 (1991)). Also, the monoclonal antibodies may be isolated from single B cell clones (N. Biotechnol. 28 (5): 253-457 (2011)).

Humanized antibodies are also called reshaped human antibodies. Specifically, for example, a humanized antibody consisting of a non-human animal (e.g., mouse) antibody CDR-grafted human antibody is known in the art. General gene recombination approaches are also known for obtaining the humanized antibodies. Specifically, for example, overlap extension PCR is known in the art as a method for grafting mouse antibody CDRs to human FRs.

DNA encoding an antibody variable region containing three CDRs and four FRs linked and DNA encoding a human antibody constant region can be inserted into an expression vector such that these DNAs are fused in frame to prepare a vector for humanized antibody expression. The vector having the inserts is transfected into hosts to establish recombinant cells. Then, the recombinant cells are cultured for the expression of DNA encoding the humanized antibody to produce the humanized antibody into the cultures of the cultured cells (see European Patent Publication No. 239400 and International Publication No. WO1996/002576).

If necessary, FR amino acid residues may be substituted such that the CDRs of the reshaped human antibody form an appropriate antigen binding site. For example, a mutation can be introduced to the amino acid sequence of FR by the application of the PCR method used in the mouse CDR grafting to the human FRs.

The desired human antibody can be obtained by DNA immunization using transgenic animals having all repertoires of human antibody genes (see International Publication Nos. WO1993/012227, WO1992/003918, WO1994/002602, WO1994/025585, WO1996/034096, and WO1996/033735) as animals to be immunized In addition, a technique of obtaining human antibodies by panning using a human antibody library is also known. For example, a human antibody Fv region is expressed as a single-chain antibody (also referred to as "scFv") on the surface of phages by a phage display method. A phage expressing antigen binding scFv can be selected. The gene of the selected phage can be analyzed to determine a DNA sequence encoding the Fv region of the antigen binding human antibody. After the determination of the DNA sequence of the antigen binding scFv, the Fv region sequence can be fused in frame with the sequence of the desired human antibody C region and then inserted into an appropriate expression vector to prepare an expression vector. The expression vector is transfected into the preferred expression cells listed above for the expression of the gene encoding the human antibody to obtain the human antibody. These methods are already known in the art (see International Publication Nos. WO1992/001047, WO1992/020791, WO1993/006213, WO1993/011236, WO1993/019172, WO1995/001438, and WO1995/015388).

The molecule harboring the protease cleavage sequence in the molecule capable of binding to a ligand serves as the ligand binding moiety or molecule in the present invention. Whether the ligand binding moiety/molecule is cleaved by treatment with protease appropriate for the protease cleavage sequence can be optionally confirmed. The presence or absence of the cleavage of the protease cleavage sequence can be confirmed, for example, by contacting the protease with the molecule harboring the protease cleavage sequence in the molecule capable of binding to a ligand, and confirming the molecular weight of the protease treatment product by an electrophoresis method such as SDS-PAGE.

Furthermore, cleavage fragments after protease treatment can be separated by electrophoresis such as SDS-PAGE and quantified to evaluate the activity of the protease and the cleavage ratio of a molecule into which the protease cleavage sequence has been introduced. A non-limiting embodiment of the method of evaluating the cleavage ratio of a molecule into which a protease cleavage sequence has been introduced includes the following method: For example, when the cleavage ratio of an antibody variant into which a protease cleavage sequence has been introduced is evaluated using recombinant human u-Plasminogen Activator/Urokinase (human uPA, huPA) (R&D Systems; 1310-SE-010) or recombinant human Matriptase/ST14 Catalytic Domain (human MT-SP1, hMT-SP1) (R&D Systems; 3946-SE-010), 100 microgram/mL of the antibody variant is reacted with 40 nM huPA or 3 nM hMT-SP1 in PBS at 37 degrees C. for one hour, and then subjected to capillary electrophoresis immunoassay. Capillary electrophoresis immunoassay can be performed using Wes (Protein Simple), but the present method is not limited thereto. As an alternative to capillary electrophoresis immunoassay, SDS-PAGE and such may be performed for separation, followed by detection with Western blotting. The present method is not limited to these methods. Before and after cleavage, the light chain can be detected using anti-human lambda chain HRP-labeled antibody (abcam; ab9007), but any antibody that can detect cleavage fragments may be used. The area of each peak obtained after protease treatment is output using software for Wes (Compass for SW; Protein Simple), and the cleavage ratio (%) of the antibody variant can be determined with the following formula:

(Peak area of cleaved light chain)×100/(Peak area of cleaved light chain+Peak area of uncleaved light chain)

Cleavage ratios can be determined if protein fragments can be detected before and after protease treatment. Thus, cleavage ratios can be determined not only for antibody variants but also for various protein molecules into which a protease cleavage sequence has been introduced.

The in vivo cleavage ratio of a molecule into which a protease cleavage sequence has been introduced can be determined by administering the molecule into animals and detecting the administered molecule in blood samples. For example, an antibody variant into which a protease cleavage sequence has been introduced is administered to mice, and plasma is collected from their blood samples. The antibody is purified from the plasma by a method known to those skilled in the art using Dynabeads Protein A (Thermo; 10001D), and then subjected to capillary electrophoresis immunoassay to evaluate the protease cleavage ratio of the antibody variant. Capillary electrophoresis immunoassay can be performed using Wes (Protein Simple), but the present method is not limited thereto. As an alternative to capillary electrophoresis immunoassay, SDS-PAGE and such may be performed for separation, followed by detection with Western blotting. The present method is not limited to these methods. The light chain of the antibody variant collected from mice can be detected using anti-human lambda chain HRP-labeled antibody (abcam; ab9007), but any antibody that can detect cleavage fragments may be used. Once the area of each peak obtained by capillary electrophoresis immunoassay is output using software for Wes (Compass for SW; Protein Simple), the ratio of the remaining light chain can be calculated as [Peak area of light chain]/[Peak area of heavy chain] to determine the ratio of the full-length light chain that remain uncleaved in the mouse body. In vivo cleavage efficiencies can be determined if protein fragments collected from a living organism are detectable. Thus, cleavage ratios can be determined not only for antibody variants but also for various protein molecules into which a protease cleavage sequence has been introduced. Calculation of cleavage ratios by the above-mentioned methods enables, for example, comparison of the in vivo cleavage ratios of antibody variants into which different cleavage sequences have been introduced, and comparison of the cleavage ratio of a single antibody variant between different animal models such as a normal mouse model and a tumor-grafted mouse model.

The present invention also relates to a polynucleotide encoding the fusion protein of the present invention.

The polynucleotide according to the present invention is usually carried by (or inserted in) an appropriate vector and transfected into host cells. The vector is not particularly limited as long as the vector can stably retain an inserted nucleic acid. For example, when *E. coli* is used as the host, a pBluescript vector (manufactured by Stratagene Corp.) or the like is preferred as a vector for cloning. Various commercially available vectors can be used. In the case of using the vector for the purpose of producing the fusion protein of the present invention, an expression vector is particularly useful. The expression vector is not particularly limited as long as the vector permits expression of the fusion protein in vitro, in *E. coli*, in cultured cells, or in organism individuals. The expression vector is preferably, for example, a pBEST vector (manufactured by Promega Corp.) for in vitro expression, a pET vector (manufactured by Invitrogen Corp.) for *E. coli*, a pME18S-FL3 vector (GenBank Accession No. AB009864) for cultured cells, and a pME18S vector (Mol Cell Biol. 8: 466-472 (1988)) for organism individuals. The insertion of the DNA of the present invention into the vector can be performed by a routine method, for example, ligase reaction using restriction sites (Current protocols in Molecular Biology edit. Ausubel et al. (1987) Publish. John Wiley & Sons. Section 11.4-11.11).

The host cells are not particularly limited, and various host cells are used according to the purpose. Examples of the cells for expressing the fusion protein can include bacterial cells (e.g., *Streptococcus, Staphylococcus, E. coli, Streptomyces,* and *Bacillus subtilis*), fungal cells (e.g., yeasts and *Aspergillus*), insect cells (e.g., *Drosophila* S2 and *Spodoptera* SF9), animal cells (e.g., CHO, COS, HeLa, C127, 3T3, BHK, HEK293, and Bowes melanoma cells) and plant cells. The transfection of the vector to the host cells may be performed by a method known in the art, for example, a calcium phosphate precipitation method, an electroporation method (Current protocols in Molecular Biology edit. Ausubel et al., (1987) Publish. John Wiley & Sons. Section 9.1-9.9), a Lipofectamine method (manufactured by GIBCO-BRL/Thermo Fisher Scientific Inc.), or a microinjection method.

An appropriate secretory signal can be incorporated into the fusion protein of interest in order to secrete the fusion protein expressed in the host cells to the lumen of the endoplasmic reticulum, periplasmic space, or an extracellular environment. The signal may be endogenous to the fusion protein of interest or may be a foreign signal.

When the fusion protein of the present invention is secreted into a medium, the recovery of the fusion protein in the production method is performed by the recovery of the medium. When the fusion protein of the present invention is produced into cells, the cells are first lysed, followed by the recovery of the fusion protein.

A method known in the art including ammonium sulfate or ethanol precipitation, acid extraction, anion- or cation-exchange chromatography, phosphocellulose chromatography, hydrophobic interaction chromatography, affinity chromatography, hydroxyapatite chromatography, and lectin chromatography can be used for recovering and purifying the fusion protein of the present invention from the recombinant cell cultures.

It should be understood by those skilled in the art that arbitrary combinations of one or more embodiments described in the present specification are also included in the present invention unless there is technical contradiction on the basis of the technical common sense of those skilled in the art. Also, the present invention excluding arbitrary combinations of one or more embodiments described in the present specification is intended in the present specification and should be interpreted as the described invention, unless there is technical contradiction on the basis of the technical common sense of those skilled in the art.

EXAMPLES

Example 1. Preparation of IL-12 Fused Antibodies with Protease Cleavable Linkers IL-12 is pro-inflammatory cytokine that activates various cells such as T, NK, and B cells. IL-12 is known to show anti-tumor efficacy although its systemic exposure caused severe toxicity, hampering sufficient dosing to show efficacy. In order to overcome this limitation, IL-12 releasing antibodies that can release IL-12 only around tumor by exploiting tumor specific proteases have been developed.

1-1.Preparation of IL-12 Release Type

Various IL-12 release type antibodies were constructed by fusing IL-12 molecules, which is composed of p40 (SEQ ID NO: 871) and p35 (SEQ ID NO: 872), with anti-IL-12 antibodies through protease-cleavable linker (SEQ ID NO: 873) in a different manner. The anti-IL-12 antibody, Mab80 (WO2010017598) was employed. Unless otherwise noted, Fc region is a modified IgG1 Fc region which contains mutations (L235R/G236R in EU numbering) to abolish Fc gamma R binding.

F2 bivalent IL-12 release Mab80 is a homo-dimer of a pair of light chain (SEQ ID NO: 874) and heavy chain (SEQ ID NO: 875). In light chain p40 subunit was attached to N-terminal of Mab80VL-k0 (SEQ ID NO: 876) via cleavable linker (SEQ ID NO: 877). In heavy chain, cleavable linker (SEQ ID NO: 873) was introduced into elbow hinge region between Mab80VH (SEQ ID NO: 878) and CH1 domains. GS linker was inserted in hinge region and p35 subunit was attached to C-terminal of Fc domain via cleavable linker (SEQ ID NO: 879). Once these cleavable linkers were digested by proteases, active IL-12 molecules are released (FIG. 1A).

Figure 1B:
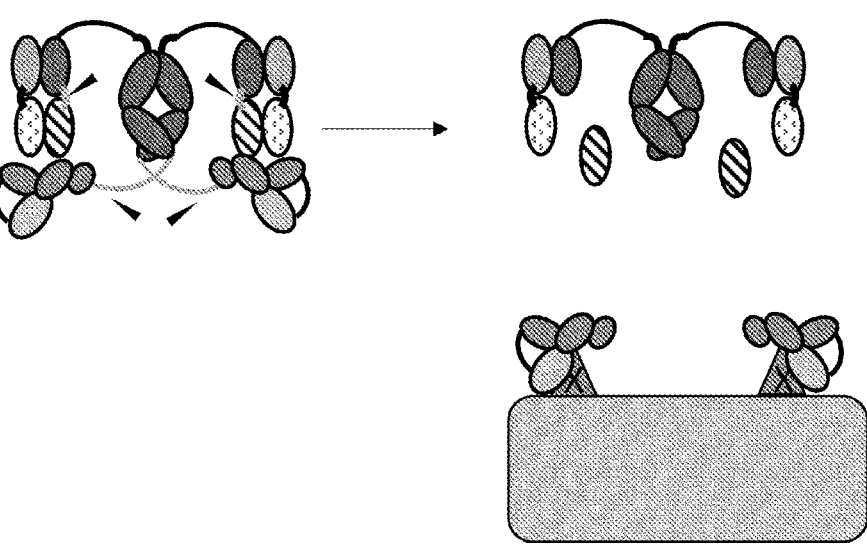
FIG. 1B is a diagram showing a fusion protein of an IgG antibody and IL-12 in which antibody and IL-12 molecules are fused via cleavable linkers. Cleavable linkers indicated by black triangles are cleaved by proteases and active free IL-12 molecules are released after cleavage.
Figure 1C:
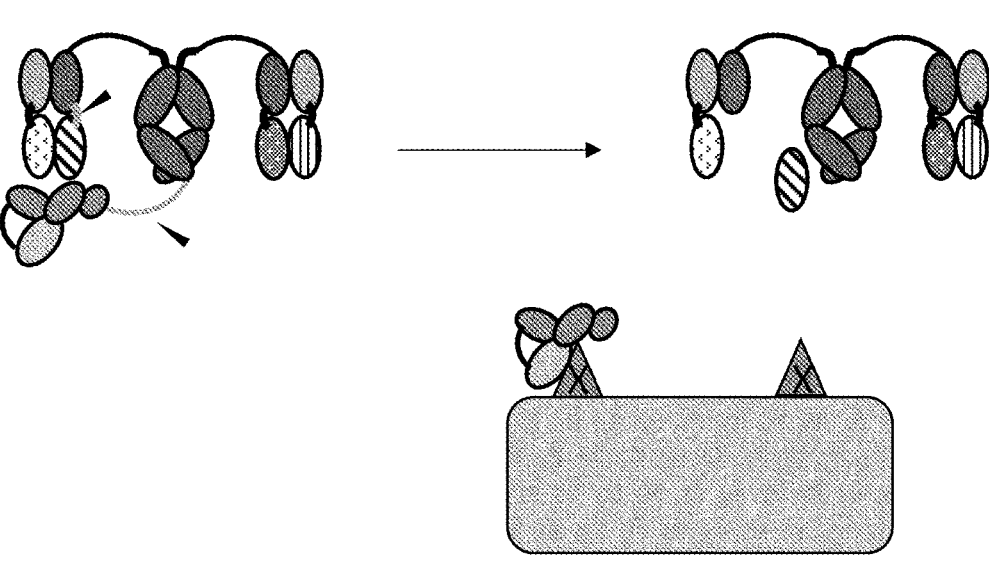
FIG. 1C is a diagram showing a fusion protein of an IgG antibody and IL-12 in which antibody and IL-12 molecules are fused via cleavable linkers. Cleavable linkers indicated by black triangles are cleaved by proteases and active free IL-12 molecules are released after cleavage.

F4 bivalent IL-12 release Mab80 (FIG. 1B) is a homo-dimer of a light chain (SEQ ID NO: 876) and heavy chain (SEQ ID NO: 880). Mab80VL-k0 (SEQ ID NO: 876) was employed as light chain without modification. In heavy chain, cleavable linker was introduced into elbow hinge region between Mab80VH (SEQ ID NO: 878) and CH1 domains. GS linker was inserted in hinge region and single-chain IL-12 was attached to C-terminal of Fc domain via cleavable linker (SEQ ID NO: 879). Once these cleavable linkers were digested by proteases, active IL-12 molecules are released (FIG. 1B)

F4 monovalent IL-12 release Mab80 (FIG. 1C) is a hetero-dimer of a pair of light chain 1 (SEQ ID NO:

876)/heavy chain 1(SEQ ID NO: 881) and light chain 2(SEQ ID NO: 882)/heavy chain 2(SEQ ID NO: 883). In heavy chain 1 (SEQ ID NO: 881), cleavable linker was introduced into elbow hinge region between Mab80VH (SEQ ID NO: 878) and CH1 domains. Anti-KLH antibody was used as variable regions in heavy chain 2 and light chain 2. In order to promote hetero-dimerization and precise association of heavy and light chains, knobs-into-holes mutations (Nat. Biotechnol, 1998, 16, 677-681) were introduced in heavy chain CH3 domains and CrossMab technology (PNAS, 2011, 108, 11187-11192) was employed in heavy chain 2 and light chain 2. Mab80VL-k0 (SEQ ID NO: 876) was employed as light chain 1 without modification. Heavy chain 1 and heavy chain 2 contain knob mutations (Y349C/T366W) and hole mutations (E356C/T366S/L368A/Y407V), respectively. Light chain 2 was composed of VH domain of anti-KLH with human kappa constant region. Heavy chain 2 was composed of VL domain of anti-KLH and modified IgG1 Fc region.

Expression vectors of each chain were prepared by a method known to those skilled in the art, and expressed using Expi293 (Life Technologies Corp.) by combining each chain as shown in Table 2. Purification of antibodies was done using affinity purification by MabSelect SuRe (Cat. No: 17-5438-01, GE Healthcare) followed by size exclusion chromatography using Superdex 200 gel filtration column (Cat. No: 28-9893-35, GE Healthcare). Any aggregates present in the elution from affinity chromatography were removed using size exclusion chromatography.

TABLE 2

| IL-12 releasing antibodies and sequence IDs of each chain. | | | | |
|---|---|---|---|---|
| IL-12 releasing antibodies | Light chain 1 | Heavy chain 1 | Light chain 2 | Heavy chain 2 |
| F2 bivalent IL-12 release Mab80 | SEQ ID NO: 874 | SEQ ID NO: 875 | None | None |
| F4 bivalent IL-12 release Mab80 | SEQ ID NO: 876 | SEQ ID NO: 880 | None | None |
| F4 monovalent IL-12 release Mab80 | SEQ ID NO: 876 | SEQ ID NO: 881 | SEQ ID NO: 882 | SEQ ID NO: 883 |

1-2. Preparation of IL-12 Fusion Type

IL-12 fusion type antibodies were constructed by fusing IL-12 molecules, which is composed of p40 (SEQ ID NO: 871) and p35 (SEQ ID NO: 872), with anti-IL-12 antibodies through GS linkers. As anti-IL-12 antibody, Mab80 (WO2010017598), Ustekinumab (WO2002012500) and J695 (WO2000056772) were employed. Unless otherwise noted, Fc region is a modified IgG1 Fc region which contains mutations (L235R/G236R in EU numbering) to abolish Fc gamma R binding.

Figure 2A:
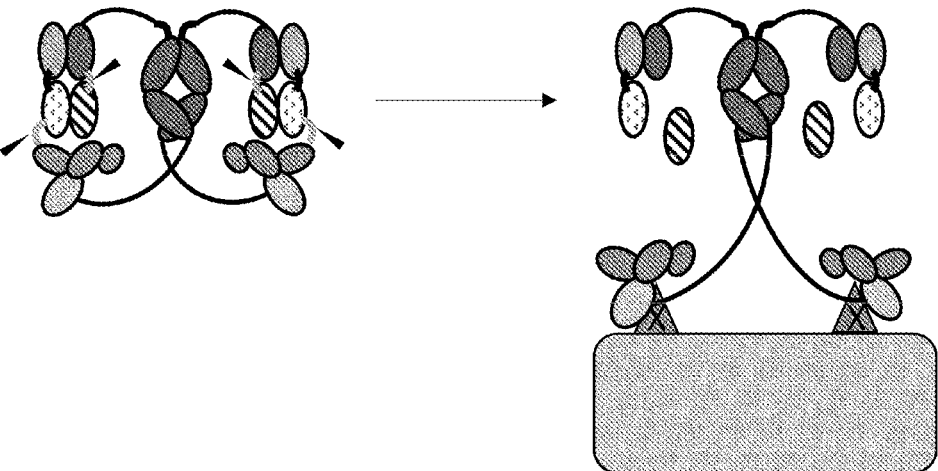
FIG. 2A is a diagram showing a fusion protein of an IgG antibody and IL-12 in which antibody Fc domain and IL-12 molecules are fused via non-cleavable linkers. Cleavable linkers indicated by black triangles are cleaved by proteases and active IL-12 molecules are released as antibody fusion after cleavage.

F2 bivalent IL-12 fusion Mab80 is a homo-dimer of a pair of light chain (SEQ ID NO: 874) and heavy chain (SEQ ID NO: 884). In light chain p40 subunit was attached to N-terminal of Mab80VL-k0 (SEQ ID NO: 876) via cleavable linker (SEQ ID NO: 877). In heavy chain, cleavable linker was introduced into elbow hinge region between Mab80VH (SEQ ID NO: 878) and CH1 domains. GS linker was inserted in hinge region and p35 subunit was attached to C-terminal of Fc domain via GS linker. Once these cleavable linkers were digested by proteases, active IL-12 molecules fused Fc are released (FIG. 2A).

Figure 2B:
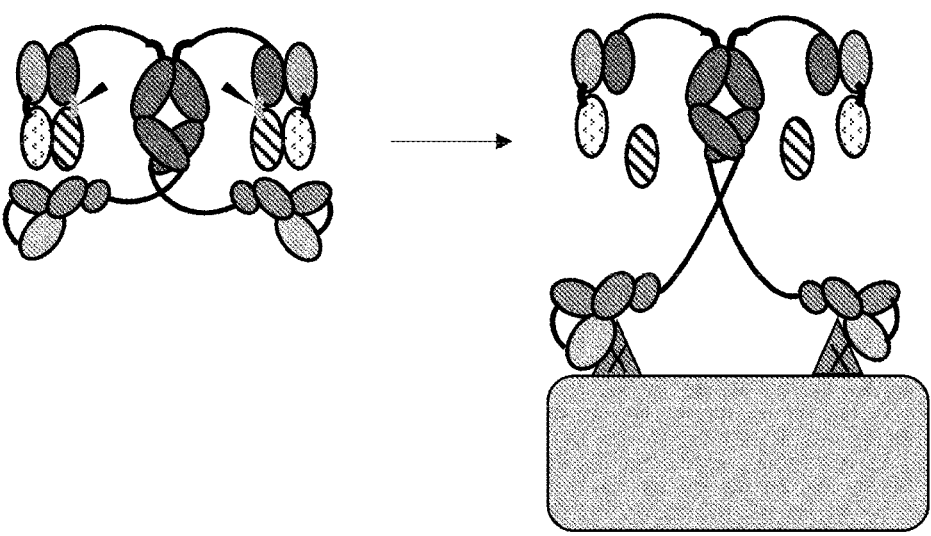
FIG. 2B is a diagram showing a fusion protein of an IgG antibody and IL-12 in which antibody Fc domain and IL-12 molecules are fused via non-cleavable linkers. Cleavable linkers indicated by black triangles are cleaved by proteases and active IL-12 molecules are released as antibody fusion after cleavage.
Figure 2C:
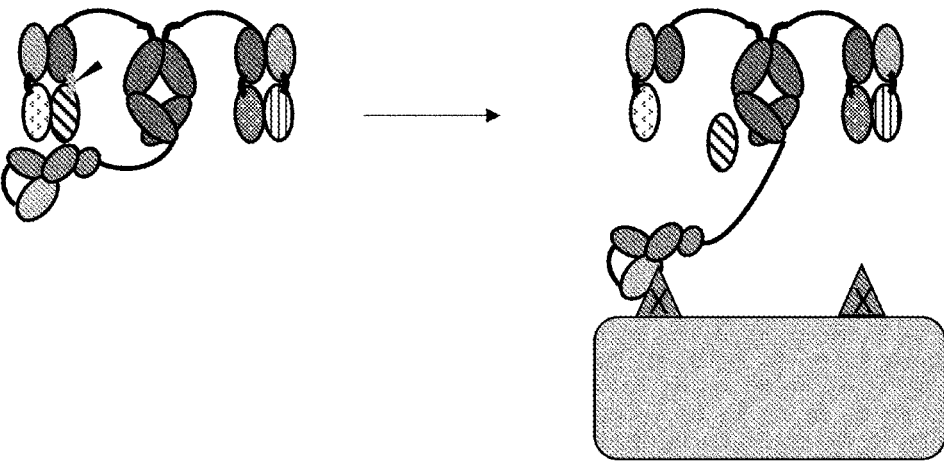
FIG. 2C is a diagram showing a fusion protein of an IgG antibody and IL-12 in which antibody Fc domain and IL-12 molecules are fused via non-cleavable linkers. Cleavable linkers indicated by black triangles are cleaved by proteases and active IL-12 molecules are released as antibody fusion after cleavage.
Figure 2D:
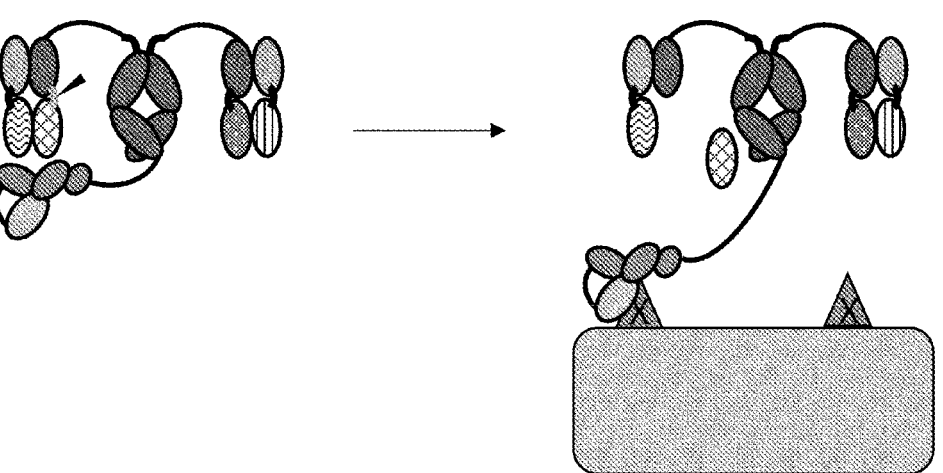
FIG. 2D is a diagram showing a fusion protein of an IgG antibody and IL-12 in which antibody Fc domain and IL-12 molecules are fused via non-cleavable linkers. Cleavable linkers indicated by black triangles are cleaved by proteases and active IL-12 molecules are released as antibody fusion after cleavage.
Figure 2E:
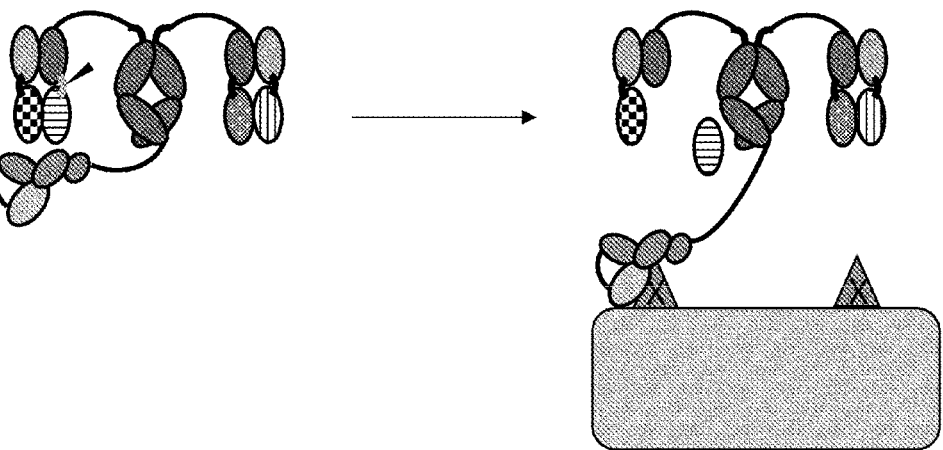
FIG. 2E is a diagram showing a fusion protein of an IgG antibody and IL-12 in which antibody Fc domain and IL-12 molecules are fused via non-cleavable linkers. Cleavable linkers indicated by black triangles are cleaved by proteases and active IL-12 molecules are released as antibody fusion after cleavage.

F4 bivalent IL-12 fusion Mab80 (FIG. 2B) is a homo-dimer of a light chain (SEQ ID NO: 876) and heavy chain (SEQ ID NO: 885). Mab80VL-k0 (SEQ ID NO: 876) was employed as light chain without modification. In heavy chain, cleavable linker was introduced into elbow hinge region between Mab80VH (SEQ ID NO: 878) and CH1 domains. GS linker was inserted in hinge region and single-chain IL-12 was attached to C-terminal of Fc domain via GS linker. Once these cleavable linkers were digested by proteases, active IL-12 molecules fused Fc are released (FIG. 2B).

F4 monovalent IL-12 fusion Mab80 (FIG. 2C) is a hetero-dimer of a pair of light chain 1 (SEQ ID NO: 876)/heavy chain 1(SEQ ID NO: 886) and light chain 2(SEQ ID NO: 882)/heavy chain 2(SEQ ID NO: 883). In heavy chain 1 (SEQ ID NO: 886), cleavable linker was introduced into elbow hinge region between Mab80VH (SEQ ID NO: 878) and CH1 domains. Anti-KLH antibody was used as variable regions in heavy chain 2 and light chain 2. In order to promote hetero-dimerization and precise association of heavy and light chains, knobs-into-holes mutations were introduced in heavy chain CH3 domains and CrossMab technology was employed in heavy chain 2 and light chain 2. Mab80VL-k0 (SEQ ID NO: 876) was employed as light chain 1 without modification.

Heavy chain 1 and heavy chain 2 contain knob mutations (Y349C/T366W) and hole mutations (E356C/T366S/L368A/Y407V), respectively. Light chain 2 was composed of VH domain of anti-KLH with human kappa constant region. Heavy chain 2 was composed of VL domain of anti-KLH and modified IgG1 Fc region.

F4 monovalent IL-12 fusion UstK (FIG. 2D) is a hetero-dimer of a pair of light chain 1 (SEQ ID NO: 887)/heavy chain 1 (SEQ ID NO: 888) and light chain 2 (SEQ ID NO: 882)/heavy chain 2 (SEQ ID NO: 883). In heavy chain 1 (SEQ ID NO: 888), cleavable linker was introduced into elbow hinge region between UstKVH (SEQ ID NO: 889) and CH1 domains. Anti-KLH antibody was used as variable regions in heavy chain 2 and light chain 2. In order to promote hetero-dimerization and precise association of heavy and light chains, knobs-into-holes mutations were introduced in heavy chain CH3 domains and CrossMab technology was employed in heavy chain 2 and light chain 2. UstkVL (SEQ ID NO: 887) was employed as light chain 1 without modification.

Heavy chain 1 and heavy chain 2 contain knob mutations (Y349C/T366W) and hole mutations (E356C/T366S/L368A/Y407V), respectively. Light chain 2 was composed of VH domain of anti-KLH with human kappa constant region. Heavy chain 2 was composed of VL domain of anti-KLH and modified IgG1 Fc region.

F4 monovalent IL-12 fusion J695 (FIG. 2E) is a hetero-dimer of a pair of light chain 1 (SEQ ID NO: 890)/heavy chain 1 (SEQ ID NO: 891) and light chain 2 (SEQ ID NO: 882)/heavy chain 2 (SEQ ID NO: 883). In heavy chain 1 (SEQ ID NO: 891), cleavable linker was introduced into elbow hinge region between J695VH (SEQ ID NO: 892) and CH1 domains. Anti-KLH antibody was used as variable regions in heavy chain 2 and light chain 2. In order to promote hetero-dimerization and precise association of heavy and light chains, knobs-into-holes mutations were introduced in heavy chain CH3 domains and CrossMab technology was employed in heavy chain 2 and light chain 2. J695VL (SEQ ID NO: 890) was employed as light chain 1 without modification.

Heavy chain 1 and heavy chain 2 contain knob mutations (Y349C/T366W) and hole mutations (E356C/T366S/

L368A/Y407V), respectively. Light chain 2 was composed of VH domain of anti-KLH with human kappa constant region. Heavy chain 2 was composed of VL domain of anti-KLH and modified IgG1 Fc region.

Expression vectors of each chain were prepared by a method known to those skilled in the art, and expressed using Expi293 (Life Technologies Corp.) by combining each chain as shown in Table 3. Purification of antibodies was done using affinity purification by MabSelect SuRe (Cat. No: 17-5438-01, GE Healthcare) followed by size exclusion chromatography using Superdex 200 gel filtration column (Cat. No: 28-9893-35, GE Healthcare). Any aggregates present in the elution from affinity chromatography were removed using size exclusion chromatography.

TABLE 3

IL-12 releasing antibodies with Fc fusion and sequence IDs of each chain.

| IL-12 fused antibodies | Light chain 1 | Heavy chain 1 | Light chain 2 | Heavy chain 2 |
|---|---|---|---|---|
| F2 bivalent IL-12 fusion Mab80 | SEQ ID NO: 874 | SEQ ID NO: 884 | | |
| F4 bivalent IL-12 fusion Mab80 | SEQ ID NO: 876 | SEQ ID NO: 885 | | |
| F4 monovalent IL-12 fusion Mab80 | SEQ ID NO: 876 | SEQ ID NO: 886 | SEQ ID NO: 882 | SEQ ID NO: 883 |
| F4 monovalent IL-12 fusion UstK | SEQ ID NO: 887 | SEQ ID NO: 888 | SEQ ID NO: 882 | SEQ ID NO: 883 |
| F4 monovalent IL-12 fusion J695 | SEQ ID NO: 890 | SEQ ID NO: 891 | SEQ ID NO: 882 | SEQ ID NO: 883 |

Figure 3A:
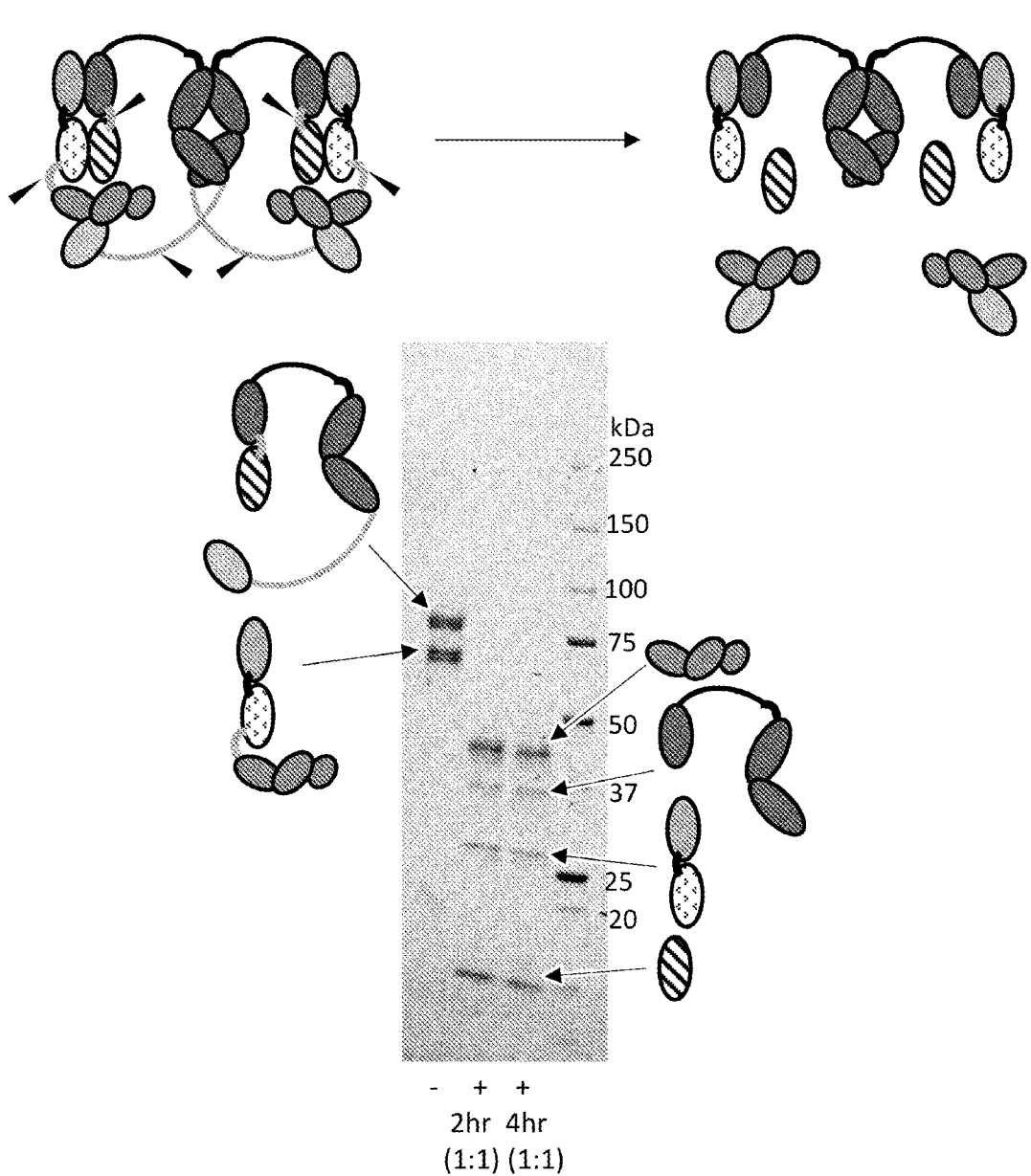
FIG. 3A shows the SDS-PAGE for cleaved products obtained after MTSP1 digestion of IL-12 release type molecules.
Figure 3B:
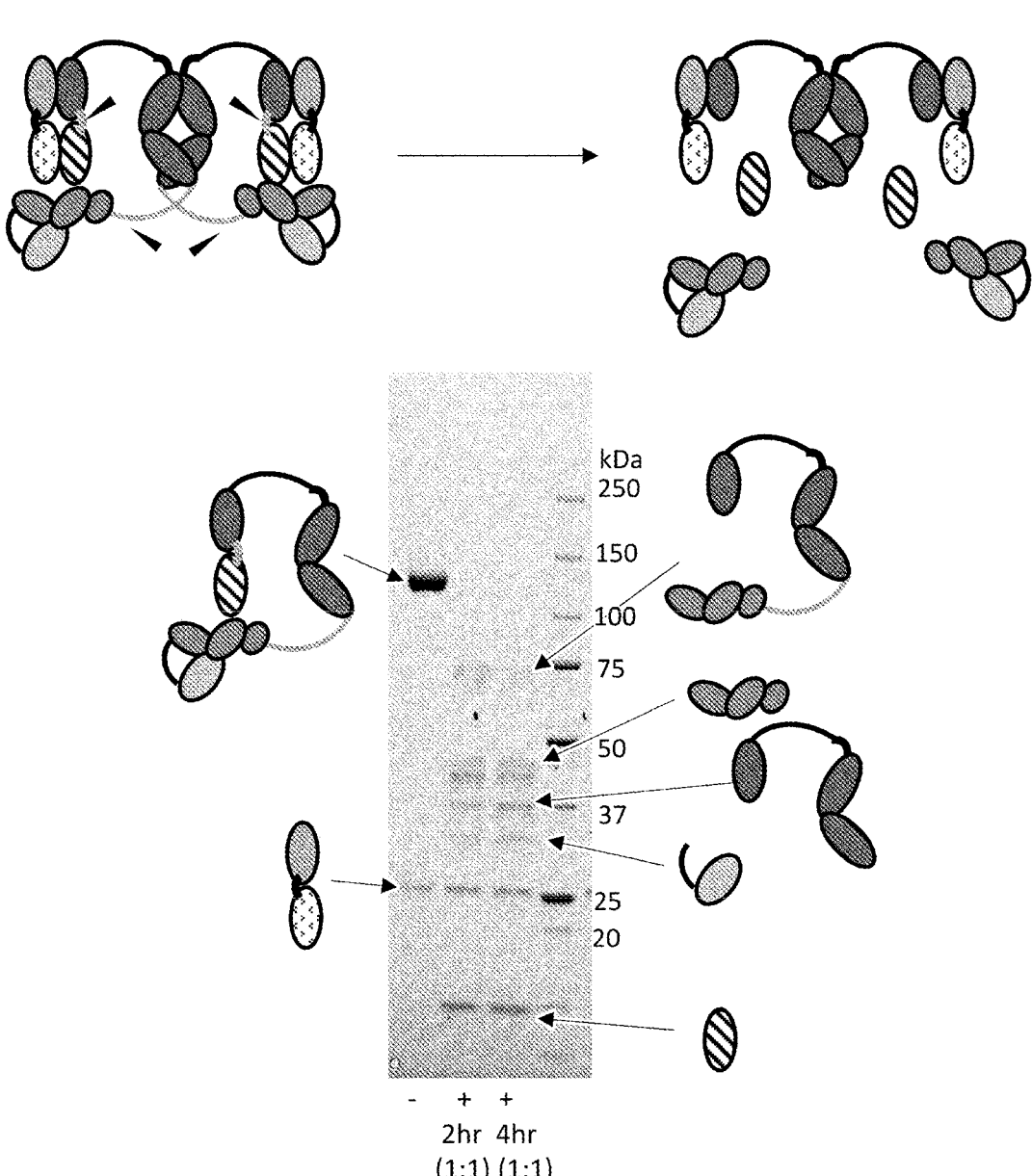
FIG. 3B shows the SDS-PAGE for cleaved products obtained after MTSP1 digestion of IL-12 release type molecules.
Figure 4A:
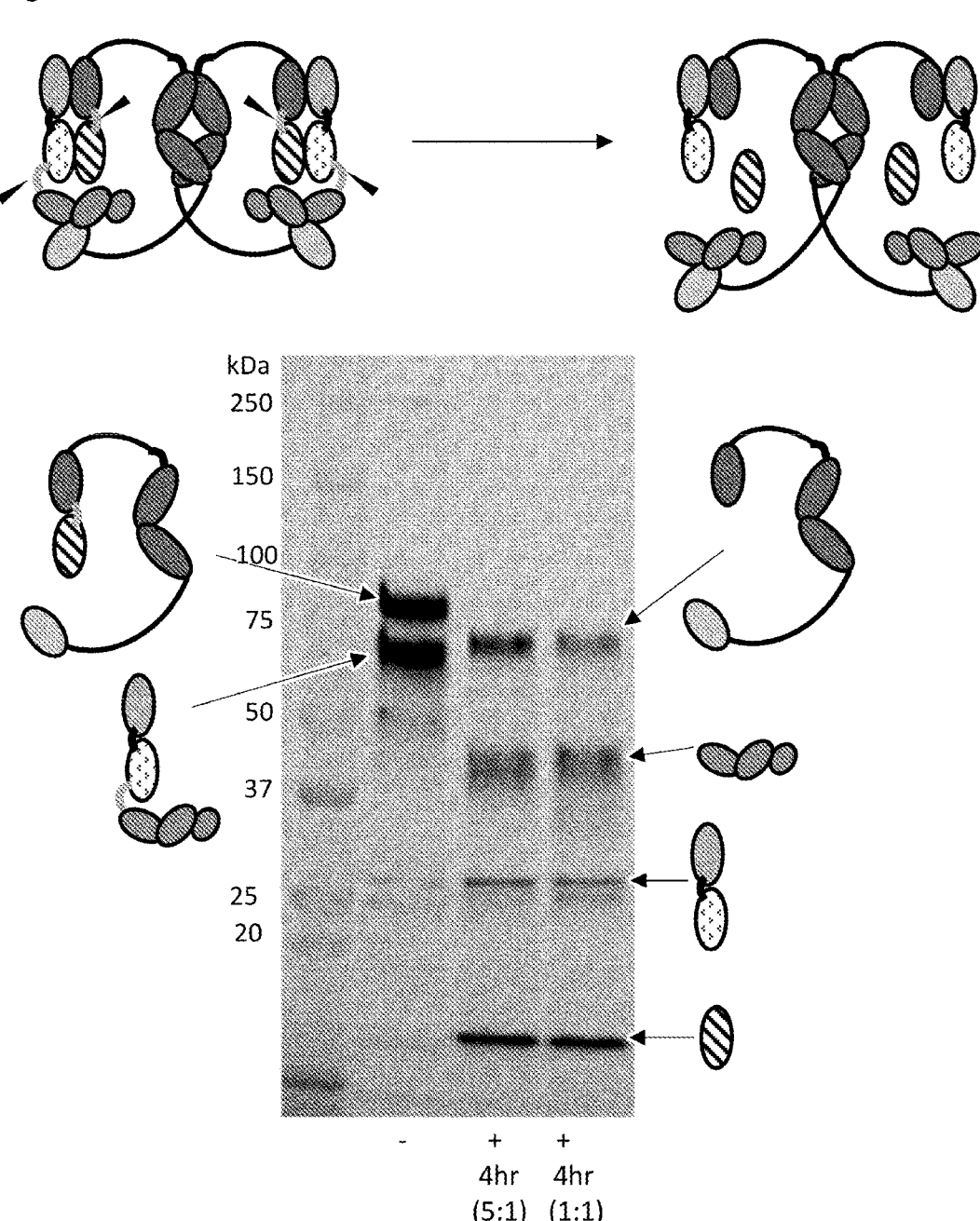
FIG. 4A shows the SDS-PAGE for cleaved products obtained after MTSP1 digestion of IL-12 fusion type molecules.
Figure 4B:
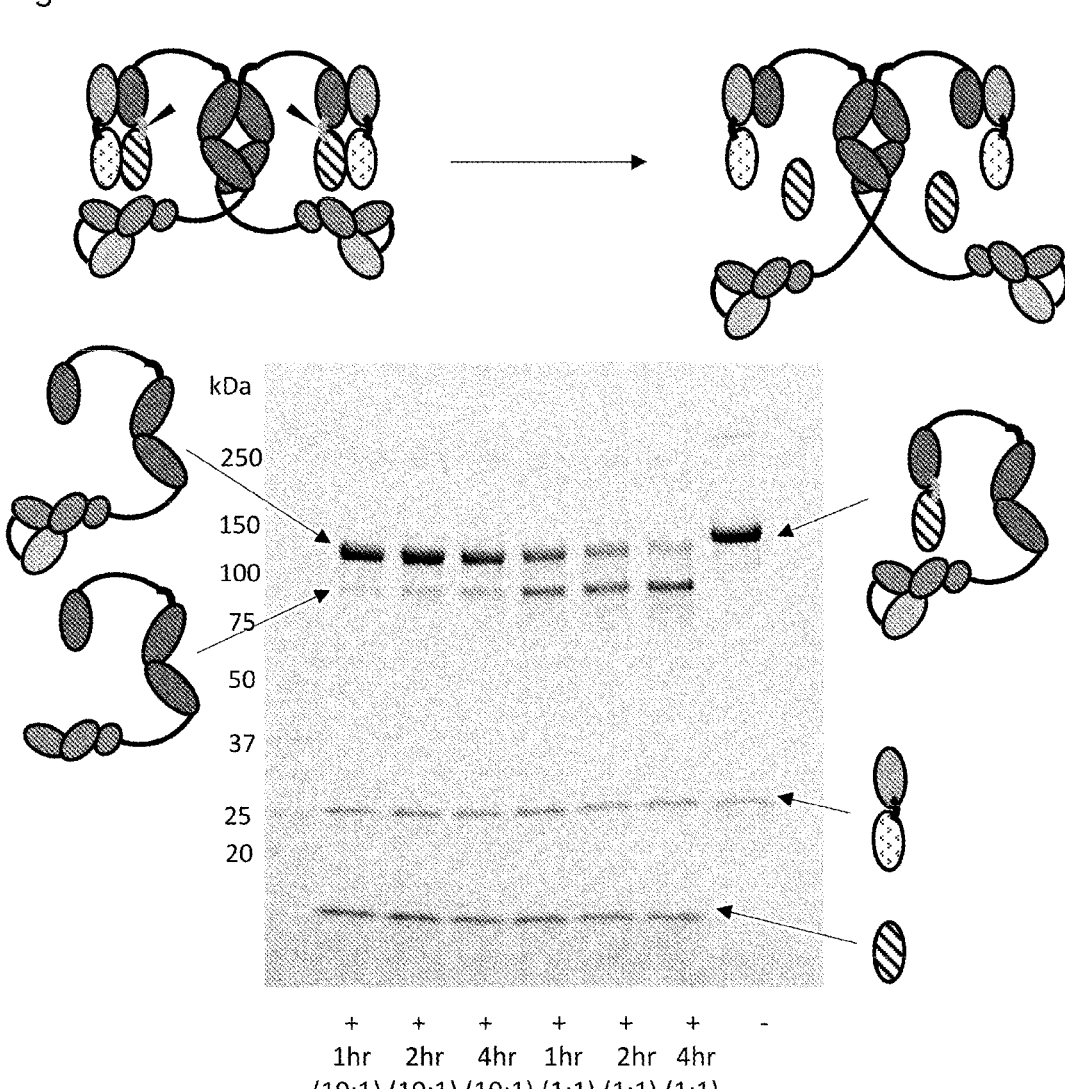
FIG. 4B shows the SDS-PAGE for cleaved products obtained after MTSP1 digestion of IL-12 fusion type molecules.
Figure 4C:
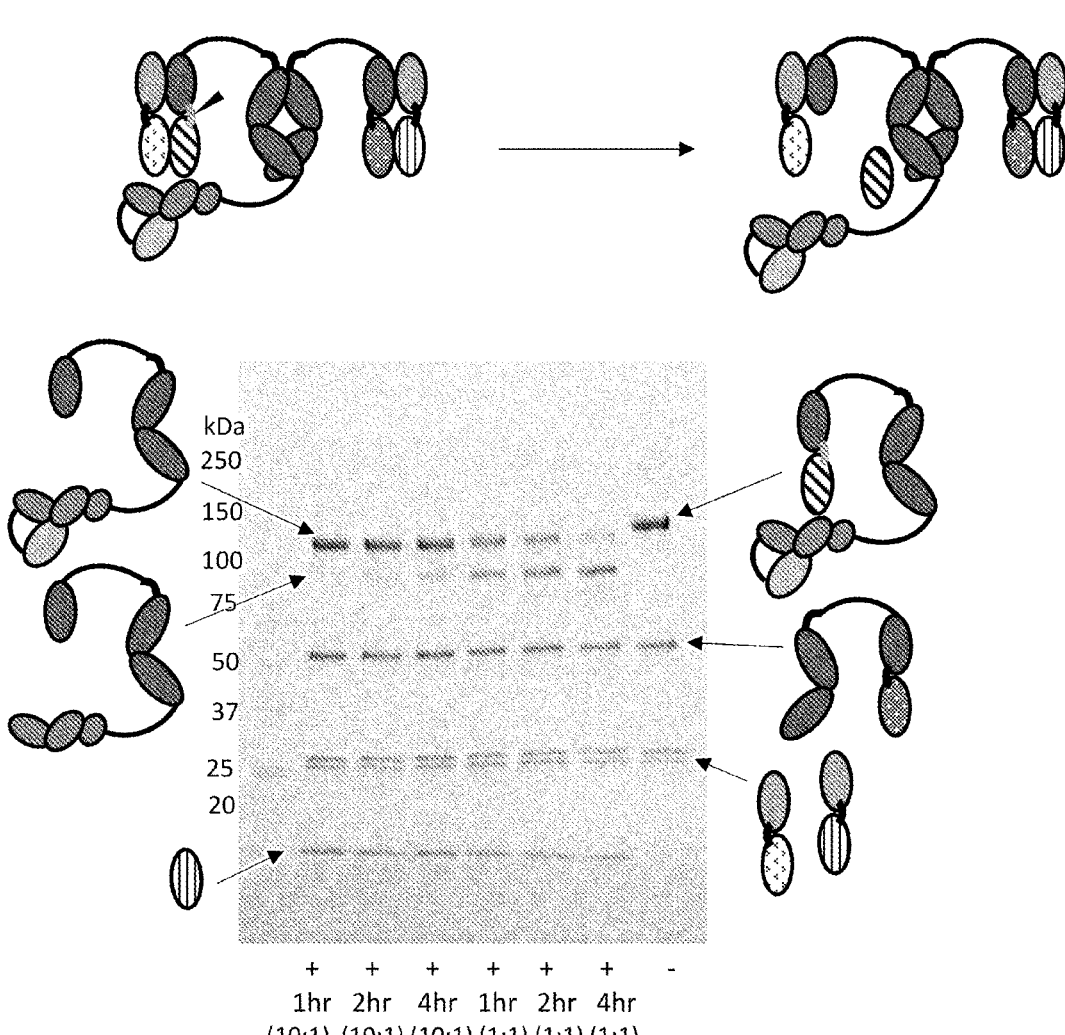
FIG. 4C shows the SDS-PAGE for cleaved products obtained after MTSP1 digestion of IL-12 fusion type molecules.
Figure 4D:
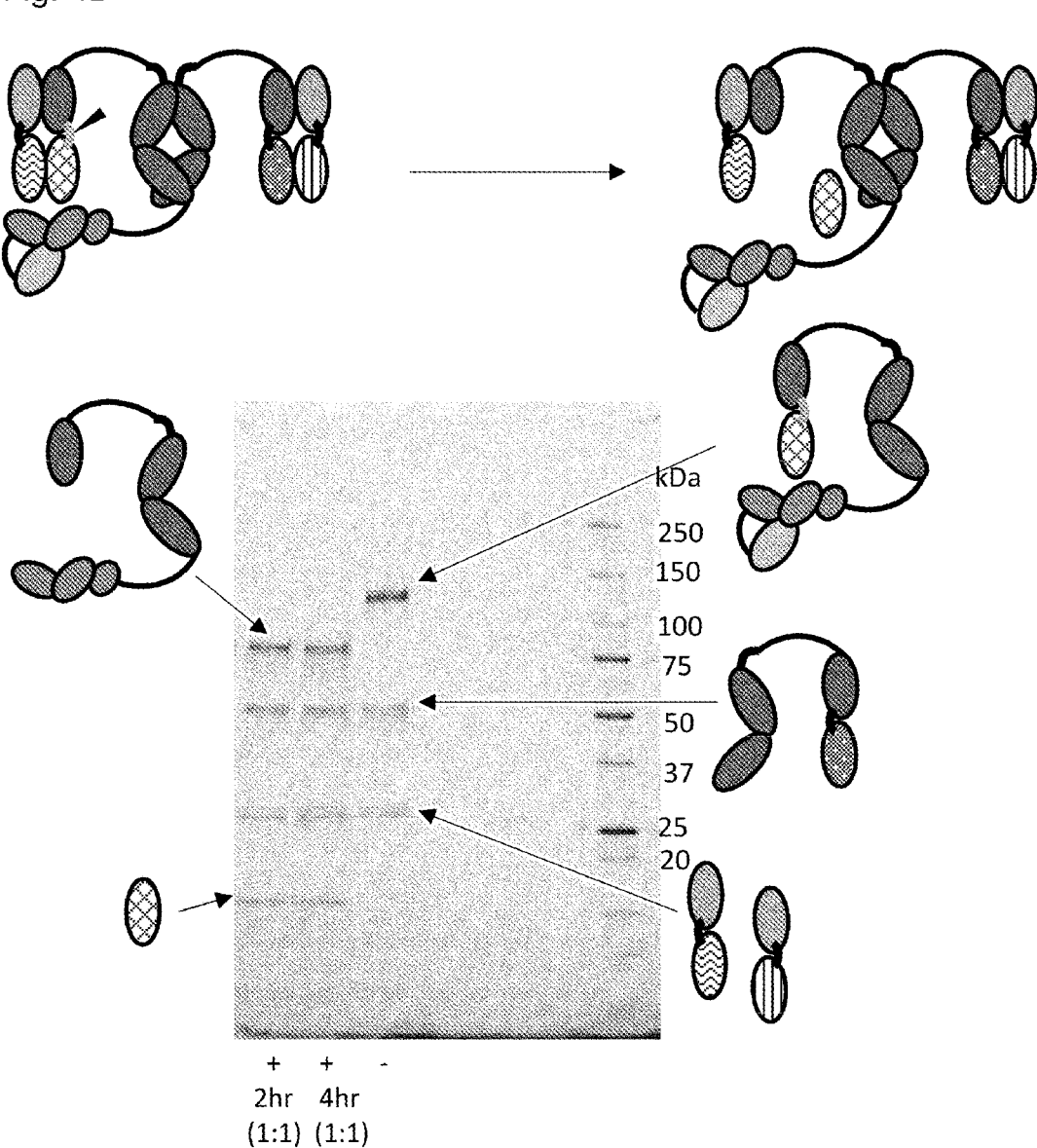
FIG. 4D shows the SDS-PAGE for cleaved products obtained after MTSP1 digestion of IL-12 fusion type molecules.
Figure 4E:
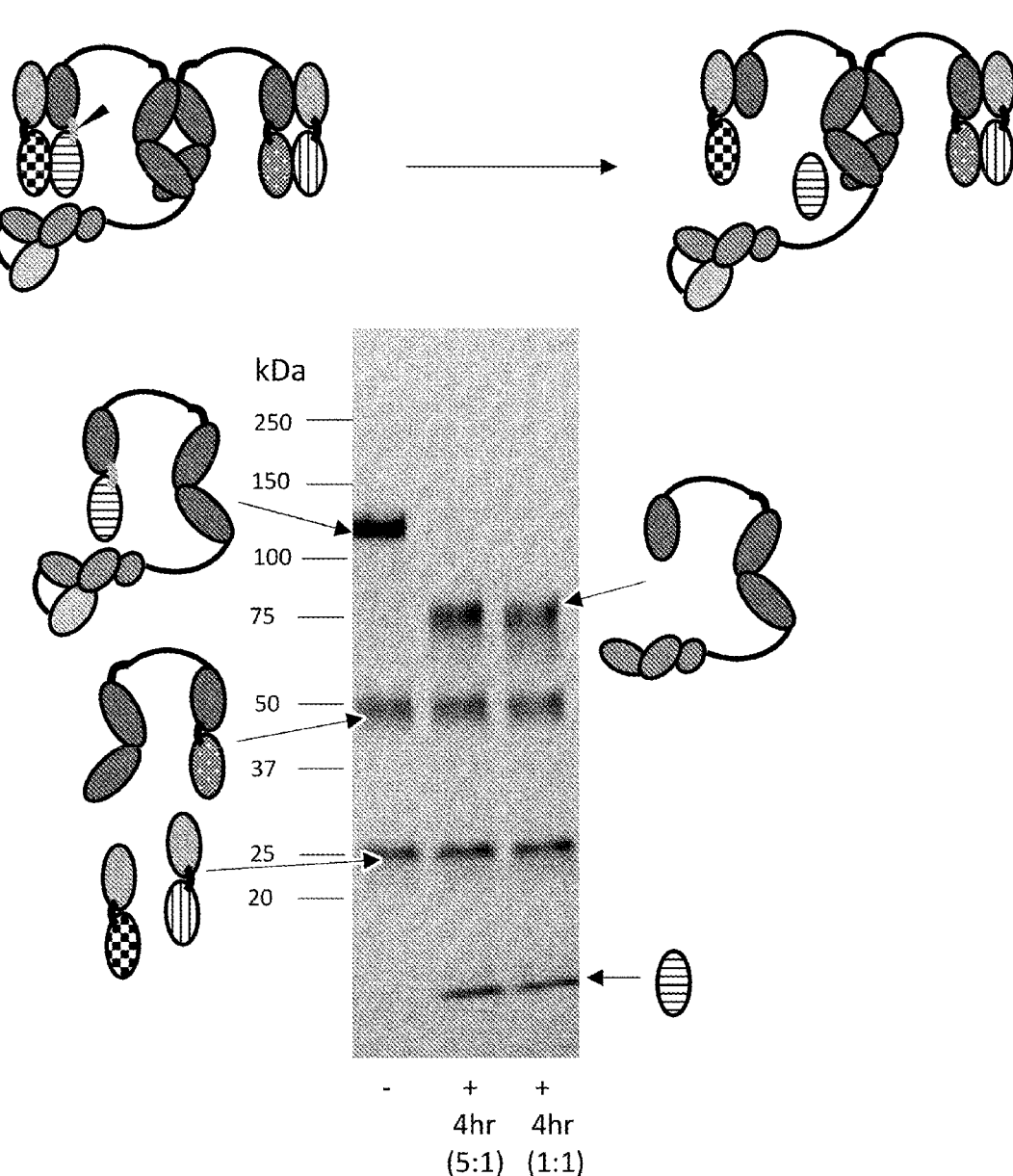
FIG. 4E shows the SDS-PAGE for cleaved products obtained after MTSP1 digestion of IL-12 fusion type molecules.

Example 2. Protease Cleavage Evaluation of IL-12 Releasing Antibody Harboring Protease Cleavage Sequence and Flexible Linker Sequence Whether the antibodies prepared in Example 1 would be cleaved by protease was verified. Recombinant Human Matriptase/ST14 Catalytic Domain (MT-SP1) (R&D Systems, Inc., 3946-SE-010) was used as the protease. 500 nM protease and 500 nM of each antibody were reacted in PBS under a condition of 37 degrees C. for 1 or 2 or 4 hours. Then, cleavage by the protease was evaluated by reducing SDS-PAGE. The results are shown in FIGS. 3 & 4. As a result of protease digestion for IL-12 release type F2 and F4 (FIG. 3), VH and IL-12 are cleaved from the antibody. As a result of protease digestion for IL-12 fusion type F2 and F4 (FIG. 4), VH is cleaved from the antibody and the IL-12 is fused to the VH less antibody. Apart from the digestion observed at protease site, non-specific digestion of IL12 was also observed (FIG. 3B-C; FIG. 4B-D). It was due to the presence of sequence recognized by MTSP1 at the C-terminus of p40. Thus cleaved p40 released or fused to Fc was observed after protease digestion although p40 and p35 are fused with GS linker (FIG. 3B-C; FIG. 4B-D). However, as the p35 lacks Trp, the stain free gels could not show a precise band corresponding to p35.

Example 3. Evaluation of In Vitro Activity 3-1. Evaluation of In Vitro Activity of Release Type Variants IL12 was purified by co-expression of vectors expressing p40 (SEQ ID NO: 871) and p35 (SEQ ID NO: 872) with TEV site followed (His)$_6$ tag fused at the C-terminus. Expression vectors of each chain were prepared by a method known to those skilled in the art, and expressed using Expi293 (Life Technologies Corp.) by combining each chain. Purification of antibodies was done using affinity purification by Ni Sepharose excel (Cat. No: 17-3712-02, GE Healthcare) followed by size exclusion chromatography using Superdex 200 gel filtration column (Cat. No: 28-9893-35, GE Healthcare). Any aggregates present in the elution from affinity chromatography were removed using size exclusion chromatography.

To assess IL-12 bioactivity of IL-12 release type antibodies with or without protease treatment, IL-12 luciferase assay was conducted. Briefly, $2.5 \times 10^4$ cells/well IL-12 bioassay cell (Promega, Cat #CS2018A02A) which express human IL-12Rb1, IL-12Rb2, and STAT4, were plated in 96-well plate and incubated overnight. Then, IL-12 or IL-12 releasing antibodies were added to the culture plate and incubated for 18 hours. For protease-treated samples, IL-12 or IL-12 releasing antibodies were treated with equimolar concentration of MTSP1 for 4 hours and serial diluents were prepared. Luciferase activity was detected with Bio-Glo luciferase assay system (Promega, G7940) according to manufacturer's instructions. Luminescence was detected using GloMax (registered trademark) Explorer System (Promega #GM3500). Data analysis was done by Microsoft (registered trademark) Excel (registered trademark) 2013 and the analyzed data was plotted using GraphPad Prism 7.

F4 monovalent IL-12 release Mab80, F4 bivalent IL-12 release Mab80, and F2 bivalent IL-12 release Mab80 were subjected to the IL-12 luciferase assay. All the three variants showed lower IL-12 bioactivity than hIL-12_His tag in the absence of MTSP1, and the IL-12 bioactivity was recovered to the same level to hIL-12_His tag upon MTSP1 treatment (FIG. 5A-C).

3-2. Evaluation of In Vitro Activity of Fusion Variants

To assess the IL-12 bioactivity of IL-12 fusion type antibodies, the IL-12 luciferase assay mentioned above was employed.

F4 monovalent IL-12 fusion Mab80, F4 monovalent IL-12 fusion Ustk, F4 monovalent IL-12 fusion J695, F2 bivalent IL-12 fusion Mab80, and F4 bivalent IL-12 fusion Mab80 were subjected to the IL-12 luciferase assay. All the five variants showed lower IL-12 bioactivity than hIL-12_His tag in the absence of MTSP1, and the IL-12 bioactivity was recovered upon MTSP1 treatment (FIG. 6A-E). Comparing F4 bivalent IL-12 fusion Mab80 and F2 bivalent IL-12 fusion Mab80, F4 monovalent IL-12 fusion Mab80 indicated lower IL-12 bioactivity than F2 bivalent IL-12 fusion Mab80 in the absence of MTSP1, meaning F4 had stronger IL-12 neutralizing activity than F2 in the case of Mab80 (FIG. 6D).

Example 4: Preparation of IL-12 Fusion Type Antibodies with Improved Homogeneity The presence of the GS linker in the hinge region between the Fab and Fc resulted in heterogeneity in the disulphide bond formation between heavy chain constant region (HC) and light chain constant region (LC) of Mab80-L1-C1-L4-IL12 (F4 bivalent IL-12 fusion Mab80). Mab80-L1-C1-L4-IL12 is a homo-dimer of a light chain (SEQ ID NO: 876) and heavy chain (SEQ ID NO: 885). SEQ ID NO: 876 was employed as a light chain without modification. In the heavy chain, a cleavable linker (L1, SEQ ID NO: 873) was introduced into the elbow hinge region between Mab80VH (SEQ ID NO: 878) and Constant region 1 (C1, SEQ ID NO: 901). Single-chain IL-12 (SEQ ID NO: 902) was attached to the C-terminus of Fc domain via the GS linker (L4, SEQ ID NO: 903) (FIG. 2B). To promote homogeneity, 3 variants of IL-12 fusion type antibodies were generated.

Mab80-L1-C2-L4-IL12 is a homo-dimer of a light chain (SEQ ID NO: 876) and heavy chain (SEQ ID NO: 904). SEQ ID NO: 876 was employed as a light chain without modification. In the heavy chain, cleavable linker (SEQ ID NO: 873) was introduced into the elbow hinge region between Mab80VH (SEQ ID NO: 878) and Constant region 2 (C2, SEQ ID NO: 905). In the Constant region 2, the GS linker present in the hinge region (GGGGSGGGGSEPKSCDKTHTCPPCP) (SEQ ID NO: 937) was shifted to (EPKSCGGGGSGGGGSDKTH-TCPPCP) (SEQ ID NO: 935) to promote cysteine (cys) bond formation between C220 of the heavy chain (SEQ ID NO: 904) and C214 of the light chain (SEQ ID NO: 876). Single-chain IL-12 (SEQ ID NO: 902) was attached to the C-terminus of Fc domain via the GS linker (L4, SEQ ID NO: 903).

Mab80-L1-C3-L4-IL12 is a homo-dimer of a light chain (SEQ ID NO: 906) and heavy chain (SEQ ID NO: 907). SEQ ID NO: 906 was employed as a light chain with C214S modification and SEQ ID NO: 907 was employed as a heavy chain with C220S modification, which resulted in no disulfide bond formation between heavy chain and light chain. In the heavy chain, a cleavable linker (SEQ ID NO: 873) was introduced into the elbow hinge region between Mab80VH (SEQ ID NO: 878) and Constant region 3 (C3, SEQ ID NO: 908). Single-chain IL-12 (SEQ ID NO: 902) was attached to the C-terminus of Fc domain via the GS linker (L4, SEQ ID NO: 903).

Mab80-L1-C4-L4-IL12 is a homo-dimer of a light chain (SEQ ID NO: 876) and heavy chain (SEQ ID NO: 909). SEQ ID NO: 876 was employed as a light chain without modification. SEQ ID NO: 909 was employed as a heavy chain with S131C and C220S modification, which resulted in disulfide bond formation between heavy chain and light chain. In the heavy chain, a cleavable linker (SEQ ID NO: 873) was introduced into the elbow hinge region between Mab80VH (SEQ ID NO: 878) and Constant region 4 (C4, SEQ ID NO: 910). Single-chain IL-12 (SEQ ID NO: 902) was attached to the C-terminus of Fc domain via the GS linker (L4, SEQ ID NO: 903).

Expression vectors of each chain were prepared by a method known to those skilled in the art, and expressed using Expi293 (Life Technologies Corp.) by combining each chain as shown in Table 4. Purification of antibodies was done using affinity purification by MabSelect SuRe (Cat. No: 17-5438-01, GE Healthcare) followed by size exclusion chromatography using Superdex 200 gel filtration column (Cat. No: 28-9893-35, GE Healthcare). Any aggregates present in the elution from affinity chromatography were removed using size exclusion chromatography.

TABLE 4

| IL-12 fusion type antibodies with improved homogeneity and sequence IDs of each chain | | |
| --- | --- | --- |
| IL-12 fused antibodies | Light chain | Heavy chain |
| Mab80-L1-C1-L4-IL12 | SEQ ID NO: 876 | SEQ ID NO: 885 |
| Mab80-L1-C2-L4-IL12 | SEQ ID NO: 876 | SEQ ID NO: 904 |
| Mab80-L1-C3-L4-IL12 | SEQ ID NO: 906 | SEQ ID NO: 907 |
| Mab80-L1-C4-L4-IL12 | SEQ ID NO: 876 | SEQ ID NO: 909 |

Figure 7A:
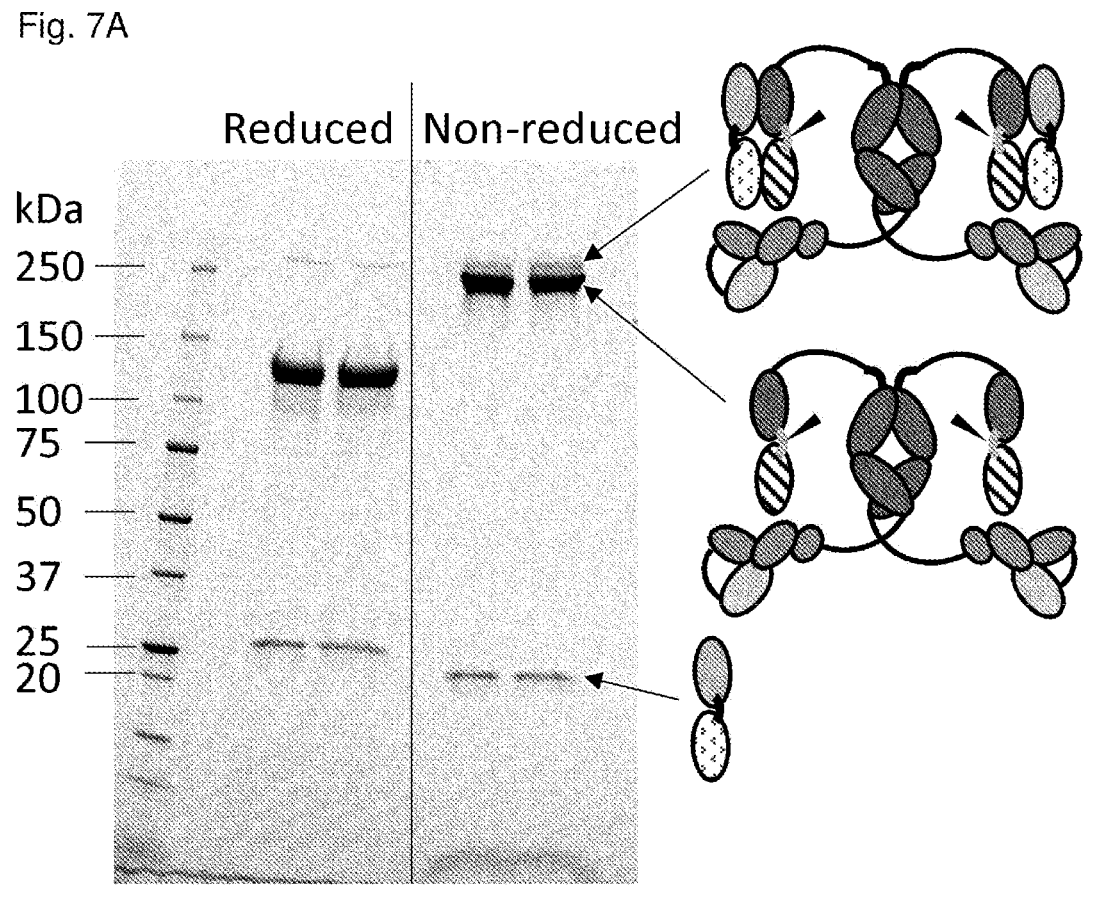
Figure 7B:
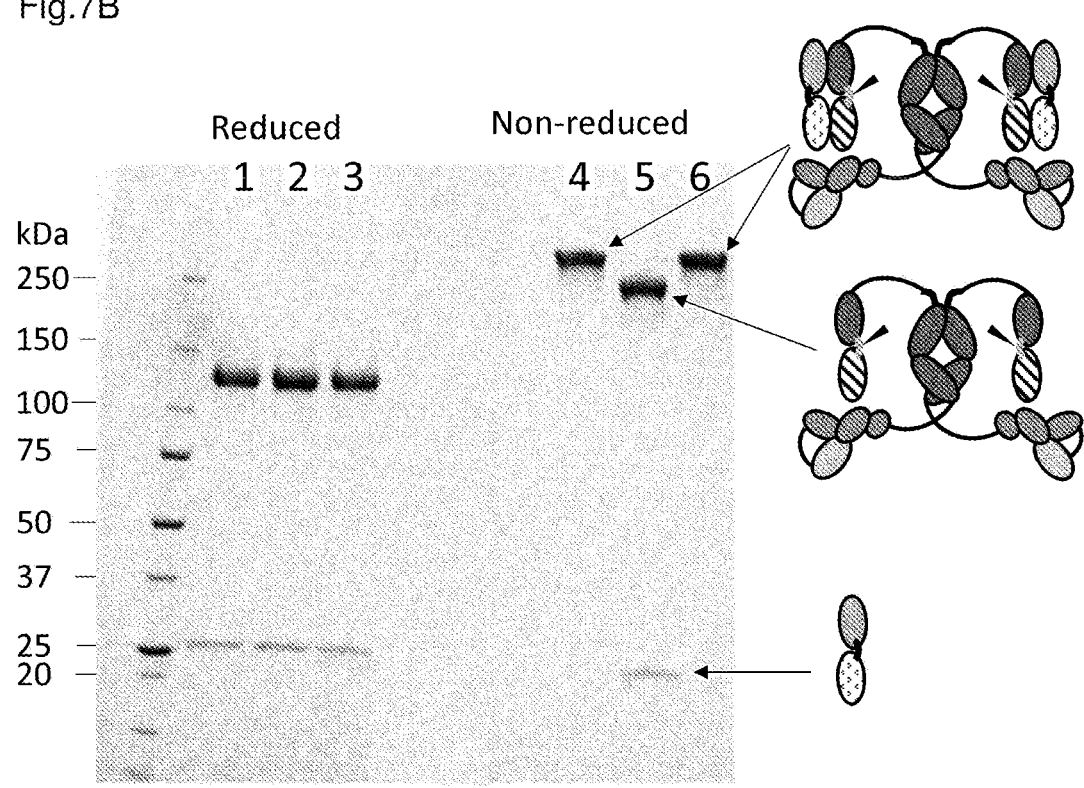
FIG. 7B shows the results of SDS-PAGE under reducing and non-reducing conditions for Mab80-L1-C2-L4-IL12 (lane 4), Mab80-L1-C3-L4-IL12 (lane 5), and Mab80-L1-C4-L4-IL12 (lane 6).

Example 5: SDS-PAGE Analysis for IL12 Fusion Type Antibodies with Improved Homogeneity SDS-PAGE was performed under reducing and non-reducing conditions. FIG. 7A shows the SDS-PAGE results for Mab80-L1-C1-L4-IL12 (F4 bivalent IL-12 fusion Mab80). Under the non-reducing conditions, Mab80-L1-C1-L4-IL12 shows multiple upper bands which correspond to Mab80-L1-C1-L4-IL12 with LC forming cys bond with HC and Mab80-L1-C1-L4-IL12 where LC are dissociating from HC, and the corresponding LC is visible closer to 20 kDa (lower band) under the non-reduced conditions. The presence of multiple bands under non-reduced conditions show the existence of heterogeneity due to the cys bonds between HC and LC, representing the presence of heterogeneity. FIG. 7B shows the SDS-PAGE results for Mab80-L1-C2-L4-IL12, Mab80-L1-C3-L4-IL12 and Mab80-L1-C4-L4-IL12 which show improved homogeneity. Mab80-L1-C2-L4-IL12 and Mab80-L1-C4-L4-IL12 (lanes 4 & 6) show single bands in non-reduced conditions, representing the presence of cys bond between heavy chain and light chain. Whereas, Mab80-L1-C3-L4-IL12 (lane 5) shows the presence of heavy chain and light chain in non-reduced conditions, showing the absence of cys bond between heavy chain and light chain due to the mutations.

Example 6: Evaluation of In Vitro Activity of IL12 Fusion Type Antibodies with Improved Homogeneity To assess IL-12 bioactivity of IL-12 fusion type antibodies with or without protease treatment, IL-12 luciferase assay was conducted. Briefly, $2.5 \times 10^4$ cells/well IL-12 bioassay cell (Promega, Cat #CS2018A02A) which express human IL-12Rb1, IL-12Rb2, and STAT4, were plated in 96-well plate and incubated overnight. Then, IL-12 or IL-12 releasing antibodies were added to the culture plate and incubated for 18 hours. For protease-treated samples, IL-12 or IL-12 releasing antibodies were treated with equimolar concentration of MTSP1 for 4 hours and serial diluents were prepared. Luciferase activity was detected with Bio-Glo luciferase assay system (Promega, G7940) according to manufacturer's instructions. Luminescence was detected using GloMax (registered trademark) Explorer System (Promega #GM3500). Percentage of effective concentration for wild type IL-12 was calculated and captured values were plotted using GraphPad Prism 7.

Figure 8:
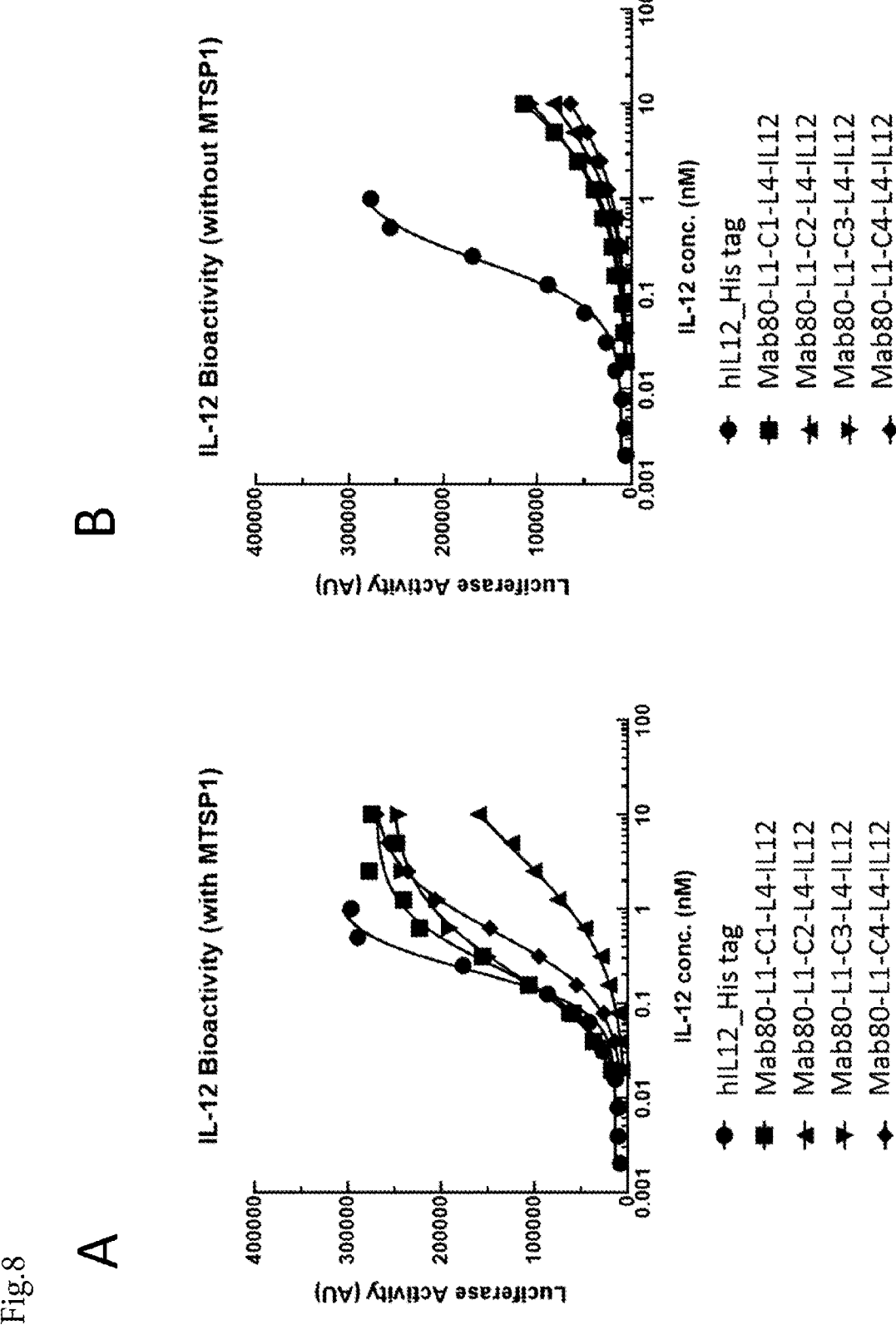
FIG. 8 shows IL-12 bioactivity of intact and MTSP1-cleaved Mab80-L1-C1-L4-IL12, Mab80-L1-C2-L4-IL12, and Mab80-L1-C3-L4-IL12.

Mab80-L1-C1-L4-IL12, Mab80-L1-C2-L4-IL12, Mab80-L1-C3-L4-IL12, and Mab80-L1-C4-L4-IL12 were subjected to the IL-12 luciferase assay. All the four variants showed lower IL-12 bioactivity than hIL-12_His tag in the absence of MTSP1, and the IL-12 bioactivity was recovered upon MTSP1 treatment (FIGS. 8A & 8B). Of all the variants, Mab80-L1-C4-L4-IL12 showed the lowest activity of all the variants in the absence of MTSP1 followed by Mab80-L1-C1-L4-IL12 and Mab80-L1-C2-L4-IL12.

Example 7: Preparation of IL-22 Fused Antibodies with Protease Cleavable Linkers 7-1. Preparation of IL-22 Release Type Various IL-22 fused antibodies were constructed by fusing IL-22 molecules (SEQ ID NO: 911), with anti-IL-22 antibodies through protease-cleavable linker (SEQ ID NOs: 873 and 879). The anti-IL-22 antibody, 087B03 (Gill et. al., US20070243589A1) was employed. Unless otherwise noted, the Fc region is a modified IgG1 Fc region which contains mutations (L235R/G236R in EU numbering) to abolish Fc gamma R binding.

087B03-L1-C1-L3-IL22 is a homo-dimer of a light chain (SEQ ID NO: 912) and heavy chain (SEQ ID NO: 913). SEQ ID NO: 912 was employed as a light chain without modification. In the heavy chain, a cleavable linker (L1, SEQ ID NO: 873) was introduced into the elbow hinge region between 087B03VH (SEQ ID NO: 914) and Constant region 1 (C1, SEQ ID NO: 901). IL-22 was attached to the C-terminus of Fc domain via a cleavable linker (L3, SEQ ID NO: 879) as shown in FIG. 9A.

087B03-L1-C3-L3-IL22 is a homo-dimer of a light chain (SEQ ID NO: 915) and heavy chain (SEQ ID NO: 916). SEQ ID NO: 915 was employed as a light chain with C214S modification and SEQ ID NO: 916 was employed as a heavy chain with C220S modification, which resulted in no di-sulfide bond formation between heavy chain and light chain. In the heavy chain, a cleavable linker (L1, SEQ ID NO: 873) was introduced into the elbow hinge region between 087B03VH (SEQ ID NO: 914) and Constant region 3 (C3, SEQ ID NO: 908). IL-22 was attached to the C-terminus of Fc domain via a cleavable linker (L3, SEQ ID NO: 879).

7-2. Preparation of IL-22 Non-Release Type

087B03-C1-L4-IL22 is a homo-dimer of a light chain (SEQ ID NO: 912) and heavy chain (SEQ ID NO: 917). SEQ ID NO: 912 was employed as a light chain without modi-fication. In the heavy chain, there was no cleavble linker introduced into the elbow hinge region between 087B03VH (SEQ ID NO: 914) and Constant region 1 (C1, SEQ ID NO: 901). IL-22 was attached to the C-terminus of Fc domain via the GS linker (L4, SEQ ID NO: 903) as shown in FIG. 9B. 087B03-C1-L4-1L22 represents a non-cleavable form of IL22 fused antibodies.

Expression vectors of each chain were prepared by a method known to those skilled in the art, and expressed using Expi293 (Life Technologies Corp.) by combining each chain as shown in Table 1. Purification of antibodies was done using affinity purification by MabSelect SuRe (Cat. No: 17-5438-01, GE Healthcare) followed by size exclusion chromatography using Superdex 200 gel filtration column (Cat. No: 28-9893-35, GE Healthcare). Any aggregates present in the elution from affinity chromatography were removed using size exclusion chromatography.

TABLE 5

IL-22 fusion type Abs with improved homogeneity and sequence IDs of each chain.

| IL-22 fused antibodies | Light chain | Heavy chain |
|---|---|---|
| 087B03-L1-C1-L3-IL22 | SEQ ID NO: 912 | SEQ ID NO: 913 |
| 087B03-L1-C3-L3-IL22 | SEQ ID NO: 915 | SEQ ID NO: 916 |
| 087B03-C1-L4-IL22 | SEQ ID NO: 912 | SEQ ID NO: 917 |

Example 8. Protease Cleavage Evaluation of IL-22 Releasing Antibody Harboring Protease Cleavage Sequence and Flexible Linker Sequence FIGS. 9A & B shows a schematic diagram of exemplary IL-22 fused antibodies, with and without protease cleavage sites, to illustrate the cleavage by protease. For IL-22 fused antibody with a cleavable linker such as 087B03-L1-C1-L3-1L22, protease treatment will result in the cleavage of the linker between the variable and CH1 regions of the heavy chain region. This will destabilize the antigen binding frag-ment (Fab) region of the antibody, and IL-22 can be released from the Fab region. In addition, proteolytic digestion of the linker between IL-22 and the C-terminal of the antibody heavy chain will allow IL-22 to be released from the fragment crystallizable region (Fc region) of the antibody. In contrast, IL-22 fused antibodies with a non-cleavable linker such as 087B03-C1-L4-IL22, will not result in the release of IL-22 as the linkers cannot be cleaved by the protease. As such, IL-22 will remain neutralized by the antigen binding fragment (Fab) region of the antibody.

To verify if proteolytic digestion of the linkers could release IL-22, a proteolytic reaction was set up using recom-binant human u-Plasminogen Activator/Urokinase (uPA) (Cat No: 1310-SE, R&D Systems) and the antibodies listed in Table 5. IL-22 fused antibodies and uPA protease were diluted with PBS (Gibco), mixed at a final concentration of 2000 nM antibody and 2000 nM uPA protease, and incu-bated overnight at 37 degrees Celsius (C) in a Thermocycler (2720 Applied Biosystems). The reaction was prepared in a PCR plate (Axygen) to minimize evaporation. As controls, HEK293-derived recombinant human IL-22 (Cat No: Z03081-50, Genscript) or PBS was added instead of IL-22 fused antibodies. Cleavage of antibodies by protease was evaluated by reducing sodium dodecyl sulphate-polyacryl-amide gel electrophoresis (SDS-PAGE) using 4-20% Mini-PROTEAN TGX Stain-Free Precast Gels (Bio-Rad). The gel was activated for 45 seconds with ultraviolet light using ChemiDoc Imaging system (Bio-Rad) and an image of the gel was obtained.

Figure 10A:
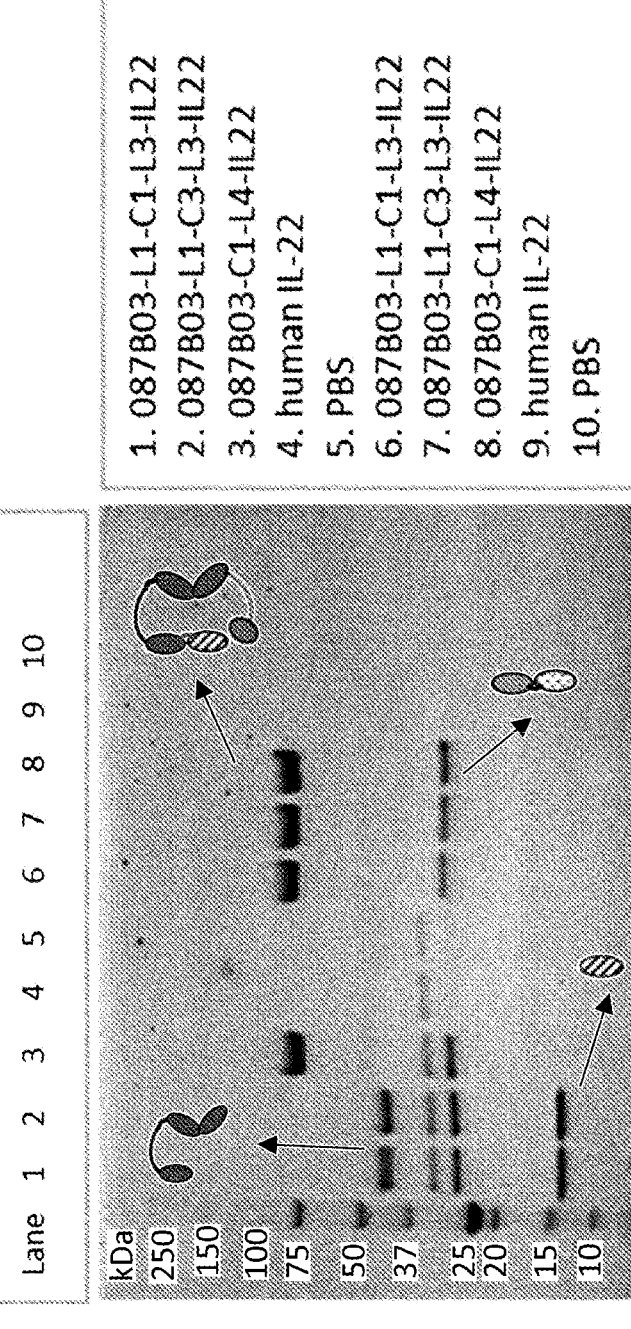
FIG. 10A shows the SDS-PAGE results for cleaved products obtained after uPA digestion of IL-22 release type molecules.

As shown in FIG. 10A, VH and IL-22 were released from the antibody 087B03-L1-C1-L3-IL22 and 087B03-L1-C3-L3-IL22 as a result of protease digestion. This can be seen by comparing the lanes 1 and 2 where the 75 kDa band is absent, with lanes 6 and 7 where it is present. As 087B03-C1-L4-IL22 has non-cleavable linkers, protease digestion did not result in release of VH and IL-22 in lanes 3 and 8. The released VH appears at approximately 15 kDa.

The released IL-22 could not be clearly visualized in FIG. 10A because IL-22 lacks tryptophan residues for visualiza-tion on the stain-free gel, and also because it is a glycosy-lated protein which will appear as a diffused smear instead of a sharp band. As such, western blotting was used to demonstrate IL-22 release by uPA protease.

To do this, samples were prepared in the same manner as FIG. 10A, subjected to reducing SDS-PAGE, and transferred to a PVDF membrane (Bio-Rad) using the Trans-Blot Turbo Transfer System (Bio-Rad) Immunodetection was done by iBind Western Device (Invitrogen). Goat anti-human IL-22 antibody (Cat No: AF782, R&D Systems) and donkey anti-goat IgG HRP (Cat No. ab98519, Abcam) were used for detection. Chemiluminescent detection was performed using SuperSignal™ West Femto substrate (ThermoFisher) and ChemiDoc Imaging system (Bio-Rad). The procedures were performed according to the each manufacturer's recommen-dation.

Figure 10B:
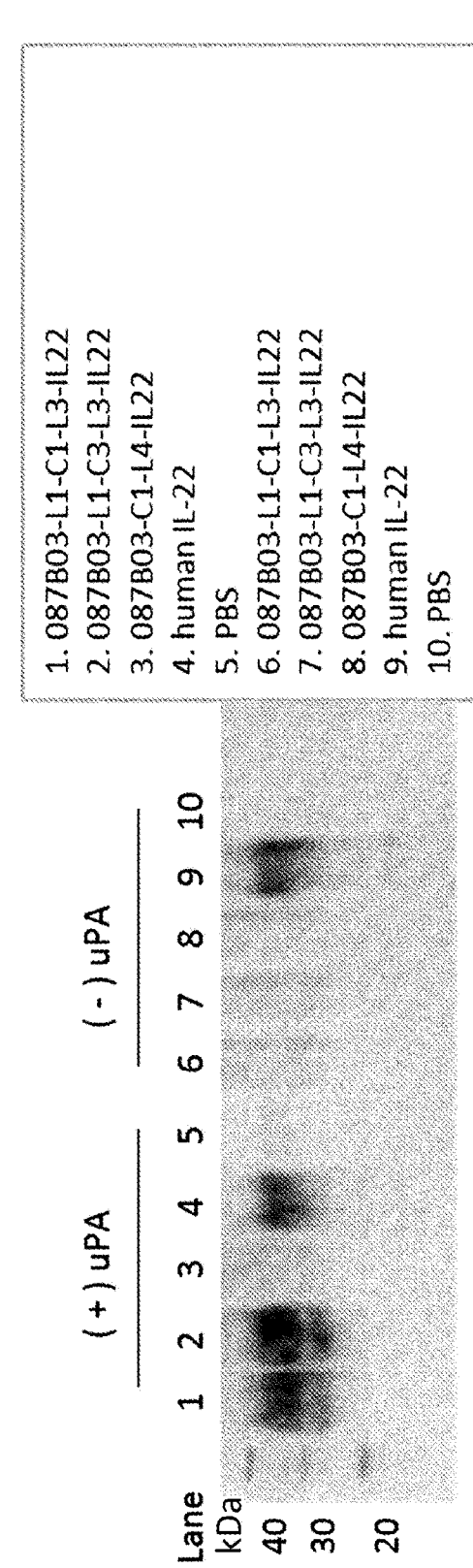
FIG. 10B shows the western blotting results demonstrating IL-22 release from the IL-22 release type molecules after uPA digestion.

As shown in FIG. 10B, IL-22 released by uPA proteolytic cleavage was detected in lanes 1-2, but not in lanes 3, 6, 7 and 8, which was consistent with the release of VH in FIG. 10A. Together, these data demonstrate that proteolytic diges-tion of the linkers in the IL-22 fused antibodies could release IL-22.

Example 9. Evaluation of In Vitro Activity

To assay for the bioactivity of released IL-22 after cleav-age of IL-22 fused antibodies, the following assay was set up. Firstly, IL-22 fused antibodies and recombinant human uPA protease were diluted with PBS (Gibco), mixed at a final concentration of 2000 nM antibody and 2000 nM uPA protease, and incubated overnight at 37 degrees C. in a Thermocycler (2720 Applied Biosystems) to allow for cleavage of the linker and release of IL-22. For controls, HEK293-derived recombinant human IL-22 (Cat No: Z03081-50, Genscript) or PBS (Gibco) were incubated with uPA.

Next, the bioactivity of released IL-22 was assayed using COLO205 colon carcinoma cells (Cat No: CCL-222, ATCC) which respond to IL-22 by secreting IL-10 (Int Immuno-pharmacol. 2004 May; 4(5):679-91). After trypsinization with 0.25% trypsin (Gibco), COLO205 cells were filtered through a 70 micrometer cell strainer (Corning) to remove cell clumps. Cell counts were performed using Luna Dual Fluorescence Cell Counter (Logos Biosystem), and 3E4 cells in 50 microliter were seeded into each well of a flat bottom 96-well plate. The cells were incubated for a minimum of 4 hours at 37 degrees C. in a 5% CO2 incubator to allow cells to attach to the plate. Cleaved IL-22 fused antibodies previously incubated with uPA were serially diluted to 6 times of the final desired concentration, and 10 microliter was added to the cells for a final assay volume of 60 microliter. The assay plate was further incubated overnight at 37 degrees C. in a 5% CO2 incubator. After overnight incubation, the assay plate was centrifuged at 300 g for 3 minutes at 25 degrees C. Cell supernatant samples were collected to quantify the amount of IL-10 produced by COLO205 cells using Human IL-10 DuoSet ELISA (R&D Systems). The procedures for Human IL-10 ELISA were performed according to the manufacturer's recommendation except for the preparation of IL-10 standard and samples. IL-10 standard was diluted in COLO205 culture media, RPMI 1640 medium (Gibco) containing 10% Fetal Bovine Serum (Sigma) and 1% Penicillin-Streptomycin (Gibco), so that the cell supernatant samples could be assayed without dilution for more sensitive IL-10 detection. Where dilutions of the sample were necessary, samples were diluted in COLO205 culture media for ELISA. The absorbance of samples were measured at 450 nm and 595 nm using MultiSkan GO plate reader (Thermo Scientific).

Figure 11:
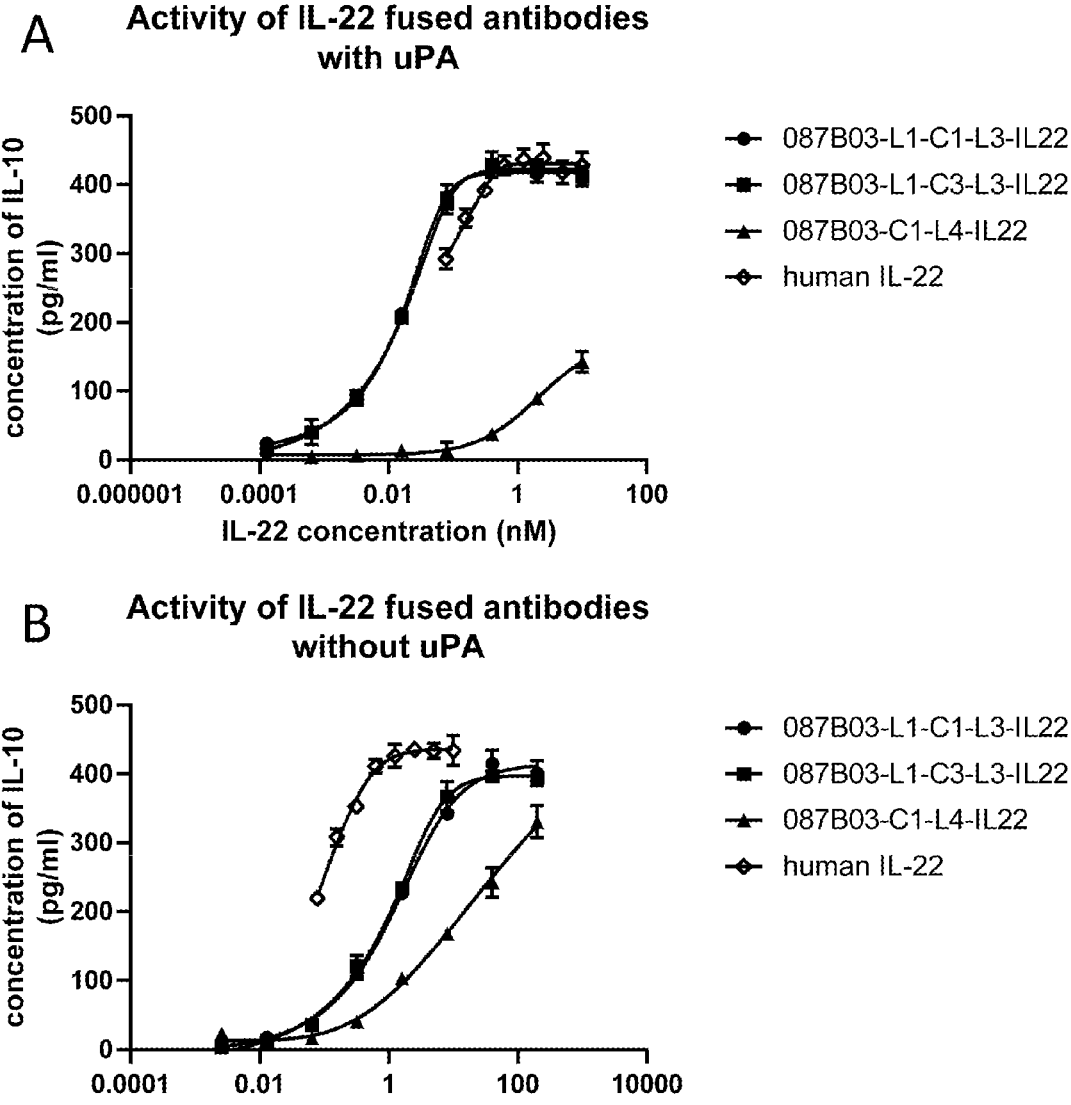
FIG. 11 shows IL-22 bioactivity of uPA-cleaved and intact IL-22 release type molecules.

Example 10. Protease Cleaved IL-22 Fused Antibodies Showed Stronger Bioactivity as Compared to Non-Protease Treated Antibodies As shown in FIG. 11A, the IL-22 released after protease digestion of 087B03-L1-C1-L3-IL22 and 087B03-L1-C3-L3-IL22 which have cleavable linkers, was able to bind to IL-22 receptors on COLO205 cells and trigger IL-10 secretion. In contrast, 087B03-C1-L4-IL22 with non-cleavable linkers only showed weak IL-10 response at extremely high doses of IL-22, indicating that IL-22 was not released and remained neutralized. Similarly, in FIG. 11B where no protease was added to the IL-22 fused antibodies, IL-22 bioactivity was weaker as compared to recombinant human IL-22 alone, indicating that the IL-22 in the fused antibody was less available for binding to IL-22R on the COLO205 cell.

Example 11: Preparation of IL-22 Fused Antibodies with Improved Homogeneity

The presence of the GS linker in the hinge region between the Fab and Fc resulted in heterogeneity in the disulfide bond formation between heavy chain constant region (HC) and light chain constant region (LC) of 087B03-L1-C1-L3-IL22. To promote homogeneity, two variants of IL-22 fused antibodies were generated, following the design of the IL-12 fusion type antibodies with improved homogeneity described in Example 4.

087B03-L1-C2-L3-IL22 is a homo-dimer of a light chain (SEQ ID NO: 912) and heavy chain (SEQ ID NO: 929). SEQ ID NO: 912 was employed as a light chain without modification. In the heavy chain, cleavable linker (L1, SEQ ID NO: 873) was introduced into the elbow hinge region between 087B03VH (SEQ ID NO: 914) and Constant region 2 (C2, SEQ ID NO: 905). In the Constant region 2, the GS linker present in the hinge region (GGGGSGGGGSEPKSCDKTHTCPPCP) (SEQ ID NO: 937) was shifted to (EPKSCGGGGSGGGGSDKTHTCPPCP) (SEQ ID NO: 935) to promote cysteine (cys) bond formation between C220 of the heavy chain (SEQ ID NO: 929) and C214 of the light chain (SEQ ID NO: 912). IL-22 (SEQ ID NO: 911) was attached to the C-terminus of Fc domain via a cleavable linker (L3, SEQ ID NO: 879).

087B03-L1-C4-L3-IL22 is a homo-dimer of a light chain (SEQ ID NO: 912) and heavy chain (SEQ ID NO: 930). SEQ ID NO: 912 was employed as a light chain without modification. SEQ ID NO: 930 was employed as a heavy chain with S131C and C220S modification, which resulted in disulfide bond formation between heavy chain and light chain. In the heavy chain, a cleavable linker (L1, SEQ ID NO: 873) was introduced into the elbow hinge region between 087B03VH (SEQ ID NO: 914) and Constant region 4 (C4, SEQ ID NO: 910). IL-22 (SEQ ID NO: 911) was attached to the C-terminus of Fc domain via a cleavable linker (L3, SEQ ID NO: 879).

Expression vectors of each chain were prepared by a method known to those skilled in the art, and expressed using Expi293 (Life Technologies Corp.) by combining each chain as shown in Table 6. Purification of antibodies was done using affinity purification by MabSelect SuRe (Cat. No: 17-5438-01, GE Healthcare) followed by size exclusion chromatography using Superdex 200 gel filtration column (Cat. No: 28-9893-35, GE Healthcare). Any aggregates present in the elution from affinity chromatography were removed using size exclusion chromatography.

| IL-22 fusion type antibodies with improved homogeneity and sequence IDs of each chain | | |
|---|---|---|
| IL-22 fused antibodies | Light chain | Heavy chain |
| 087B03-L1-C2-L3-IL22 | SEQ ID NO: 912 | SEQ ID NO: 929 |
| 087B03-L1-C4-L3-IL22 | SEQ ID NO: 912 | SEQ ID NO: 930 |

Example 12: SDS-PAGE Analysis for IL-22 Releasing Antibodies with Improved Homogeneity FIG. 12 shows the SDS-PAGE results for cleavable IL-22 releasing antibodies with and without improved homogeneity under reducing and non-reducing conditions. Under non-reducing conditions, 087B03-L1-C1-L3-IL22 (lane 1) shows multiple bands, which show the existence of heterogeneity of cys bonds between HC and LC. The uppermost band corresponds to 087B03-L1-C1-L3-IL22 with cys bond between LC and HC. The lower bands correspond to 087B03-L1-C1-L3-IL22 when the LC does not form a cys bond with HC. In the absence of a Cys bond with HC, the LC is visible at approximately 25 kDa under non-reducing conditions. In lane 2, the LC is also visible under non-reducing conditions as 087B03-L1-C3-L3-IL22 has no disulfide bond between LC and HC due to introduction of C220S modification in the HC and C214S modification in the LC.

In contrast, IL-22 releasing antibodies with improved homogeneity 087B03-L1-C2-L3-IL22 (lane 3) and 087B03-L1-C4-L3-IL22 (lane 4) show single bands under non-reducing conditions, representing the presence of cys bond between heavy chain and light chain.

Figure 13:
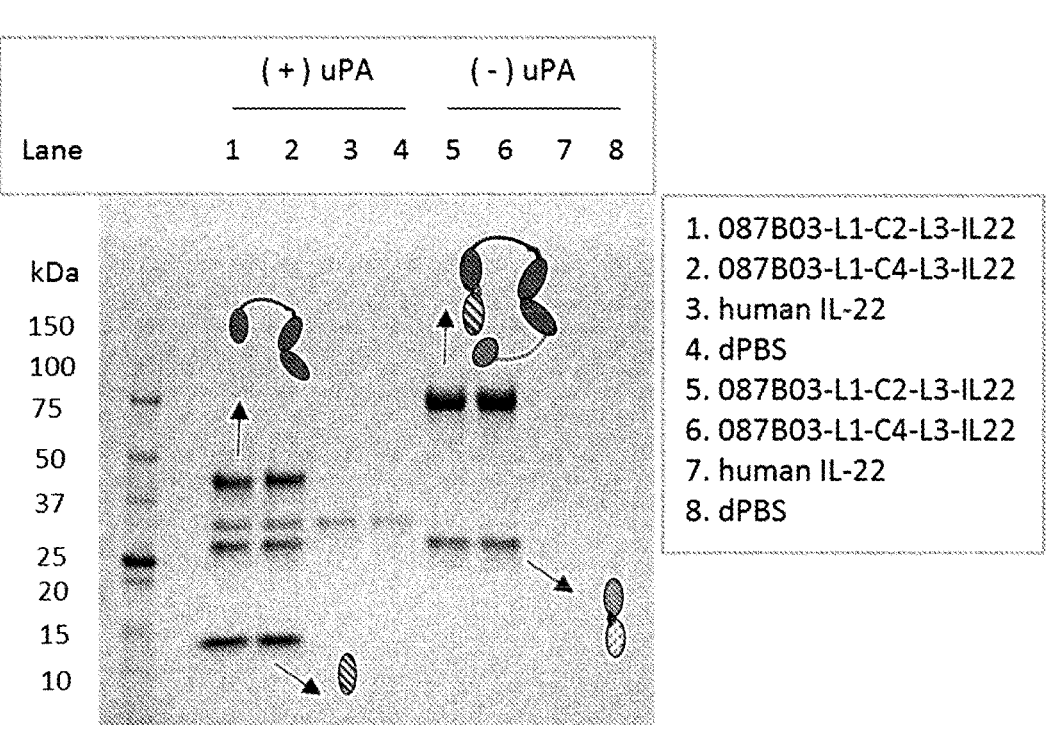
FIG. 13 shows the SDS-PAGE results for cleaved products obtained after uPA digestion of IL-22 release type molecules 087B03-L1-C2-L3-IL22 and 087B03-L1-C4-L3-IL22.
Figure 14:
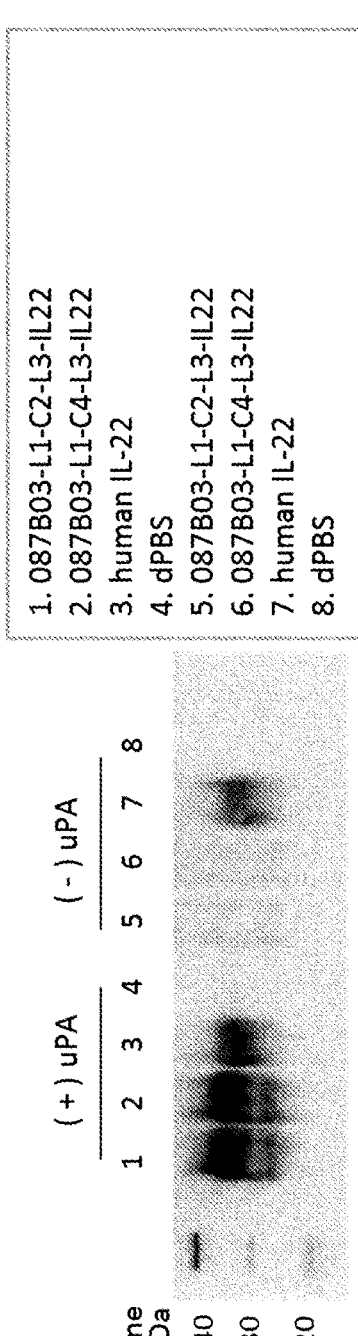
FIG. 14 shows the western blotting results demonstrating IL-22 release from the IL-22 release type molecules 087B03-L1-C2-L3-IL22 and 087B03-L1-C4-L3-1L22 after uPA digestion.

Example 13. Protease Cleavage Evaluation of IL-22 Releasing Antibody Harboring Protease Cleavage Sequence and Flexible Linker Sequence with Improved Homogeneity To verify if proteolytic digestion of the linkers could release IL-22 from the antibodies with improved homogeneity, a proteolytic reaction was set up using recombinant human u-Plasminogen Activator/Urokinase (uPA) (Cat No: 1310-SE, R&D Systems) using the method described in Example 8. As shown in FIG. 13, VH and IL-22 were released from the antibody 087B03-L1-C2-L3-IL22 and 087B03-L1-C4-L3-IL22 as a result of uPA protease digestion. This can be seen by comparing the lanes 1 and 2 where the 75 kDa band is absent, with lanes 5 and 6 where it is present. The released VH appears at approximately 15 kDa. Western blotting to detect released IL-22 by uPA protease was also performed using the method described in Example 8. As shown in FIG. 14, IL-22 released by uPA proteolytic cleavage was detected in lanes 1 and 2, but not in lanes 5 and 6, which was consistent with the release of VH in FIG. 13.

Example 14: Evaluation of In Vitro Activity of IL22 Fused Antibodies with Improved Homogeneity The bioactivity of released IL-22 after cleavage of IL-22 fused antibodies with improved homogeneity was evaluated using the method described in Example 9. As shown in FIG. 15A, in the presence of protease, the IL-22 released from 087B03-L1-C2-L3-IL22 and 087B03-L1-C4-L3-IL22 was able to bind to IL-22 receptors on COLO205 cells and trigger IL-10 secretion. In contrast, as shown in FIG. 15B where no protease was added to the IL-22 fused antibodies, IL-22 bioactivity was weaker as compared to recombinant human IL-22 alone, indicating that the IL-22 in the fused antibody was less available for binding to IL-22R on the COLO205 cell.

Example 15: Preparation of IL-2 Fused Antibodies with Protease Cleavable Linkers IL-2 promotes T cell-dependent immune response while it is also essential to maintain functional Tregs to regulating immune responses. In order to control its function in either promoting or regulating immune responses, engineering of IL-2 has been studied. For example, it is reported that IL-2 N88D mutein showed reduced binding to IL-2R beta gamma and thus it works as Treg-selective IL-2 molecule (J. Auto-immun., 2018, 95, 1). On the other hand, another IL-2 mutein with reduced binding to IL-2R alpha to avoid preferential activation of Tregs has also been reported (Onco-immunology, 2017, 6, e1277306). By combining these cytokine-engineering approach with disease specific protease activation, expanding therapeutic index can be expected. In order to demonstrate susceptibility of IL-2 mutein with site specific activation by disease-specific proteases, IL-2 fused antibodies with protease cleavable linkers were tested.

Various IL-2 fused antibodies were constructed by fusing IL-2 mutein, with anti-IL-2 antibodies or control antibody through GS linker (SEQ ID NO: 927). IL2.N88D (SEQ ID NO: 918) was employed as an example of IL-2 muteins. which is a modified IL-2 containing two mutations (N88D to reduce binding to IL-2R beta gamma, C145A to reduce unexpected binding to other molecules) and purification tag (His-tag in its C-terminus). Anti-IL-2 antibody, Cx (Onur et. al., WO2017121758A1) and 16C3 (Isaac et. al., WO2015/109212A1) were employed. Anti-KLH antibody were employed as a control antibody which does not bind to IL-2 and thus IL-2 is not neutralized regardless of protease cleavage. Unless otherwise noted, Fc region is a modified IgG1 Fc region which contains mutations (L235R/G236R/A327G/A330S/P331S in EU numbering) to abolish Fc gamma R binding.

Cx-L1-C5-L5-IL2.N88D is a homo-dimer of a heavy chain (SEQ ID NO: 919) and light chain (SEQ ID NO: 920). In heavy chain, cleavable linker (L1, SEQ ID NO: 873) was introduced into elbow hinge region between CxH (SEQ ID NO: 931) and Constant region 5 (C5, SEQ ID NO: 932). SEQ ID NO: 920 was employed as light chain without modification. IL-2 N88D was attached to C-terminal of Fc domain via flexible linker (SEQ ID NO: 927) as shown in FIG. 16A.

Cx-L6-C5-L5-IL2.N88D is a homo-dimer of a heavy chain (SEQ ID NO: 921) and light chain (SEQ ID NO: 920). In heavy chain, GS linker (SEQ ID NO: 928) was introduced into elbow hinge region between CxH (SEQ ID NO: 931) and Constant region 5 (C5, SEQ ID NO: 932). SEQ ID NO: 920 was employed as light chain without modification. IL-2 N88D was attached to C-terminal of Fc domain via flexible linker (SEQ ID NO: 927) as shown in FIG. 16B.

16C3-L1-C5-L5-IL2.N88D is a homo-dimer of a heavy chain (SEQ ID NO: 922) and light chain (SEQ ID NO: 923). In heavy chain, cleavable linker (L1, SEQ ID NO: 873) was introduced into elbow hinge region between 16C3VH (SEQ ID NO: 933) and Constant region 5 (C5, SEQ ID NO: 932). SEQ ID NO: 923 was employed as light chain without modification. IL-2 N88D was attached to C-terminal of Fc domain via flexible linker (SEQ ID NO: 927).

16C3-L6-C5-L5-IL2.N88D is a homo-dimer of a heavy chain (SEQ ID NO: 924) and light chain (SEQ ID NO: 923). In heavy chain, GS linker (SEQ ID NO: 928) was introduced into elbow hinge region between 16C3VH (SEQ ID NO: 933) and Constant region 5 (C5, SEQ ID NO: 932). SEQ ID NO: 923 was employed as light chain without modification. IL-2 N88D was attached to C-terminal of Fc domain via flexible linker (SEQ ID NO: 927).

KLH-L6-C5-L5-IL2.N88D is a homo-dimer of a heavy chain (SEQ ID NO: 925) and light chain (SEQ ID NO: 926). In heavy chain, GS linker (SEQ ID NO: 928) was introduced into elbow hinge region between KLH VH (SEQ ID NO: 934) and Constant region 5 (C5, SEQ ID NO: 932). SEQ ID NO: 926 was employed as light chain without modification. IL-2 N88D was attached to C-terminal of Fc domain via flexible linker (SEQ ID NO: 927) as shown in FIG. 16C.

Expression vectors of each chain were prepared by a method known to those skilled in the art, and expressed using Expi293 (Life Technologies Corp.) by combining each chain as shown in Table 7. Purification of IL-2 N88D without antibody molecule was done using affinity purification by HisTrap excel (Cat. No: 17371206, GE Health-care) followed by size exclusion chromatography using Superdex 75 increase gel filtration column (Cat. No: 29148721, GE Healthcare). Purification of IL-2 fused antibodies was done using affinity purification by HisTrap excel (Cat. No: 17371206, GE Healthcare) followed by size exclusion chromatography using Superdex 200 increase gel filtration column (Cat. No: 28990944, GE Healthcare). Any aggregates present in the elution from affinity chromatography were removed using size exclusion chromatography.

TABLE 7

List of IL-2 fused antibodies and sequence IDs of each chain

| IL-2 fused antibodies | Heavy chain | Light chain |
| --- | --- | --- |
| Cx-L1-C5-L5-IL2.N88D | SEQ ID NO. 919 | SEQ ID NO: 920 |
| Cx-L6-C5-L5-IL2.N88D | SEQ ID NO: 921 | SEQ ID NO: 920 |
| 16C3-L1-C5-L5-IL2.N88D | SEQ ID NO: 922 | SEQ ID NO: 923 |
| 16C3-L6-C5-1.5-IL2.N88D | SEQ ID NO; 924 | SEQ ID NO: 923 |
| KLH-L6-C5-L5-IL2.N88D | SEQ ID NO: 925 | SEQ ID NO: 926 |

Example 16: Protease Cleavage Evaluation of IL-2 Fused Antibodies

FIG. 16 shows a schematic diagram of exemplary IL-2 N88D fused antibodies, with and without protease cleavage sites, to illustrate the cleavage by protease. For IL-2 N88D fused antibody with a cleavable linker such as Cx-L1-05-L5-IL2.N88D and 16C3-L1-C5-L5-IL2.N88D, protease treatment will result in the cleavage of the linker between the VH and CH1 regions in the heavy chains (A). This will destabilize the Fab regions of the antibody and IL-2 N88D can be released from neutralization. In contrast, IL-2 N88D fused antibodies with a non-cleavable linker such as Cx-L6-C5-L5-IL2.N88D and 16C3-L6-C5-L5-IL2.N88D, will not result in the release of IL-2 N88D as the linkers cannot be cleaved by the protease (B). As such, IL-2 N88D will remain neutralized. IL-2 N88D fused control antibodies with a non-cleavable linker such as KLH-L6-C5-L5-IL2.N88D, will remain active regardless of protease treatment(C).

To verify if proteolytic digestion of the linkers could release IL-2 N88D, a proteolytic reaction was set up using recombinant human u-Plasminogen Activator/Urokinase (uPA) (Cat No: 755304, Biolegend) and the antibodies listed in Table 7. IL-2 N88D fused antibodies and uPA protease were diluted with PBS (Wako), mixed at a final concentration of 0.1 mg/mL antibody and 100 nM uPA protease, and incubated 2 hours at 37 degree C. in a Thermocycler (2720 Applied Biosystems). The reaction was run in a PCR tube (Applied Biosystems) to minimize evaporation. As controls, E. coli-derived recombinant human IL-2 (Cat No: AF 02, PEPROTECH) or purified IL-2 N88D was added instead of IL-2 fused antibodies. Cleavage of antibodies by protease was evaluated by reducing sodium dodecyl sulphate-polyacrylamide gel electrophoresis (SDS-PAGE) using 4-20% Mini-PROTEAN TGX Stain-Free Precast Gels (Bio-Rad). The gel was stained with Quick CBB (Cat No: 299-50101, FUJIFILM) and images of the gel was obtained by Chemi-Doc Imaging system (Bio-Rad).

As shown in FIG. 17, VH was released from the antibody Cx-L1-C5-L5-1L2.N88D and 16C3-L1-C5-L5-IL2.N88D as a result of protease digestion. This can be confirmed by comparing the lanes 8 and 9 where the 75 kDa band is absent, with lanes 1 and 2 where it is present. The released VH appeared at approximately 15 kDa in lane 8 and 9. As KLH-L6-C5-L5-IL2.N88D, Cx-L6-C5-L5-IL2.N88D, and 16C3-L6-C5-L5-IL2.N88D have non-cleavable linkers, protease digestion did not result in release of VH in lanes 10, 11, and 12.

Example 17: Evaluation of In Vitro Activity of IL-2 Fused Antibodies

Figure 18:
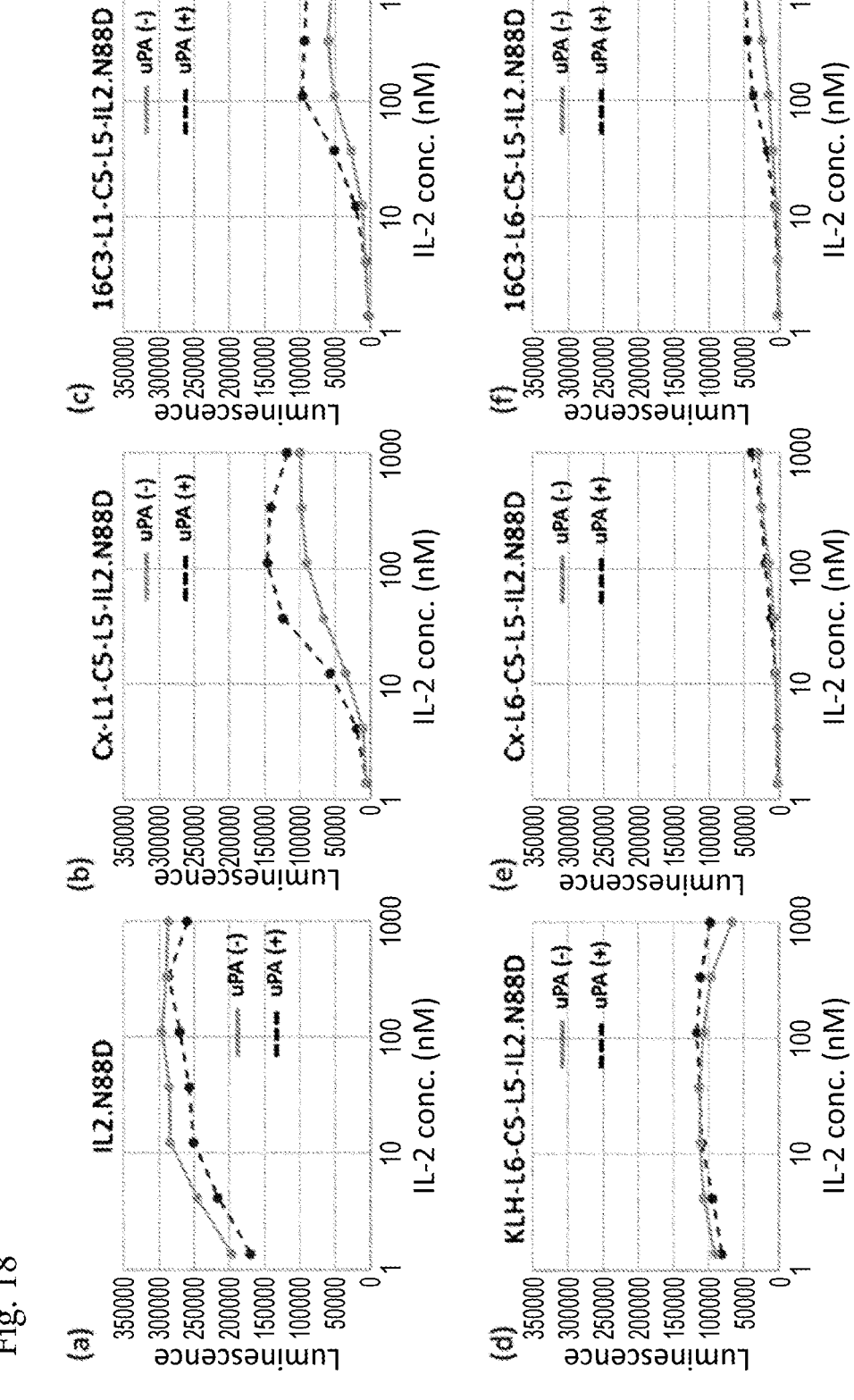
FIG. 18 shows a result of IL-2 bioassay to evaluate bioactivity of IL-2 released from IL-2 fused antibodies.

To evaluate bioactivity of IL-2 released from IL-2 fused antibodies, IL-2 bioassay (Promega, JA2205) was used with the following procedures. $2.4 \times 10^4$ of effector cells in 20 microliter of RPMI were plated in each well in 384-well plate and IL-2 fused antibodies in 10 microliter of RPMI were added at the final concentration of 1000 nM to 1.4 nM with or without uPA protease at the final concentration of 100 nM (Biolegend). Plates were incubated at 37 degree C. at 5% $CO_2$ for 18 hours and 30 microliter of Bio-Glo luciferase assay reagent was applied to each well. Activity of IL-2 was evaluated by measuring luminescence with 2104 EnVision (Perkin Elmer). Results of this assay were shown in FIG. 18.

Recombinant IL2.N88D (a) and KLH-L6-C5-L5-IL2.N88D (d) showed activity regardless of uPA treatment due to their non-neutralized forms. On the other hand, Cx-L1-C5-L5-IL2.N88D (b) and 16C3-L1-C5-L5-IL2.N88D (c) both of which are IL-2 fused antibodies with protease cleavable linkers showed recovery of activity upon uPA treatment while activities were suppressed without uPA treatment. Activities of these molecules with non-cleavable linker (e and f) were kept suppressed even upon uPA treatment. These results indicate that IL-2 fused antibodies with protease cleavable linkers can be kept neutralized without protease activity and activated upon protease-mediated cleavage of protease cleavable linkers.

The invention claimed is:

1. A fusion protein which comprises a ligand-binding moiety and is represented by formula (I):

[Ligand-binding domain]-[Lx]-[Cx]-[Ly]-[Ligand moiety]     (I)

wherein:

Lx represents a first peptide linker comprising a first protease cleavage site;

Cx represents a constant region comprising a second peptide linker and one or more amino acid residues which are modified from or to cysteine;

Ly represents a third peptide linker, and wherein the ligand-binding domain comprises a VH region and a VL region, binds to the ligand moiety, and is capable of releasing the ligand moiety in the presence of a protease, wherein the constant region comprises an antibody heavy chain comprising a CH1 region and an Fc region and an antibody light chain comprising a CL region,

(a) wherein the second peptide linker is positioned in a hinge region so that disulfide bond formation between Cys at position 220 of the heavy chain and Cys at position 214 of the light chain is promoted, with all positions according to EU numbering;

(b) wherein amino acid residues in the heavy chain and the light chain are modified so that no disulfide bond is formed between position 220 of the heavy chain and position 214 of the light chain, with all positions according to EU numbering; or (c) wherein the heavy chain is modified to allow disulfide bond formation between position 131 of the heavy chain and position 214 of the light chain, with all positions according to EU numbering; and wherein the first protease cleavage site of Lx is located between the VH or VL region and the CH1 or CL region, respectively.

2. The fusion protein of claim 1, which comprises two sets of the ligand-binding domain, ligand moiety, first peptide linker, constant region, and a third peptide linker.

3. A polynucleotide encoding the fusion protein of claim 1.

4. A vector comprising the polynucleotide of claim 3.

5. A host cell comprising the polynucleotide of claim 3.

6. A method for producing a fusion protein comprising culturing the host cell of claim 5.

7. The fusion protein of claim 1 or 2, wherein Ly comprises a second protease cleavage site.

8. The fusion protein of claim 1 or 2, wherein the fusion protein comprises a full-length antibody.

9. The fusion protein of claim 1, wherein Lx comprises more than one protease cleavage site which is located between the VH or VL region and the CH1 or CL region.

10. The fusion protein of claim 1 or 2, wherein the Fc region comprises a CH3 region, and wherein the ligand moiety is connected to an amino acid residue exposed on the surface of the CH3 region of the Fc region via Ly.

11. The fusion protein of claim 1 or 2, which further comprises a second protease cleavage site, wherein the ligand moiety is connected to an N-terminal region of the ligand binding moiety via the second protease cleavage site.

12. The fusion protein of claim 1 or 2, wherein the ligand moiety is a molecule having a biological activity, wherein binding of the ligand-binding domain to the ligand moiety inhibits the biological activity of the ligand moiety.

13. The fusion protein of claim 11, wherein the ligand moiety is a cytokine or chemokine.

14. A pharmaceutical composition comprising the fusion protein of claim 1 or 2.

* * * * *